United States Patent
Liu et al.

(10) Patent No.: US 9,220,915 B2
(45) Date of Patent: *Dec. 29, 2015

(54) DEVICES AND METHODS FOR RADIATION-BASED DERMATOLOGICAL TREATMENTS

(75) Inventors: Harvey I-Heng Liu, Fremont, CA (US); John P. Beale, Mountain View, CA (US)

(73) Assignee: TRIA BEAUTY, INC., Dublin, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/443,821

(22) Filed: Apr. 10, 2012

(65) Prior Publication Data

US 2012/0283803 A1    Nov. 8, 2012

Related U.S. Application Data

(63) Continuation-in-part of application No. 13/366,202, filed on Feb. 3, 2012.

(60) Provisional application No. 61/439,353, filed on Feb. 3, 2011, provisional application No. 61/444,079, filed (Continued)

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 2017/00154* (2013.01);
(Continued)

(58) Field of Classification Search
CPC .............. A61B 18/203; A61B 2018/2085; A61N 5/06; A61N 5/0616; A61N 2005/0626–2005/0628; A61N 2005/0644
USPC ............................ 606/9; 607/88–89
See application file for complete search history.

(56) References Cited

U.S. PATENT DOCUMENTS

| | | | |
|---|---|---|---|
| 3,360,659 A | 12/1967 | Young | 250/236 |
| 3,517,202 A | 6/1970 | Kennedy | 250/568 |

(Continued)

FOREIGN PATENT DOCUMENTS

| | | | | |
|---|---|---|---|---|
| WO | 2008/124839 A1 | 10/2008 | | A61B 18/18 |
| WO | 2011/010239 A1 | 1/2011 | | A61B 18/20 |

OTHER PUBLICATIONS

Doss, James D., "Method for Calculation of Corneal Profile and Power Distribution," Arch. Ophthalmol, vol. 99, 6 pages, July 1981.

(Continued)

*Primary Examiner* — Lynsey Crandall
*Assistant Examiner* — Nathan J Jenness
(74) *Attorney, Agent, or Firm* — Slayden Grubert Beard PLLC

(57) ABSTRACT

A self-contained, hand-held device for providing a dermatological treatment includes a handheld device body, a radiation source supported in the device body, an automated scanning system, an application end, and a displacement control system. The automated scanning system is configured to receive an input beam generated by the radiation source and scan the received input beam to provide a series of output beams for delivery to the skin via the application end of the device to form a pattern of treatment spots on the skin. The application end is configured to be manually moved across the surface of the skin during a treatment session. The displacement control system includes a displacement sensor configured to determine a displacement of the device relative to the skin, and electronics configured to control at least one operational parameter of the device based on the determined displacement of the device relative to the skin.

19 Claims, 73 Drawing Sheets

Related U.S. Application Data on Feb. 17, 2011, provisional application No. 61/469,316, filed on Mar. 30, 2011, provisional application No. 61/533,641, filed on Sep. 12, 2011, provisional application No. 61/533,677, filed on Sep. 12, 2011, provisional application No. 61/533,786, filed on Sep. 12, 2011, provisional application No. 61/545,481, filed on Oct. 10, 2011, provisional application No. 61/563,491, filed on Nov. 23, 2011, provisional application No. 61/594,128, filed on Feb. 2, 2012, provisional application No. 61/613,778, filed on Mar. 21, 2012.

(51) Int. Cl.
*A61B 17/00* (2006.01)
*A61B 18/00* (2006.01)
*A61B 19/00* (2006.01)
*A61N 5/067* (2006.01)

(52) U.S. Cl.
CPC .......... *A61B2017/00769* (2013.01); *A61B 2018/0047* (2013.01); *A61B 2018/00458* (2013.01); *A61B 2018/00476* (2013.01); *A61B 2018/00732* (2013.01); *A61B 2018/2035* (2013.01); *A61B 2018/2085* (2013.01); *A61B 2019/409* (2013.01); *A61B 2019/461* (2013.01); *A61B 2019/465* (2013.01); *A61N 2005/067* (2013.01); *A61N 2005/0644* (2013.01); *H01L 2224/48091* (2013.01)

(56) References Cited

U.S. PATENT DOCUMENTS

| | | | |
|---|---|---|---|
| 4,094,576 A | 6/1978 | Heiling | 359/18 |
| 4,739,177 A | 4/1988 | Borden | 250/574 |
| 4,799,164 A | 1/1989 | Hellekson et al. | 235/462.4 |
| 5,070,509 A | 12/1991 | Meyers | 372/45.01 |
| 5,186,184 A | 2/1993 | Aindow et al. | 131/281 |
| 5,445,608 A | 8/1995 | Chen et al. | 604/20 |
| 5,452,181 A | 9/1995 | Hoover | 361/697 |
| 5,475,452 A | 12/1995 | Kuhn et al. | 351/212 |
| 5,522,813 A | 6/1996 | Trelles | 606/2 |
| 5,646,674 A | 7/1997 | Bacon | 347/257 |
| 5,658,323 A | 8/1997 | Miller | 607/89 |
| 5,710,631 A | 1/1998 | Bou-ghannam et al. | 356/495 |
| 5,726,793 A | 3/1998 | Boardman et al. | 359/216.1 |
| 5,758,951 A | 6/1998 | Haitz | 362/259 |
| 5,790,576 A | 8/1998 | Waarts et al. | 372/50.23 |
| 6,003,997 A | 12/1999 | Downes, Jr. | 359/857 |
| 6,057,871 A | 5/2000 | Peterson | 347/238 |
| 6,106,316 A | 8/2000 | Barringer et al. | 439/263 |
| 6,171,302 B1* | 1/2001 | Talpalriu et al. | 606/9 |
| 6,234,687 B1 | 5/2001 | Hall et al. | 385/88 |
| 6,243,407 B1 | 6/2001 | Mooradian et al. | 372/92 |
| 6,339,577 B1 | 1/2002 | Hineno | 369/112.24 |
| 6,392,813 B1 | 5/2002 | Reardon et al. | 359/641 |
| 6,527,460 B2 | 3/2003 | Cohen et al. | 385/94 |
| 6,529,542 B1 | 3/2003 | Karlsen et al. | 372/108 |
| 6,758,845 B1 | 7/2004 | Weckwerth et al. | 606/9 |
| 6,771,686 B1 | 8/2004 | Ullman et al. | 372/92 |
| 7,090,670 B2 | 8/2006 | Sink | 606/9 |
| 7,118,563 B2 | 10/2006 | Weckwerth et al. | 606/9 |
| 7,184,184 B2 | 2/2007 | Debenedictis et al. | 359/201.1 |
| 7,372,606 B2 | 5/2008 | Broome et al. | 359/216.1 |
| 7,420,996 B2 | 9/2008 | Schulte et al. | 372/36 |
| 7,515,346 B2 | 4/2009 | Govorkov et al. | 359/641 |
| 7,633,486 B2 | 12/2009 | Lai et al. | 345/156 |
| 7,636,186 B2 | 12/2009 | Debenedictis et al. | 359/205.1 |
| 7,684,660 B2 | 3/2010 | Braunisch et al. | 385/14 |
| 7,777,173 B2 | 8/2010 | Price et al. | 250/221 |
| 8,523,849 B2 | 9/2013 | Liu et al. | 606/9 |
| 8,679,102 B2 | 3/2014 | Reichert et al. | 606/9 |
| 8,685,008 B2 | 4/2014 | Weckwerth et al. | 606/9 |
| 2002/0128695 A1 | 9/2002 | Harth et al. | 607/88 |
| 2003/0171795 A1 | 9/2003 | Walmsley et al. | 607/88 |
| 2004/0036975 A1 | 2/2004 | Slatkine | 359/584 |
| 2004/0152943 A1 | 8/2004 | Zimmerman et al. | 600/13 |
| 2004/0167501 A1 | 8/2004 | Island et al. | 606/9 |
| 2004/0176754 A1 | 9/2004 | Island et al. | 606/9 |
| 2004/0230260 A1 | 11/2004 | Macfarland et al. | 607/89 |
| 2005/0045189 A1 | 3/2005 | Jay | 128/898 |
| 2005/0141068 A1 | 6/2005 | Debenedictis et al. | 359/201.1 |
| 2005/0154380 A1* | 7/2005 | DeBenedictis et al. | 606/9 |
| 2006/0149343 A1 | 7/2006 | Altshuler et al. | 607/90 |
| 2006/0155266 A1 | 7/2006 | Manstein et al. | 606/17 |
| 2006/0200114 A1 | 9/2006 | Ferren et al. | 606/9 |
| 2006/0227836 A1 | 10/2006 | Omori et al. | 372/50.124 |
| 2007/0060819 A1 | 3/2007 | Altshuler et al. | 600/475 |
| 2007/0060984 A1 | 3/2007 | Webb et al. | 607/89 |
| 2007/0093798 A1 | 4/2007 | Debenedictis et al. | 606/12 |
| 2007/0179481 A1 | 8/2007 | Frangineas et al. | 606/9 |
| 2007/0198004 A1 | 8/2007 | Altshuler et al. | 606/9 |
| 2007/0213698 A1 | 9/2007 | Altshuler et al. | 606/12 |
| 2007/0260230 A1 | 11/2007 | Youngquist et al. | 606/9 |
| 2008/0058782 A1 | 3/2008 | Frangineas et al. | 606/9 |
| 2008/0058783 A1 | 3/2008 | Altshuler et al. | 606/9 |
| 2008/0077198 A1 | 3/2008 | Webb et al. | 607/88 |
| 2008/0139901 A1 | 6/2008 | Altshuler et al. | 600/306 |
| 2008/0172047 A1 | 7/2008 | Altshuler et al. | 606/9 |
| 2008/0262484 A1 | 10/2008 | Hawkins et al. | 606/12 |
| 2008/0294150 A1 | 11/2008 | Altshuler et al. | 606/3 |
| 2009/0069741 A1 | 3/2009 | Altshuler et al. | 604/22 |
| 2009/0131922 A1 | 5/2009 | Dewey et al. | 606/9 |
| 2009/0137996 A1 | 5/2009 | Debenedictis | 606/9 |
| 2009/0270848 A1 | 10/2009 | Weckwerth et al. | 606/9 |
| 2010/0130969 A1 | 5/2010 | Batterson et al. | 606/9 |
| 2010/0152718 A1 | 6/2010 | Fujikawa | 606/9 |
| 2010/0211055 A1 | 8/2010 | Eckhouse et al. | 606/9 |
| 2011/0098691 A1 | 4/2011 | Chan et al. | 606/9 |
| 2012/0022510 A1 | 1/2012 | Welches et al. | 606/3 |
| 2012/0050849 A1 | 3/2012 | Schreiber | 359/371 |
| 2012/0197357 A1* | 8/2012 | Dewey et al. | 607/89 |

OTHER PUBLICATIONS

Jacques, Steven L., "Skin Optics," Oregon Medical Laser Center News, 7 pages, Jan. 1998.

Song, Dae-Sung et al., "Single-Fundamental-Mode Phototonic-Crystal Vertical-Cavity Surface-Emitting Lasers," Applied Physics Letters 80, 3901 (2002), DOI: 10.1063/1.1481984, 3 pages, 2002.

Internet Webpage, Wikipedia, the free encyclopedia, <http://en.wikipedia.org/wiki/Lens_(optics)> archived on Dec. 18, 2008 (retrieved on Feb. 6, 2013), backdated using the Internet archive website <URL: http://web.archive.org/web/20081218164923/http://en.wikipedia.org/wiki/Lens_(optics)>, 10 pages, Dec. 18, 2008.

Liu, Anjin et al., "Reduced Divergence Angle of Photonic Crystal Vertical-Cavity Surface-Emitting Laser," Appl. Phys. Lett. 94, 3 pages, 2009.

Sardar, Dhiraj K. et al., "Optical Absorption and Scattering of Bovine Cornea, Lens, and Retina in the Visible Region," Laser Med. Sci., 24(6), 18 pages, Nov. 2009.

Kang, Zhou et al., "Reduction of Far-Field Divergence Angle of 850 nm Multi-Leaf Holey Vertical Cavity Surface Emitting Laser," Chin. Phys. Lett., vol. 28, No. 8, 3 pages, 2011.

International PCT Search Report and Written Opinion, PCT/US2012/023894, 12 pages, May 3, 2012.

International PCT Search Report and Written Opinion, PCT/US2012/023880, 12 pages, May 3, 2012.

International PCT Search Report and Written Opinion, PCT/US2012/023887, 12 pages, May 3, 2012.

International PCT Search Report and Written Opinion, PCT/US2012/023890, 12 pages, May 3, 2012.

International PCT Search Report and Written Opinion, PCT/US2012/023885, 12 pages, May 3, 2012.

International PCT Search Report and Written Opinion, PCT/US2012/023893, 12 pages, May 3, 2012.

International PCT Search Report and Written Opinion, PCT/US2012/054146, 19 pages, Jan. 28, 2013.

(56) References Cited

OTHER PUBLICATIONS

U.S. Non-Final Office Action, U.S. Appl. No. 13/443,717, 14 pages, Jun. 9, 2015.
U.S. Non-Final Office Action, U.S. Appl. No. 13/366,202, 24 pages, Jul. 2, 2015.
U.S. Final Office Action, U.S. Appl. No. 13/443,844, 19 pages, Feb. 9, 2015.
U.S. Final Office Action, U.S. Appl. No. 13/443,863, 16 pages, Feb. 5, 2015.
U.S. Final Office Action, U.S. Appl. No. 13/443,876, 22 pages, Feb. 9, 2015.
U.S. Final Office Action, U.S. Appl. No. 13/366,237, 20 pages, Nov. 25, 2014.
U.S. Final Office Action, U.S. Appl. No. 13/366,256, 17 pages, Dec. 17, 2014.
U.S. Final Office Action, U.S. Appl. No. 13/366,177, 23 pages, Nov. 25, 2014.
U.S. Non-Final Office Action, U.S. Appl. No. 14/016,221, 18 pages, Feb. 13, 2015.
U.S. Final Office Action, U.S. Appl. No. 14/016,221, 18 pages, Aug. 24, 2015.
Aquarius Series 437nm Blue Laser Pointer, LaserGlow Technologies Inc., URL: https://wvvw.laserglow.com/GAP#, 6 pages.
U.S. Non-Final Office Action, U.S. Appl. No. 13/366,237, 29 pages.
U.S. Non-Final Office Action, U.S. Appl. No. 13/366,177, 30 pages.
U.S. Non-Final Office Action, U.S. Appl. No. 13/366,256, 19 pages.
U.S. Non-Final Office Action, U.S. Appl. No. 13/443,844, 22 pages.
U.S. Non-Final Office Action, U.S. Appl. No. 13/443,876, 27 pages.

* cited by examiner

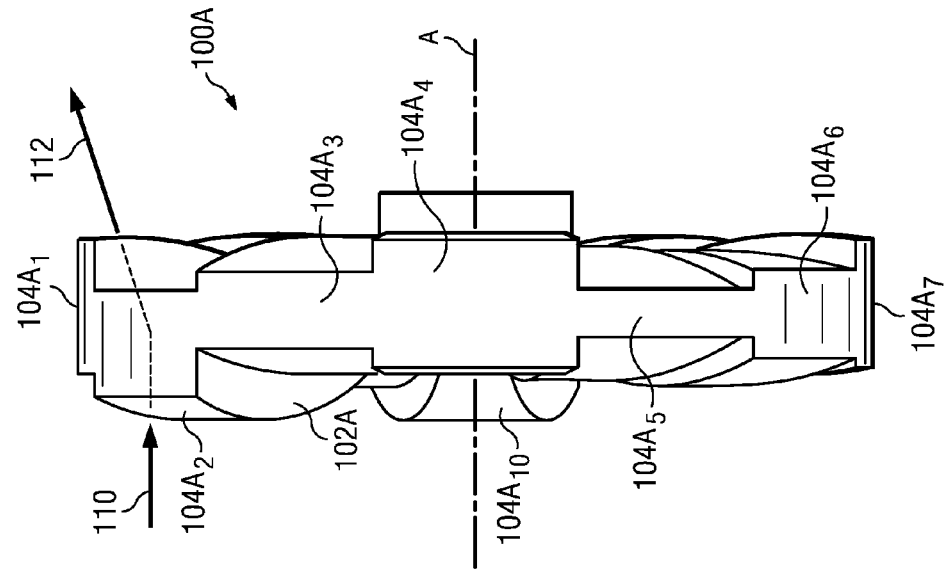
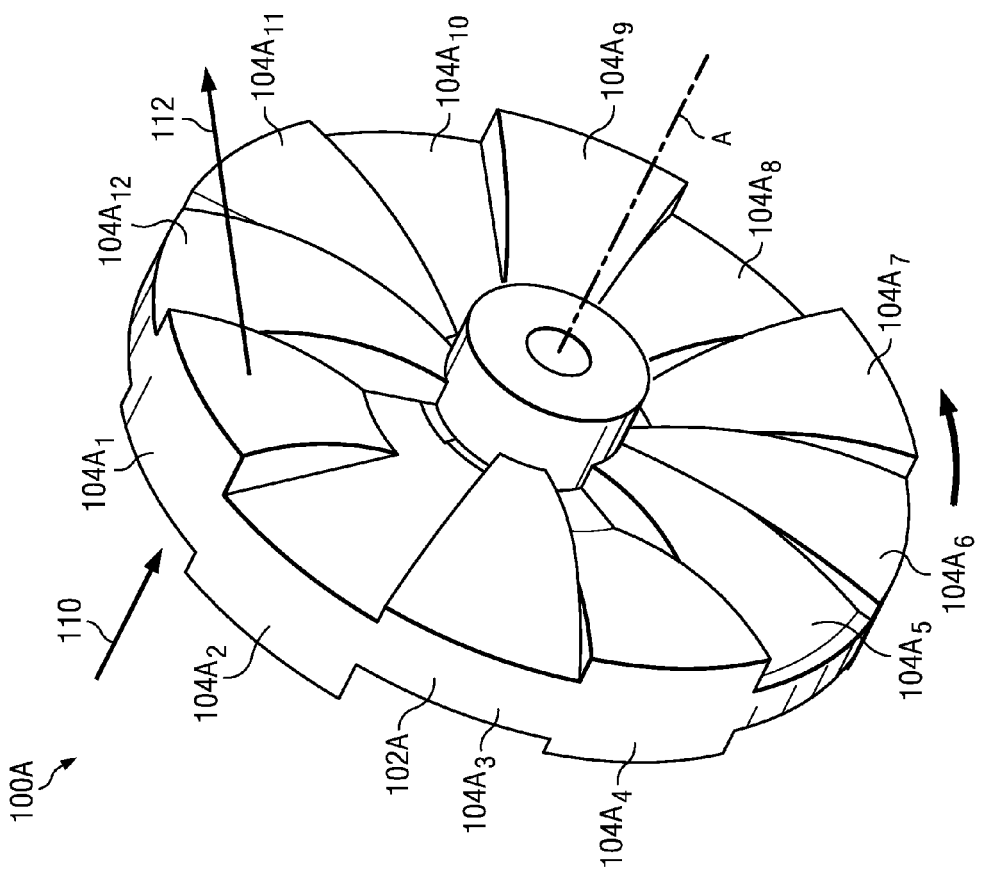

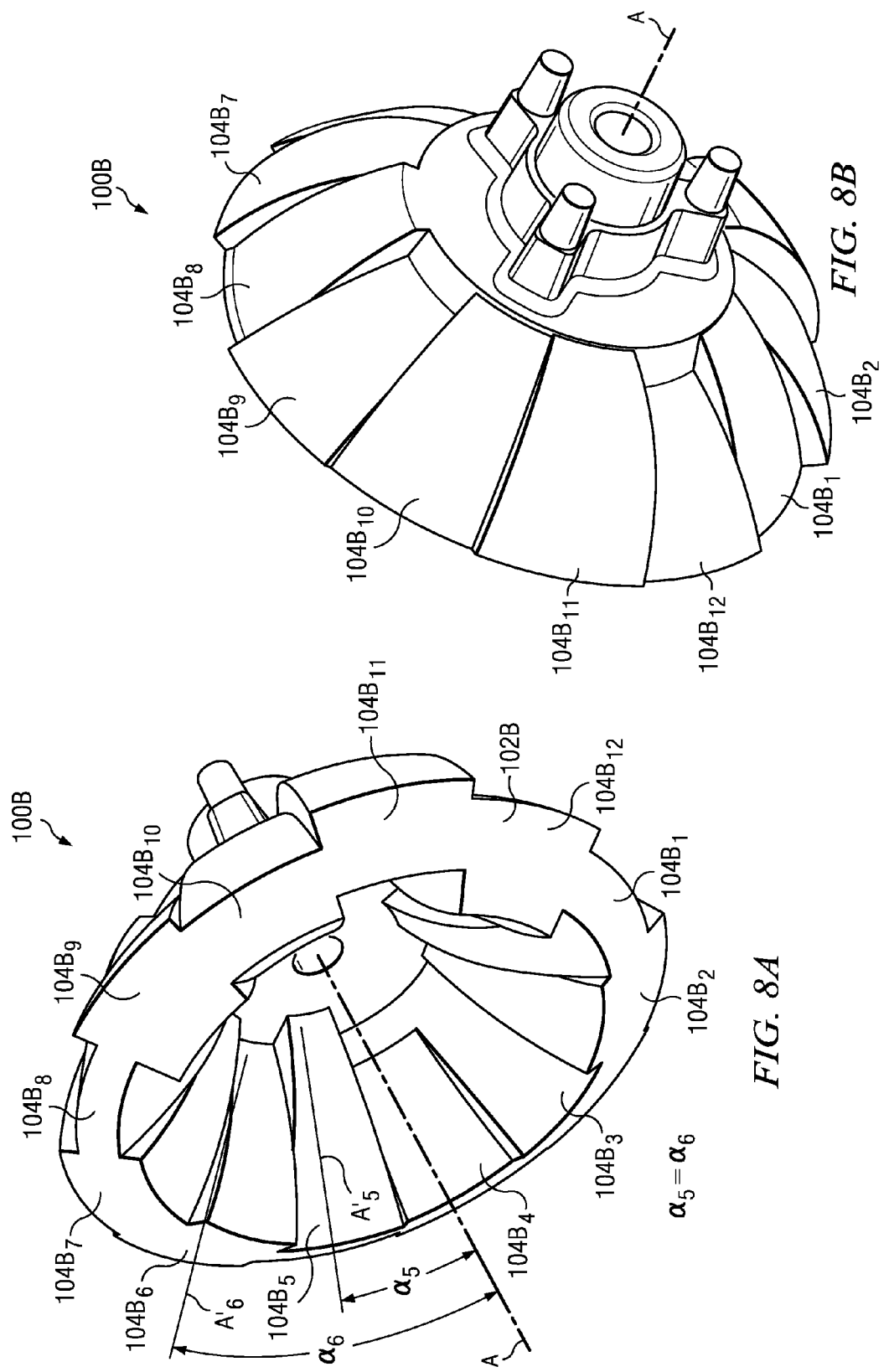

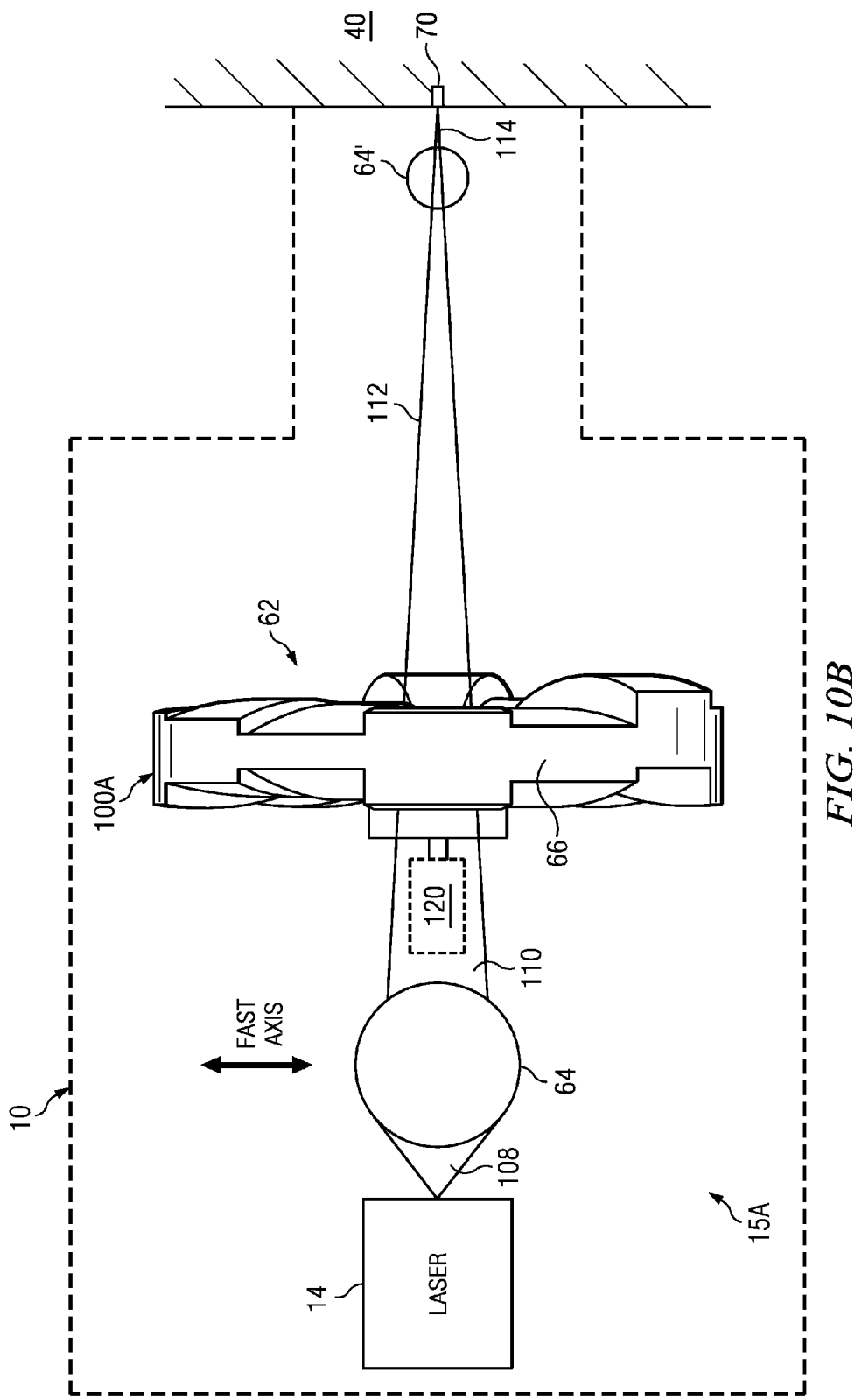

OAE = OBF = OCG = ODH

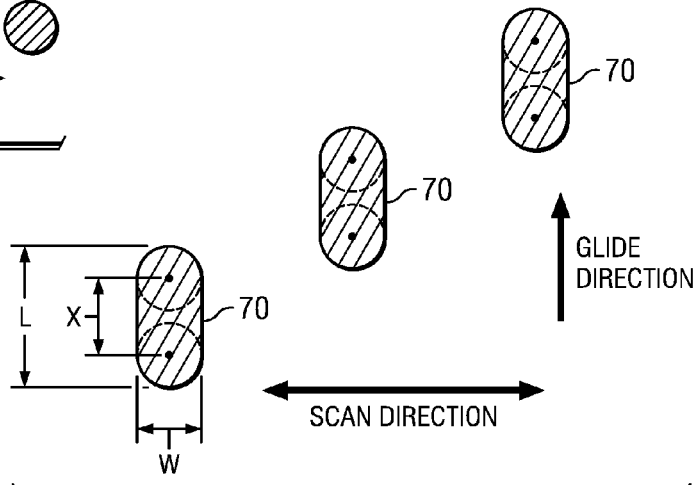
FIG. 26A
FIG. 26B
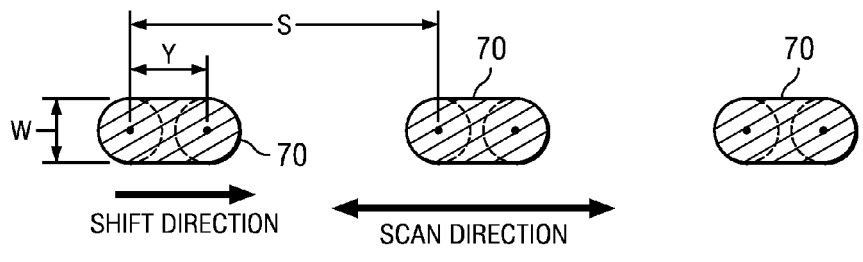
FIG. 27A
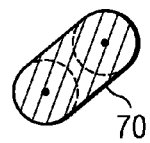
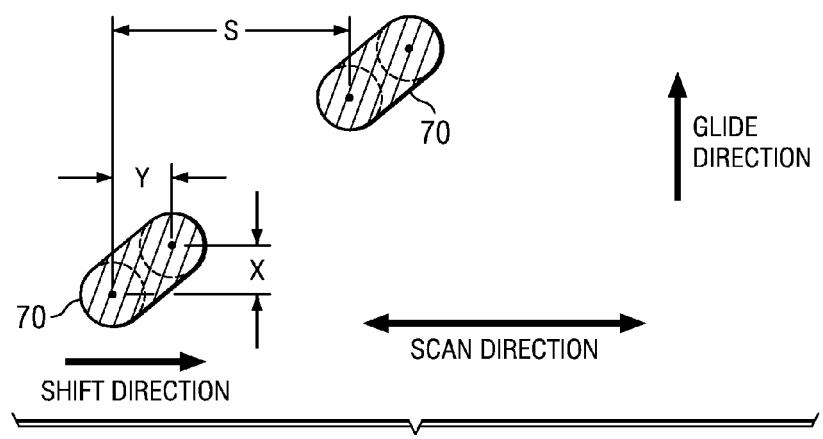
FIG. 27B

DEVICES AND METHODS FOR RADIATION-BASED DERMATOLOGICAL TREATMENTS

CROSS-REFERENCE TO RELATED APPLICATIONS

This application is a Continuation-In-Part of U.S. patent application Ser. No. 13/366,202 filed on Feb. 3, 2012, which claims priority from U.S. Provisional Application No. 61/439,353 filed on Feb. 3, 2011; U.S. Provisional Application No. 61/444,079 filed on Feb. 17, 2011; U.S. Provisional Application No. 61/469,316 filed on Mar. 30, 2011; U.S. Provisional Application No. 61/533,641 filed on Sep. 12, 2011; U.S. Provisional Application No. 61/533,677 filed on Sep. 12, 2011; U.S. Provisional Application No. 61/533,786 filed on Sep. 12, 2011; U.S. Provisional Application No. 61/545,481 filed on Oct. 10, 2011; U.S. Provisional Application No. 61/563,491 filed on Nov. 23, 2011 and U.S. Provisional Application No. 61/594,128 filed on Feb. 2, 2012, all of which applications are hereby incorporated by reference in their entirety.

This application also claims priority from U.S. Provisional Application No. 61/613,778 filed on Mar. 21, 2012, which application is hereby incorporated by reference in its entirety.

This application is also related to Co-Pending U.S. patent application Ser. No. 13/443,717 filed on Apr. 10, 2012; Co-Pending U.S. patent application Ser. No. 13/443,788 filed on Apr. 10, 2012; Co-Pending U.S. patent application Ser. No. 13/443,808 filed on Apr. 10, 2012; Co-Pending U.S. patent application Ser. No. 13/443,844 filed on Apr. 10, 2012; Co-Pending U.S. patent application Ser. No. 13/443,863 filed on Apr. 10, 2012, Co-Pending U.S. patent application Ser. No. 13/443,880 filed on Apr. 10, 2012; and Co-Pending U.S. patent application Ser. No. 13/443,876 filed on Apr. 10, 2012, all of which co-pending applications are hereby incorporated by reference in their entirety.

TECHNICAL FIELD

The present disclosure is related to radiation-based dermatological treatment devices and methods, e.g., laser-based devices for providing fractional treatment, or devices using any other type of radiation source for providing any other suitable type of dermatological treatment. Some embodiments include an automated scanning system for scanning a beam to multiple locations on the skin.

BACKGROUND

Light-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering light or laser radiation to an area of tissue on a person's body, e.g., the skin or internal tissue, to treat the tissue in a photochemical, photobiological, thermal, or other manner, which can be ablative or non-ablative, among other properties, depending on the particular application.

Light-based treatment devices include various types of radiation sources, such as lasers, LEDs, flashlamps, etc. For example, laser diodes are particularly suitable for certain light-based treatments and devices for providing such treatments. Laser diodes are compact, as they are typically built on one chip that contains the major necessary components for light generation other than a power source. Further, laser diodes typically provide an efficiency of up to 50% or higher, which enables them to be driven by low electrical power compared to certain other lasers. Laser diodes allow direct excitation with small electric currents, such that conventional transistor based circuits can be used to power the laser.

Other characteristics typical of laser diodes include high temperature sensitivity/tunability, and a highly divergent beam compared to certain other lasers. Laser diodes typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-based treatment devices typically include optics downstream of the laser source to scan, shape, condition, direct, and/or otherwise influence the laser radiation to the target tissue as desired. Such optics may include lenses, mirrors, and other reflective and/or transmissive elements, for controlling optical parameters of the beam, such as the direction, propagation properties or shape (e.g., convergent, divergent, collimated), spot size, angular distribution, temporal and spatial coherence, and/or intensity profile of the beam, for example. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide complete coverage of a target area of tissue. For other applications, e.g., certain wrinkle treatments, vascular treatments, pigmentation treatments, anti-inflammatory treatments, and other skin rejuvenation treatments, the scanned radiated areas may be spaced apart from each other by non-irradiated areas such that only a fraction of the overall target area of the tissue is radiated during a treatment session. Thus, in such applications, there are generally regions of untreated tissue between regions of treated tissue. This type of treatment is known as "fractional" treatment (or more specifically, fractional photothermolysis in some cases) because only a fraction of the target area is irradiated during a treatment session.

Some known scanning systems move the radiation source itself relative to the device housing or structure in order to form the scanned pattern of radiated areas. Other known scanning systems utilize one or more moving optical elements (e.g., mirrors and/or lenses) in order to scan a radiation beam into a pattern of radiated areas, rather than moving the radiation source relative to the device housing or structure.

SUMMARY

The present disclosure is related to radiation-based dermatological treatment devices and methods, e.g., laser-based devices for providing fractional treatment.

In some embodiments, a hand-held compact device is provided for providing radiation-based dermatological treatments, e.g., skin resurfacing, skin rejuvenation, wrinkle treatment, removal or reduction of pigmentation, hair removal, acne treatment, skin tightening, redness, vascular treatments such as telangectasia or port-wine stains, stretch marks, anti-aging, or anti-inflammatory skin treatments such as treating rosacea, acne, or vitiligo. Other embodiments may apply to non-skin tissue treatment, such as eye tissue or internal organs. In particular embodiments, the device includes one or more radiation sources (e.g., one or more lasers) and an automated scanning system for delivering an array of scanned beams to the skin, while the device is manually moved across the skin, to produce an array of discrete treatment spots on the skin, e.g., to provide a fractional thermal treatment. In other embodiments, the device may be configured for full coverage of a treatment area (i.e., non-fractional treatment), e.g., for skin tightening. In some embodiments, the device may provide a non-thermal treatment, e.g., a photochemical treatment such as a blue light treatment that acts on bacterial porphyrins, photobiological treatment such as low-level light therapy that acts on mitochondria, photodynamic therapy (PDT), etc.

The device may include one or more radiation sources that radiate energy in the form of one or more beams to produce one or more irradiated areas on the skin that provide a dermatological treatment. As used herein, "radiation" may include any radiative energy, including electromagnetic radiation, UV, visible, and IP light, radio frequency, ultrasound, microwave, etc. A radiation source may include any suitable device for radiating one or more coherent or incoherent energy beams, e.g., a laser, LED, flashlamp, ultrasound device, RF device, microwave emitter, etc. Energy beams may be generated in any suitable manner, such as pulsed, continuous wave (CW), or otherwise (depending on the particular embodiment, application, or device setting), and then scanned by an automated scanning system to deliver a scanned array of output beams to the skin. In some embodiments, the radiation source is a laser, e.g., an edge emitting laser diode, laser diode bar, HeNe laser, YAG laser, VCSEL laser, or other types of laser, that generates one or more laser beams that are scanned and delivered to the skin to effect a treatment. It should be understood that references herein to a radiation source or an energy beam in the singular should be interpreted to mean at least one radiation source or at least one energy beam, unless otherwise specified, e.g., references to a single radiation source or a single energy beam, or references to radiation sources or energy beams (or references to multiple radiation sources or multiple energy beams).

In some embodiments, the device provides automatically scanned and/or pulsed energy beams to the skin to provide a fractional dermatological treatment, e.g., skin resurfacing, skin rejuvenation, wrinkle treatment, removal or reduction of pigmentation, treatment of coarse skin caused by photodamage, etc. Each scanned and/or pulsed energy beam delivered to the skin is referred to herein as a "delivered beam." In embodiments that provide a fractional treatment, each delivered beam forms an irradiated treatment spot (or "treatment spot") on the surface of the skin, and a three-dimensional volume of thermally damaged (or otherwise influenced, such as photochemically) skin extending below the surface of the skin, referred to herein as a micro thermal zone (MTZ). Each MTZ may extend from the skin surface downward into the skin, or may begin at some depth below the skin surface and extend further downward into the skin, depending on the embodiment, device settings, or particular application. The device may be configured to generate an array of MTZs in the skin that are laterally spaced apart from each other by volumes of untreated (i.e., non-irradiated or less irradiated) skin. For example, an application end of the device may be manually moved (e.g., in a gliding manner) across the surface of the skin during a treatment session. An automatically scanned array of beams may be delivered to the skin (to generate an array of MTZs in the skin) during the movement of the device across the skin, which is referred to herein as a "gliding mode" treatment, or between movements of the device across the skin, which is referred to herein as a "stamping mode" treatment, or a combination of these modes, or a different mode of operation. The skin's healing response, promoted by the areas of untreated (i.e., non-irradiated) skin between adjacent MTZs, provides fractional treatment benefits in the treatment area (e.g., skin resurfacing or rejuvenation, wrinkle removal or reduction, pigment removal or reduction, etc.). In some embodiments or applications, the compact, hand-held device may yield results similar to professional devices, but leverages a home use model to more gradually deliver the equivalent of a single professional dose over multiple treatments or days (e.g., a 30 day treatment routine or a two treatment sessions per week treatment routine). Skin rejuvenation generally includes at least one or more of treatments for wrinkles, dyschromia, pigmented lesions, actinic keratosis, melasma, skin texture, redness or erythema, skin tightening, skin laxity, and other treatments.

As used herein, "fractional" treatment means treatment in which individual treatment spots generated on the skin surface are physically separated from each other by areas of non-irradiated (or less irradiated) skin (such that the MTZs corresponding to such treatment spots are generally physically separated from each other). In other words, in a fractional treatment, adjacent treatment spots (and thus their corresponding MTZs) do not touch or overlap each other. In some embodiments in which a radiation source (e.g., laser) is automatically scanned and/or pulsed to generate a successive array of treatment spots on the skin, the automated scan rate and/or the pulse rate may be set and/or controlled based on various factors, such as a typical or expected speed at which the device is manually moved or glided across the skin, referred to herein as the "manual glide speed" (e.g., in a gliding mode operation of the device). In particular, the automated scan rate and/or the pulse rate may be set and/or controlled such that for a range of typical or expected manual (or mechanically-driven) glide speeds, adjacent treatment spots or adjacent rows of treatment spots are generally physically separated from each other by areas of non-treated skin (i.e., fractional treatment is provided). In some embodiments, the device delivers a successive series of automatically scanned rows of beams to the skin while the device is manually glided across the skin, to produce successive rows of treatment spots on the skin. In such embodiments, the automated scan rate may be set or selected such that for a range of typical or expected manual glide speeds, adjacent rows of treatment spots are physically separated from each other from a predetermined minimum non-zero distance, e.g., 1500 μm.

In some embodiments, the device may be configured to provide 3D fractional treatment, by generating MTZs at various depths in the skin. For example, this may be achieved (a) by scanning beams to generate MTZs at different depths, e.g., using scanning optics configured to provide different focal depths, or by controlling wavelengths, pulse energies, pulse durations, etc. for different scanned beams, (b) by dynamically moving or adjusting one or more radiation sources, scanning optics or other optics, e.g., to dynamically adjust the focal points of the delivered beams, (c) by providing multiple radiation sources configured to generate MTZs at different depths, e.g., by using multiple radiation sources arranged at different distances from the skin surface, focal depths, wavelengths, pulse energies, pulse durations, or other parameters, or (d) in any other suitable manner.

The device may include any suitable beam scanning system including any suitable (transmissive, reflective, or otherwise) beam scanning optics. In some embodiments, the device may include a transmissive disk-shaped multi-sector beam scanning element including multiple sectors (e.g., lenslets) arranged circumferentially around the scanning element. The multiple sectors or lenslets of the disk-shaped scanning element may be configured to that scan an input beam into a sequential array of output beams, each being angularly and/or translationally offset from at least one other output beam, to provide an array of treatment spots at different locations on the skin.

In other embodiments, the device may include a transmissive cup-shaped multi-sector beam scanning element including multiple sectors (e.g., lenslets) arranged circumferentially around the scanning element. The multiple sectors or lenslets of the cup-shaped scanning element may be configured to that scan an input beam into a sequential array of output beams, each being angularly and/or translationally offset from at least one other output beam, to provide an array of treatment spots at different locations on the skin.

In other embodiments, the device may include a reflective stair-stepped beam scanning element including multiple sectors (e.g., reflective surfaces) arranged circumferentially around the scanning element. The multiple sectors or reflective surfaces of the stair-stepped scanning element may be configured to that scan an input beam into a sequential array of output beams, each being angularly and/or translationally offset from at least one other output beam, to provide an array of treatment spots at different locations on the skin.

In any of these embodiments, the beam scanning element may be configured to provide "constant angular deflection" output beams, wherein each output beam from the scanning element maintains a constant or substantially constant angle of deflection with respect to the device housing (i.e., a constant propagation direction) for the duration of that output beam (i.e., for the duration that the input beam acts on the scanning element sector that produces that output beam). In other words, with constant angular deflection output beams, if the device is held stationary on the skin, each output beam creates a stationary or substantially stationary treatment spot on the skin.

In some embodiments, the device includes a displacement-based control system including a displacement sensor and electronics configured to measure or estimate the lateral displacement of the device across the skin and control one or more aspect of the device (e.g., on/off status of the radiation source, pulse rate, automated scan rate, etc.) based on the determined displacement of the device. For example, the displacement-based control system may control the delivery of scanned beams to provide a desired spacing between scanned rows of treatment spots (for a fractional treatment) and/or to prevent or reduce the incidence or likelihood of treatment spot overlap. For example, as the device generates and delivers a series of scanned beam rows to create a series of treatment spot rows, the displacement monitoring and control system may allow the next scanned beam row (or individual beams within the row) to be generated and/or delivered only if the device has been displaced a predetermined distance from a previous treatment location (e.g., the device location at the beginning of the previously delivered scanned beam row). Otherwise, the device may interrupt the generation and/or delivery of beams until the displacement of the device meets or exceeds the predetermined distance. In some embodiments, the predetermined distance is based on a predetermined number of consecutive surface features in the skin that may be detected by a displacement sensor. In other embodiments, the displacement may be measured with other types of distance detection such as mechanical rollers, optical mouse sensors, etc. In other embodiments, a dwell sensor and/or a motion sensor may be used to reduce the risk of repeatedly treating the same skin region.

In some embodiments, the device includes a single radiation source, e.g., an edge emitting laser diode, a VCSEL having a single micro-emitter zone, an LED, or a flashlamp. For certain treatments, the single radiation source may be automatically scanned to provide a line or array of delivered beams extending generally in a "scan direction," while the device is glided across the skin in a "glide direction" generally perpendicular to the scan direction, thus form a generally two-dimensional array of treatment spots on the skin. A larger array of treatment spots can thus be created by gliding the device across the skin multiple times in any suitable direction(s) or pattern(s).

In other embodiments, the device includes multiple radiation sources, e.g., multiple edge emitting laser diodes, an laser diode bar having multiple emitters (or multiple laser diode bars), a VCSEL having multiple micro-emitter zones (or multiple VCSELs), or multiple LEDs. The multiple radiation sources may be collectively scanned by an automated scanning system or separately scanned by multiple automated scanning systems, to form an array of delivered beams to the skin as desired.

In some embodiments, the device is fully or substantially self-contained in a compact, hand-held housing. For example, in some battery-powered embodiments of the device, the radiation source(s), user interface(s), control electronics, sensor(s), battery or batteries, fan(s) or other cooling system (if any), scanning system, and/or any other optics, are all contained in a compact, hand-held housing. Similarly, in some wall-outlet-powered embodiments of the device, the radiation source(s), user interface(s), control electronics, sensor(s), battery or batteries, fan(s) or other cooling system (if any), scanning system, and/or any other optics, are all contained in a compact, hand-held housing, with only the power cord extending from the device.

In other embodiments, one or more main components of the device may be separate from the device housing, and connected by any suitable physical or wireless means (e.g., wire, cable, fiber, wireless communications link, etc.)

In some embodiments, the device provides eye safe radiation, e.g., by delivering a substantially divergent energy beam (e.g., using an edge emitting laser diode with no downstream optics), and/or using an eye safety control system including one or more sensors, and/or by any other suitable manner. In some laser-based embodiments or settings, the device meets the Class 1M or better (such as Class 1) eye safety classification per the IEC 60825-1, referred to herein as "Level 1 eye safety" for convenience. In other embodiments or settings, the device exceeds the relevant Maximum Permissible Exposure (MPE) (for 700-1050 nm wavelength radiation) or Accessible Emission Limit (AEL) (for 1400-1500 nm or 1800-2600 nm wavelength radiation) by less than 50%, referred to herein as "Level 2 eye safety" for convenience. In still other embodiments or settings, the device exceeds the relevant MPE (for 700-1050 nm wavelength radiation) or AEL (for 1400-1500 nm or 1800-2600 nm wavelength radiation) by less than 100%, referred to herein as "Level 3 eye safety" for convenience. The Accessible Emission Limit (AEL), as specified in IEC 60825-1, e.g., for 700-1050 nm wavelength radiation, is discussed below. Maximum Permissible Exposure (MPE), which is relevant, e.g., for 700-1050 nm wavelength radiation, is not discussed below but is specified in IEC 60825-1:2007. In other embodiments or settings, the device meets the next highest eye safety classification after Class 1M per the IEC 60825-1, i.e., Class 3B, referred to herein as "Level 4 eye safety" for convenience.

In some embodiments, the device may be suitable for providing a fractional treatment using a home-use treatment plan that includes treatment sessions of a few minutes or less, once or twice a day. In some embodiments, a treatment session of 4 minutes, for example, may allow an effective treatment of about 300 cm$^2$ (about 4 in$^2$), e.g., for a full-face treatment. Further, certain embodiments permits the use a small battery, and allow for thermal control without any fan(s). For example, in some embodiments, a small cylindrical block of copper can absorb the waste heat from a laser during a treatment session, preventing excessive temperature rise of the diode without the use of a fan. Other embodiments may include at least one fan for increased cooling of the device components.

In some embodiments, the device may deliver a predetermined number of beams (thus providing a predetermined number of treatment spots on the skin), which may correspond to a selected treatment area (e.g., full face, periorbital area, etc.), operational mode, energy level, power level, and/or other treatment parameters. In some embodiments, the device may be glided at any speed across the skin within the target area, and repeatedly glided over the target area multiple times until the predetermined number of beams have been delivered, at which point the device may automatically terminate the treatment.

In some embodiments, the device may be controlled to prevent, limit, or reduce the incidence or likelihood of treatment spot overlap, excessive treatment spot density, or other non-desirable treatment conditions, e.g., based on feedback from one or more sensors (e.g., one or more dwell sensors, motion/speed sensors, and/or displacement sensors). For example, the device may monitor the speed or displacement of the device relative to the skin and control the radiation source accordingly, e.g., by turning off the radiation source, reducing the pulse rate, etc. upon detecting that the device has not been displaced on the skin a minimum threshold distance from a prior treatment location. Further, in some embodiments, the pulse rate may be automatically adjustable by the device and/or manually adjustable by the user, e.g., to accommodate different manual glide speeds and/or different comfort levels or pain tolerance levels of the user.

BRIEF DESCRIPTION OF THE DRAWINGS

Some embodiments of the disclosure may be understood by referring, in part, to the following description and the accompanying drawings wherein:

FIGS. 7A-7C illustrate an example disk-shaped rotating beam-scanning element, according to certain embodiments.

FIGS. 8A-8E illustrate an example cup-shaped rotating beam-scanning element, according to certain embodiments.

FIGS. 10A and 10B illustrate top and side views, respectively, of a beam generation and delivery system that includes a disk-shaped rotating scanning element, according to certain embodiments.

FIGS. 26A and 26B illustrate the smearing of treatment spots created by "constant angular deflection" beams, due to movement of the device during the delivery of the beams, according to certain embodiments.

FIGS. 27A and 27B illustrate the smearing and/or shifting of treatment spots created by "shifting deflection" beams, according to certain embodiments.

DETAILED DESCRIPTION OF THE DRAWINGS

Some embodiments of the disclosure may be understood by referring, in part, to the following description and the accompanying drawings, in which like reference numbers refer to the same or like parts.

Figure 1:
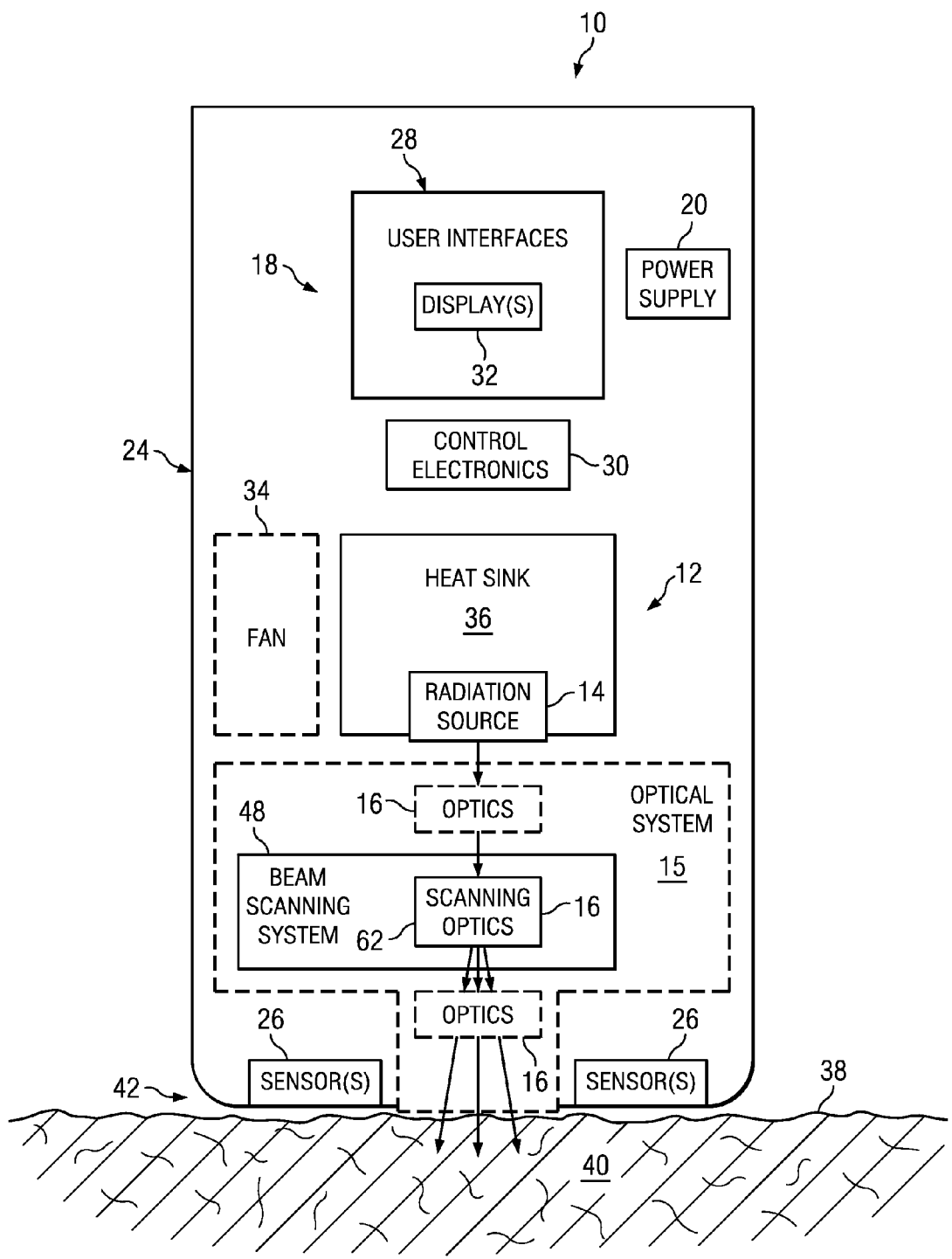
FIG. 1 illustrates components of an example radiation-based treatment device configured to deliver scanned beams to a user (e.g., to the user's skin), according to certain embodiments.

FIG. 1 illustrates various components of an example held-held radiation-based treatment device 10, according to certain embodiments. Radiation-based treatment device 10 may include a radiation source 14 including a radiation source 14 configured to generate an energy beam, an optical system 15 for scanning, conditioning, and/or delivering a series of scanned energy beams to a treatment area of the skin 40, control systems 18, one or more power supplies 20, and/or one or more fans 34.

In some embodiments, the main components of device 10 may be substantially self-contained in a held-held structure or outer housing 24. Held-held housing 24 may define an application end (or "treatment tip") 42 configured to be placed in contact with the skin (or other target surface) during treatment of a treatment area of the skin 40. Application end 42 may include or house various user interfaces, including the treatment delivery interface for delivering scanned beams to the user, as well as one or more sensors 26 for detecting various characteristics of the skin (or other surface) and/or energy delivered by device 10. In some embodiments, application end 42 may include an aperture or window 44 through which the scanned beams are delivered to the target surface, or alternatively, an optical element 16 (e.g., a lens) may be located at application end 42 and configured for direct contact or close proximity with the skin during treatment.

Device 10 may include any other components suitable for providing any of the functionality discussed herein or other related functionality known to one of ordinary skill in the art.

Radiation source 14 may include one or more radiation sources 14, such as one or more lasers, LEDs, and/or flashlamps, ultrasound devices, RF devices, or microwave emitters, for example. Embodiments including lasers as the radiation source 14 may include any type or types of lasers, e.g., one or more edge emitting laser diodes (single emitter edge emitting laser diodes or multiple emitter edge emitting laser diodes), laser diode bars, VCSEL lasers (Vertical Cavity Surface Emitting Lasers), $CO_2$ lasers, Erbium YAG lasers, pulsed dye lasers, fiber lasers, other types of lasers, or any combination thereof.

Radiation source 14 may include one or more radiation source, each operable to generate a beam of radiation. For example, radiation source 14 may comprise one or more laser sources, e.g., one or more laser diodes, $CO_2$ lasers, Erbium YAG lasers, pulsed dye lasers, fiber lasers, etc. In some embodiments, radiation source 14 may comprise one or more single-emitter edge emitting laser diode, multi-emitter edge emitting laser diode (e.g., as described in co-pending U.S. patent application Ser. No. 13/426,995 filed Mar. 21, 2012 and entitled "Dermatological Treatment Device with One or More Multi-Emitter Laser Diode," the entire contents of which application are hereby incorporated by reference), laser diode bars, or VCSEL lasers. In some embodiments, radiation source 14 may comprise one non-laser sources, e.g., one or more LEDs or flashlamps, for example.

For the sake of simplicity, this disclosure often refers to a singular radiation source or laser source (e.g., "a radiation source," "the radiation source," "a laser," or "the laser"), or to a device including a single radiation source or a single laser source. However, it should be understood that unless explicitly stated otherwise, any reference herein to a single radiation source is intended to mean at least one radiation source or laser source. Thus, for example, disclosure herein of a device including a laser source that generates a beam should be interpreted as disclosing a device including a singular laser source that generates a single beam, as well as a device including multiple laser sources each generating a respective beam.

In some embodiments, the beam emitted from the radiation source diverges in at least one direction. For example, in embodiments including an edge emitting laser diode or multi-radiation source laser diode bar, the emitted beam may diverge in both a fast axis and a slow axis. Thus, in such embodiments, optical system 15 may include optics directed to the fast axis and the slow axis beam profiles, either together or independently, as discussed below in greater detail. In embodiments including a VCSEL laser, the emitted beam or beams may diverge symmetrically in both axes.

In some embodiments, radiation source 14 may be configured for and/or operated at any suitable wavelength to provide the desired dermatological treatment. For example, radiation source 14 may be a laser configured for and/or operated at a wavelength that is absorbed by water in the skin, e.g., between 1400 nm and 2000 nm, e.g., for certain photothermolysis or other treatments. In some embodiments, radiation source 14 may be a laser configured for and/or operated at a wavelength of between 1400 nm and 1550 nm, e.g., for acne treatment or certain fractional non-ablative skin treatments, e.g., skin rejuvenation or resurfacing, wrinkle treatment, or treatment of pigmented legions (e.g., age spots, sun spots, moles, etc.). In other embodiments, radiation source 14 may be a laser configured for and/or operated at a wavelength of between 1700 nm and 1800 nm, e.g., for sebaceous gland related treatment like acne. In still other embodiments, radiation source 14 may be a laser configured for and/or operated at a wavelength of about 1926 nm, e.g., for pigmented lesion treatment like solar lentigo. As another example, radiation source 14 may be a laser configured for and/or operated at a wavelength of about 810 nm for providing hair removal treatment or melanin-based treatments. In some embodiments that include multiple radiation sources, different radiation sources may emit light at different wavelengths. For example, a device may include one or more first radiation sources that emit a wavelength of about 1400 nm-1550 nm and one or more second radiation sources that emit a wavelength of about 1926 nm. As another example, the wavelength may be in the UV (e.g., such as to effect DNA or micro-organisms), may be in the visible spectrum (e.g., such as to affect melanin, hemoglobin, oxyhemoglobin, or photosensitive elements like mitochondria or fibroblasts) or in the IR spectrum (e.g., such as to affect melanin, water, lipids). Likewise, the radiation may be in the ultrasound spectrum (e.g., such as to perform focused ultrasound fractional skin rejuvenation or tightening) or in the radio frequency spectrum (e.g., such as to perform fractional or bulk heating).

Radiation source 14 may be configured for or operated at any suitable energy or power level. For example, in some embodiments, radiation source 14 may emit a total energy of between about 2 mJ and about 30 mJ per delivered beam (i.e., per treatment spot). For example, radiation source 14 may emit between about 5 mJ and about 20 mJ per delivered beam. In particular embodiments, radiation source 14 emits about 10-15 mJ per delivered beam. In some embodiments, each delivered beam results from a pulse of a pulsed radiation source, which pulse is then scanned by an automated scanning system 48 to provide an output beam that is delivered to the skin as a delivered beam. Thus, in such embodiments, radiation source 14 may emit a total energy of between about 2 mJ and about 30 mJ per pulse, e.g., between about 5 mJ and about 20 mJ per pulse, e.g., about 10-15 mJ per pulse.

In some embodiments, device 10 controls radiation source 14 to generate radiation as continuous wave (CW) radiation, pulsed radiation, or in any other manner, depending on the particular embodiment, application, or device setting. For the purposes of this disclosure, pulsed or continuous wave radiation refers to the radiation emitted by radiation source 14, not the radiation delivered to the skin, as the radiation emitted by radiation source 14 is scanned to different locations by the automated scanning system 48. Thus, in some embodiments, radiation generated as CW radiation is delivered to the skin essentially as a series of pulses at different locations, as the CW radiation is rapidly scanned to different distinct treatment spots on the skin, with each treatment spot receiving a brief duration of the CW radiation, which is essentially a pulse. Thus, in embodiments that employ a scanning system, both CW and pulsed radiation sources may deliver energy in a pulsed manner.

Thus, to clarify the discussion, as used herein, a "generated pulse" refers to a pulse emitted by a pulsed radiation source 14, while a "delivered pulse" refers to a pulse delivered out of the application end 42 of the device 10. A delivered pulse is also referred to herein as a delivered beam 114, which is defined as the radiation output from one deflection sector of the relevant scanning element and delivered out of the application end 42 of the device 10, during any one particular scan of the scanning element. Thus, delivered pulses may be provided by both CW and pulsed radiation sources. A delivered pulse may include a single, continuous delivery of radiation, or multiple high-frequency pulses (e.g., in the form of a modulated pulse, pulse train, or super pulse) output from one deflection sector of the scanning element and delivered out of application end 42 during any one particular scan of the scanning element.

Embodiments in which radiation source 14 generates pulsed radiation may utilize any suitable pulse parameters, e.g., pulse rate or frequency, pulse on time, pulse off time, duty cycle, pulse profile, etc. In some embodiments, radiation source 14 may be pulsed at a rate between 0.5 and 75 Hz. For example, radiation source 14 may be pulsed at a rate between 2 and 30 Hz. In particular embodiments, radiation source 14 may be pulsed at a rate between 10 and 20 Hz, e.g., about 15 Hz. The energy per pulse on a given treatment spot can be achieved by a single pulse or by multiple repetitive pulses.

As used herein, a "treatment spot" means a contiguous area of skin irradiated by a radiation source—during a delivered pulse (as defined above)—to a degree generally sufficient to provide a desired treatment in the skin at that location. For some types of radiation source, including laser radiation sources for example, the boundaries of the treatment spot are defined by the "$1/e^2$ width," i.e., the treatment spot includes a contiguous area of the skin surface that is irradiated by a radiation intensity equal to at least $1/e^2$ (or 0.135) times the maximum radiation intensity at any point on the skin surface. A treatment spot may include the full extent of the surface (or volume) irradiated. A treatment spot may include the full extent of the tissue being influenced by the irradiation, which may be smaller than the irradiated area or volume, or may be larger (e.g., due to thermal conductivity). Further, reference to a treatment spot "on the skin" or similar language refers to radiation pattern on the skin which generally produces a radiation pattern within the skin, whether or not it produces a treatment effect on the surface of the skin.

A treatment spot includes any increased areas due to smearing, blurring, or other elongation in any one or more direction due to movement of device 10 across the skin during a delivered pulse, e.g., in a gliding mode operation of device 10. For example, due to smearing or blurring effects, the treatment spot generated by each delivered beam 114 may be 10% to 500% larger than the size of the instantaneous irradiated area of skin by that delivered beam 114, depending on a number of factors.

Optical system 15 is configured for scanning, delivering, conditioning, and/or otherwise controlling or affecting radiation from radiation source 14 to the target surface (e.g., the skin), and may include any number and/or type(s) of optics, or optical elements, 16 for providing such functionality. In some embodiments, optical system 15 includes (a) a beam scanning system 48 including any suitable optics 16 configured to convert, or "scan," an input beam (e.g., a pulsed or CW input beam) into a successive series of output beams for delivery to the skin, and (b) any other optical elements 16 (if any) upstream and/or downstream of the scanning system 48. The optics 16 of scanning system 48 are referred to herein as scanning optics 62, while the other optics 16 of optical system 15 (if any) are referred to herein as non-scanning optics 60, as discussed in more detail below with reference to FIG. 3A.

As used herein, an "optic" or "optical element" may mean any reflective or transmissive element that influences the angular distribution profile (e.g., angle of convergence, divergence, or collimation) of a beam in at least one axis, influences the focus of the beam in at least one axis, influences the propagation direction of the beam (e.g., by reflection or deflection), or otherwise affects a property of the radiation. Thus, optics include planar and non-planar reflective elements such as mirrors and other reflective surfaces, as well as transmissive elements such as lenses, prisms, light guides, gratings, filters, etc. For the purposes of this disclosure, optics do not generally include planar or substantially planar transmissive elements such as transmissive windows or films, e.g., a window or film that serves as a transmissive aperture for protecting internal components of the device. Reference herein to "optics" or "optical elements" means one or more optical elements.

Controls

Control systems 18 may be configured to control one or more components of device 10 (e.g., radiation source 14, beam scanning system 48, fan 34, displays 32, etc.). Control systems 18 may include, for example, any one or more of the following: a radiation source control system for controlling aspects of the generation, treatment, and delivery of radiation to the user; a scanning system control system for controlling automated scanning system 48 for scanning a beam to generate a pattern of treatment spots on the area; a displacement-based control system for controlling aspects of device 10 based on the determined displacement of device 10 across to the skin (e.g., as device is glided across the skin during treatment), e.g., relative to a prior treatment position; a temperature control system; an eye safety control system to help prevent exposure of the eyes (e.g., the cornea) to the treatment radiation (an eye safety control system may be omitted in embodiments in which the laser radiation emitted from device 10 is inherently eye-safe, e.g., certain direct exposure embodiments of device 10); and/or a battery/power control system.

Control systems 18 may include one or more sensors 26 and/or user interfaces 28 for facilitating user interaction with device 10, and control electronics 30 for processing data (e.g., from sensors 26 and/or user interfaces 28) and generating control signals for controlling various components of device 10. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

Control systems 18 may control components or operational parameters of device 10 based on feedback from sensors 26, user input received via user interfaces 28, and/or logic instructions/algorithms. For example, control systems 18 may control the treatment level (e.g., low power level, medium power level, or high power level) or treatment mode (e.g., gliding mode vs. stamping mode; or rapid-pulse mode vs. slow-pulse mode; or initial treatment mode vs. subsequent treatment mode; etc.), the status of radiation source 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (e.g., the operation of a rotating-element beam scanning system 48, as discussed below), and/or any other aspects of device 10. In some embodiments, control systems 18 may control the operation of radiation source 14 and/or component(s) of beam scanning system 48 (e.g., a rotating scanning element) based at least on feedback from a displacement sensor. Thus, for example, control systems 18 may control radiation source 14 and/or a rotating scanning element based on signals from a displacement sensor indicating that device 10 or treatment tip 42 has been translated a certain distance across treatment area 40 from a prior treatment position.

Sensors 26 may include any one or more sensors or sensor systems for sensing or detecting data regarding device 10, the user, the operating environment, or any other relevant parameters. For example, as discussed in greater detail below with respect to FIG. 2, sensors 26 may include one or more of the following types of sensors: (a) one or more displacement sensor for determining the displacement of device 10 relative to the skin, (b) one or more motion/speed sensor for determining the speed, rate, or velocity of device 10 moving ("gliding") across the skin, (c) an encoder sensor for monitoring the speed of a motor of the beam scanning system 48 and/or the position of a rotating scanning element), (d) one or more skin-contact sensor for detecting proper contact between device 10 and the skin, (e) one or more pressure sensor for detecting the pressure of device 10 pressed against the skin, (f) one or more temperature sensor for detecting the temperature of the skin and/or components of device 10, (g) one or more radiation sensor for detecting one or more parameters of radiation (e.g., intensity, fluence, wavelength, etc.) delivered or indicative of delivered to the skin, (h) one or more color/pigment sensor for detecting the color or level of pigmentation in the skin, (i) one or more eye safety sensor for preventing unwanted eye exposure to light from radiation source 14, (j) one or more dwell sensor for detecting if the device is stationary or essentially stationary with respect to the skin, (k) one or more roller-type sensors for detecting the displacement and/or glide speed of the device, and/or any (l) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touch screens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating, conditioning, or supplying power to the various components of device 10. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 20 include one or more rechargeable or non-rechargeable batteries, e.g., one or more Li containing cells or one or more A, AA, AAA, C, D, prismatic, or 9V rechargeable or non-rechargeable cells. In one example embodiment, device 10 uses an LiFePO4 18650XP, 3.2V, 1100 mAh rechargeable battery from Shenzhen Mottcell Battery Technology Co., China.

Figure 2:
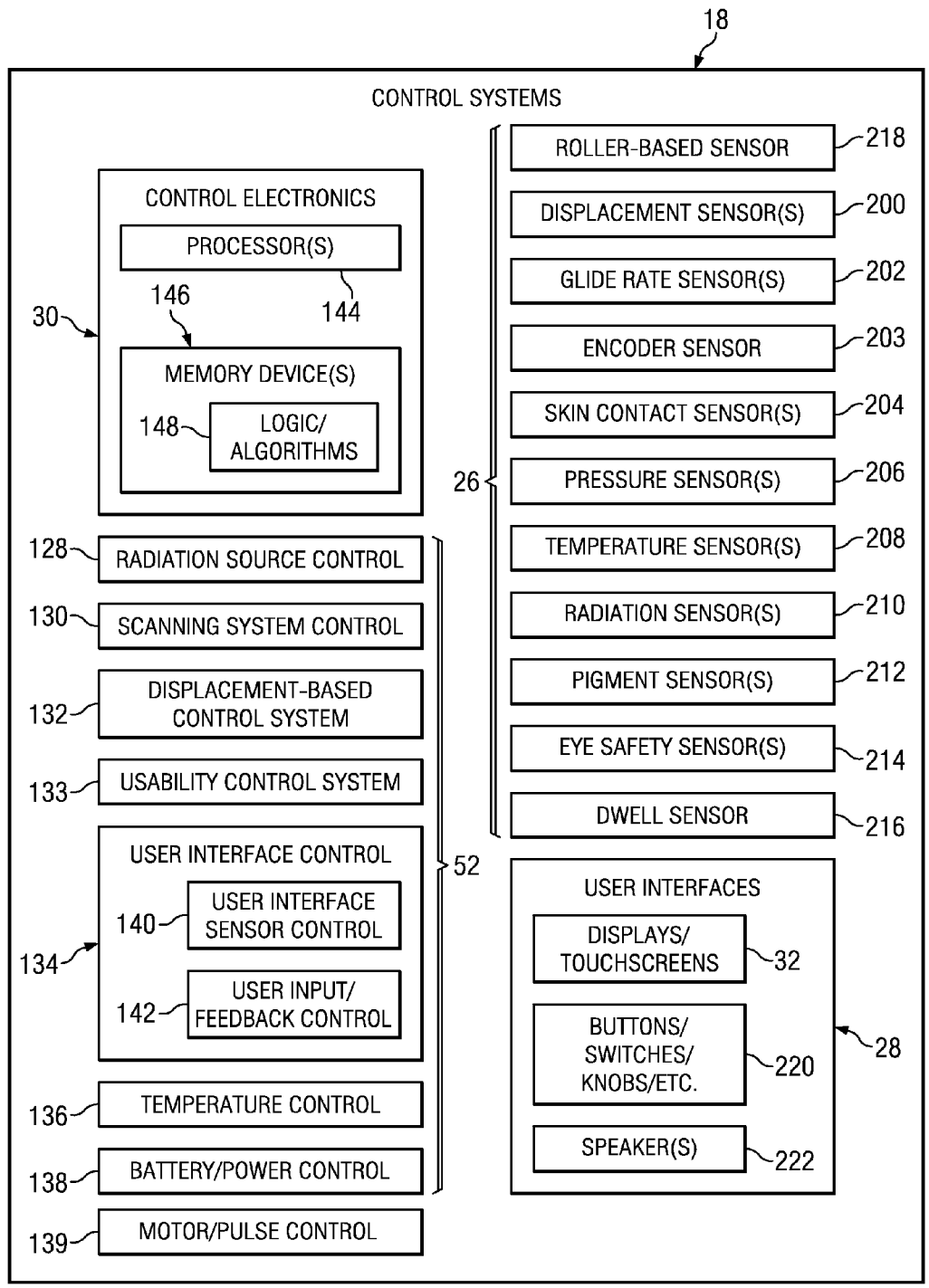
FIG. 2 illustrates an example control system for the radiation-based treatment device of FIG. 1, according to example embodiments.

FIG. 2 illustrates example components of control systems 18 for controlling aspects of device 10, according to certain embodiments. Control systems 18 may include control electronics 30, sensors 26, user interfaces 28, and a number of control subsystems 52. Control subsystems 52 are configured to control one or more components of device 10 (e.g., radiation source 14, fans 34, displays 32, etc.). In some embodiments, control subsystems 52 may include a radiation source control system 128, a scanning system control system 130, a displacement-based control system 132, a usability control system 133, a user interface control system 134, a temperature control system 136, a battery/power control system 138, a motor/pulse control system 139, and/or any other suitable control systems for controlling any of the functionality disclosed herein. User interface control system 134 may include a user interface sensor control system 140 and a user input/display/feedback control system 142.

Each control subsystem 52 may utilize any suitable control electronics 30, sensors 26, user interfaces 28, and/or any other components, inputs, feedback, or signals related to device 10. Further, any two or more control systems may be at least partially integrated. For example, the functionality of control systems 128-139 may be at least partially integrated, e.g., such that certain algorithms or processes may provide certain functionality related to multiple or all control systems 128-139.

Each control subsystem 52 (e.g., subsystems 128-139) may be configured to utilize any suitable control electronics 30, sensors 26, and user interfaces 28. In some embodiments, control electronics 30 may be shared by more than one, or all, control subsystems 52. In other embodiments, dedicated control electronics 30 may be provided by individual control subsystems 52.

Control electronics 30 may include one or more processors 144 and memory device 146 for storing logic instructions or algorithms 148 or other data. Memory devices 146 may include any one or more device for storing electronic data (including logic instructions or algorithms 148), such as any type of RAM, ROM, Flash memory, or any other suitable volatile and/or non-volatile memory devices. Logic instructions or algorithms 148 may be implemented as hardware, software, firmware, or any combination thereof. Processors 144 may include any one or more devices, e.g., one or more microprocessors and/or microcontrollers, for executing logic instructions or algorithms 148 to perform at least the various functions of device 10 discussed herein. Control electronics 30 may include exclusively analog electronics or any combination of analog and digital electronics.

Sensors 26 may include any one or more sensors or sensor systems for sensing or detecting data regarding device 10, the user, the operating environment, or any other relevant parameters. For example, sensors 26 may include one or more of the following types of sensors:

(a) At least one displacement sensor 200 for detecting, measuring, and/or calculating the displacement of device 10 relative to the skin 40, or for generating signals from which the displacement is determined. In some embodiments, e.g., as discussed below with reference to FIGS. 40A-44, displacement sensor 200 may be a single-pixel sensor configured to determine a displacement of device 10 by identifying and counting intrinsic skin features in the skin. In other embodiments, e.g., as discussed below with reference to FIGS. 45-46, displacement sensor 200 may be a multiple-pixel sensor, such as a mouse-type optical imaging sensor utilizing a two-dimensional array of pixels.

In other embodiments, e.g., as discussed below with reference to FIGS. 48A-48G, displacement sensor 200 may be a roller-type sensor 218 in which the amount of roller rotation indicates the linear displacement of the device. For example, a roller-type sensor displacement sensor 200 may include a mechanical roller having one or more indicia, a detection device (e.g., an optical or other scanner) for identifying such indicia as they roll past the detection device, and processing electronics for determining the displacement of device 10 based on the detection of such indicia. In some embodiment, the roller may also be actively driven by a motor to facilitate a gliding treatment.

In still other embodiments, displacement sensor 200 may comprise a capacitive sensor, as described below. Displacement sensor 200 may use any number of other devices or techniques to calculate, measure, and/or calculate the displacement of device 10.

Displacement sensor 200 may be used for (i) detecting, measuring, and/or calculating linear displacements of device 10 in one or more directions, (ii) detecting, measuring, and/or calculating the degree of rotation traveled by device 10 in one or more rotational directions, or (iii) any combination thereof.

Figure 68A:
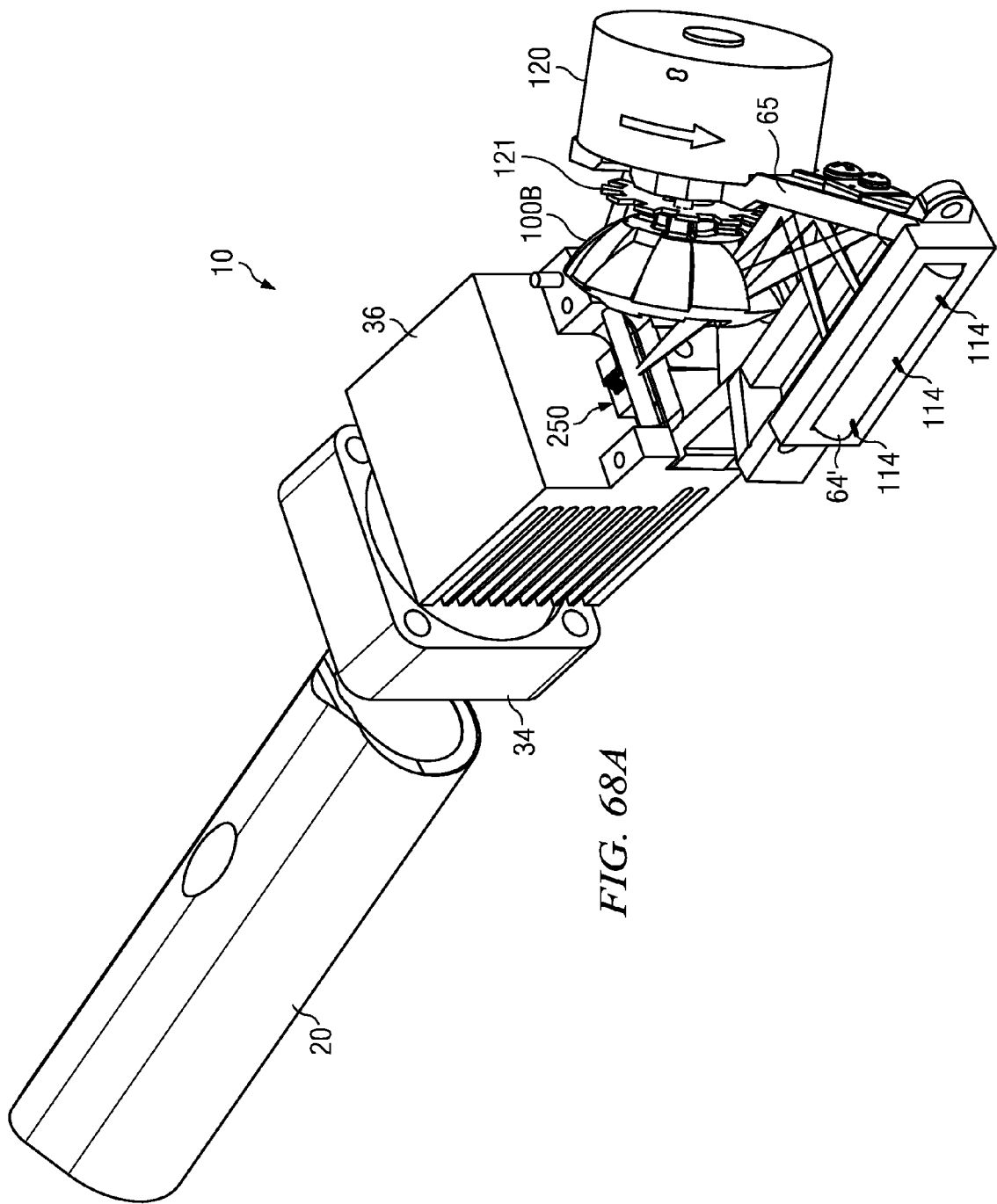
FIGS. 68A-68C illustrate an example arrangement of components (FIGS. 68A and 68B) and an assembled view of such components within a device housing (FIG. 68C) for an example scanned-beam treatment device, according to an another example embodiment.
Figure 68B:
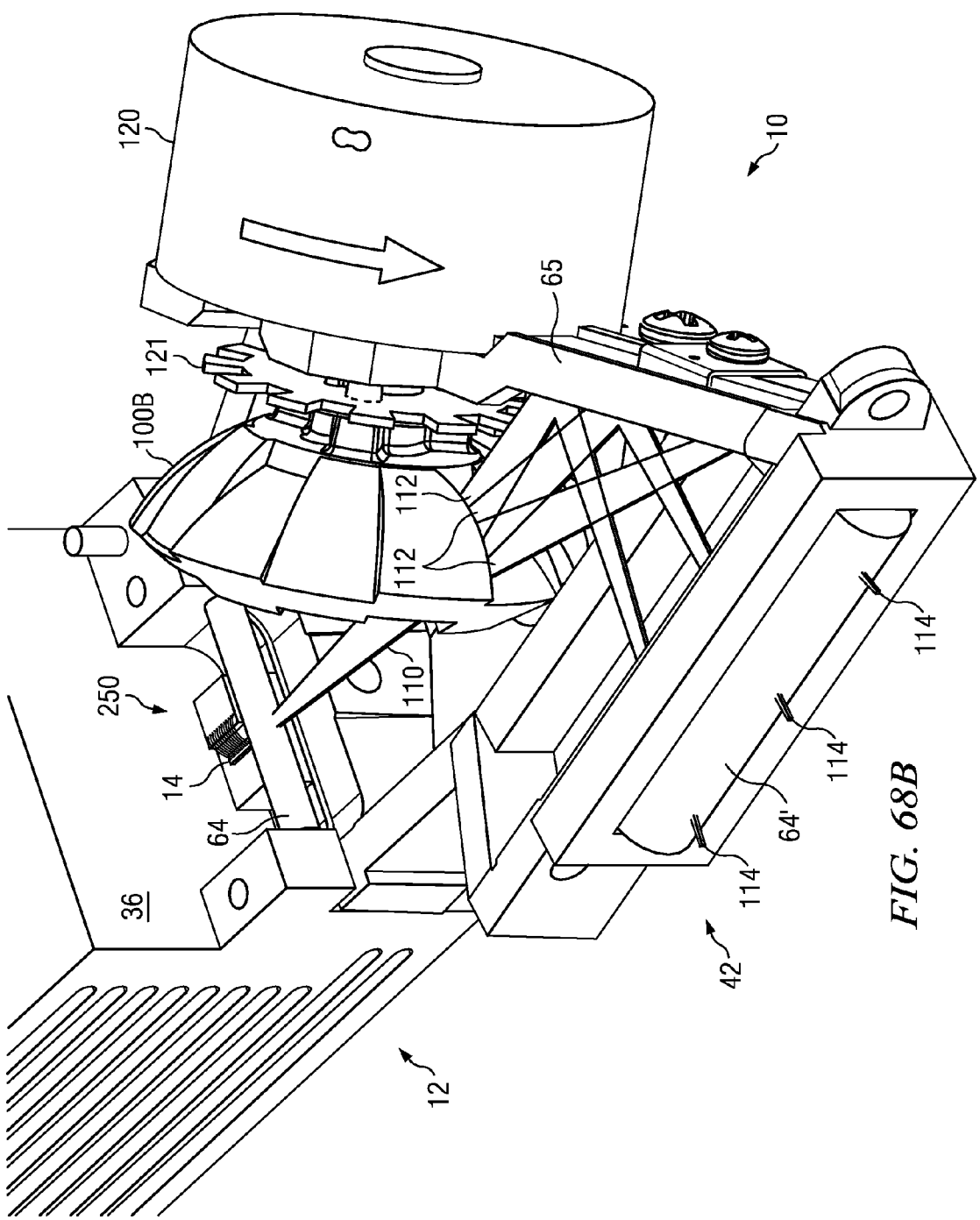

(b) At least one motion/speed sensor 202 for detecting, measuring, and/or calculating the rate, speed, or velocity of device 10 moving across the treatment area 40 (the "manual glide speed"), or for generating signals from which the manual glide speed is determined;

(c) At least one encoder sensor 203 for detecting the rotation and/or position of an encoder fixed to a scanning system motor 120 (e.g., encoder wheel 121 shown in FIGS. 68A and 68B). For example, encoder sensor 203 may be an optical sensor configured to read the rotation and/or position of the encoder as the encoder is rotated by motor 120. The signal from encoder sensor 203 can be used for determining the motor speed and/or the position of a rotating scanning element, e.g., for controlling the timing of beam pulses delivered to the scanning element.

(d) At least one skin-contact sensor 204 for detecting contact between device 10 and the skin or treatment area 40. For example, device 10 may include one or more capacitive contact sensors 204 for detecting contact with the user's skin.

(e) At least one pressure (or force) sensor 206 for detecting the pressure (or force) of device 10 against the skin or treatment area 40.

(f) At least one temperature sensor 208 for detecting the temperature of the treatment area 40, a region of the treatment area 40 (such as the treatment spot 70 before, during, and/or after treatment), components of device 10, or other object.

(g) At least one radiation sensor 210 for detecting levels or other parameters of radiation delivered to the treatment area 40 or indicative of the radiation delivered to the treatment area 40 (e.g., per light pulse, per individual beam/treatment spot, per delivered array of scanned beams/treatment spots 70, per a specific number of individual delivered beams/treatment spots 70 or scanned arrays of beams/treatment spots 70, or per a specific time period). For example, device 10 may include a photodiode to measure the pulse duration of the treatment beam.

(h) At least one color/pigment sensor 212 for detecting the color or level of pigmentation in the treatment area 40.

(i) At least one eye safety sensor 214 for helping to prevent unwanted eye exposure to light from the treatment radiation source 14. Example eye safety sensors 214 are discussed below with reference to FIGS. 48-51.

(j) At least one dwell sensor 216 for detecting whether device 10 is stationary or essentially stationary with respect to the skin.

(k) At least one roller-based sensor 218 that may be used as a displacement sensor 200, a motion/speed sensor 202, a dwell sensor 216 or all, for detecting signals indicative of the displacement of device 10, the manual glide speed of device 10, or stationary status of device 10, or both.

(l) any other type of sensors.

User interfaces 28 may include any systems for facilitating user interaction with device 10, e.g., displaying data or providing feedback to a user visually and/or audibly, and/or palpably (e.g., via vibration), and receiving commands, selections, or other input from the user. For example, user interfaces 28 may include one or more displays 32 (one or more of which may be interactive touch screens), one or more manual devices 220 (e.g., buttons, switches, knobs, sliders, touch screens, keypads, etc.), one or more speakers 222, and/or any other devices for providing data, information, or feedback to a user or receiving input or information from a user.

Control subsystems 52 may be configured to control one or more controllable operational parameters of device 10, based on feedback from sensors 26, user input received via user interfaces 28, and/or execution of logic instructions/algorithms 148. As used herein, "controllable operational parameters" may include any aspects or parameters of device 10 that may be controlled by any of control subsystem 52.

For example, one or more control subsystems 52 may control any aspects of the operation of radiation source 14, such as for example:

(a) selecting and/or switching the treatment mode (discussed below),
(b) controlling the on/off status of radiation source 14 (which may involve controlling individual light sources separately or as a group), and the timing of such on/off status: e.g., pulse trigger delay, pulse duration, pulse duty cycle, pulse frequency, temporal pulse pattern, etc.,
(c) controlling one or more parameters of the radiation: e.g., wavelength, intensity, power, fluence, etc. (e.g., by controlling the power supplied to radiation source 14), and/or
(d) controlling any other aspect of radiation source 14.

As another example, one or more control subsystems 52 may control any aspects of the operation of scanning system 48, such as for example:

(a) controlling the starting/stopping of rotation of a rotating scanning element 100,
(b) controlling the rotational speed of rotating scanning element 100 (e.g., by controlling motor 120), and/or
(c) controlling any other aspect of scanning system 48.

Control subsystems 52 (e.g., control systems 128-139) may control components or aspects of device 10 based on feedback from sensors 26, user input received via user interfaces 28, and/or logic instructions/algorithms 148. For example, in some embodiments, control system 128 may control the operation of radiation source 14 and/or beam scanning system 48 (e.g., the rotation of a scanning element 100) based on feedback from one or more displacement sensors 200 and/or skin contact sensors 204. As another example, control system 128 may control the operation of radiation source 14 and/or beam scanning system 48 based on feedback from one or more displacement sensors 200, skin contact sensors 204, and eye safety sensors 214. In other embodiments, control system 128 may control the operation of radiation source 14 and/or beam scanning system 48 based on feedback from one or more glide rate sensors 202 and skin contact sensors 204. In other embodiments, control system 128 may control the operation of radiation source 14 and/or beam scanning system 48 based on feedback from one or more dwell sensors 216 and skin contact sensors 204. In other embodiments, control system 128 may control the operation of radiation source 14 and/or beam scanning system 48 based on feedback from both a displacement sensor 200 or dwell sensor 216 and a glide rate sensor 202, in addition to one or more other sensors 204-218.

Optical System

As discussed above, device 10 may include an optical system 15 configured for scanning, delivering, conditioning, and/or otherwise controlling or affecting radiation from radiation source 14 to the target surface (e.g., the skin), and may include any number and/or type(s) of optics, or optical elements, 16 for providing such functionality. Optical system 15 may include (a) a beam scanning system 48 including any suitable beam scanning optics 62 for scanning an input beam to generate a successive series of output beams for delivery to the skin, and (b) any other optical elements 16 (if any) upstream and/or downstream of the scanning system 48.

Figure 3A:
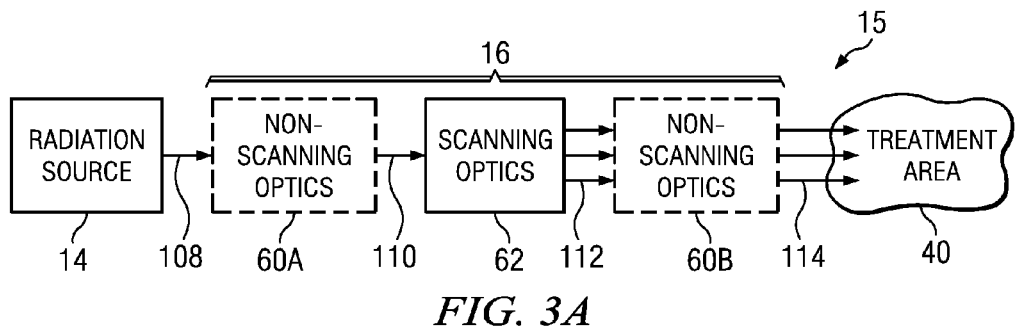
FIGS. 3A-3D illustrate representations of optical systems 15 for a scanned-beam radiation-based treatment device, according to example embodiments.

FIG. 3A illustrates aspects of the general components of an example optical system 15 for device 10, according to certain embodiments. In such embodiments, optical system 15 may include beam scanning optics 62 of beam scanning system 48 and (optionally) non-scanning optics 60. Beam scanning optics 62 may be configured to scan an input beam into a sequentially-delivered series or array of output beams to create a pattern of treatment spots 70 (e.g., spots, lines, or other shapes) in the target area 40. Non-scanning optics 60 (if any) may include non-scanning optics 60A upstream of scanning optics 62, non-scanning optics 60B downstream of scanning optics 62, or both upstream non-scanning optics 60A and downstream non-scanning 60B. Some embodiments include upstream non-scanning optics 60A and no downstream non-scanning optics 60B.

With reference to FIG. 3A, a beam generated by radiation source 14 is referred to herein as a generated beam 108. At the point of being received at scanning optics 62, the beam is referred to herein as an input beam 110. The scanning optics 62 scan the input beam 110 into a plurality of scanned beams referred to herein as output beams 112. At the point of exiting the application end 42 of device 10, the scanned beams are referred to herein as delivered beams 114.

Figure 3B:
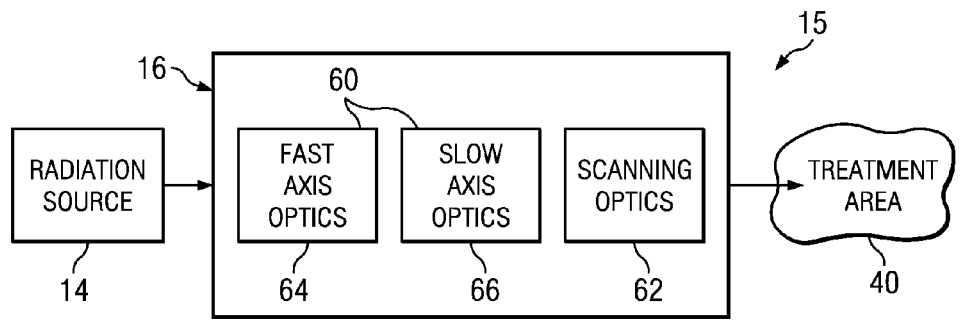

FIG. 3B illustrates aspects of the general components of an example optical system 15 for device 10, according to certain embodiments. In particular, FIG. 3B illustrates that optics 16 may include axis-asymmetric elements that act on different optical axes of an incident beam differently. For example, optics 16 may include first optics configured to influence an incident beam primarily in a first optical axis, and second optics configured to influence the beam primarily in a second optical axis orthogonal to the first axis. Influencing the beam primarily in a particular optical axis may include affecting the intensity profile of the beam in the particular optical axis to a greater extent than in an orthogonal optical axis. As used herein, the intensity profile of the beam along a particular optical axis refers to (a) the shape of the intensity profile along the particular optical axis (e.g., Gaussian, flat-topped, etc.); (b) whether the beam is converging, diverging, or collimated; (c) the degree of convergence or divergence of the beam; etc.

In some embodiments, such axis-asymmetric optical elements are used for controlling or treating a radiation source 14 that generates an asymmetric beam, e.g., a laser diode, which generates a generally rectangular cross-sectioned beam that diverges relatively quickly in a first axis (referred to as the "fast axis") and diverges relatively slowly in an orthogonal second axis (referred to as the "slow axis").

Thus, in the example shown in FIG. 3B, non-scanning optics 60 include separate fast axis optics 64 (or fast axis optics 64) and slow axis optics 66 (or slow axis optics 66). Fast axis optics 64 include one or more optical elements 16 configured to primarily affect the fast axis intensity profile of the beam (as compared with the effects on the slow axis intensity profile), while slow axis optics 66 include one or more optical elements configured to primarily affect the slow axis intensity profile of the beam (as compared with the effects on the fast axis intensity profile). In certain embodiments, fast axis optics 64 are configured to affect the fast axis intensity profile without substantially affecting the slow axis intensity profile. Further, in certain embodiments, slow axis optics 66 are configured to affect the slow axis intensity profile without substantially affecting the fast axis intensity profile. In particular embodiments, both of these features are provided: fast axis optics 64 affect the fast axis intensity profile without substantially affecting the slow axis intensity profile, and slow axis optics 66 affect the slow axis intensity profile without substantially affecting the fast axis intensity profile.

Alternatively, fast axis optics 64 and slow axis optics 66 may be partially or fully integrated. For example, a particular optical element (e.g., mirror or lens) may significantly affect both the fast axis and slow axis intensity profiles. Such element may be referred to as a multi-axes optical element, and may or may not be symmetrical about all axes (e.g., spherical). Some embodiments may include one or more multi-axes optical elements, along with one or more separate fast axis optical elements; or one or more multi-axis optical elements, along with one or more separate slow axis optical elements; one or more multi-axis optical elements, along with one or more separate slow axis optical elements and one or more separate fast axis optical elements; or any other combination thereof.

Fast axis optics 64, slow axis optics 66, and beam scanning optics 62 may be arranged in any order along the path of the beam propagation. For example, optics 64 and 66 may be arranged upstream of beam scanning optics 62, or downstream of beam scanning optics 62, or beam scanning optics 62 may be arranged between optics 64 and 66, beam scanning optics 62 may act as either one or both of optics 64 and 66. Further, where beam scanning optics 62 also acts as a fast axis optic 64, a slow axis optic 66, or both, optical system 15 may also include one or more separate fast axis optic 64, slow axis optic 66, or both, respectively Further, each of fast axis optics 64 and slow axis optics 66 may be separate from, or integral with, beam scanning optics 62. In other words, scanning optics 62 may influence either one, both, or neither of the fast axis and slow axis intensity profiles. Thus, for example, scanning optics 62 may act as fast axis optics 64, with slow axis optics 66 being provided separately. Alternatively, scanning optics 62 may act as slow axis optics 66, with fast axis optics 64 being provided separately. Alternatively, scanning optics 62 may significantly affect both the fast axis and slow axis intensity profiles.

Figure 3C:
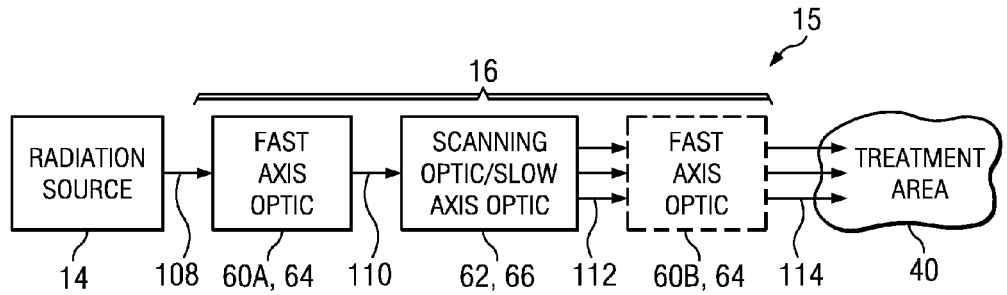

FIG. 3C illustrates the general configuration of an example optical system 15 for particular example embodiments of device 10. In this example configuration, optical system 15 includes an upstream fast axis optic 60A, 64; a beam scanning optic 62 that also act as slow axis optics 66, and optionally (depending on the particular embodiment) a downstream fast axis optic 60B. Upstream fast axis optic 60A and optional downstream fast axis optic 60B may each comprise, for example, a cylindrical or "rod" lens, an aspheric lens, or any other suitable optical element. Beam scanning optic 62, which also acts as a slow axis optic 66, may comprise, for example, a rotating multi-sector scanning element, e.g., scanning element 100A or 100B discussed below. Optical system 15 may also include one or more planar mirrors configured to direct the beams as desired. For example, a planar mirror may be positioned downstream of beam scanning optic 62 (and upstream of downstream fast axis lens 60B, if present) to direct the scanned array of output beams 112 toward the application end 42 of device 10.

Figure 3D:
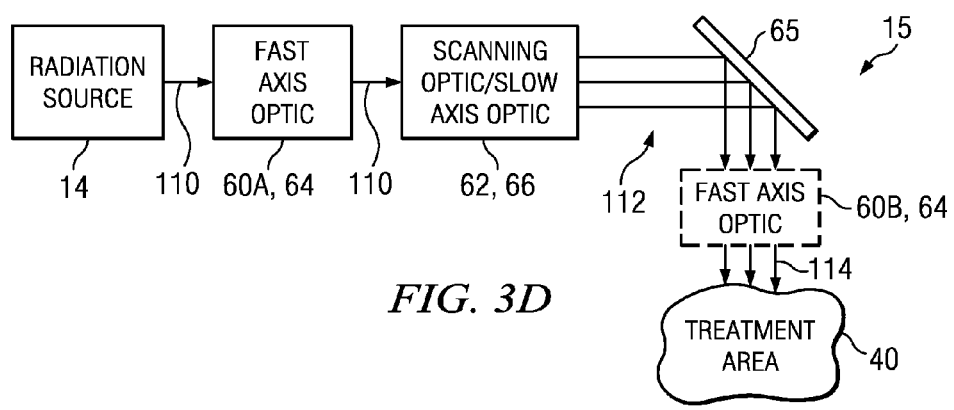

In particular embodiments, radiation source 14 is a laser diode configured to emit a pulsed or CW generated beam 108. Upstream fast axis optic 60A reduces the divergence of the generated beam 108 in the fast axis, and the resulting input beam 110 is received at the beam scanning optic 62, which scans the input beam 110 to produce a sequential series of output beams 112. In some embodiments, the output beams 112 may be redirected by one or more planar mirrors (e.g., as shown in FIG. 3D, discussed below) and/or further influenced by downstream fast axis optic 60B. In other embodiments, the output beams 112 may be delivered to the skin as delivered beams 114, without any optics 16 downstream of scanning optic 62.

In some embodiments, the scanning optic 62 (e.g., scanning element 100A or 100B discussed below) may provide a sequential array of output beams 112 that are angularly offset from each other in a scan direction. The optional downstream fast axis optic 60B may extend in the scan direction in order to receive and act on the array of output beams 112. For example, fast axis optic 60B may comprise a rod lens extending in the scan direction and configured to reduce the divergence/increase the convergence of each output beam 112 for delivery to the skin as a delivered beam 114.

FIG. 3D illustrates a configuration similar to the configuration shown in FIG. 3C, but further including a planar turning mirror 65, according to example embodiments. In some such embodiments, the scanning optic 62 (e.g., scanning element 100A or 100B discussed below) may provide a sequential array of output beams 112 that are angularly offset from each other in a scan direction. The scan direction of the output beams 112 may be shifted, or turned, by mirror 65. The optional downstream fast axis optic 60B may extend in the same direction as the shifted or turned scan direction in order to receive and act on the array of output beams 112. For example, fast axis optic 60B may comprise a rod lens extending in the scan direction and configured to reduce the divergence/increase the convergence of each output beam 112 for delivery to the skin as a delivered beam 114.

In addition, other embodiments discussed below relate to various configurations of optical system 15. For instance, in the example embodiments shown in FIGS. 10A-11B, beam scanning optics 62 also act as slow axis optics 66, while fast axis optics 64 are provided separately. In the example embodiments shown in FIGS. 19 and 20, both fast axis optics 64 and slow axis optics 66 are provided separately from beam scanning optics 62.

As discussed above, the term "optics" as used herein may include a single optical element or multiple optical elements. In some embodiments, e.g., the example embodiments shown in FIGS. 10A-10B, 11A-11B, 19, and 20, device 10 includes only a single fast axis optical element 64 and a single slow axis optical element 66. Also, embodiments according to FIG. 3C in which downstream fast axis optics 60B are omitted include only a single fast axis optical element 64 and a single slow axis optical element 66. In these embodiments, beam scanning optic 62 acts as the slow axis optic 66 (e.g., each sector of the rotating multi-sector scanning element 62 influences the input beam 110 primarily in the slow axis, such that at any particular position of the rotating scanning element 62, a beam from generation 108 to delivery 114 is significantly affected in the slow axis by only a single optical element: the respective sector of the rotating scanning element 62. Such embodiments also include a single fast axis optical element 64 separate from the scanning optic 62.

Figure 19:
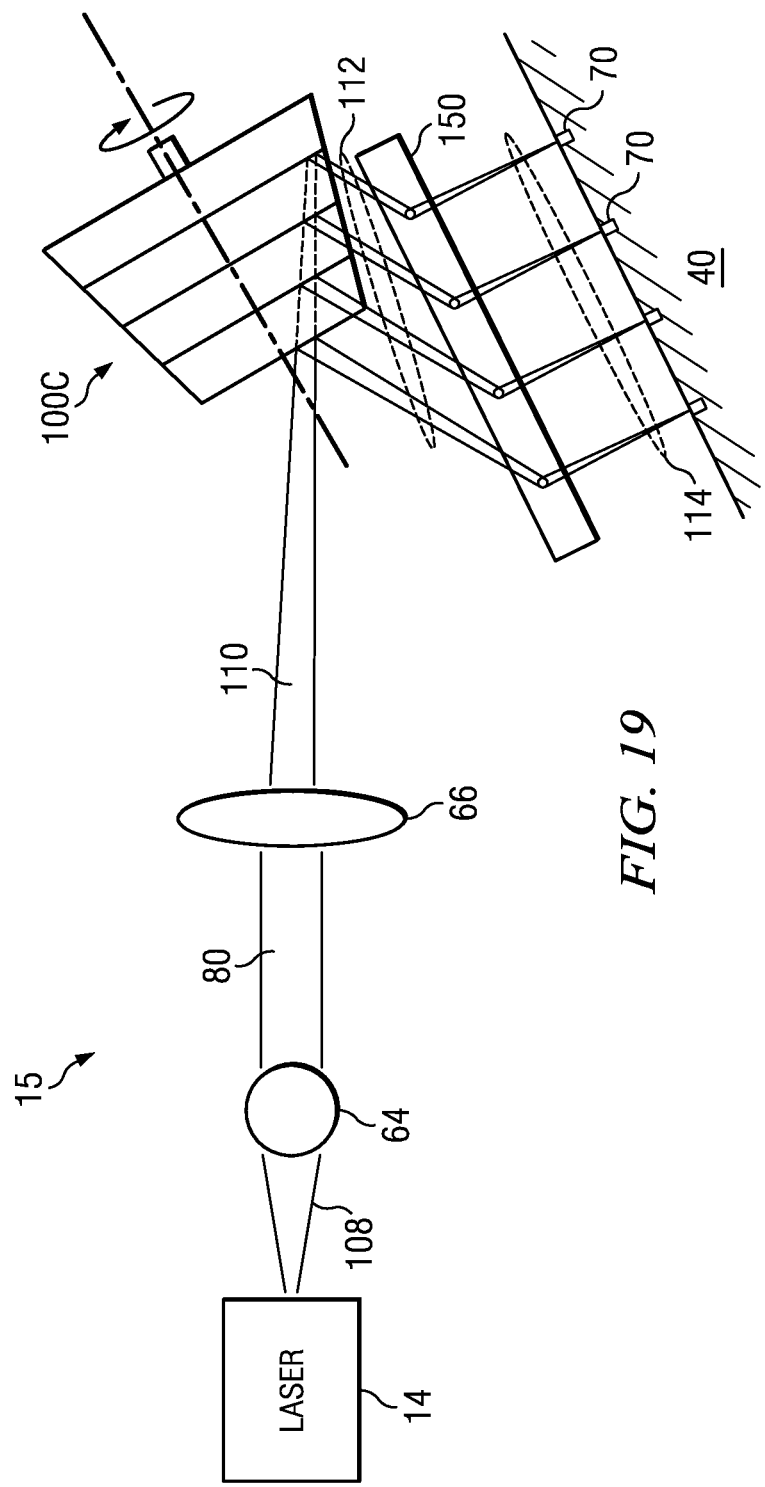
FIGS. 19 and 20 illustrate two example optical systems that include a stair-stepped rotating scanning element for scanning an input beam to create a scanned array of treatment spots on the skin, according to certain embodiments.
Figure 20:
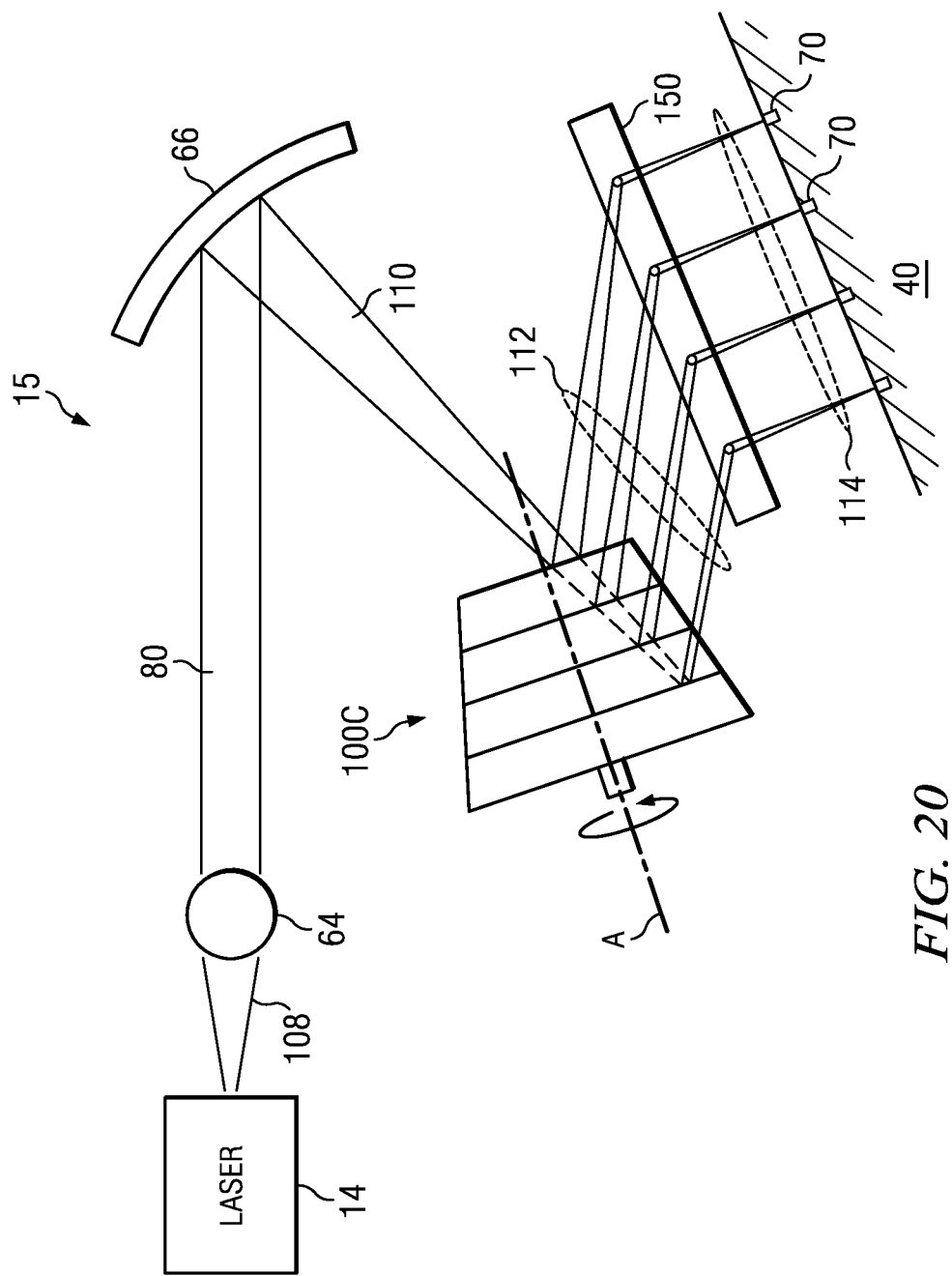

In the embodiments of FIGS. 19 and 20, the fast axis optical element 64 and slow axis optical element 66 are separate from the scanning optic 62, which utilizes planar mirror facets and thus does not influence the beam in either the fast or slow axis except for planar deflection.

In other embodiments, device 10 includes more than one fast axis optical element 64, more than one slow axis optical element 66, or both. For example, any of the embodiments shown in FIGS. 10A-10B, 11A-11B, 19, and 20 may further include one or more fast-axis optical elements 64 and/or slow-axis optical elements 66 to further influence the beam in the respective axes.

In still other embodiments, device 10 includes one or more axis-symmetric optics 16, in place of, or in addition to, fast axis optics 64 and/or slow axis optics 66. For example, optics 16 of optical system 15 may include one or more spherical optical elements, axis-symmetrical parabolic optical elements, and/or any other type of axis-symmetric optical elements. Such axis-symmetric optical elements may be used, for example, in embodiments of device 10 that utilize a radiation source 14 that generates an axis-symmetric beam, such as a fiber laser, Vertical Cavity Surface Emitting Laser (VCSEL), LED, or lamp, for example. One or more axis-symmetric optical elements may also be used in certain embodiments of device 10 that utilize a radiation source 14 that generates an axis-asymmetric beam, such as a laser diode, for example.

Example Device Schematic

Figure 4:
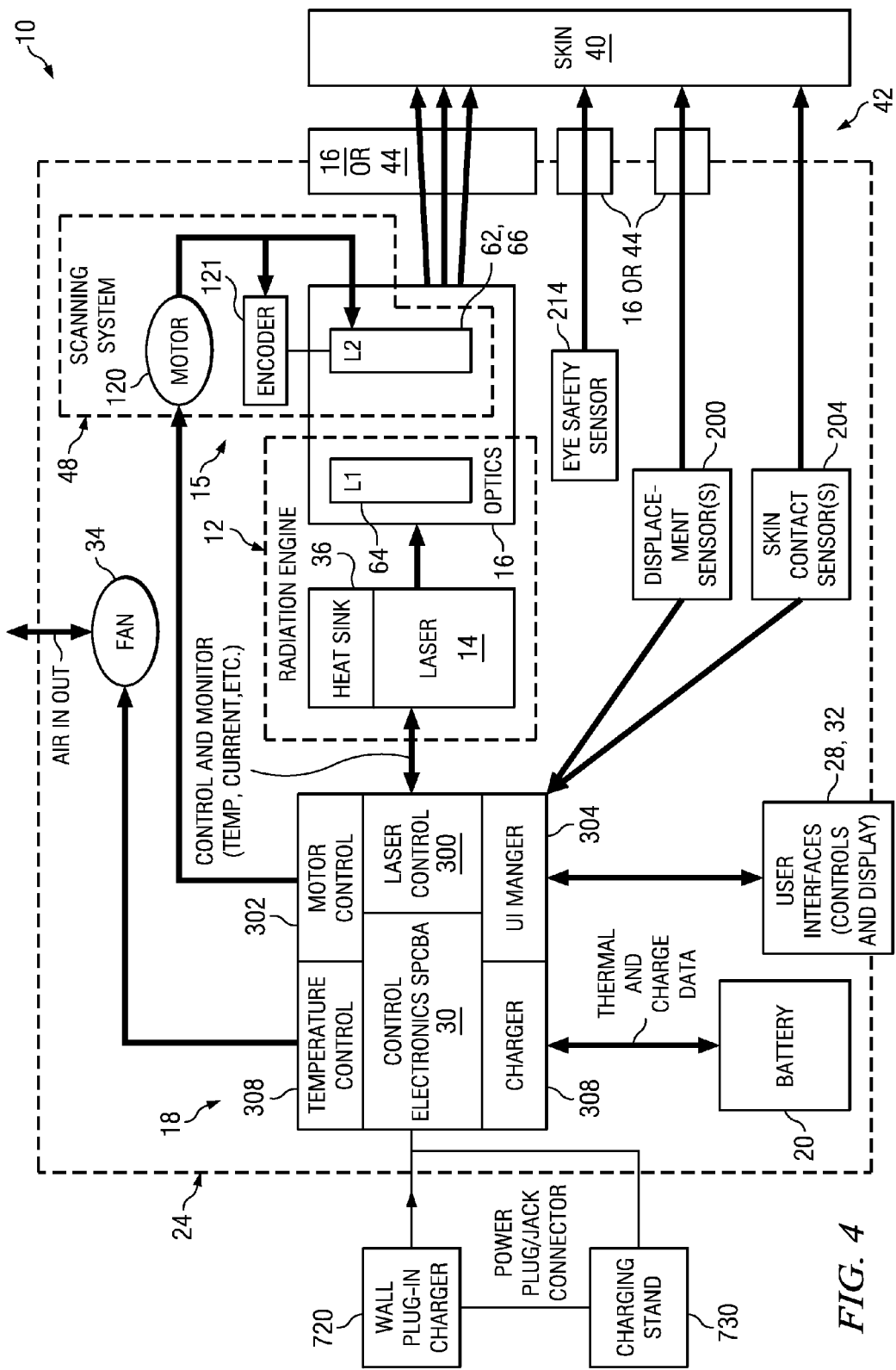
FIG. 4 illustrates a schematic layout of various components of a scanned-beam radiation-based treatment device, according to example embodiments.

FIG. 4 illustrates a functional block diagram of an example device 10, according to certain example embodiments. As shown, device 10 may include various components contained in a housing 24, including a radiation source 14, an optical system 15 including a beam scanning system 48, a control system 18, user interfaces 28 including displays 32, a power source (in this example, a battery) 20, various sensors 26, and a cooling fan 34.

Radiation source 14 includes a radiation source 14 (in this example, a laser diode) coupled to a heat sink 36, and a fast axis optical element 64. Optical system 15 may include upstream fast axis optical element 64, a slow axis optical element 66, and an optional downstream optical element 16. In this example, fast axis optical element 64 (e.g., a rod lens) is mounted to the heat sink 36 of the radiation source 14, and thus may be considered a component of radiation source 14. Further, in this example slow axis optical element 66 is a multi-sector rotating scanning element 62 (e.g., element 100A or 100B) of a beam scanning system 48. Thus, in this example, a rotating scanning element 62 acts as both a scanning element and a slow axis optical element. Beam scanning system 48 includes a motor 120 configured to rotate scanning element 62 and an encoder 121, e.g., an indicator wheel fixed to scanning element 62. In operation, radiation source 14 emits a generated beam 108, which is influenced by fast axis optical element 64 to provide an input beam 110 to scanning element 62. The input beam 110 is scanned by the multi-sector rotating scanning element 62 to generate a successive array of offset output beams 112 (e.g., angularly offset from each other). The output beams 112 are delivered through a downstream optic 16 (e.g., a fast axis rod lens), which further influences the beams, or a protective output window 44 that does not influence the beams, and to the skin 40 as delivered beams 114 to generate an array of treatment spots on the skin.

Device 10 may include one or more displacement sensors 200, skin contact sensors 204, and/or eye safety sensors 214 (and/or any other type or types of sensors 26 discussed herein). Displacement sensor 200 may monitor the lateral displacement of device 10 relative to the skin, e.g., as device 10 is moved across the skin in a gliding mode or stamping mode of operation. Skin contact sensors 204 may determine whether device 10, in particular an application end 42, is in contact with or sufficiently close to the skin for providing treatment to the user. Eye safety sensor 214 may determine whether the application end 42 of device 10 (e.g., an optical element 16 or window 44 at the application end 42), is positioned over the skin or the eye, such that device 10 can be controlled (e.g., radiation source 14 turned off) when the eye is detected, in order to prevent unintended exposure of the eye.

As discussed above, control system 18 may include any suitable subsystems for controlling the various components and aspects of device 10. In this example, control system 18 includes a radiation source control system 128, a scanning control system 130, a displacement-based control system 132, a usability control system 133, a user interface control system 134, a temperature control system 136, a battery/charger control system 138, and/or a motor/pulse control system 139. Each control subsystem 128-139 may utilize or interact with control electronics 30, sensors 26, and user interfaces 28, as appropriate.

Radiation source control system 128 may monitor and control various aspects of radiation source 14. For example, system 128 may turn radiation source 14 on and off, and monitor and control the intensity of generated beam (e.g., by controlling the current to radiation source 14). As another example, in embodiments or configurations in which radiation source 14 is pulsed, system 128 may monitor and/or control the pulse duration, pulse on time, pulse off time, trigger delay time, duty cycle, pulse profile, or any other parameters of generated pulses from radiation source 14. As another example, system 128 may monitor the temperature of radiation source 14, which data may be used by temperature control system 136, e.g., for controlling the pulse duration, the motor speed of motor 120, the operation of cooling fan 34, etc. In addition, system 128 may turn radiation source 14 off, or reduce power to radiation source 14 based on the monitored temperature of radiation source 14 (e.g., to prevent overheating). Radiation source control system 128 may utilize data or signals from any other control subsystems (e.g., scanning control system 130, user interface control system 134, temperature control system 136, battery/charger control system 138, and/or motor/pulse control system 139) for controlling aspects of radiation source 14.

Scanning control system 130 may monitor and control various aspects of laser scanning system 48, e.g., motor 120 which is configured to rotate a multi-sector scanning element 62 in certain embodiments. For example, system 130 may turn motor 120 on and off, and monitor and control the rotational speed, direction of rotation, and/or other parameters of motor 120. Scanning control system 130 may communicate data or signals with, or otherwise cooperate with, other control subsystems, e.g., radiation source control system 128, displacement-based control system 132, usability control system 133, user interface control system 134, and/or motor/pulse control system 139.

User interface control system 134 may include a user interface sensor control system 140 for monitoring and controlling displacement sensor 200, skin contact sensors 204, eye safety sensor 214, and/or other sensors 26. For example, system 134 may receive signals detected by each sensor, and send control signals to each sensor. User interface control system 134 may include a user input/display/feedback control system 142 for monitoring and controlling user interfaces 28 and displays 32. For example, system 134 may receive user input data from various user interfaces 28, and control information communicated to the user via displays 32 (e.g., visually, audibly, tangibly (e.g., by vibration), palpably, etc.). Scanning control system 130 may communicate data or signals with, or otherwise cooperate with, other control subsystems, e.g., radiation source control system 128, scanning control system 130, displacement-based control system 132, usability control system 133, temperature control system 136, battery/charger control system 138, and/or motor/pulse control system 139.

Temperature control system 136 may be configured to monitor and control the temperature of one or more components of device 10, e.g., radiation source 14, motor 120 of scanning system 48, battery 20, etc. Thus, temperature control system 136 may receive data from one or more temperature sensors 208, and control one or more fans 34 based on such data. In addition to controlling fan(s) 34, temperature control system 136 may generate control signals for controlling radiation source 14, motor 120, etc. based on temperature data. For example, temperature control system 136 may communicate signals to radiation source control system 128 and/or scanning system control system 130 to control the operation of radiation source 14 and/or motor 120 based on detected temperature signals, e.g., to dynamically compensate for changes in the radiated wavelength associated with changes in the laser temperature, e.g., as discussed below with reference to FIG. 63. As another example, temperature control system 136 may communicate signals to radiation source control system 128 and/or scanning system control system 130 to turn off or otherwise control radiation source 14 and/or motor 120 to avoid overheating (or in response to a detected overheating) of such component(s), to maintain such components within predefined performance parameters, or for any other purpose. Temperature control system 136 may communicate data or signals with, or otherwise cooperate with, radiation source control system 128, scanning control system 130, user interface control system 134, battery/charger control system 138, and/or motor/pulse control system 139.

Battery/charger control system 138 may be configured to monitor and control the charging of battery 20. In some embodiments, multiple batteries 20 are included in device 10. In some embodiments, battery 20 may be removable from device 10, e.g., for replacement. As shown in FIG. 3, device 10 may be configured for connection to a wall plug-in charger 720 and/or a charging stand 730 via control electronics 30, for charging battery 20. System 138 may monitor the current charge and/or temperature of battery 20, and regulate the charging of battery 20 accordingly. Battery/charger control system 138 may communicate data or signals with, or otherwise cooperate with, other control subsystems, e.g., user interface control system 134, and/or temperature control system 136.

Motor/pulse control system 139 may monitor and control various aspects of radiation source 14 and/or scanning system 48, and may incorporate or combine various aspects of other subsystems discussed above, including aspects of radiation source control system 128, scanning system control system 130, displacement-based control system 132, usability control system 133, user interface control system 134, and temperature control system 136. For example, motor/pulse control system 139 may turn radiation source 14 on and off, control the pulse duration, pulse on time, pulse off time, trigger delay time, duty cycle, pulse profile, or any other parameters of generated pulses from radiation source 14 (e.g., by controlling the current to radiation source 14), control a motor 120 of scanning system 48 (e.g., to control the speed, position, etc. of a rotating beam-scanning element 100), etc. Motor/pulse control system 139 may control such parameters based on signals from various sensors 26 and/or by monitoring the rotation and/or position of an encoder 121, which may be arranged to indicate the rotation and/or position of a rotating beam-scanning element 100). Motor/pulse control system 139 may utilize data or signals from any other control subsystems 128-138 for controlling aspects of radiation source 14 and/or scanning system 48. Example aspects of motor/pulse control system 139 are discussed in greater detail below with reference to FIGS. 55-59.

Device 10 may include a delivery end, referred to herein as application end 42, configured to be placed against the skin 40. Application end 42 may include or house various user interfaces, including the treatment delivery interface for delivering output beams 112 to the user, as well as one or more sensors for detecting various characteristics of the target surface and/or treatment delivered by device 10. For example, in the illustrated embodiment, application end 42 provides an interface for one or more displacement sensors 200, skin contact sensors 204, and/or eye safety sensors 214, allowing these sensors to interface with the skin 40. As shown in FIG. 4, some sensors 26 (e.g., radiation reflection-based displacement sensors 200 and/or eye safety sensors 214) may interface with the skin 40 via an optical element 16 or window 44 provided at the application end 42, while other sensors 26 (e.g., capacitance-based contact sensors 204) may interface directly with the skin 40.

General Operation of Scanning System

Figure 5A:
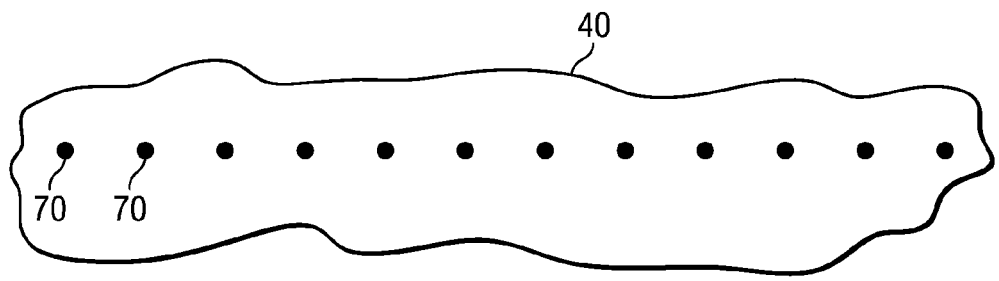
FIGS. 5A and 5B illustrate the general concept of creating rows of treatment spots on the skin using a scanned-beam radiation-based treatment device, according to example embodiments.

FIG. 5A illustrates an example pattern or array of treatment spots 70—in this example, a row 72 of treatment spots 70—delivered by one full scan of an input beam 110 by scanning system 48, with device 10 held stationary on the skin. For example, one full scan of an input beam 110 by scanning system 48 may be correspond to one full rotation of a multi-sector rotating scanning element, e.g., scanning element 100A, 100B, or 100C discussed below. In this example, scanning system 48 delivers 12 output beams 112 to create 12 treatment spots 70 on the skin during a single scan of the input beam 110. Thus, in such embodiment, scanning system 48 may utilize a 12-sector rotating scanning element.

As discussed above, in some embodiments or settings, device 10 may be operated in a "gliding mode" in which the device is manually moved, or glided, across the skin while delivering scanned radiation to the skin. Scanning system 48 may repeatedly scan rows 72 of treatment spots 70 onto the target area 40 as device 10 is glided across the skin, thus producing a two-dimensional array of treatment spots on the skin 40.

In other embodiments, device 10 is configured to be used in a "stamping mode" in which device 10 is held relatively stationary at different locations on the skin, with one or more scanned rows or arrays of treatment spots 70 (overlapping or not overlapping) delivered at each location of device 10 on the skin. Thus, device 10 may be positioned at a first location on the skin, at which point one or more scanned rows or arrays of treatment spots 70 may then be delivered to the skin while device 10 is held relatively stationary, after which device 10 may then be moved—by lifting device 10 and repositioning it or by gliding device 10 across the surface of the skin—to a new location, at which point one or more scanned rows or arrays of treatment spots may then be delivered at this new location, and so on, in order to cover an area of the skin 40 as desired. In still another embodiment, beam scanning system 48 is configured to provide a generally two-dimensional array of treatment spots 70 in a single scan of input beam 110 (or multiple input beams 110), even assuming device 10 is held stationary on the skin. For example, the scanning system 48 may include a first rotating element that scans the beam(s) in one direction and a second rotating element that scans the beam(s) in the orthogonal direction. As another example, a single rotating element can be can be configured to provide multiple scanned rows of output beams, or a two-dimensional array of output beams, during a single scan, as discussed below.

In other embodiments, device 10 may be configured for use in both a "gliding mode" and "stamping mode," as selected by the user.

Figure 5B:
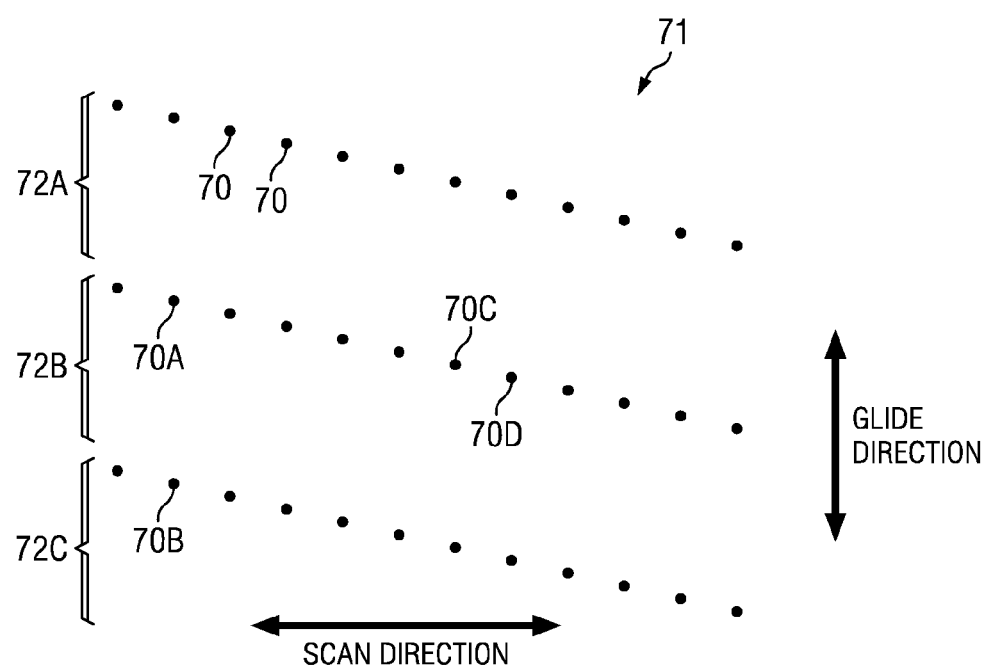

FIG. 5B illustrates an example array of treatment spots generated by an example device 10 used in a gliding mode. In particular, the figure shows three scanned rows 72 of treatment spots 70, indicated as rows 72A, 72B, and 72C, aligned relative to each other in the glide direction, which forms a two-dimensional array 71 of treatment spots 70. Each row 72 extends generally diagonally with respect to the scan direction due to the movement of device 10 in the glide direction during the successive delivery of individual treatment spots 70 in each row 72.

The degree to which each row 72 is aligned diagonally with respect to the scan direction, which may influence the spacing of adjacent treatment spots aligned in the glide direction (e.g., treatment spots 70A and 70B), may depend on one or more various factors, e.g., (a) the manual glide speed (the speed at which device 10 is glided across the skin), (b) the scanning rate (e.g., the rate at which treatment spots are successively delivered to the skin and the time between scans, (c) any displacement-based control, which may enforce a predetermined minimum spacing between adjacent rows in the glide direction, e.g., by interrupting the delivery of radiation to ensure the predetermined minimum spacing, and/or (d) any other relevant factor. In some embodiments, the scanning rate or particular aspects of the scanning rate (e.g., pulse on time, pulse off time, pulse frequency, etc.), and/or the predetermined minimum spacing between rows as controlled by a displacement-based control system, may be selectable or adjustable automatically by control system 18, manually by a user, or both.

Further, the distance between adjacent treatment spots 70 in the scan direction (e.g., treatment spots 70C and 70D) may depend on one or more various factors, e.g., the scanning rate, the distance between the center points of adjacent treatment spots, the size and shape of individual treatment spots, etc., which factors may be defined by the configuration of the beam scanning optics 62, other optics 16 or aspects of optical system 15, or other factors. In some embodiments, one or more of these factors may be selectable or adjustable automatically by control system 18, manually by a user, or both. In some embodiments or device settings, adjacent treatment spots in the scan direction are spaced apart from each other by areas of non-irradiated skin, thus providing a fractional treatment. In some embodiments or device settings, adjacent treatment spots in the scan direction may abut each other edge-to-edge, or may overlap each other, in order to provide contiguous rows of irradiated areas. Such contiguous rows may be spaced apart from each other in the glide direction, may abut each other edge-to-edge, or may overlap each other to provide a fully covered (i.e., non-fractional) irradiated area, as defined by a variety of factors such as those discussed above, which may or may not be manually and/or automatically selectable or adjustable.

Thus, it should be clear that the fractional pattern of treatment spots shown in FIG. 5B, in which treatment spots are spaced apart from each other in both the glide direction and scan direction, is merely one example pattern. Device 10, and in particular optical system 15 (including scanning system 48), may be configured for providing various different treatment spot patterns, e.g., as discussed above, and as shown in the example of FIGS. 21-25, which are discussed below in more detail.

Beam scanning system 48 may include any suitable beam scanning optics 62 and other component for scanning an individual radiation beam into a sequentially-delivered array of beams to form a pattern of treatment spots in the skin 40. For example, as discussed below with respect to FIGS. 6-20, scanning system 48 may include a rotating beam scanning element having a number of deflection sectors that successively deflect (e.g., reflect or transmit with a deflection) a single input beam 110 to provide an array of successively delivered output beams 112, which may be offset from each other (e.g., angularly offset, translationally offset, or both). This process of using a scanning element to successively deflect an input beam 110 to provide an array of successively delivered output beams 112 (which are offset from each other in some aspect) is referred to as "scanning" the input beam 110.

Figure 7A:
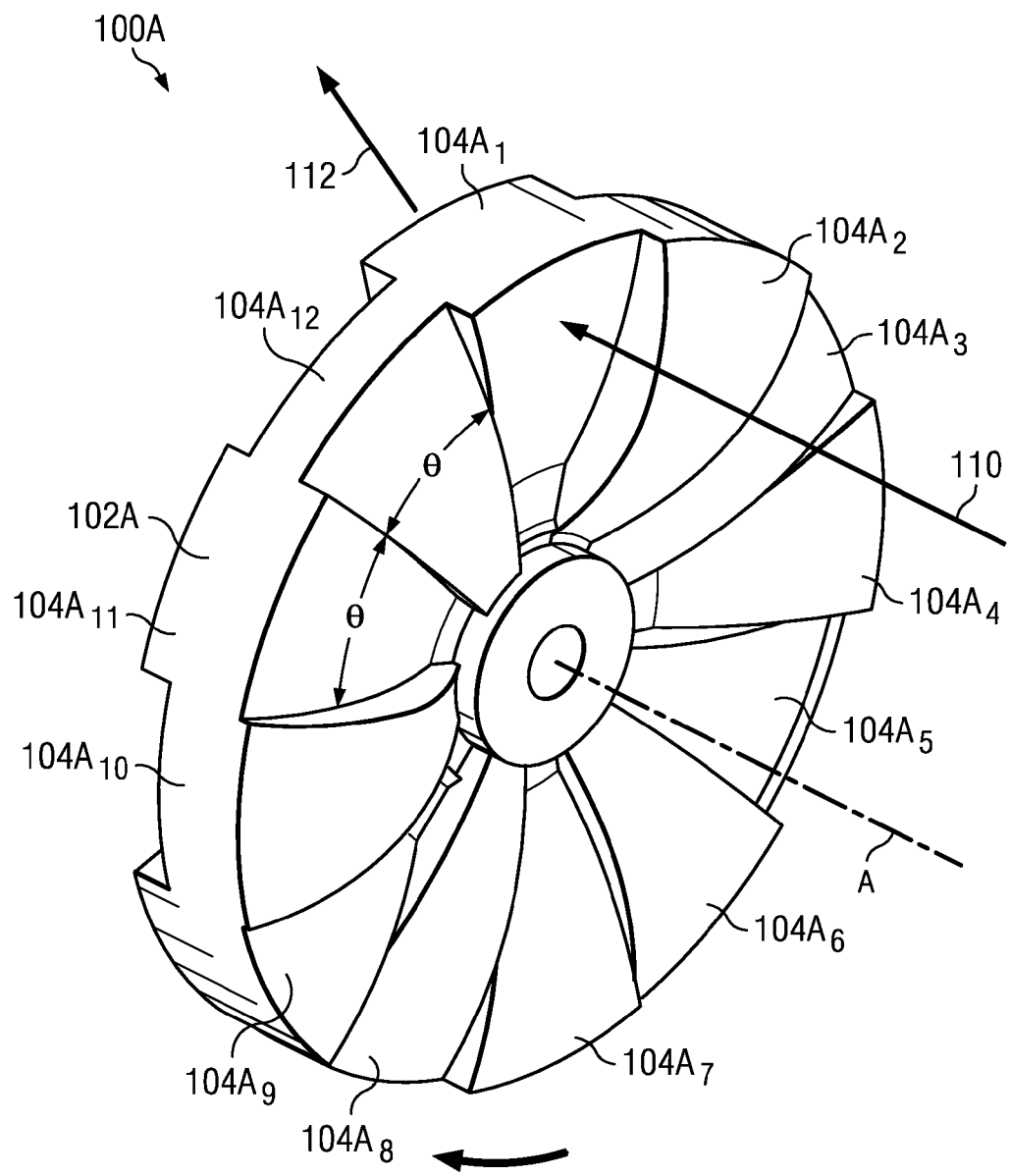

In some embodiments, the rotating multi-sector scanning element may be generally disc-shaped (e.g., as shown in FIGS. 7A-7C) or generally cup-shaped (e.g., as shown in FIGS. 8A-8E). The multiple deflection sectors may be arranged around a circumference of the scanning element and may be configured to successively deflect the incident input beam 110 by different angles to provide a successive array of deflected output beams 112 that are angularly offset from each other. The angularly offset array of output beams 112 may be delivered directly to the skin 40, or may be influenced by further optics 16 before being delivered to the skin 40 as delivered beams 114. For example, optics 16 may be provided to parallelize the array of output beams 112, or to influence the divergence or convergence of individual output beams 112, before being delivered to the target area 40 as delivered beams 114.

As another example, as discussed below with respect to FIGS. 12-20, beam scanning system 48 may include a generally stair-stepped rotating scanning element with a number of reflection sectors that successively reflect an incident input 110 beam to provide an array of successive output beams 112 that are translationally and/or angularly offset from each other. In some embodiments, the reflection sectors of the scanning element include planar reflection surfaces that are offset from each other in order to provide a successive array of reflected output beams 112 that are translationally offset from each other and either parallel to each other or angularly offset from each other. The translationally (and/or angularly) offset array of reflected output beams 112 may be delivered directly to the skin 40, or may be influenced by further optics 16 before being delivered to the skin 40 as delivered beams 114. For example, optics 16 may be provided to parallelize the array of output beams 112, or to influence the divergence or convergence of individual output beams 112, before being delivered to the target area 40 as delivered beams 114.

Scanning System May Include a Rotating Multi-Sector Scanning Element

FIGS. 6-20 illustrate various aspects and embodiments of a rotating multi-sector beam scanning element 100 for use in certain embodiments of scanning system 48. More particularly, FIGS. 6A-6C illustrate the general structure and operation of a rotating multi-sector scanning element 100 for scanning an input beam 110, while FIGS. 7-20 are directed to three example types of rotating multi-sector scanning elements 100 for use in scanning system 48: an example disc-shaped multi-sector transmissive scanning element 100A; an example cup-shaped multi-sector transmissive scanning element 100B; and an example stair-stepped reflective scanning element 100C.

Figure 6A:
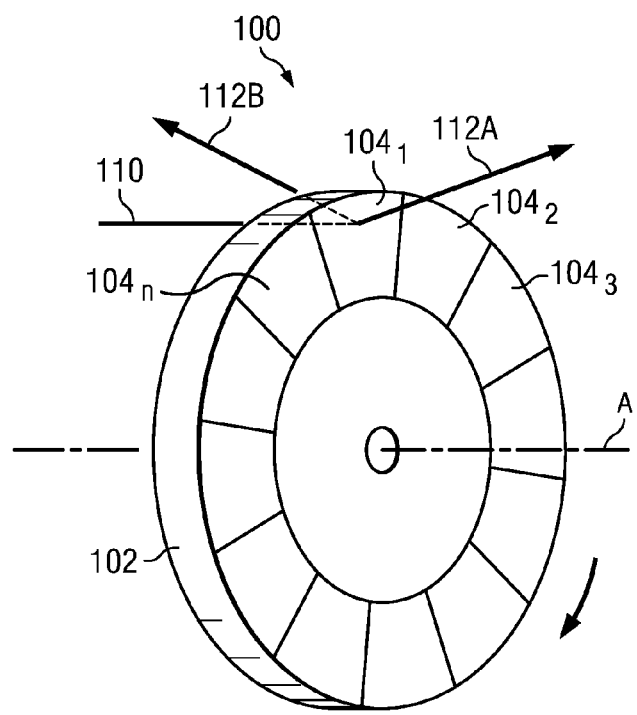
FIG. 6A illustrates a basic structure of an example rotating element for scanning an input beam to form an array of output beams, according to certain embodiments.
Figure 6B:
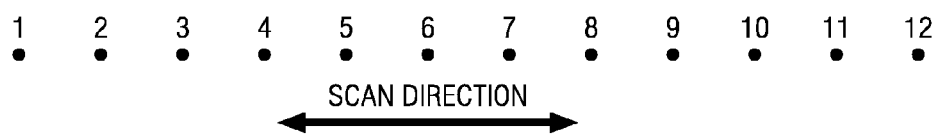
FIGS. 6B and 6C illustrate example patterns treatment spots created by the beam-scanning element of FIG. 6A, according to certain embodiments.
Figure 6C:
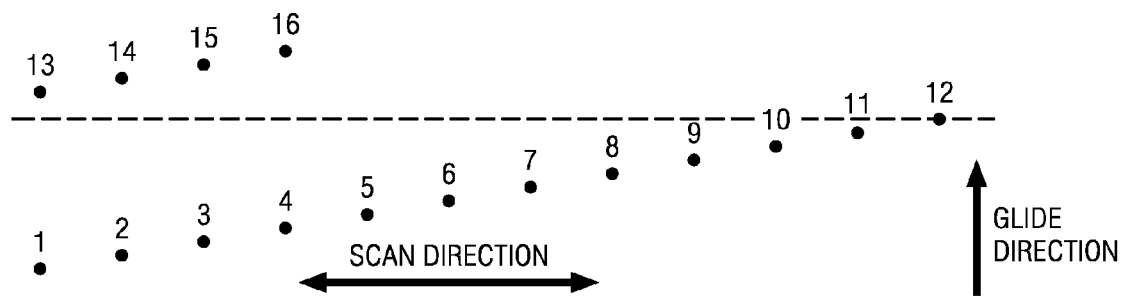

FIG. 6A illustrates a basic structure of a rotating element 100, according to some embodiments. Element 100 has a body 102 configured to rotate about an axis A. Body 102 includes a plurality of sectors 104 generally arranged around the circumference or periphery of the body 12 and configured to deflect and/or otherwise optically influence an input beam 110 into an array of output beams 112 offset from each other. Depending on the particular embodiment, each sector 104 may transmit but deflect and/or otherwise optically influence the input beam 110, as indicated by example arrow 112A (e.g., where element 100 is a disc-shaped transmissive element 100A or cup-shaped transmissive element 100B, as discussed below) or reflect and/or otherwise optically influence the input beam 110, as indicated by example arrow 112B (e.g., where element 100 is a stair-stepped reflective element 100C, as discussed below). In some embodiments, as each individual sector 104 rotates through the input beam 110, the angular deflection of the corresponding output beam 112 may remain constant or substantially constant so that each output beam 112 is stationary or substantially stationary with respect to device 10 for the duration of that output beam 112. Such sectors are referred to herein as "constant angular deflection" sectors. Alternatively, the deflection of each output beam 112 may vary during the rotation of the corresponding sector 104 through the input beam 110 so that each output beam 112 traces a pattern, e.g., a line or arc.

As shown in FIG. 6A, sectors $104_1$-$104_n$ arranged circumferentially around axis A are configured to deflect (reflect or transmissively deflect) an input beam 110 to produce an array of offset output beams 112. Thus, as the rotating element 100 rotates through the input beam 110 for one full revolution (i.e., one full scan of input beam 110), sectors $104_1$-$104_n$ produce a successively scanned array of n output beams 112, each offset from one, some, or all other output beams 112 in the scanned array, to provide a scanned row or array of treatment spots 70 on the skin 40.

As used herein, unless otherwise specified, an "array" means any pattern of elements (e.g., output beams 112 or treatment spots 70) arranged in any manner, e.g., in a linear row, a non-linear row, a regular two-dimensional pattern, an irregular two-dimensional pattern, or any other pattern.

Further, as used herein, unless otherwise specified, "offset" means angularly offset (e.g., diverging or converging lines), translationally offset (e.g., offset parallel lines), or both angularly and translationally offset. Thus, output beams 112 that are "offset" from each other may be angularly offset (e.g., output beams 112 generated by transmissive sectors 104A and 104B of certain embodiments of elements 110A and 100B, respectively), translationally offset (e.g., output beams 112 generated by reflective sectors 104C of certain embodiments of stair-stepped element 110C), or both angularly and translationally offset (e.g., output beams 112 generated by reflective sectors 104C of certain other embodiments of stair-stepped element 110C).

FIG. 6B illustrates an example pattern of treatment spots delivered by one rotation of element 100 (i.e., one scan of input beam 110), assuming device 10 is held stationary with respect to the target area, for the purpose of illustration. The treatment spots are labeled 1 through 12, indicating the sequential order in which each treatment spot is produced, beginning with treatment spot 1 produced by sector $104_1$, followed by treatment spot 2 produced by sector $104_2$, and so on. In this example, each sector 104 has been configured to provide a constant deflection as that sector rotates through the input beam 110, such that each sector 104 produces a stationary or substantially stationary spot 70 on the skin.

Sectors $104_1$ to $104_n$ may be configured such that the array of treatment spots 70 may be delivered in any desired sequential order, e.g., in terms of a particular direction of the array. For example, in the example shown in FIG. 6B, sectors $104_1$ through $104_{12}$ are configured to produce treatment spots 1-12 in sequential order along the scan direction. However, treatment spots may be delivered in any other sequential order, based on the particular design and configuration of element 100, e.g., as discussed below with reference to FIGS. 22-25.

FIG. 6C illustrates an example pattern of treatment spots delivered by one rotation of element 100 (i.e., one scan of input beam 110), assuming device 10 is glided over the target area in a direction substantially perpendicular to the scan direction (e.g., device 10 operating in a gliding mode, as discussed above). As with the example shown in FIG. 6B, in the example shown in FIG. 6C, sectors $104_1$ to $104_n$ are configured to deliver a pattern of treatment spots in sequential order along the scan direction. This configuration of element 100 produces a generally linear row of treatment spots aligned diagonally with respect to the scan direction, due to the movement of the device 10 in the glide direction. Again, it should be understood that treatment spots may be delivered in any other sequential order, based on the particular design and configuration of element 100, which may provide a variety of different two-dimensional treatment spot patterns as device is glided across the skin 40, as discussed in greater detail below.

Disc-Shaped Rotating Scanning Element

FIGS. 7A-7C illustrate an example embodiment of a rotating disc-shaped, multi-sector beam scanning element 100A for use in certain embodiments of beam scanning system 48. In particular, FIG. 7A is an isometric front (i.e., upstream) view of disc-shaped element 100A; FIG. 7B is an isometric rear (i.e., downstream) view of disc-shaped element 100A; and FIG. 7C is a side view of disc-shaped element 100A.

As shown, disc-shaped element 100A has a body 102A configured to rotate about axis A (e.g., driven by a motor 120). In this example, body 102A includes 12 sectors $104A_1$ to $104A_{12}$ arranged circumferentially around axis A. Each sector $104A_1$ to $104A_{12}$ comprises a transmissive lenslet configured to (a) deflect an input beam 110 in a different angular direction, and (b) focus (i.e., influence the divergence/convergence of) the input beam 110 in at least one axis (e.g., the fast axis, the slow axis, or both). As element 100A rotates one full revolution through the input beam 110 (i.e., one full scan), lenslets $104A_1$ to $104A_{12}$ produce a successively scanned array of 12 output beams 112 that are angularly offset from each other, to provide a scanned array of 12 treatment spots on the skin 40.

In some embodiments, each transmissive lenslet $104A_1$ to $104A_{12}$ is configured to (a) deflect the input beam 110 in a different angular direction, such that the output beams 112 are offset from each other along one axis (e.g., the slow axis or the fast axis), and (b) focus the input beam 110 along that same axis (e.g., the slow axis or the fast axis), while not substantially affecting the beam along the orthogonal axis (e.g., the other of the slow axis and fast axis). For example, in an example embodiment, each transmissive lenslet is configured to (a) deflect the input beam 110 in a different angular direction such that the output beams 112 are offset from each other in the slow axis direction, and (b) focus the slow axis profile of the beam, while not substantially affecting the fast axis profile of the beam. Thus, in such example embodiment, scanning element 100A acts as both a beam scanning element 62 and a slow axis element 66, e.g., as discussed above with reference to FIGS. 3C and 3D.

As discussed above, lenslets 104A may be configured such that the array of treatment spots may be generated in any desired sequential order, e.g., in terms of one or more particular directions. In this example embodiment, lenslets $104A_1$ to $104A_{12}$ are configured such that the 12 corresponding treatment spots are delivered along a linear scan direction in a pseudo-random order, e.g., as discussed below with reference to FIG. 22C.

In the example illustrated embodiment, each lenslet 104A has a toroid shape defined by rotating a cross-sectional shape around the rotational axis A of element 100A. The rotated cross-sectional shape may be defined by a pair of opposing edges that form the opposing surfaces of the lenslet upon rotation of the cross-sectional shape. The pair of opposing edges may have any suitable shapes. For example, the pair of opposing arcs may be a pair of opposing arcs (with each arc being circular or non-circular, and with the opposing arcs being symmetrical or non-symmetrical with respect to each other), an arc and an opposing non-arc (e.g., a linear segment or other shape), or any other suitable shapes for forming the desired surfaces of the lenslet upon rotation of the cross-sectional shape. A geometric "centerline" of the cross-sectional shape of each lenslet may be defined between the pair of opposing edges. Further, each toroidal lenslet may define a "lenslet apex," defined herein as the thickest portion of the lenslet, in the direction from edge-to-edge of the cross-sectional shape.

In some embodiments, each lenslet has a toroid shape defined by rotating a cross-sectional shape around the rotational axis A, wherein the cross-sectional shape is defined by a pair of opposing arcs. In other embodiments, each lenslet has a toroid shape defined by rotating a cross-sectional shape around the rotational axis A of element 100A, wherein the cross-sectional shape is defined by an arc opposed by a linear segment.

Thus, while the input beam 110 is incident on any particular lenslet 104A, it is affected in a manner similar to the shifted lens shown in FIGS. 9A-9B (discussed below). The different shapes of lenslets $104A_1$ to $104A_{12}$ of element 100A are generated in effect by varying the radial distance from input beam 110 to the lenslet apex, thus presenting the incoming laser beam 110 with a different relative position between the beam center and lenslet apex. This difference in relative positioning results in each output beam 112 being deflected by a different angular amount for each sector. In this example, the angular deflection of each output beam 112 with respect to device 10 is constant as each respective lenslet 104 rotates through input beam 110, such that output spots (rather than lines, arcs, or other shapes) are produced from each sector. Thus, each output beam 112 may be referred to as a "constant angular deflection" output beam 112. As discussed above, in addition to deflecting the input beam 110, each lenslet also focuses the input beam 112, e.g., in the slow-axis direction, to provide a desired focal plane and/or a desired beam profile at the skin 40.

Further, in this example embodiment, along a front or rear view of element 100A, each lenslet 104A is essentially a circular sector sweeping the same circumferential or central angle (30 degrees in this example). Thus, with reference to FIG. 7A, for each lenslet, θ=30 degrees. In other embodiments of disc-shaped element 100A, different lenslets may be circular sectors that sweep different central angles. In other embodiments of disc-shaped element 100A, the lenslets may have any other suitable shapes (i.e., other than circular sectors) in the front or rear view of element 100A, and the different lenslets may sweep the same or different circumferential or central angles.

Further, although the example disc-shaped element 100A shown in FIGS. 7A-7C includes 12 lenslets, in other embodiments disc-shaped element 100A may include any other number of lenslets, more than or fewer than 12.

Cup-Shaped Rotating Scanning Element

Figure 8D:
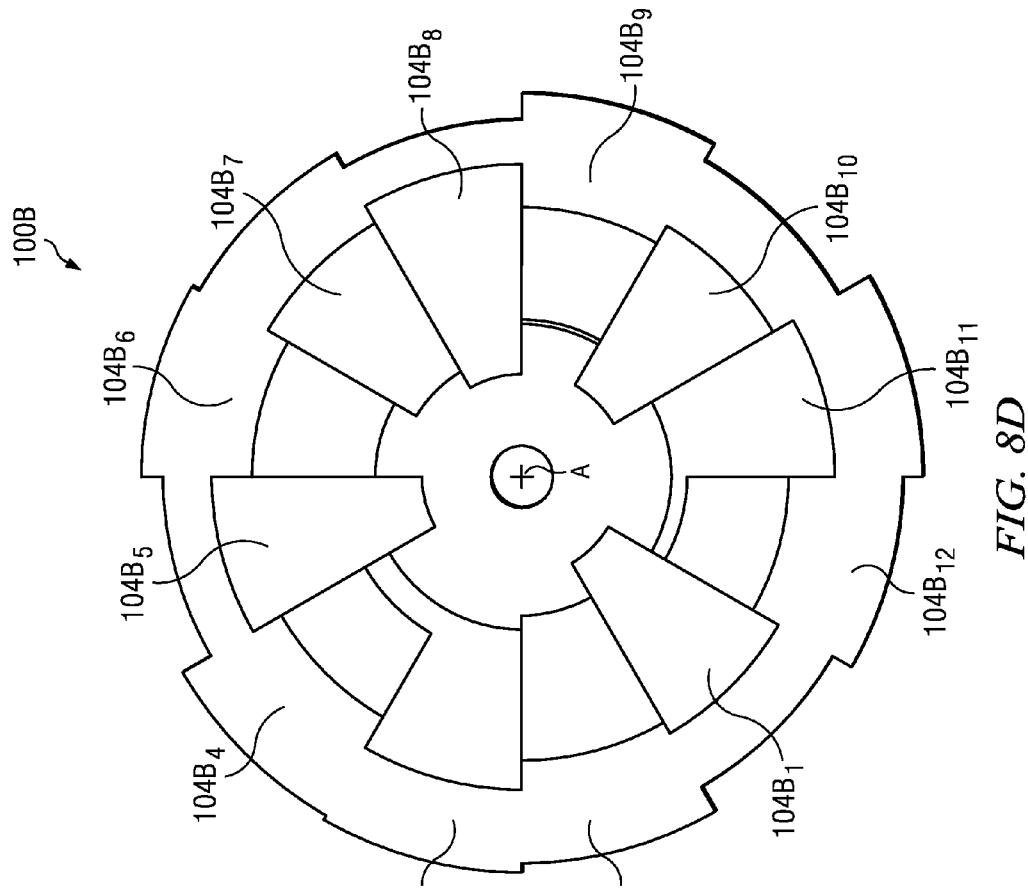
Figure 8C:
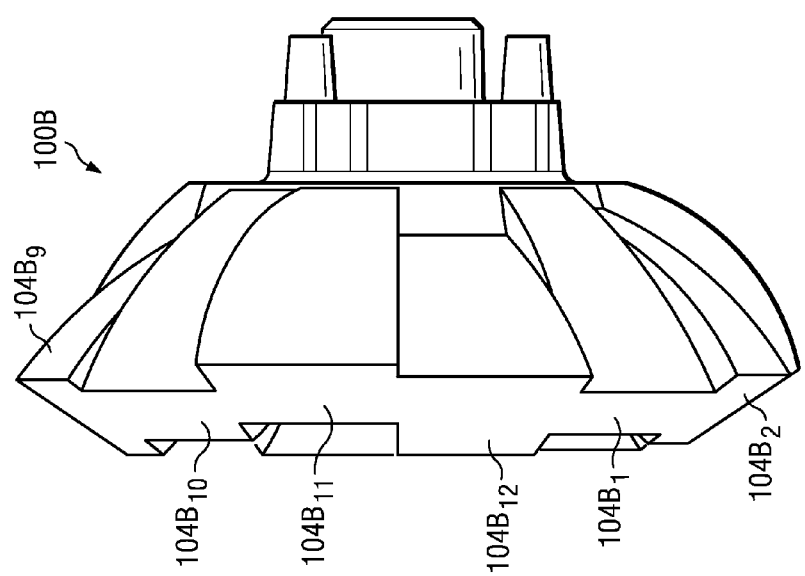
Figure 8E:
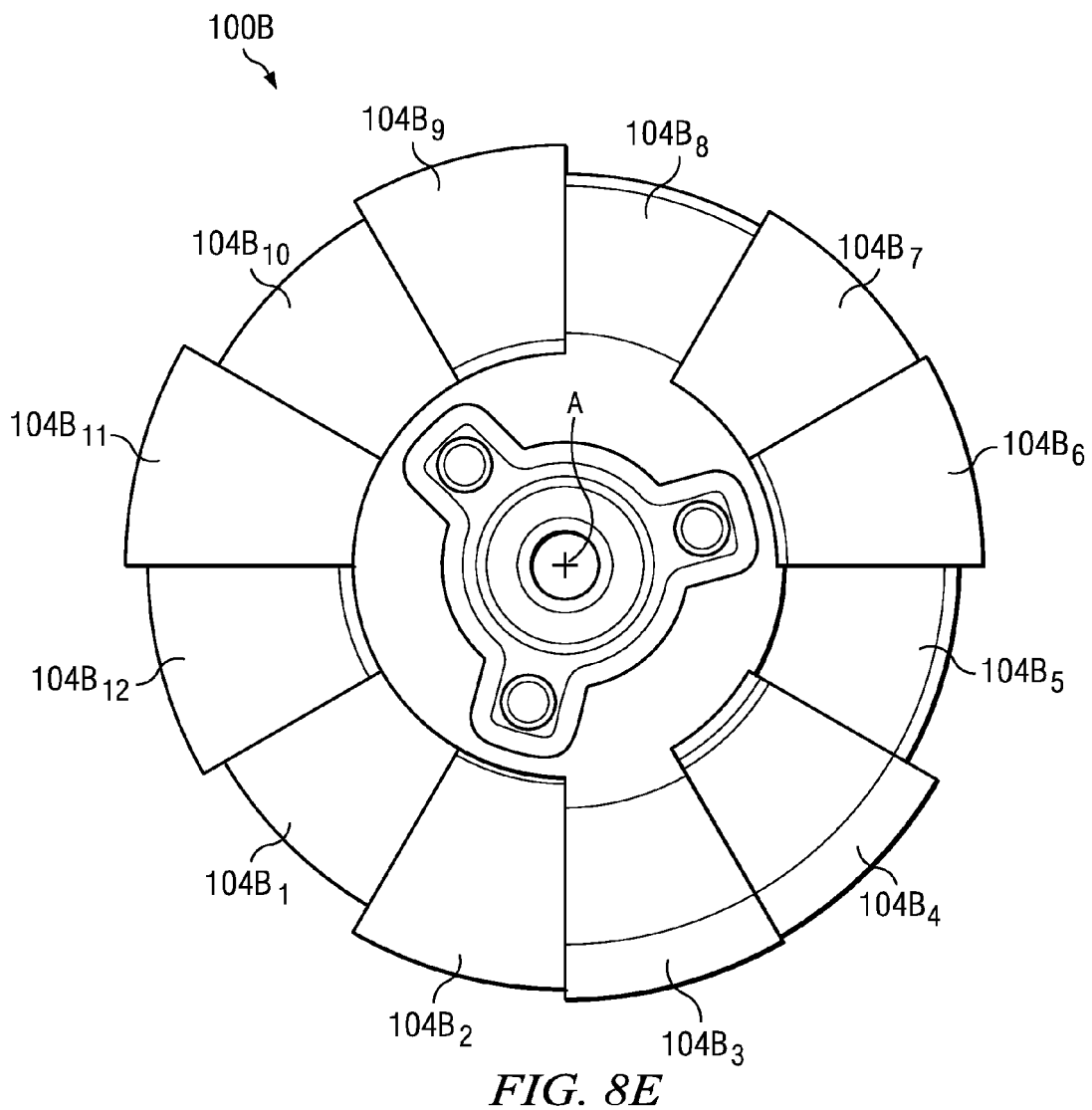

FIGS. 8A-8E illustrate various aspects and embodiments of a rotating cup-shaped, multi-sector beam scanning element 100B for use in certain embodiments of scanning system 48. In particular, FIG. 8A is an isometric front (i.e., upstream) view of cup-shaped element 100B; FIG. 8B is an isometric rear (i.e., downstream) view of cup-shaped element 100B; FIG. 8C is a side view of cup-shaped element 100B; FIG. 8D is a front view of cup-shaped element 100B; and FIG. 8E is a rear view of cup-shaped element 100B.

Cup-shaped rotating element 100B is similar to disc-shaped rotating element 100A with each lenslet "tilted" toward the axis of rotation in the upstream direction to form a cup shape lens element. Cup-shaped element 100B operates according to the same basic principle as disc-shaped element 100A discussed above, with each lenslet (a) deflecting deflect an input beam 110 in a different angular direction, and (b) focusing the input beam 110 along at least one axis (e.g., the fast axis, the slow axis, or both) to generate a sequential series of output beams 112 propagating to achieve a desired pattern of treatment spots on the skin 40. As with other embodiments discussed herein, cup-shaped element 100B can be configured such that the angular deflection produced by each lenslet 104 either (a) remains constant as that lenslet 104 rotates through the input beam 110 (e.g., to produce a spot on the skin) or (b) varies as the lenslet 104 rotates through the input beam 110 (e.g., to produce a line segment or arc on the skin).

As shown in FIGS. 8A-8E, cup-shaped element 100B has a body 102B configured to rotate about axis A (e.g., driven by a motor 120). In this example, body 102B includes 12 sectors $104B_1$ to $104B_{12}$ arranged circumferentially around axis A. Each sector $104B_1$ to $104B_{12}$ comprises a transmissive lenslet configured to (a) deflect an input beam 110 in a different angular direction, and (b) focus (i.e., influence the divergence/convergence of) the input beam 110 in at least one axis (e.g., the fast axis, the slow axis, or both). As element 100B rotates one full revolution through the input beam 110 (i.e., one full scan), lenslets $104B_1$ to $104B_{12}$ produce a successively scanned array of 12 output beams 112 that are angularly offset from each other, to provide a scanned array of 12 treatment spots on the skin 40.

In some embodiments, each transmissive lenslet $104B_1$ to $104B_{12}$ is configured to (a) deflect the input beam 110 in a different angular direction, such that the output beams 112 are offset from each other along one axis (e.g., the slow axis or the fast axis), and (b) focus the input beam 110 along that same axis (e.g., the slow axis or the fast axis), while not substantially affecting the beam along the orthogonal axis (e.g., the other of the slow axis and fast axis). For example, in an example embodiment, each transmissive lenslet is configured to (a) deflect the input beam 110 in a different angular direction such that the output beams 112 are offset from each other in the slow axis direction, and (b) focus the slow axis profile of the beam, while not substantially affecting the fast axis profile of the beam. Thus, in such example embodiment, scanning element 100B acts as both a beam scanning element 62 and a slow axis element 66, e.g., as discussed above with reference to FIGS. 3C and 3D.

As discussed above, lenslets 104b may be configured such that the array of treatment spots may be generated in any desired sequential order, e.g., in terms of one or more particular directions. In this example embodiment, lenslets 104B$_1$ to 104B$_{12}$ are configured such that the 12 corresponding treatment spots are delivered along a linear scan direction in a pseudo-random order, e.g., as discussed below with reference to FIG. 22C.

As with lenslets 104A of example disc-shaped element 100A, each lenslet 104B of example cup-shaped element 100B may have a toroid shape defined by rotating a cross-sectional shape around the rotational axis A of element 100B. The rotated cross-sectional shape may be defined by a pair of opposing edges that form the opposing surfaces of the lenslet upon rotation of the cross-sectional shape. The pair of opposing edges may have any suitable shapes. For example, the pair of opposing arcs may be a pair of opposing arcs (with each arc being circular or non-circular, and with the opposing arcs being symmetrical or non-symmetrical with respect to each other), an arc and an opposing non-arc (e.g., a linear segment or other shape), or any other suitable shapes for forming the desired surfaces of the lenslet upon rotation of the cross-sectional shape. A geometric "centerline" of the cross-sectional shape of each lenslet may be defined between the pair of opposing edges. Further, each toroidal lenslet may define a "lenslet apex," defined herein as the thickest portion of the lenslet, in the direction from edge-to-edge of the cross-sectional shape.

In some embodiments, each lenslet has a toroid shape defined by rotating a cross-sectional shape around the rotational axis A, wherein the cross-sectional shape is defined by a pair of opposing arcs. In other embodiments, each lenslet has a toroid shape defined by rotating a cross-sectional shape around the rotational axis A of element 100B, wherein the cross-sectional shape is defined by an arc opposed by a linear segment.

In some embodiments, e.g., the example embodiment shown in FIGS. 8A-8E, each lenslet 104B of cup-shaped element 100B has a respective cross-section defined by a pair of circular arcs centered around a tilted centerline A'. (The pair of arc and centerline for each lenslet are also discussed below with respect to FIG. 9B). Each centerline is "tilted" in that it is angularly offset from the rotational axis A of element 100B by a defined angle $\alpha$ (i.e., the angle at which each lenslet 104B of element 100B is "tilted" toward rotational axis A as compared to the lenslets 104A of disc-shaped element 100A). The toroid shape of each lenslet 104B of cup-shaped element 100B is defined by rotating the respective cross-section (i.e., pair of opposing arcs centered around a tilted centerline) around the rotational axis A of element 100B.

FIG. 8A illustrates (a) a tilted centerline A'$_5$ corresponding to lenslet 104B$_5$ and angularly offset from rotational axis A by an angle $\alpha_5$, and (b) a tilted centerline A'$_6$ corresponding to lenslet 104B$_6$ and angularly offset from rotational axis A by an angle $\alpha_6$. Thus, lenslet 104B$_5$ has a toroid shape defined by rotating around rotational axis A a cross-section defined by a pair of circular arcs centered around tilted centerline A'$_5$, while lenslet 104B$_6$ has a toroid shape defined by rotating around rotational axis A a cross-section defined by a pair of circular arcs centered around tilted centerline A'$_6$. The different shapes of lenslets 104B$_1$ to 104B$_{12}$ of element 100B are generated by varying a "radial" distance—specifically, along each respective tilted centerline—of the lenslet apex (i.e., the thickest part of the lenslet cross-section), as described in greater detail below with respect to FIG. 9B, thus presenting the incoming beam 110 with a different relative position between the beam center and the lenslet apex, for different lenslets. This difference in relative positioning results in each output beam 112 being deflected by a different angular amount, as discussed below with respect to FIG. 9B.

In some embodiments, cup-shaped scanning element 100B is configured such that the toroidal shape of each lenslet 104B provides a "constant angular deflection" output beam 112, as that lenslet 104B sweeps across the input beam 110.

In this embodiment, each tilted centerline A'$_1$ through A'$_{12}$ is angularly offset from rotational axis A by the same angle $\alpha$ (thus, for A'$_5$ and A'$_6$ discussed above, $\alpha_5 = \alpha_6$). In other words, each lenslet 104B is tilted by the same degree. In some embodiments, $\alpha$ is less than 80 degrees. In certain embodiments, $\alpha$ is between about 30 degrees and about 60 degrees. In particular embodiments, $\alpha$ is about 47 degrees. In other embodiments, different tilted centerline A'$_1$ through A'$_{12}$ may be angularly offset from rotational axis A by different angles (e.g., $\alpha_5 \neq \alpha_6$). In other words, each lenslet 104B may be tilted by different degrees.

FIGS. 8D and 8E illustrate the front and rear views, respectively, of cup-shaped element 100B. From these perspectives, each lenslet 104B is essentially a circular sector sweeping the same circumferential or central angle (30 degrees). Thus, with reference to FIG. 8D, for each lenslet, $\theta = 30$ degrees. In other embodiments of cup-shaped element 100B, different lenslets 104B may be aspherical sectors that sweep different central angles. In other embodiments of cup-shaped element 100B, the lenslets may have any other suitable shapes (i.e., other than aspherical sectors) in the front or rear view of element 100B, and the different lenslets may sweep the same or different circumferential or central angles.

Further, although the example cup-shaped element 100B shown in FIGS. 8A-8E includes 12 lenslets, in other embodiments cup-shaped element 100B may include any other number of lenslets, more than or fewer than 12.

Figure 9A:
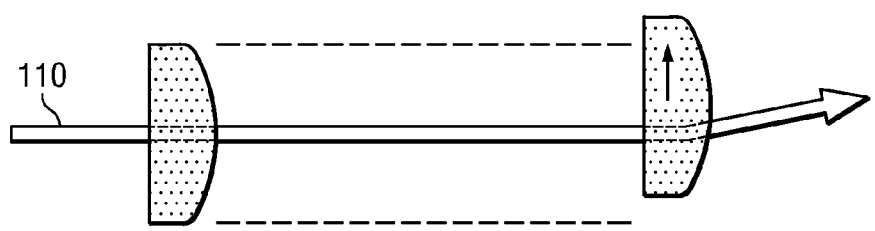
FIGS. 9A and 9B illustrate optical aspects of the example beam-scanning elements of FIGS. 7A-7C and FIGS. 8A-8E, according to certain embodiments.
Figure 9B:
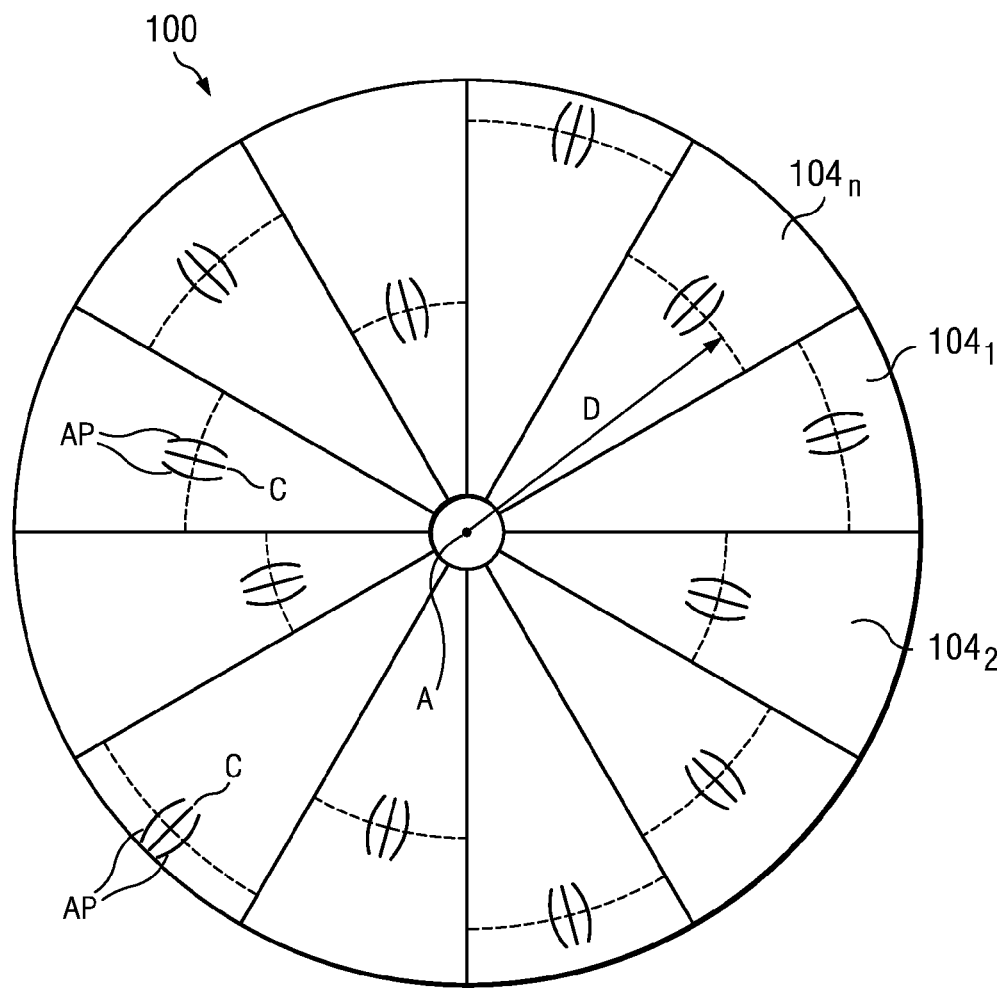

The basic illustrative theory behind the multi-lenslet elements 100A and 100B and how they deflect a radiation beam is shown in FIGS. 9A-9B. With reference to the orientation shown in FIG. 9A, the radiation beam B enters from the left and passes undeviated through the center of the lens at the left. When the lens is shifted up (off axis relative to the beam, as indicated by the vertical arrow) as shown on the right, the beam is deviated by an angle generally proportional to the shift.

Lenslets 104 may have any suitable shape or configuration to affect the beam. For example, as discussed below in greater detail, lenslets 104 may have a toroidal shape, a circular shape, an aspheric shape, or any other suitable shape or configuration.

FIG. 9B illustrates a representation of a beam scanning element 100 (e.g., element 100A or 100B) according to an example embodiment. Element 100 includes a plurality of lenslets 104 arranged around a rotational axis A. In this example, each the lenslet 104 has a toroidal shape defined by rotating a pair of arcs AP around rotational axis A, where the rotation of the arc pair AP in each sector 104 is indicated by the dashed line sweeping through each sector 104 (such that each dashed line is an arc centered on the rotational axis A). Here, each arc pair AP is shown orthogonal to its actual orientation, for the purposes of illustration. Arc pairs AP may comprise circular arcs or non-circular arcs. In some embodiments (e.g., disk-shaped scanning element 100A), the centerline C of each lenslet 104 resides in the same plane, specifically the plane of rotation of element 100 (i.e., 90 degrees from the axis of rotation A). In other embodiments (e.g., cup-shaped scanning element 100B), each lenslet 104 is tilted with respect to plane of rotation such that the centerline C of each lenslet 104 extends at an angle between plane of rotation of element 100 and the axis of rotation A). This angle of tilt may be the same for each lenslet 104 or may be different for different lenslets 104, e.g., as discussed above regarding cup-shaped scanning element 100B.

As shown, the lens apex (i.e., the thickest point) of each lenslet 104 sweeps through the dashed line in each sector 104. For each lenslet 104, the distance D of the lens apex from rotational axis A is different than some or all other lenslets 104. This difference in distance D among the different lenslets 104 provides the different angular deflections of output beam 112 produced by the respective lenslets 104.

The toroidal lenslets 104 as discussed above provide for constant angular deflection of the output beam 112 produced by each lenslet 104, as that lenslet 104 sweeps across the input beam 110.

In some embodiments, each lenslet 104 may have the same optical power, or substantially the same optical power. In other embodiments, lenslets 104 may have slightly different optical powers, in order to (a) provide a uniform focal plane for the array of output beams 112 with respect to the skin surface (e.g., the optical powers or individual lenslets 104 may be selected to compensate for the different angular deflection of each output beam 112), and/or (b) provide for distortion correction among the various output beams 112. In other embodiments, each lenslet 104 may have substantially different optical powers.

It should be understood that the specific shapes of lenslets 104 specifically shown and discussed herein are examples only, and that lenslets 104 may have any other shapes or configurations (which may or may not be toroid shaped) suitable for deflecting an input beam 110 in different angular directions.

Example Optics Systems Utilizing a Rotating Multi-Lenslet Scanning Element

FIGS. 10 and 11 illustrate example optical systems 15 that utilize a rotating multi-lenslet scanning element 100, according to certain embodiments.

Figure 10A:
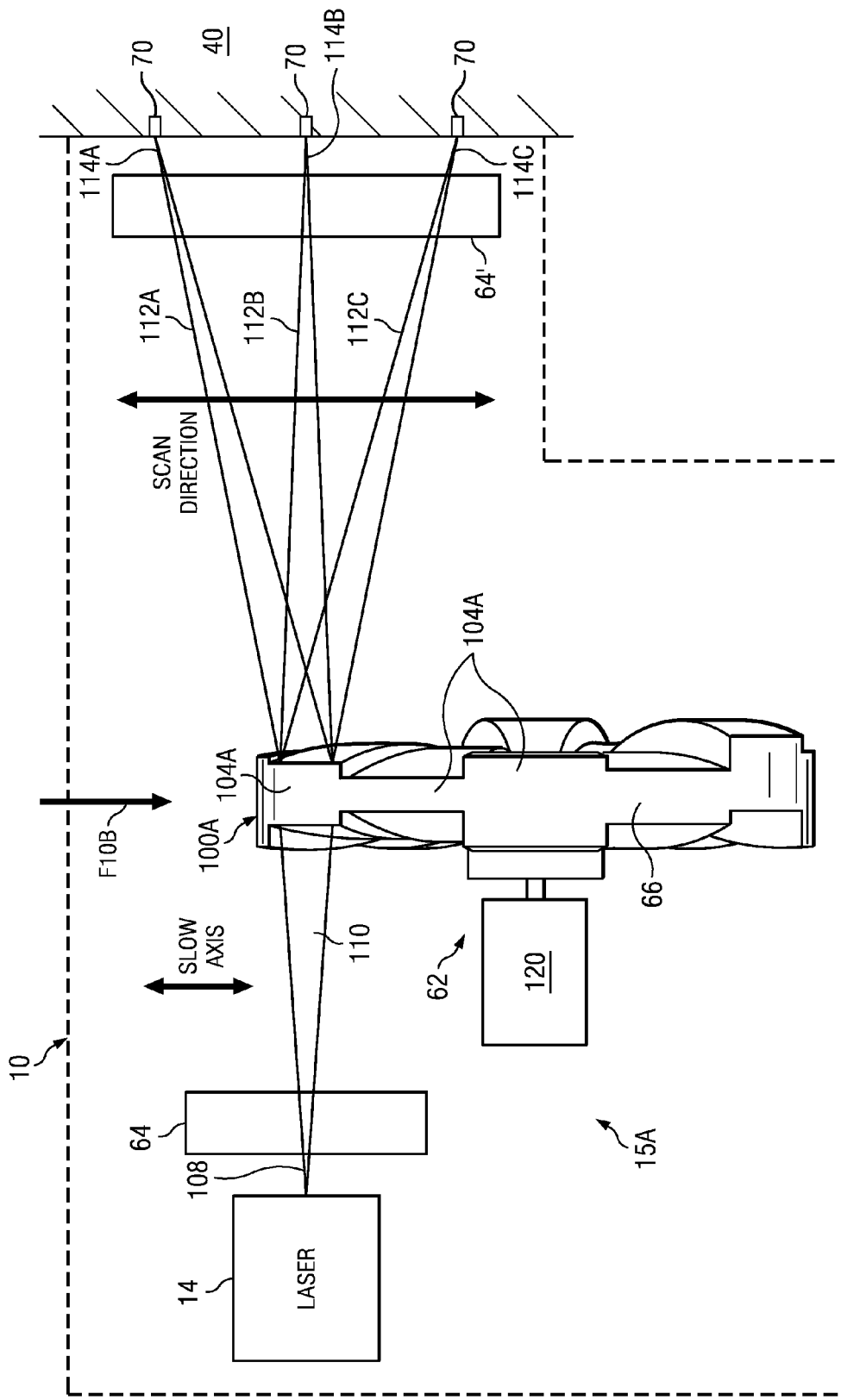

FIGS. 10A and 10B illustrate top and side views, respectively, of an optical system 15A that includes a rotating disc-shaped scanning element 100A, e.g., as described above with respect to FIGS. 7A-7C, according to certain embodiments. Optical system 15A is configured to scan and deliver radiation generated by radiation source 14 to form a pattern of treatment spots 70 on the skin 40.

In this example embodiment, the radiation source 14 is a laser diode that generates an axially-asymmetric beam 108 including a fast axis and an orthogonal slow axis. Optics 16 may include a fast axis optic 64, and a disc-shaped scanning element 100A rotated by a motor 120. In some embodiments, optics 16 may also include a downstream fast axis optic 64', whereas in other embodiments this optic is omitted.

As shown, laser 14 generates beam 108, which diverges relatively rapidly in the fast axis (as shown in FIG. 10B) and diverges relatively slowly in the slow axis (as shown in FIG. 10A). Fast axis optic 64, e.g., a rod lens, aspheric lens, or any other suitable optical element, is configured to convert the beam in the fast axis from rapidly diverging to less diverging (e.g., slowly diverging, collimated, or converging) toward target area 40, as shown in FIG. 10B. In some embodiments, fast axis lens 64 does not significantly influence the slow axis beam angular distribution profile (e.g., the convergence/divergence of the slow axis), as shown in FIG. 10A.

Fast axis optic 64 delivers an input beam 110 to rotating disc-shaped scanning element 100A, which includes multiple lenslets 104 that generate a successive series of output beam 112 toward the skin 40, as shown in FIG. 10A. In addition to deflecting the various output beams in the scan direction to form a desired pattern of treatment spots on the skin 40, lenslets 104 of element 100A also focus the beam in the slow axis, to convert the slow axis profile of the beam from slowly diverging to slowly converging (or in some embodiments, collimated). Thus, a single element 100A operates as both the beam scanning element and the slow axis optic 66, thus reducing or minimizing the number of separate components for such functions, which may be desirable. In some embodiments, lenslets 104 of element 100A do not substantially influence the fast axis beam profile, as shown in FIG. 10B.

Fast axis optic 64 and lenslets 104 of element 100A may be configured to converge the beam in the fast and slow axes, respectively, such that each output beam 112 has a focal point or focal plane located at or slightly above the surface of the skin (i.e., outside the skin). As used herein, the "focal point" or "focal plane" of each delivered beam 114 is defined as the plane perpendicular to the propagation axis of the beam 114 having the minimum cross-sectional area. For embodiments that provide axially-asymmetric delivered beams 114 (e.g., embodiments that utilize an axially-asymmetric radiation source 14, such as a laser diode), the minimum cross-sectional area is typically located between the waist of the fast axis beam profile and the waist of the slow axis beam profile.

Further, as discussed above, in some embodiments a downstream fast axis optic 64' is provided for additional focusing and/or imaging and/or treatment of output beams 112 for delivery to the skin as delivered beams 114. Other embodiments omit the downstream lens 64', and thus include only a single fast axis optic (element 64) and a single slow axis optic (element 100A). This design may thus reduce or minimize the number of optical elements as compared to existing systems or other embodiments, which may be desirable for various reasons.

Figure 11A:
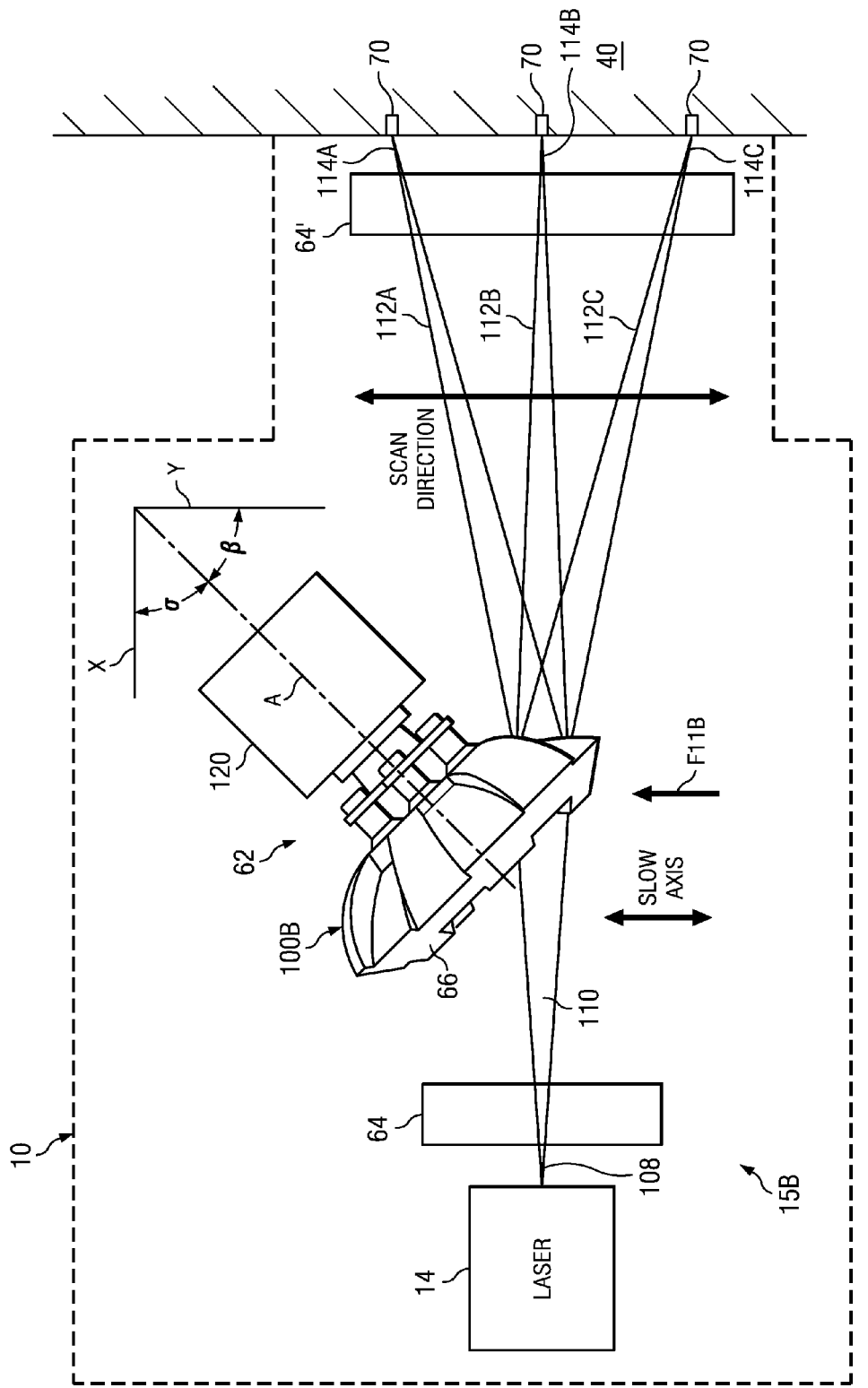
FIGS. 11A and 11B illustrate top and side views, respectively, of a beam generation and delivery system that includes a cup-shaped rotating scanning element, according to certain embodiments.
Figure 11B:
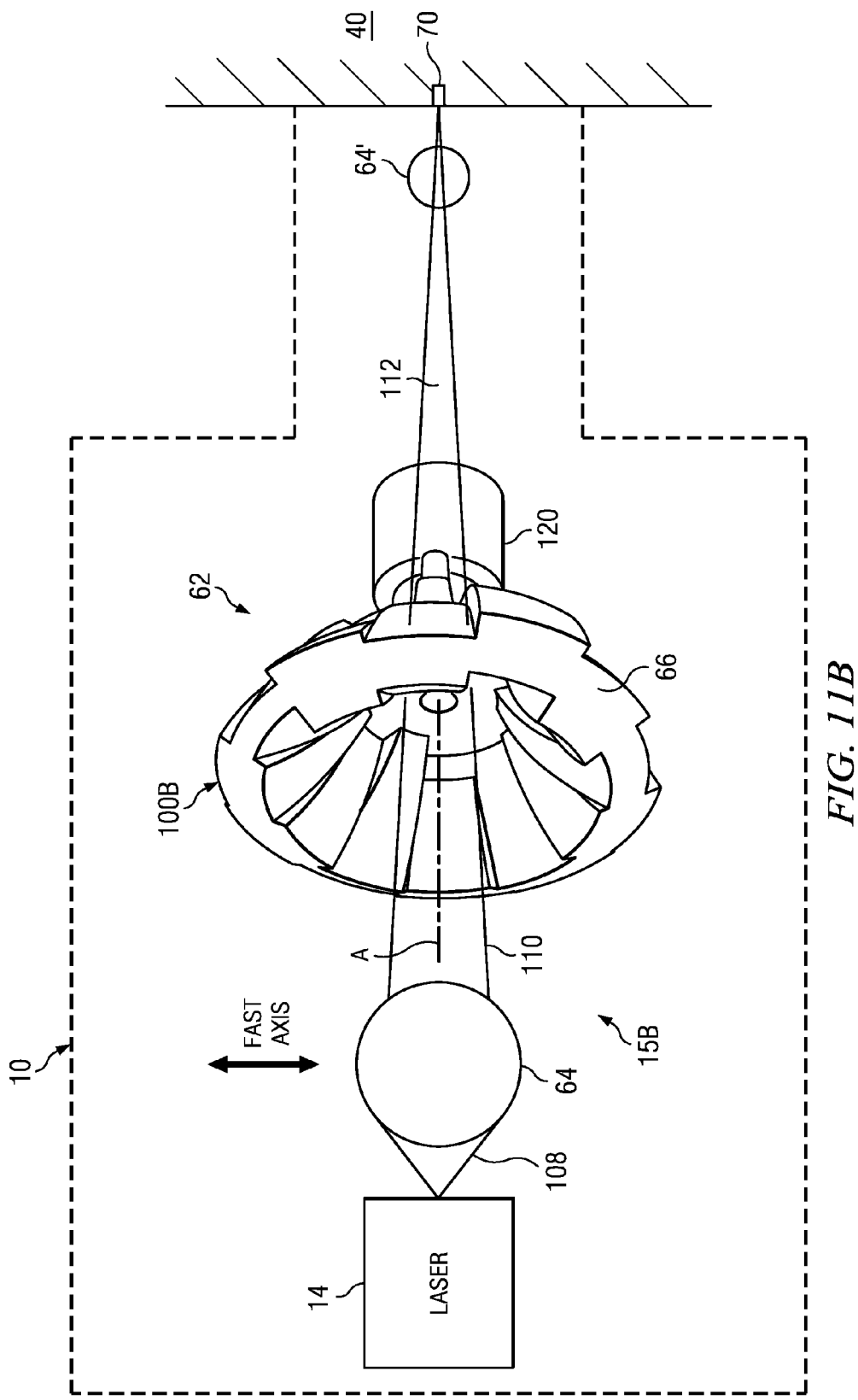

FIGS. 11A and 11B illustrate top and side views, respectively, of an optical system 15B that includes a rotating cup-shaped scanning element 100B, e.g., as described above with respect to FIGS. 8A-8E, according to certain embodiments. Optical system 15B is similar to optical system 15A, except scanning system 48 includes a cup-shaped scanning element 100B, rather than disc-shaped element 100A. Again, it is assumed in this example that the treatment radiation source 14 is a laser diode that generates an axially-asymmetric beam 108 defining a fast axis and an orthogonal slow axis. As with the example discussed above, the downstream fast axis optic 64' may be included or omitted, depending on the particular design.

As shown, laser 14 generates beam 108, which diverges relatively rapidly in the fast axis (as shown in FIG. 11B) and diverges relatively slowly in the slow axis (as shown in FIG. 11A). Fast axis optic 64, e.g., a rod lens, aspheric lens, or any other suitable optical element, is arranged to convert the beam in the fast axis from rapidly diverging to less diverging (e.g., slowly diverging, collimated, or converging) toward target area 40, as shown in FIG. 11B. In some embodiments, fast axis lens 64 does not significantly influence the slow axis beam angular distribution profile (e.g., the convergence/divergence of the slow axis), as shown in FIG. 10A.

Fast axis optic 64 delivers an input beam 110 to rotating cup-shaped scanning element 100B, which includes multiple lenslets 104 that generate a successive series of output beam 112 toward the skin 40, as shown in FIG. 11A. In addition to deflecting the various output beams in the scan direction to form a desired pattern of treatment spots in the target area 40, lenslets 104 of element 100A also focus the beam in the slow axis, to convert the slow axis profile of the beam from slowly diverging to slowly converging. (or in some embodiments, collimated). Thus, a single element 100B operates as both the beam scanning element 62 and the slow axis optic 66, thus reducing or minimizing the number of separate components for such functions, which may be desirable. In some embodiments, lenslets 104 of element 100B do not substantially influence the fast axis beam profile, as shown in FIG. 10B, as shown in FIG. 11B.

Fast axis optic 64 and lenslets 104 of element 100B may be configured to converge the beam in the fast and slow axes, respectively, such that each output beam 112 has a focal point or focal plane located at or slightly above the surface of the skin (i.e., outside the skin).

Further, as discussed above, in some embodiments a downstream fast axis optic 64' is provided for additional focusing and/or imaging and/or treatment of output beams 112 for delivery to the skin as delivered beams 114. Other embodiments omit the downstream lens 64', and thus include only a single fast axis optic (element 64) and a single slow axis optic (element 100B). This design may thus reduce or minimize the number of optical elements as compared to existing systems or other embodiments, which may be desirable for various reasons.

Cup-shaped scanning element 100B is arranged such that the rotational axis A of element 100B is aligned at an angle $\alpha$ relative to a central axis of input beam 110, indicated as axis X. In some embodiments, e.g., as shown in FIG. 11A, angle $\alpha$ is greater than zero, which may allow scanning system 48 to be arranged in housing 24 of device 10 such that one or more external dimensions of housing 24 may be reduced, e.g., as compared to a scanning system utilizing a disc-shaped scanning element, or certain known scanning systems. For example, angle $\alpha$ may be greater than 10 degrees. In certain embodiments, angle $\alpha$ is greater than 30 degrees. Further, angle $\alpha$ may be greater than 45 degrees, which may allow for particular reduction of one or more external dimensions of housing 24, or other component packaging advantages. In particular embodiments, angle $\alpha$ is between 45 and 55 degrees. In one example embodiment, angle $\alpha$ is about 47 degrees.

Further, angle $\alpha$ may be related to the angle of forward tilt of each lenslet 104, defined above as angle $\alpha$ with reference to FIG. 8A. For example, $\sigma+\alpha$ may be in the range between 60 and 120 degrees. In some embodiments, $\sigma+\alpha$ may be in the range between 80 and 100 degrees. In particular embodiments, $\sigma+\alpha$ is equal to or approximately equal to 90 degrees (i.e., angles $\sigma$ and $\alpha$ are complementary or approximately complementary angles).

Alternatively or in addition, rotational axis A of element 100B may be aligned at an angle $\beta$ relative to a scan direction, i.e., a direction of the beam deflection caused by lenslets 104, indicated as direction Y. Scan direction Y may or may not be perpendicular to the central axis X of input beam 110, depending the configuration of the particular embodiment.

In some embodiments, e.g., as shown in FIG. 11A, angle $\beta$ is less than 90 degrees, which may allow scanning system 48 to be arranged in housing 24 of device 10 such that one or more external dimensions of housing 24 may be reduced, e.g., as compared to a scanning system utilizing a disc-shaped scanning element, or certain known scanning systems. For example, angle $\beta$ may be less than 80 degrees. In certain embodiments, angle $\beta$ is less than 60 degrees. Further, angle $\beta$ may be less than 45 degrees, which may allow for particular reduction of one or more external dimensions of housing 24, or other component packaging advantages. In particular embodiments, angle $\beta$ is between 35 and 45 degrees. In one example embodiment, angle $\beta$ is about 43 degrees.

Further, angle $\beta$ may be related to the angle of forward tilt of each lenslet 104, defined above as angle $\alpha$ with reference to FIG. 8A. For example, angles $\sigma$ and $\beta$ may differ by less than 30 degrees. In some embodiments, angles $\sigma$ and $\beta$ may differ by less than 10 degrees. In particular embodiments, angles $\sigma$ and $\beta$ are equal or approximately equal.

Stair-Stepped Rotating Scanning Element

FIGS. 12-20 illustrate various aspects and embodiments of a stair-stepped rotating beam scanning element 100C and example scanning systems 48 including a stair-stepped scanning element 100C.

Figure 12:
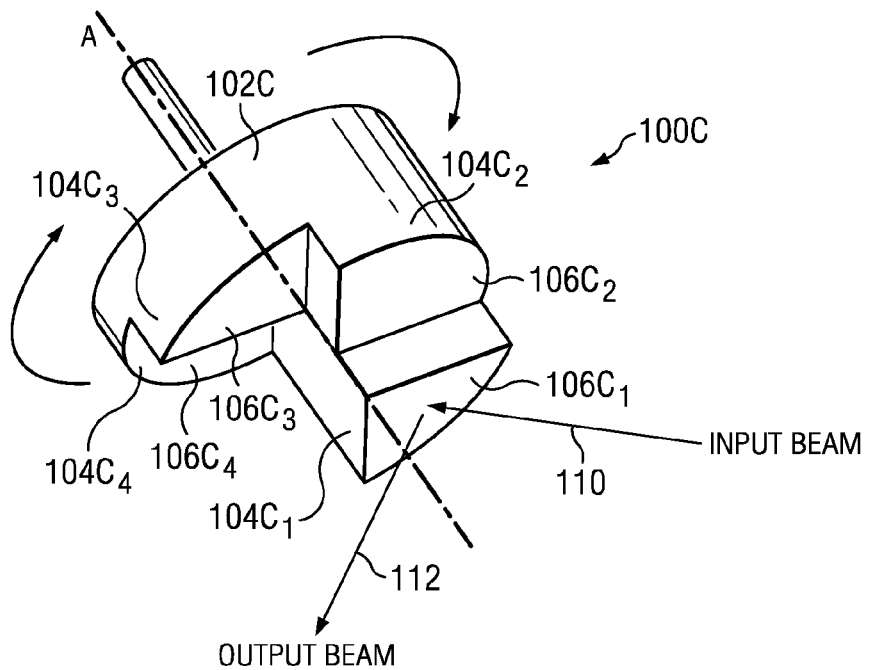
FIG. 12 illustrates an example stair-stepped rotating scanning element, according to an example embodiment.

FIG. 12 illustrates an example stair-stepped rotating element 100C. Rotating element 100C has a body 102C configured to rotate about an axis A. Body 102C defines a plurality of reflection sectors $104C_1$-$104C_4$ arranged circumferentially around axis A, and respectively defining a plurality of reflection surfaces $106C_1$-$106C_4$ arranged in a generally stair-stepped manner. Reflection surfaces $106C_1$-$106C_4$ are configured to reflect an input beam 110 (received directly from radiation source 14 or from optics arranged upstream from rotating element 100C or otherwise) such that the input beam 110 reflects off each reflection surface $106C_1$-$106C_4$ in succession, one at a time, as the rotating element rotates about axis A, to generate a successive array of output beams 112.

As shown, reflection surfaces $106C_1$-$106C_4$ are offset from each other in the direction along rotational axis A. As a result, the different reflection sectors $104C_1$-$104C_4$ generate a successive array of offset output beams 112 that are translationally (and/or angularly) offset from each other, as explained below in greater detail.

In some embodiments, reflection surfaces $106C_1$-$106C_4$ are planar surfaces that are parallel to each other, such that the array of reflected output beams 112 produced by the input radiation beam successively reflecting off the reflection surfaces $106C_1$-$106C_4$ as element 100C rotates are translationally offset and parallel to each other, e.g., as discussed with reference to the array of output beams 112A-112D shown in FIG. 13. In some embodiments, the plane of each respective reflection surface $106C_1$-$106C_4$ is perpendicular to rotational axis A. In other embodiments, the planes of reflection surfaces $106C_1$-$106C_4$ may be parallel to each other, but arranged at any non-perpendicular angle relative to rotational axis A.

In other embodiments, reflection surfaces $106C_1$-$106C_4$ are planar surfaces arranged at angles relative to each other such that the array of reflected radiation beams are both translationally offset and angularly offset (i.e., not parallel) from each other; for example, the reflected array of beams (as opposed to the individual reflected beams) may diverge or converge, or form multiple rows of treatment spots, as opposed to a single linear row.

Forming reflection surfaces $106C_1$-$106C_4$ as planar surfaces perpendicular to the rotational axis provides the effect that for the duration of time that the radiation beam is reflected off each reflection surface 106C, the angular direction of the resulting output beam 112 (relative to the device structure or housing 24) remains constant over the duration of time, which may be referred to as "constant angular deflection" output beams 112. "Constant angular deflection" is discussed in greater detail below with reference to FIGS. 26A-26B. Thus, in such embodiments, reflection sectors $104C_1$-$104C_4$ may be referred to as constant angular deflection reflection sectors 104C, similar to the constant angular deflection lenslets 104A and 104B discussed above with respect to certain embodiments of the disc-shaped and cup-shaped scanning elements 100A and 100B.

In some embodiments, some or all reflection surfaces $106C_1$-$106C_4$ may be non-planar, e.g., concave or convex along one or more axes. In such embodiments, each output beam 112 may either (a) move relative to the device structure or housing 24 during the time that the input beam 110 is incident upon the respective non-planar reflection surface 106C, or (b) remain substantially stationary relative to the device structure or housing 24 during the time that the input beam 110 is incident upon the respective non-planar reflection surface 106C, depending on the specific non-planar shape of reflection surfaces $106C_1$-$106C_4$ and/or other aspects of the configuration of optics 16, for example.

For example, reflection surfaces $106C_1$-$106C_4$ may be shaped or configured as "shifting deflection" surfaces that provide shifting deflection output beam 112, similar to the shifting deflection lenslets 104A and 104B discussed above with respect to certain embodiments of the disc-shaped and cup-shaped scanning elements 100A and 100B. "Shifting deflection" is discussed in greater detail below with reference to FIGS. 27A-27B.

As discussed above, reflection surfaces $106C_1$-$106C_4$ may be offset from each other in the direction of the axis A. Reflection surfaces $106C_1$-$106C_4$ may be offset from each other along the axis A by the same distance between each surface, or alternatively, by different distances. The offset distance between different reflection surfaces $106C_1$-$106C_4$ may be selected to provide the desired spacing between the respective output beams 112 reflected off reflection surfaces $106C_1$-$106C_4$.

Figure 13:
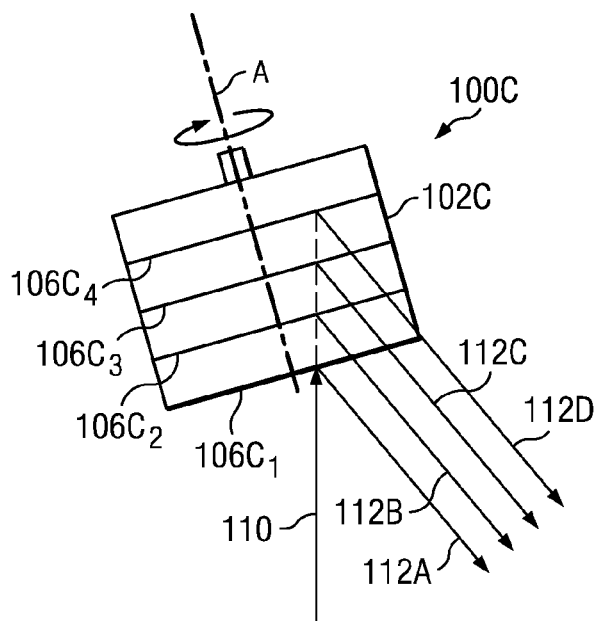
FIGS. 13 and 14 illustrate the basic operation of a stair-stepped rotating scanning element, according to an certain embodiments.

FIG. 13 illustrates a representational side view of rotating element 100C, with each reflection surface $106C_1$-$106C_4$ represented by a line extending across the diameter of body 102C, for illustration purposes. An input beam 110 reflects off each reflection surface $106C_1$-$106C_4$ in succession, one at a time, as rotating element 100C rotates about axis A, to produce a successive array of output beams 112A-112D. In this example, reflection surfaces $106C_1$-$106C_4$ are planar surfaces and parallel to each other, such that reflected output beams 112A-112D are translationally offset and parallel to each other, and stationary with respect to the device structure or housing 24 (i.e., constant angular deflection output beams).

Figure 14:
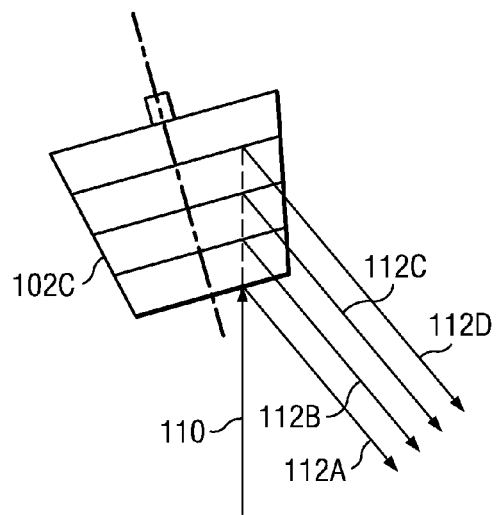

FIG. 14 illustrates a side view of another rotating element 100C, wherein the element body 102C has a tapered shape, according to certain embodiments. As with FIG. 13, each reflection surface $106C_1$-$106C_4$ is represented by a line extending across the diameter of body 102C, for illustration purposes. The tapered shape of body 102C may reduce the mass of body 102C and/or may prevent unwanted deflection or blocking of the input beam 110 and/or output beams 112A-112D by the structure of body 102C.

Downstream Optics for Stair-Stepped Scanning System

As mentioned above, the successive array of output beams 112 may be delivered directly to the skin 40 as delivered beams 114, or may be influenced by one or more downstream optics 60B (with reference to FIG. 3A) before being delivered to the skin 40 as delivered beams 114. In some embodiments, one or more downstream optics 60B may be configured to redirect and/or otherwise influence the array of output beams 112. Such downstream optics 60B may include any one or more mirrors or other reflective surfaces, lenses or other optical elements configured to deflect, focus, defocus, or otherwise affect the direction, convergence/divergence, focal point, beam intensity profile, and/or other property of output beams 112.

In some embodiments, downstream optics 60B may be configured to influence the intensity profile of individual output beams 112 along one axis or multiple axes, e.g., by influencing the shape of the intensity profile along one or more axis, changing whether the beam is converging, diverging, or collimated along one or more axis, changing the degree of convergence or divergence along one or more axis, etc., For example, downstream optics 60B may be configured to define a focal point or focal plane for each output beam 112 at or slightly above the surface of the skin (i.e., outside the skin). Downstream optics 60B may influence the intensity profile of each individual output beams 112 equally or differently. For example, in some embodiments, such downstream optics may include an array of lens or mirror elements, each corresponding to an individual output beam 112 and thus operable to influence individual output beams 112 as desired, including influencing individual output beams 112 differently if desired.

In addition or alternatively, downstream optics 60B may be configured to deflect output beams 112. Downstream optics 60B may deflect output beams 112 in a manner that does not influence the propagation of output beams 112 relative to each other. For example, in the example shown in FIG. 15A, downstream optics 60B include a planar mirror 150A that reflects an array of output beams 112A-112D from rotating element 100C towards the skin 40, without influencing the propagation of output beams 112 relative to each other. In some embodiments, downstream optics 60B may be configured to deflect at least some of the output beams 112 to increase the normality (i.e., perpendicularity) of such beams 112 relative to the target surface. In other embodiments, downstream optics may be configured to deflect at least some of the output beams 112 to deliver the beams 112 at one or more predetermined normal or non-normal (i.e., non-perpendicular) angle relative to the target surface.

Alternatively, downstream optics 60B may deflect output beams 112 in a manner that influences the propagation of output beams 112 in one or more axes relative to each other, such as (a) influencing whether the array of output beams 112 (as opposed to individual output beams 112) converge, diverge, or propagate parallel to each other, and/or (b) influencing the degree with which the array of output beams 112 (as opposed to individual output beams 112) converge or diverge from each other. For example, such downstream optics 60B may include one or more lenses or mirror elements that are concave, convex, or otherwise non-planar in one or more directions.

Figure 15A:
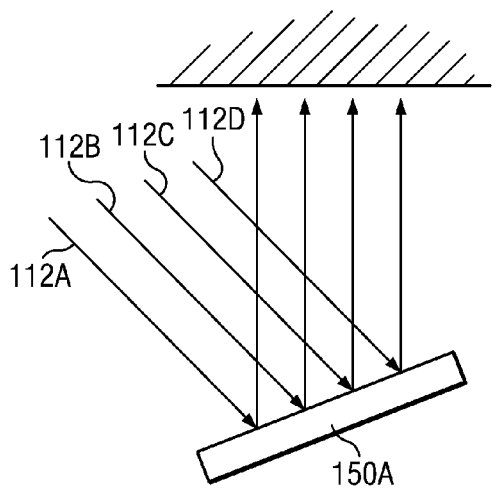
FIG. 15A-15C illustrate example downstream optics for use with a stair-stepped rotating scanning element, according to an certain embodiments.
Figure 15B:
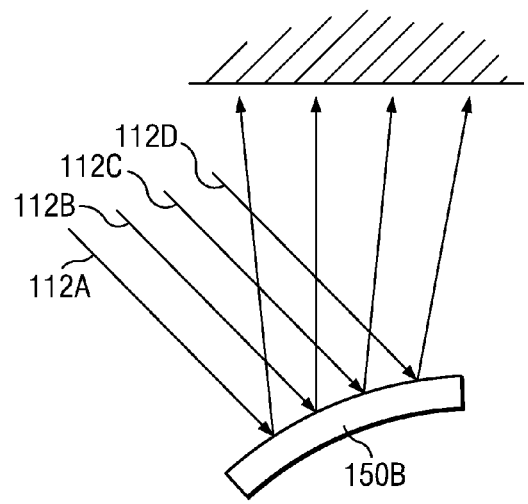
Figure 15C:
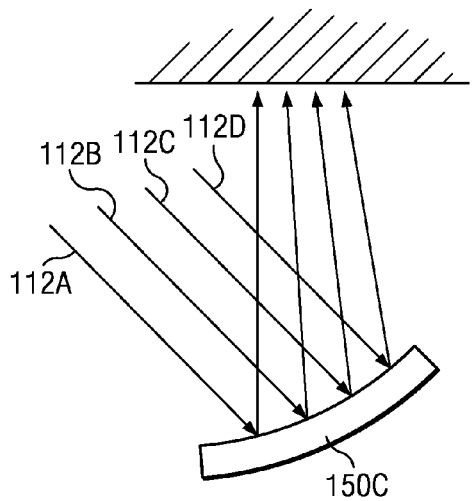

FIGS. 15B and 15C illustrate examples of such downstream optics. In the example embodiment of FIG. 15B, downstream optics include a convex mirror 150B that increases the divergence/decreases the convergence of an array of output beams 112A-112D, thus either (a) converting a parallel array to a diverging array, (b) increasing the degree of divergence of a diverging array, (c) decreasing the degree of convergence of a converging array, or (d) converting a converging array to a parallel or diverging array. In contrast, in the example embodiment of FIG. 15C, downstream optics include a concave mirror 150C that increases the convergence or decreases the divergence of an array of output beams 112A-112D, thus either (a) converting a parallel array to a converging array, (b) increasing the degree of convergence of a converging array, (c) decreasing the degree of divergence of a diverging array, or (d) converting a diverging array to a parallel or converging array.

In some embodiments, downstream optics 60B may both (a) influence the intensity profile of individual output beams 112 along one or more axis, and (b) influence the propagation of output beams 112 relative to each other along one or more axis.

Path Length Compensation

In certain applications, it may be desirable that each beam delivered to the skin 40 has an equal total path length, the total path length being defined as the total travel distance of the beam from the radiation source 14 to the skin 40. For example, in embodiments in which individual beams delivered to the skin 40 are converging, diverging, or otherwise experiencing a change in intensity profile (in one or more axis) while propagating toward the skin 40, it may be desired that each beam have an equal path length from the radiation source 14 to the skin 40 to provide a uniform size, shape, and/or intensity of treatment spots on the skin 40 created by the different individual beams.

However, as shown in the example embodiments of FIGS. 13 and 14, the input beam 110 travels different distances before reflecting off the respective reflection surface $106C_1$-$106C_4$. Thus, in some embodiments, downstream optics may include path length compensation optics 152. Path length compensation optics 152 may include any suitable one or more optical elements to reflect, deflect, or otherwise influence the output beams 112A-112D in order to provide equal total path lengths (e.g., from the radiation source 14 to the skin 40).

Figure 16:
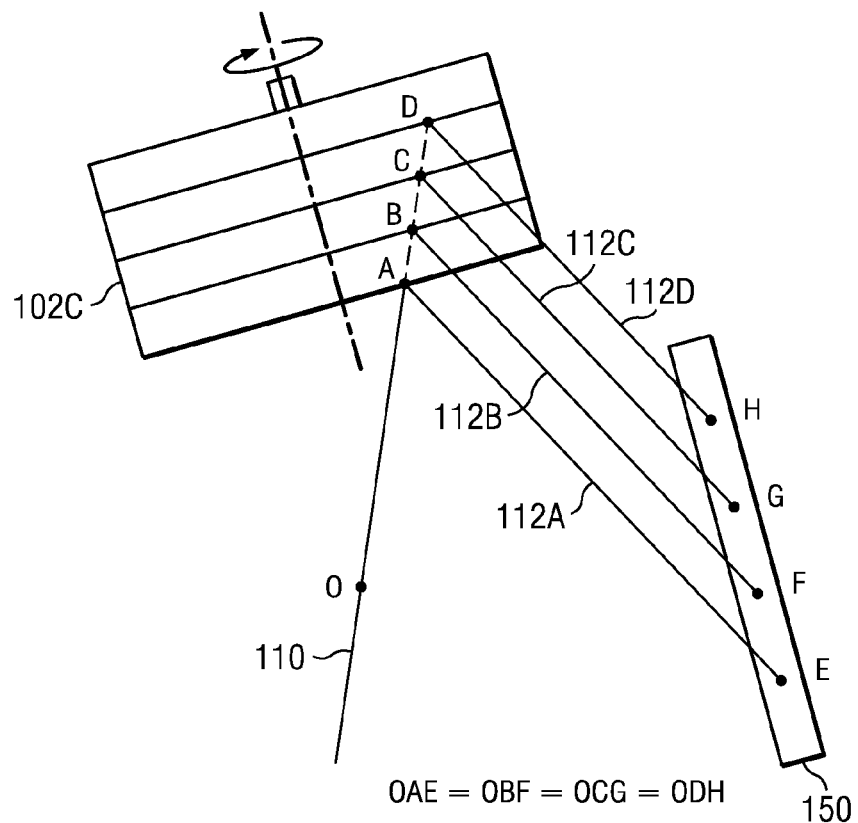
FIG. 16 illustrate example downstream optics for correcting the path length of different scanned beams in a system including a stair-stepped rotating scanning element, according to an certain embodiments.

FIG. 16 illustrates an example of path length compensation optics 152, according to certain embodiments. In this example, path length compensation optics 152 includes a single deflecting element (e.g., mirror or lens) arranged to deflect output beams 112A-112D such that the path length of each beam from the radiation source 14 to optics 152 is equal. Thus, in this example, path length OAE=path length OBF=path length OCG=path length ODH. Optics 152 may be arranged parallel to the skin 40 such that the total path length of each beam is equal. For example, optics 152 may deflect each output beam 112A-112D perpendicular to the page and toward the plane of the skin 40 arranged generally parallel to the page.

In other embodiments, path length compensation optics 152 may be arranged non-parallel to the skin 40, but still provide that the total path length of each beam is equal. For example, optics 152 may be arranged such that a portion of the path length differences from point O to points A-D on the different reflection surfaces $106C_1$-$106C_4$ is compensated for by the different respective distances between points A-D on rotating element 30 and points E-H on optics 152, while the remainder of the path length differences is compensated for by the different respective distances between points E-H on optics 152 and the skin 40.

Figure 18A:
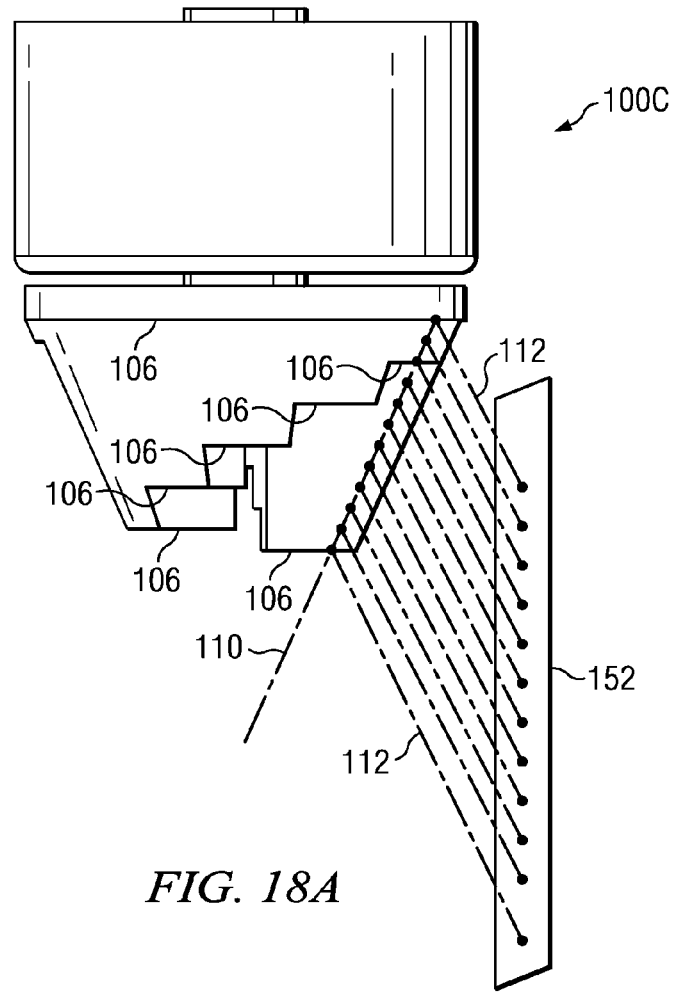
FIGS. 18A-18B illustrate example path length correcting optics for use with the stair-stepped rotating scanning element of FIGS. 17A-17B, according to an example embodiment.
Figure 18B:
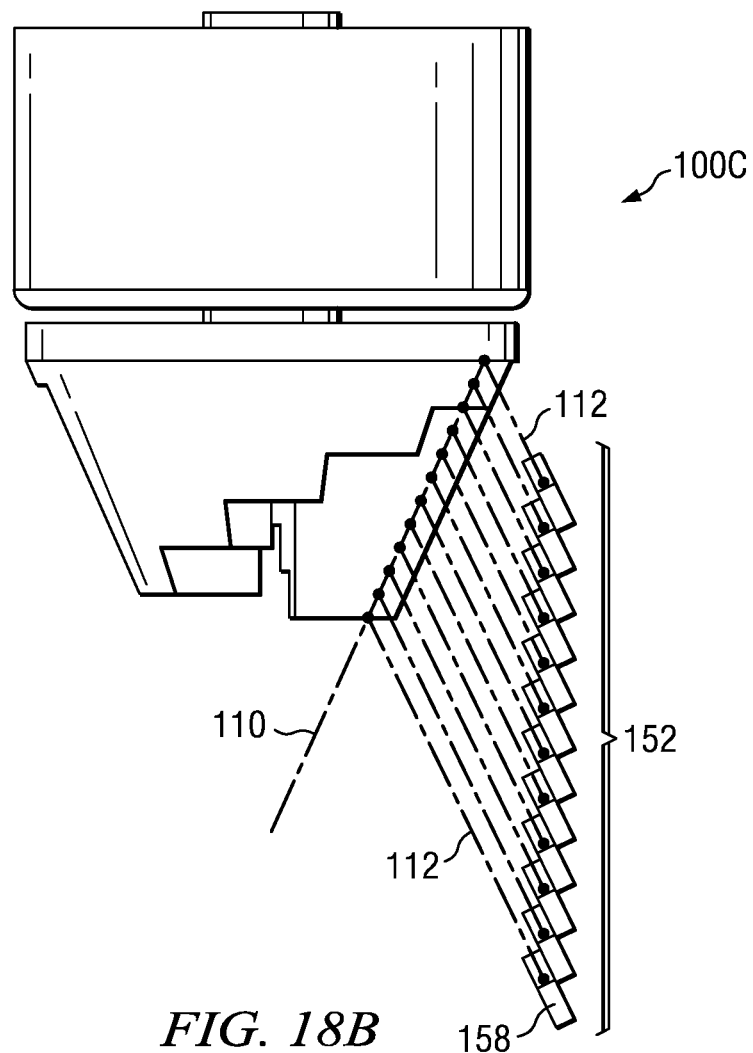

In other embodiments, e.g., as shown in FIG. 18B discussed below, path length compensation optics 152 may include multiple optical elements, each corresponding to an individual output beam 112.

As with other downstream optics discussed above, path length compensation optics 152 (a) may or may not influence the intensity profile of individual output beams 112 along one or more axis, and (b) may or may not influence the propagation of output beams 112 relative to each other along one or more axis.

Example Stair-Stepped Beam Scanning Element

Figure 17A:
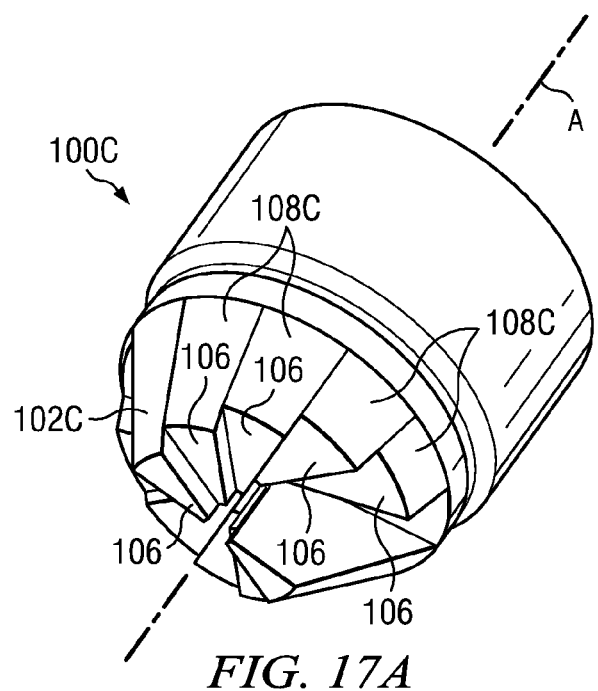
FIGS. 17A-17B illustrate three-dimensional and end views, respectively, of an example stair-stepped rotating scanning element, according to an example embodiment.
Figure 17B:
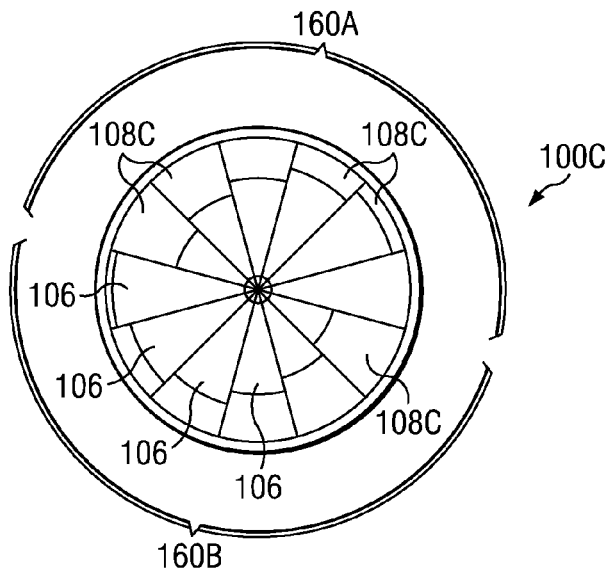

FIGS. 17 and 18 illustrate example embodiments of a rotating stair-stepped beam scanning element 100C. In particular, FIG. 17A illustrates an example three-dimensional view, FIG. 17B illustrates an example end view of element 100C viewed along the axis of rotation A, FIG. 18A illustrates an example side view of stair-stepped scanning element 100C, and including a first example path length compensation optics 152 (single element), and FIG. 18B illustrates another example side view of stair-stepped scanning element 100C, and including a second example path length compensation optics 152 (multiple elements).

As shown in FIGS. 17A and 17B, the illustrated example includes 12 reflection sectors 104C, each defining a planar reflection surface 106C that is perpendicular to the axis of rotation A of rotating element 100C, the planar reflection surfaces 106C being parallel to each other and offset from each other in the direction of the axis of rotation A. Further, each reflection sector 104C also defines a tapered side surface 108C such that the reflection sector 104C together define a generally conical stepped shape.

As shown in FIG. 18A, the 12 planar reflection surfaces 106C of rotating element 100C may reflect a stationary input beam 110 to generate a time-sequential array of 12 output beams 112 that are translationally offset from (and parallel to) each other). As discussed above, path length compensation optics 152 may be provided to compensate for the different path lengths of the input beam 110 incident on the different reflection surfaces 106C of rotating element 100C, in order to provide a uniform total path length (e.g., from radiation source 14 to the skin 40) for each output beam 112. In this embodiment, path length compensation optics 152 comprises a single optical element configured to deflect the time-sequential array of output beams 112 toward the skin 40 (or toward further downstream optics before delivery to the skin 40).

FIG. 18B illustrates an alternative embodiment of FIG. 18A, wherein path length compensation optics 152 comprises an array of optical elements 158, each arranged for deflecting one of the output beams 112 toward the skin 40 (or toward further downstream optics before delivery to the skin 40).

Reflection Sector Configuration

Returning to FIGS. 17A and 17B, the illustrated embodiment includes 12 reflection sectors $104C_1$-$104C_{12}$ arranged around the circumference in the order $104C_1$, $104C_2$, $104C_3$, . . . $104C_{12}$. The 12 reflection sectors define two sets, reflection sectors $104C_1$-$104C_6$ and reflection sectors $104C_7$-$104C_{12}$, each set defining a group of six consecutive ascending steps, and each set extending 180 degrees around body 102C.

In other embodiments, reflection sectors 104C may define one set of consecutively adjacent ascending steps around the circumference, or any multiple number of sets of consecutively adjacent ascending steps around the circumference.

Alternatively, reflection sectors 104C may be arranged in sets that are not consecutively adjacent. For example, two sets of reflection sectors $104C_1$-$104C_6$ and $104C_7$-$104C_{12}$, each forming a series of (consecutive or non-consecutive) ascending steps, may be arranged in a partial or fully alternating manner around the circumference (e.g., [$104C_1$, $104C_7$, $104C_2$, $104C_8$, . . . $104C_6$, $104C_{12}$], or [$104C_1$, $104C_2$, $104C_3$, $104C_7$, $104C_7$, $104C_9$, $104C_4$, $104C_5$, $104C_6$, $104C_{10}$, $104C_{11}$, $104C_{12}$]).

As another example, three sets of reflection sectors $104C_1$-$104C_4$, $104C_5$-$104C_8$, and $104C_9$-$104C_{12}$, each forming a series of (consecutive or non-consecutive) ascending steps, may be arranged in a partial or fully alternating manner around the circumference (e.g., [$104C_1$, $104C_5$, $104C_9$, $104C_2$, $104C_6$, $104C_{10}$, $104C_3$, $104C_7$, $104C_{11}$, $104C_4$, $104C_8$, $104C_{12}$], or [$104C_1$, $104C_2$, $104C_5$, $104C_6$, $104C_9$, $104C_{10}$, $104C_3$, $104C_4$, $104C_7$, $104C_8$, $104C_{11}$, $104C_{12}$]).

Alternatively, reflection sectors 104C may define sets that are not arranged in a consecutively adjacent or alternating order. For example, sets of reflection sectors 104C may be arranged randomly around the circumference of body 102C. For example, three sets of reflection sectors $104C_1$-$104C_4$, $104C_5$-$104C_8$, and $104C_9$-$104C_{12}$, each forming a series of consecutive ascending steps 1-4, may be arranged in an alternating random manner around the circumference (e.g., [$104C_1$, $104C_5$, $104C_{10}$, $104C_4$, $104C_8$, $104C_{12}$, $104C_3$, $104C_6$, $104C_{11}$, $104C_2$, $104C_7$, $104C_9$ (alternating between the three sets)]), or a fully random manner (e.g., [$104C_7$, $104C_2$, $104C_8$, $104C_5$, $104C_{12}$, $104C_{10}$, $104C_3$, $104C_6$, $104C_1$, $104C_{11}$, $104C_4$, $104C_9$]).

As discussed above, reflection surfaces 106C may be arranged parallel to each other, or non-parallel to each other. In the example embodiment shown in FIGS. 17A-17B, planar reflection surfaces 106C are all parallel to each other. Embodiments in which planar reflection surfaces 106C are all parallel to each other may be configured for either single-scan-direction, single-row scanning or single-scan-direction, multi-row scanning, which terms are defined below with reference to FIGS. 23A-24B. Embodiments in which at least some planar reflection surfaces 106C are not parallel to each other may be configured for multi-scan-direction scanning, which is defined below with reference to FIGS. 25A-25B.

FIGS. 19 and 20 illustrate example optical systems 15 that include a stair-stepped rotating scanning element 100C, according to certain embodiments. As shown, each of the example optical systems 15 of FIGS. 19 and 20 includes (a) fast axis optics 64, (b) slow axis optics 66, (c) stair-stepped scanning element 100C, and (d) downstream optics 60B, specifically a mirror 150. Each optical system 15 receives a beam 108 generated by a radiation source 14, treats the generated beam 108 to provide an input beam 110 to stair-stepped scanning element 100C, which converts the input beam 110 into a time-sequential series of output beams 112, and further treats the output beams 112 to provide delivered beams 114 to the skin 40 to generate a pattern of treatment spots 70. The beam extending from radiation source 14 to the skin 40 during any particular treatment spot formation, which includes generated beam 108, input beam 110, an output beam 112, and the corresponding delivered beam 114, is referred to herein as beam 80.

As discussed above, fast axis optics 64 include one or more optical elements configured to primarily affect the fast axis profile of the beam, while slow axis optics 66 include one or more optical elements configured to primarily affect the slow axis profile of the beam.

In certain embodiments, radiation source 14 may generate an axially-asymmetric beam 108 having different beam profiles in the fast axis and slow axis. For example, radiation source 14 may comprise a laser diode. In other embodiments, radiation source 14 may generate axially-symmetric beam, e.g., a fiber laser or other axially-symmetric radiation source.

Each of the example embodiments shown in FIGS. 19 and 20 includes a single fast axis optical element 64, and a single slow axis optical element 66 distinct from the fast axis optical element 64. In other embodiments, device 10 includes multiple fast axis optical elements 64 and a single slow axis optical element 66 distinct from the fast axis optical elements 64. In other embodiments, device 10 includes a single fast axis optical element 64 and multiple slow axis optical elements 28 distinct from the fast axis optical element 64.

In still other embodiments, one or more fast axis optical element 64 and slow axis optical element 66 may be integrated, i.e., a single optical element (or multiple optical elements) may substantially act on both the fast axis and slow axis intensity profiles. Such elements may be referred to as multi-axis optical elements. Such embodiments may include one or more multi-axis optical elements in combination with zero, one, or more fast axis optical elements 64, and zero, one, or more slow axis optical elements 28. Thus, as an example only, device 10 may include a single fast axis optical elements 64, a single slow axis optical elements 28, and a single multi-axis optical element.

In some embodiments, fast axis optics 64 (either a single element or multiple elements, depending on the embodiment) may be configured to affect the fast axis intensity profile of beam 80 (i.e., input beam 110 and/or output beam 112) without substantially affecting the slow axis intensity profile, and slow axis optics 66 (either a single element or multiple elements, depending on the embodiment) may be configured to affect the slow axis intensity profile of the beam 80 without substantially affecting the fast axis intensity profile. Or, fast axis optics 64 (either a single element or multiple elements, depending on the embodiment) may be configured to affect the fast axis intensity profile of the beam 80 to a significantly greater extent or degree than the slow axis intensity profile, and slow axis optics 66 (either a single element or multiple elements, depending on the embodiment) may be configured to affect the slow axis intensity profile of the beam 80 to a significantly greater extent or degree than the fast axis intensity profile.

In other embodiments, one of fast axis optics 64 (either a single element or multiple elements, depending on the embodiment) or slow axis optics 66 (either a single element or multiple elements, depending on the embodiment) substantially affects only the fast axis intensity profile or the slow axis intensity profile, while the other of fast axis optics 64 and slow axis optics 66 substantially affects both the fast axis intensity profile and the slow axis intensity profile. Or, one of fast axis optics 64 (either a single element or multiple elements, depending on the embodiment) or slow axis optics 66 (either a single element or multiple elements, depending on the embodiment) affects one of the fast and slow axis intensity profiles of beam 80 to a significantly greater extent or degree than the other of the fast and slow axis intensity profiles, while the other of fast axis optics 64 and slow axis optics 66 affects both the fast axis intensity profile and the slow axis intensity profile to a substantially similar extent or degree.

In other embodiments, each of the fast axis optics 64 (either a single element or multiple elements, depending on the embodiment) or slow axis optics 66 (either a single element or multiple elements, depending on the embodiment) are configured to significantly affect both the fast axis intensity profile and the slow axis intensity profile of the beam 80.

Returning to FIGS. 19 and 20, each of these example embodiments includes (a) a scanning system 48 including a stair-stepped rotating scanning element 100C, and (b) downstream optics 60B, specifically a mirror 150, which are both distinct from the fast axis optical element 64 and slow axis optical element 66. In this embodiment, rotating scanning element 100C utilizes planar reflection surfaces 106C such that rotating scanning element 100C does not significantly affect the intensity profile of the beam 80 in any axis. In other embodiments, reflection surfaces 106C of rotating scanning element 100C may be configured to significantly affect the intensity profile in one or more axis (e.g., the fast axis intensity profile and/or the slow axis intensity profile).

In other embodiments, stair-stepped rotating scanning element 100C may be integrated with fast axis optics 64 and/or slow axis optics 66. For example, stair-stepped rotating scanning element 100C may act as a fast axis optical element 64 (as the only fast axis optical element, or in combination with one or more other fast axis optical elements 64), with slow axis optics 66 being provided separately. Alternatively, stair-stepped rotating scanning element 100C may act as a slow axis optical element 66 (as the only slow axis optical element, or in combination with one or more other slow axis optical elements 66), with fast axis optics 64 being provided separately. Alternatively, stair-stepped rotating scanning element 100C may act as both a fast axis optical element 64 and a slow axis optical element 66 (as a single, combined scanning element/fast axis optical element/slow axis optical element; or in combination with one or more other fast axis optical elements 64 and/or one or more other slow axis optical elements 66).

Fast axis optical element 64, slow axis optical element 66, and stair-stepped rotating scanning element 100C may be arranged in any order along the path of the beam 80. For example, fast axis optical element 64 and slow axis optical element 66 may be arranged upstream of stair-stepped rotating scanning element 100C (as shown in FIGS. 19 and 20), or downstream of stair-stepped rotating scanning element 100C, or stair-stepped rotating scanning element 100C may be arranged between optical elements 64 and 66. Further, optical elements 64 and 66 may be arranged in any order with respect to each other.

In addition to deflecting an input beam 110 to generate an array of offset output beams 112 (e.g., offset along a scan direction), each sector 104 may further influence the input beam 110 in one or more axis. For example, each sector 104 may further influence the input beam 110 by having curvature in its reflection surface that provides optical power, similar to the examples provided above for the transmissive disk or cup shaped scanning elements. For example, in addition to the deflection, each sector 104 may further act as a slow axis optic and/or a fast axis optic. In some embodiments, each sector 104 may deflect the input beam 110 in the slow axis direction, and also influence the convergence/divergence of the input beam 110. For example, element 100 may receive an input beam 110 that is diverging in the slow axis direction, and each sector 104 may both (a) deflect the input beam 110 by a particular degree, and (b) convert the diverging beam into a collimated or converging beam, e.g., such that individual collimated, focused, or pseudo-focused output beams 112 can be delivered to the target area, for generating treatment spots.

Example Configurations of Rotating Element 100 and Corresponding Treatment Spot Arrays As discussed above with respect to FIGS. 6A-6C, beam scanning element 100 may be configured to provide a wide variety of treatment spot patterns on the skin 40, and treatment spots may be delivered in any desired sequential order, based on the particular configuration and arrangement of sectors $104_1$ to $104_n$.

Figure 21A:
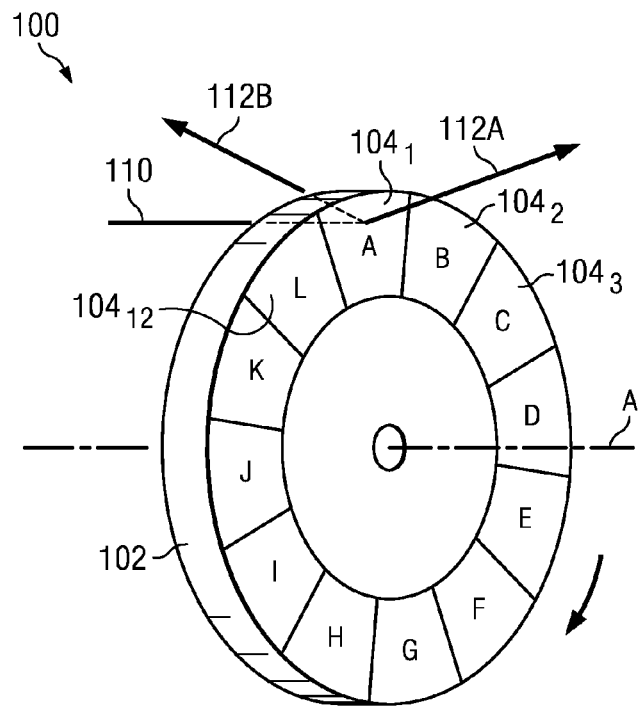
FIG. 21A-21C illustrates a first example arrangement of sectors of a rotating beam scanning element (FIG. 21A), and resulting patterns of treatment spots created by such arrangement (FIGS. 21B and 21C), according to example embodiments.

FIG. 21A illustrates an example beam scanning element 100, which may be configured as a disc-shaped scanning element (e.g., disc-shaped transmissive element 100A), a cup-shaped scanning element (e.g., cup-shaped transmissive element 100B), a stair-stepped scanning element (e.g., stair-stepped reflective element 100C), or any other type of rotating scanning element. Element 100 has a body 102 configured to rotate about an axis A. Body 102 includes a plurality of sectors 104 generally arranged around the circumference or periphery of the body 12 and configured to deflect an input beam 110 into an array of output beams 112 offset from each other. Depending on the particular embodiment, each sector 104 may transmit but deflect the input beam 110, as indicated by example arrow 112A (e.g., disc-shaped transmissive element 100A or cup-shaped transmissive element 100B discussed below) or reflect the input beam, as indicated by example arrow 112B (e.g., stair-stepped reflective element 100C discussed below).

Sectors $104_1$ to $104_n$ may be configured such that the array of treatment spots may be delivered in any desired sequential order (e.g., in terms of the amount of deflection in a particular direction) and/or to produce one, two, or more rows during each scan of element 100, as discussed below.

Sequential Order of Treatment Spots

Sectors $104_1$ to $104_n$ may be configured such that the array of treatment spots 70 may be delivered in any desired sequential order, e.g., with respect to one or more particular directions. For example, in the example shown in FIG. 21A, sectors $104_1$ to $104_n$ are labeled A through L, with sector A (sector $104_1$) producing the greatest offset (in one or more directions), sector B (sector $104_2$) producing the next greatest offset, sector C (sector $104_3$) producing the next greatest offset, and so on. As shown, sectors A-L are arranged in sequential order around the perimeter of element 100.

Figure 21B:
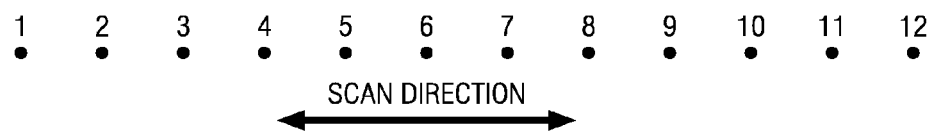

Thus, FIG. 21B illustrates the sequential order of treatment spots delivered by one full rotation of element 100 (i.e., one scan of input beam 110), assuming device 10 is held stationary with respect to the target area (e.g., device 10 operating in a stamping mode, as discussed above). As shown, the treatment spots are labeled 1 through 12, indicating the sequential order in which each treatment spot is produced, beginning with treatment spot 1 produced by sector A (sector $104_1$, followed by treatment spot 2 produced by sector B (sector $104_2$), and so on.

Figure 21C:
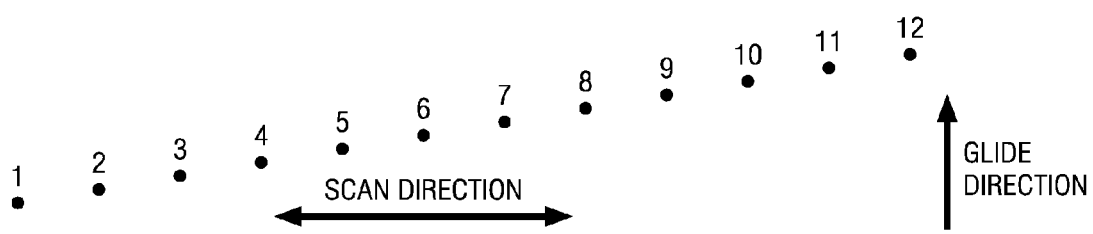

Further, FIG. 21C illustrates the sequential order of treatment spots delivered by one full rotation of element 100 (i.e., one scan of input beam 110), assuming device 10 is manually glided over the target area in a direction substantially perpendicular to the scan direction (e.g., device 10 operating in a gliding mode, as discussed above). As shown, the treatment spots are again labeled 1 through 12, indicating the sequential order in which each treatment spot is produced, beginning with treatment spot 1 produced by sector A (sector $104_1$), followed by treatment spot 2 produced by sector B (sector $104_2$), and so on. This configuration of element 100 produces a generally linear row of treatment spots aligned diagonally with respect to the scan direction due to the movement of the device in the glide direction.

Figure 22A:
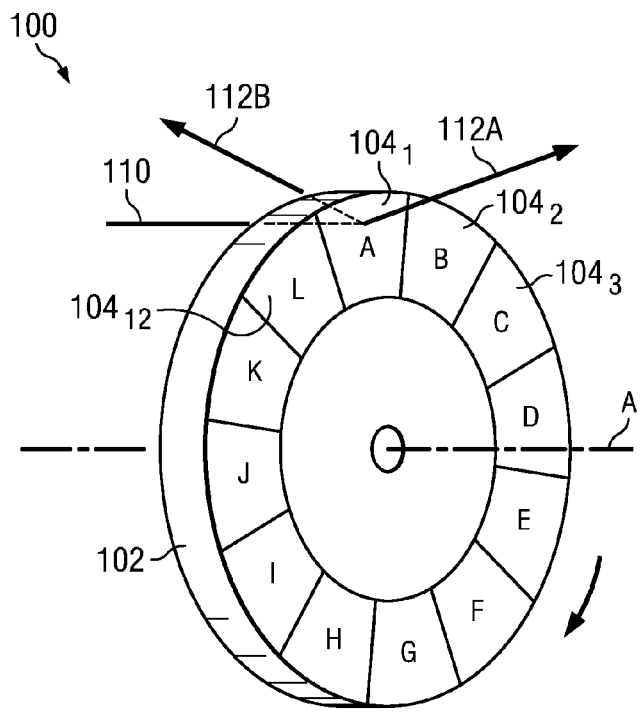
FIG. 22A-22C illustrates a second example arrangement of sectors of a rotating beam scanning element (FIG. 22A), and resulting patterns of treatment spots created by such arrangement (FIGS. 22B and 22C), according to example embodiments.

Element 100 may be configured to generate treatment spots in any other desired sequential order. For example, FIG. 22A illustrates an example element 100' that, like example element 100 discussed above, includes sectors $104_1$ to $104_n$ numbered A through K, with sector A (sector $104_1$) producing the greatest offset (in one or more directions), sector B (sector $104_2$) producing the next greatest offset, sector C (sector $104_3$) producing the next greatest offset, and so on. However, unlike element 100 discussed above, sectors A-L of element 100' are not arranged sequentially around the perimeter of element 100. Rather, sectors A-L are arranged in a specific pseudo-random order around the perimeter of element 100: A, C, E, I, G, B, D, F, K, J, H, L.

Figure 22B:

FIG. 22B illustrates the sequential order of treatment spots delivered by one full rotation of element 100' (i.e., one scan of input beam 110), assuming device 10 is held stationary with respect to the target area (e.g., device 10 operating in a stamping mode). As shown, the treatment spots are labeled 1 through 12, indicating the sequential order in which each treatment spot is produced, beginning with treatment spot 1 produced by sector A (sector $104_1$), followed by treatment spot 2 produced by sector C (sector $104_2$), followed by treatment spot 3 produced by sector E (sector $104_3$), and so on.

Figure 22C:
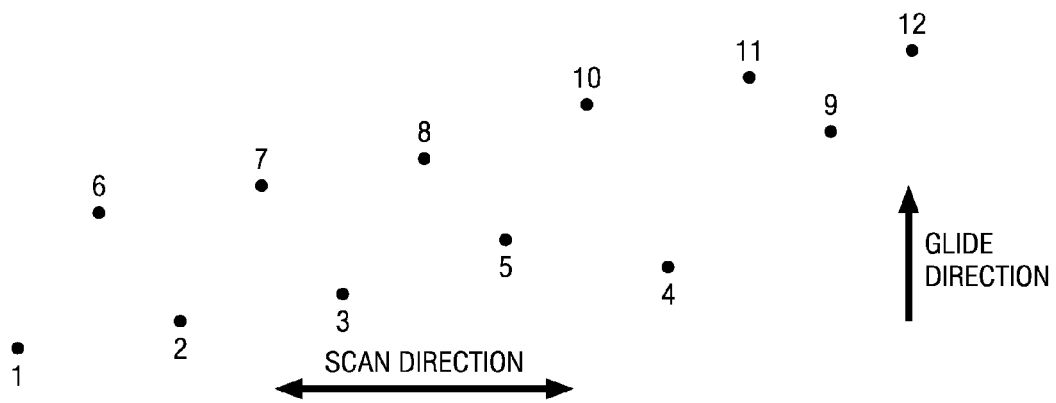

Further, FIG. 22C illustrates the sequential order of treatment spots delivered by one full rotation of element 100' (i.e., one scan of input beam 110), assuming device 10 is glided over the target area in a direction substantially perpendicular to the scan direction (e.g., device 10 operating in a gliding mode). As shown, the treatment spots are again labeled 1 through 15, indicating the sequential order in which each treatment spot is produced, beginning with treatment spot 1 produced by sector A (sector $104_1$), followed by treatment spot 2 produced by sector C (sector $104_2$), followed by treatment spot 3 produced by sector E (sector $104_3$), and so on. Thus, each scan of element 100' produces a non-linear, pseudo-random pattern of treatment spots. In some embodiments or applications, repeating a non-linear scan pattern (e.g., the pattern shown in FIG. 22C) in a gliding mode of device 10 may provide a more uniform or otherwise preferred array (e.g., generates less pain or less thermal interaction between the micro-thermal zones (MTZs) underlying the treatment spots than that produced by a linear scan pattern (e.g., the pattern shown in FIG. 21C). In other embodiments or applications, repeating a linear scan pattern in a gliding mode may provide a more uniform or otherwise preferred array of treatment spots than that produced by a non-linear scan pattern.

It should be understood that the configurations and resulting treatment spot patterns shown in FIGS. 21 and 26 are examples only, and that beam scanning element 100 may be configured to generate treatment spots in any other desired sequential order. Further, element 100 may have any other number (more or less than 12) of sectors for generating any other number (more or less than 12) of treatment spots per rotation of element 100. Further, element 100 may be produced in any suitable manner. For example, element 100 may be formed as a single, integral element. As another example, the individual sectors 104 may be formed separately and then secured to each other to form element 100. As a further example, it can be understood by one of ordinary skill in the filed that element 100 may be produced by many well-known fabrication methods including injection molding, grinding, machining, electroforming, and further including with or without secondary processes such as polishing, platings, or coatings.

Other Example Treatment Spot Patterns Generated by Element 100

In addition to the sequential order of treatment spot generated by beam scanning element 100, the number of rows of treatment spots 70 generated by each rotation of element 100 (i.e., each scan of input beam 110) may vary based on the configuration of element 100. For example, element 100 may be configured to provide "single-scan-direction, single-row scanning," "single-scan-direction, multi-row scanning," or "multi-scan-direction, multi-row scanning," as discussed below.

1. Single-Scan-Direction, Single-Row Scanning

Figure 23A:
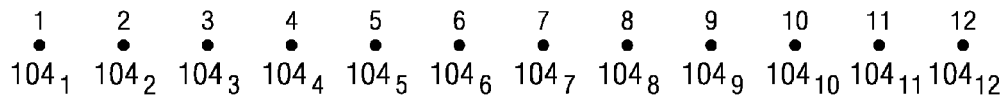
FIGS. 23A-23B, 24A-24B, and 25A-25B illustrates example patterns of treatment spots created by various configurations of a rotating beam scanning element, according to example embodiments.
Figure 23B:
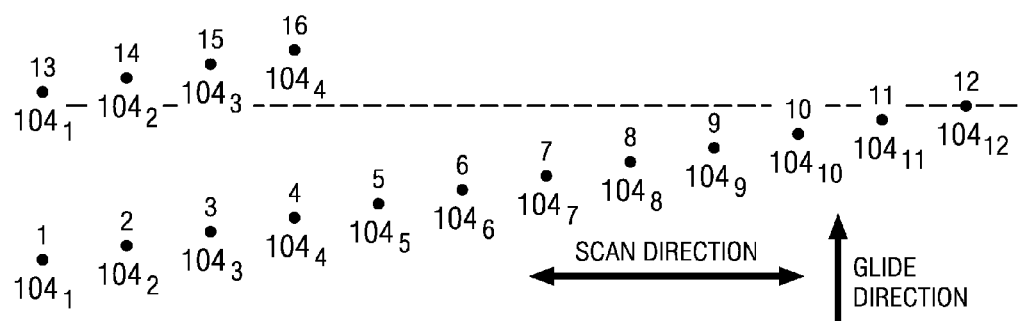

FIGS. 23A-23B illustrate example radiation patterns generated by a single-scan-direction, single-row scanning element 100 that includes 12 sectors $104_1$-$104_{12}$ arranged in the order $104_1$, $104_2$, $104_3$ . . . $104_{12}$. The sectors $104_1$-$104_{12}$ are configured such that the treatment spots are generated in a single row, in order along the direction of row (i.e., each new treatment spot being adjacent to the previous treatment spot). For stair-stepped scanning element 100C, single-scan-direction, single-row scanning can be provided where the reflective sectors 104C are arranged as a single series of consecutive ascending steps around the perimeter of element 100C.

FIG. 23A illustrates the treatment spot pattern formed on the skin 40 during one full rotation of element 100 (i.e., one scan of input beam 110) if the device 10 is held stationary relative to the skin 40, as well as indicating the sequential order of the generated treatment spots (1-12) and the sector $104_1$-$104_{12}$ that produced each treatment spot. FIG. 23B illustrates the treatment spot pattern formed on the skin 40 if the device 10 is moved at a relatively constant speed across the skin 40 during the scanning and radiation delivery process in a glide direction generally perpendicular to the scan direction. FIG. 23B shows a first scan, indicated as "Scan 1", created by one rotation of element 100, and the first four spots of a second scan, indicated as "Scan 2," as well as indicating the sequential order of the generated treatment spots (1-16) and the sector $104_1$-$104_{12}$ that produced each treatment spot.

As shown, a full scan (i.e., a full rotation of element 100) generates one row of treatment spots. Thus, such patterns are referred to herein as "single-scan-direction, single-row scanning patterns." A two-dimensional array of treatment spots can be produced in the skin 40 by repeating (continuously or non-continuously) the single-scan-direction, single-row scanning pattern while device 10 is physically moved across the skin 40.

2. Single-Scan-Direction, Multi-Row Scanning

Figure 24A:
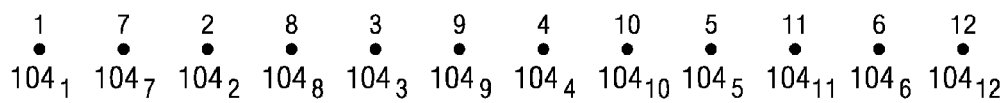
Figure 24B:
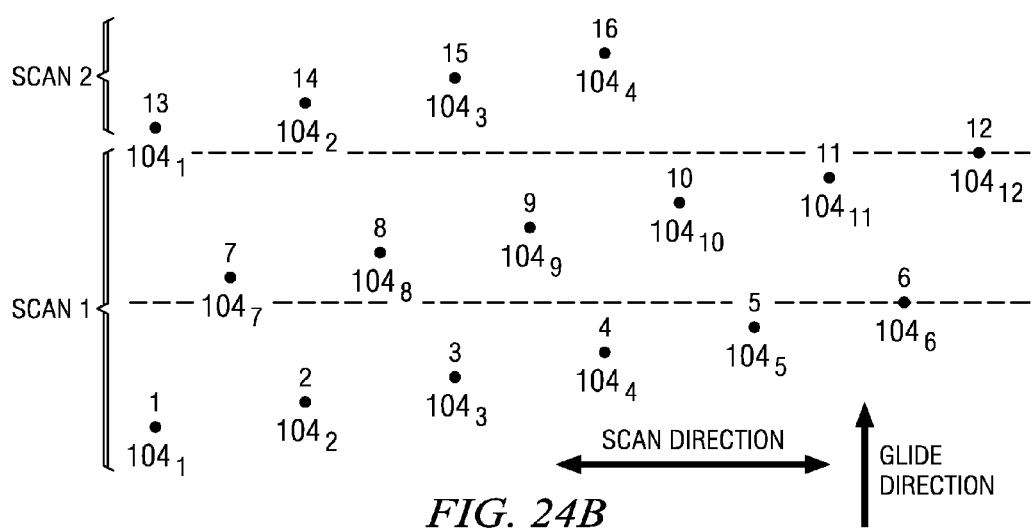

FIGS. 24A-24B illustrate example radiation patterns generated by a single-scan-direction, multi-row scanning element 100 that includes 12 sectors $104_1$-$104_{12}$ arranged in the order $104_1$, $104_2$, $104_3$ . . . $104_{12}$. The sectors $104_1$-$104_{12}$ are configured such that the treatment spots are generated in a single row, but out of order along the direction of the row. FIG. 24A illustrates the treatment spot pattern formed on the skin 40 during one rotation of element 100 if the device 10 is held stationary relative to the skin 40, as well as the sequential order of the generated treatment spots (1-12) and the sector $104_1$-$104_{12}$ that produced each treatment spot.

FIG. 24B illustrates the treatment spot pattern formed on the skin 40 if the device 10 is moved at a relatively constant speed across the skin 40 during the scanning and radiation delivery process in a glide direction generally perpendicular to the scan direction. As shown, a full scan (i.e., a full rotation of element 100) essentially generates two rows of treatment spots, one corresponding to sectors $104_1$-$104_6$ and one corresponding to sectors $104_7$-$104_{12}$.

Thus, FIG. 24B shows a first scan, indicated as "Scan 1", created by one rotation of element 100, and the first three spots of a second scan, indicated as "Scan 2," as well as indicating the sequential order of the generated treatment spots (1-15) and the sector $104_1$-$104_{12}$ that produced each treatment spot. The first scan includes a first row created by sequentially scanning sectors $104_1$-$104_6$, followed by a second row created by sequentially scanning sectors $104_7$-$104_{12}$. In this manner, a multi-row scanning pattern can be created using a single-scan-direction scanner (e.g., a single-scan-direction scanning element 100). Such patterns are referred to herein as "single-scan-direction, multi-row scanning patterns."

Single-scan-direction, multi-row scanning patterns have any other number of rows (i.e., more than two) can be similarly created. For example, an element 100 may include 12 sectors $104_1$-$104_{12}$ configured such that sectors $104_1$-$104_4$ generate a first row, sectors $104_5$-$104_8$ generate a second row, and sectors $104_9$-$104_{12}$ generate a third row. Thus, the sectors may be arranged around element 100 in the order: $104_1$, $104_5$, $104_9$, $104_2$, $104_6$, $104_{10}$, $104_3$, $104_7$, $104_{11}$, $104_4$, $104_8$, $104_{12}$.

Further, a larger two-dimensional array of treatment spots can be produced in the skin 40 by repeating (continuously or non-continuously) such single-scan-direction, multi-row scanning patterns while device 10 is physically moved across the skin 40.

For stair-stepped scanning element 100C, single-scan-direction, multi-row scanning can be provided by arranging the reflective sectors 104C in multiple groups of consecutively ascending steps around the perimeter of element 100C, with each group of consecutively ascending steps generating a row of treatment spots during a gliding operation. For example, to produce the example pattern shown in FIG. 24B a stair-stepped scanning element 100C having 12 reflection sectors arranged in order $104_1$-$104_{12}$ around the perimeter of element 100C may consist of two groups of consecutively ascending steps: sectors $104_1$-$104_6$ define a first set of ascending steps (which generate the first row of spots), and sectors $104_7$-$104_{12}$ define a second set of ascending steps (which generate the second row of spots). The embodiment of stair-stepped scanning element 100C shown in FIGS. 17A-17B illustrates an example of such a configuration.

In other embodiments, the single-scan-direction rotating element may be otherwise configured to deliver beams in any other sequential order along the scan direction, e.g., based on the number and arrangement of sets of sectors 104. Further, any of such single-scan-direction radiation patterns may be repeated (continuously or non-continuously) while device 10 is moved across the skin 40 in order to form a larger two-dimensional array of treatment spots.

3. Multi-Scan-Direction Scanning

Figure 29A:
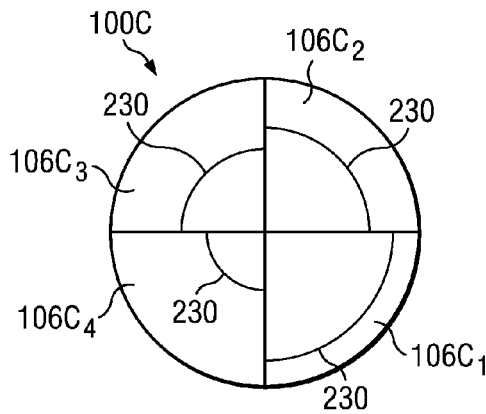
FIGS. 29A-29F illustrate the same various radiation modes with respect to an example stair-stepped type rotating element having four deflection sectors, according to certain embodiments.
Figure 29B:
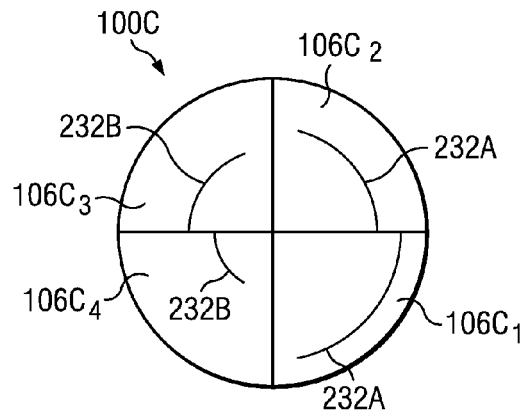

In other embodiments, a multi-scan-direction rotating element 100 is used. A multi-scan-direction rotating element 100 scans an input beam 110 in multiple directions, such that treatment spots generated by a single scan (i.e., a single rotation of the rotating element 100) are not aligned in a single linear row, even when the device 10 is held stationary during the scan. For example, a multi-scan-direction rotating element 100 may be configured to produce multiple offset rows of treatment spots in a single rotation of the scanning element. Such resulting patterns are referred to herein as "multi-scan-direction, multi-row scanning patterns." As opposed to a single-scan-direction element 100 configured to form multiple rows in a single scan by moving the device 10 across the skin 40 during the scan, a multi-scan-direction rotating element 100 can form multiple rows in a single scan as a result of the beam scanning itself, regardless of whether the device 10 is moved across the skin 40 during the scan. For example, a single scan of multi-scan-direction rotating element 100 may form multiple rows of treatment spots, in which each row is scanned in a primary scan direction, and the rows are offset from each other in a secondary scan direction, which may be orthogonal to the primary scan direction (e.g., as shown in FIGS. 29A and 29B discussed below).

In some embodiments, multi-scan-direction rotating elements 100 include multiple subsets of sectors 104, each configured to produce a different row of treatment spots, regardless of whether the device 10 is moved across the skin 40 during the scan. For example, element 100 for generating three rows of treatment spots (while device 10 remains stationary) may include a first set of sectors $104_1$-$104_n$ configured to generate a first row of treatment spots, a second set of sectors $104_{n+1}$-$104_{2n}$ configured to generate a second row of treatment spots, and a third set of sectors $104_{2n+1}$-$104_{3n}$ configured to generate a third row of treatment spots.

In embodiments in which sectors 104 are lenslets (e.g., element 100A or 100B), the lenslets may be shaped or aligned to deflect input beam 110 to form rows of output beams 112 offset from each other in a secondary scan direction. Embodiments of stair-stepped element 100C may include multiple sets of reflection sectors 104, each set having reflection surfaces 106 parallel with each other but angularly offset from the reflection surfaces 106 of the other set(s) of reflection sectors 104. Thus, each set of sectors 104 may generate a separate row of treatment spots offset from each other. An example is discussed below with respect to FIGS. 29A-29B. Sectors 104 of such a multi-scan-direction rotating element 100 may be configured in any suitable number of sets to produce any suitable number of rows of treatment spots during a single scan.

Figure 25A:
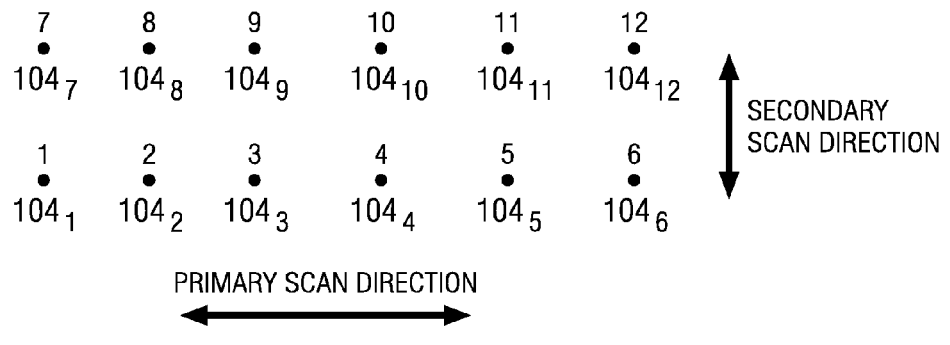
Figure 25B:
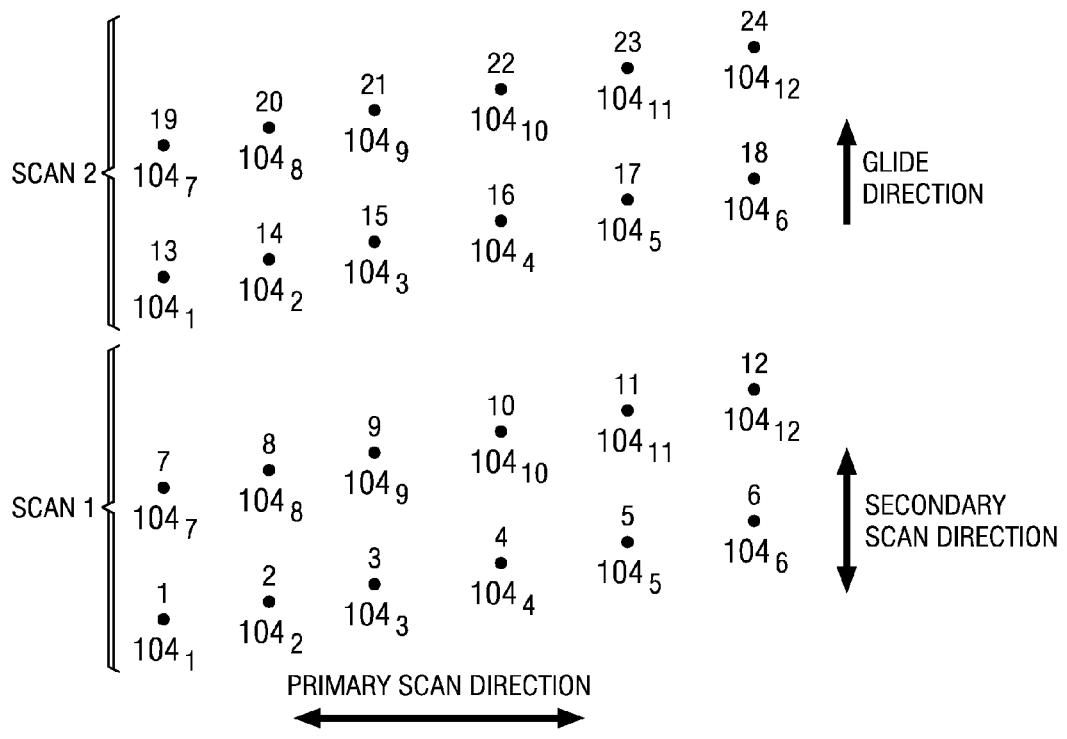

FIGS. 25A-25B illustrate example multi-scan-direction, multi-row scanning patterns generated using a multi-scan-direction scanning element 100. FIG. 25A illustrates the treatment spot pattern formed on the skin 40 during one rotation of the example multi-scan-direction scanning element 100 discussed above, where the device 10 is held stationary relative to the skin 40, as well as indicating the sequential order of the generated treatment spots (1-12) and the sector 104 ($104_1$-$104_{12}$) that produced each treatment spot.

FIG. 25B illustrates the treatment spot pattern formed by the example multi-scan-direction scanning element 100 if the device 10 is moved at a constant speed across the skin 40 during the scanning and radiation delivery process in a glide direction generally perpendicular to the scan direction. As shown, each full scan (i.e., a full rotation of element 100) essentially generates two rows of treatment spots, one corresponding to each of the two sets of sectors $104_1$-$104_6$ and $104_7$-$104_{12}$. Thus, FIG. 25B shows a full first scan, indicated as "Scan 1", created by one rotation of element 100, and a full second scan, indicated as "Scan 2," as well as indicating the sequential order of the generated treatment spots (1-24) and the sector 104 ($104_1$-$104_{12}$) that produced each treatment spot. Each of the two full scans includes a first row created by sequentially scanning sectors $104_1$-$104_6$, followed by a second row created by sequentially scanning sectors $104_7$-$104_{12}$.

Multi-scan-direction scanning element 100 may be configured in any suitable manner. For example, a stair-stepped scanning element (e.g., element 100C) may be configured for multi-scan-direction scanning. Such scanning element may be similar to the stair-stepped scanning element 100C shown in FIGS. 17A-17B, but wherein the two sets of sectors $104_1$-$104_6$ and $104_7$-$104_{12}$ are configured to generate two offset rows of treatment spots during a single scan (i.e., a single rotation of element 100), even when device 10 is held stationary relative to the skin 40. Like scanning element 100 shown in FIGS. 17A-17B, each set of sectors $104_1$-$104_6$ and $104_7$-$104_{12}$ of the example multi-scan-direction scanning element 100 defines a group of six consecutive ascending steps. However, unlike scanning element 100C of FIGS. 17A-17B in which all 12 reflection surfaces 106 are parallel to each other, for the multi-scan-direction scanning element 100 the reflection surfaces $106_1$-$106_6$ of sectors $104_1$-$104_6$ are angularly offset from (i.e., non-parallel to) reflection surfaces $106_7$-$106_{12}$ of sectors $104_7$-$104_{12}$. In other words, reflection surfaces $106_1$-$106_6$ of sectors $104_1$-$104_6$ are parallel to each other, and reflection surfaces $106_7$-$106_{12}$ of sectors $104_7$-$104_{12}$ are parallel to each other, but the two sets are angularly offset from each other. Thus, reflection surfaces $106_1$-$106_6$ generate a first row of six treatment spots, and reflection surfaces $106_7$-$106_{12}$ generate a second row of six treatment spots, offset from the first row.

In other embodiments, the multi-scan-direction rotating element may be otherwise configured to deliver beams in any other sequential order along the scan direction, e.g., based on the number and arrangement of sets of sectors 104, to form a desired two-dimensional array of treatment spots on the skin 40. Further, any of such multi-scan-direction radiation patterns may be repeated (continuously or non-continuously) while device 10 is moved across the skin 40 in order to form a larger two-dimensional array of treatment spots, e.g., as discussed above with reference to FIG. 25B.

"Constant Deflection" and "Shifting Deflection" Sectors

In addition to the various aspects of element 100 and sectors 104 discussed above, in some embodiments, individual sectors 104 may be configured to produce output beams 112 having a constant deflection (angular or translative, depending on the embodiment), or a variable or "shifting" deflection, as that sector 104 rotates through the input beam 110.

Each sector 104 (or least some of the sectors 104) of element 100 (e.g., element 100A, 100B, or 100C) may be a "constant angular deflection" sector, which is defined a sector that deflects the input beam 110 such that the angular deflection of the output beam 112 relative to the input beam 110 remains constant or substantially constant as that sector 104 rotates through the input beam 110. In other words, the angular direction of each output beam 112 remains constant or substantially constant relative to the input beam 110 (and relative to the structure of device 10) during the time that each corresponding sector 104 rotates through the input beam 110. Some embodiments of element 100 (e.g., embodiments of transmissive elements 110A and 100B, and certain embodiments of reflective stair-stepped element 100C) generate an array of constant angular deflection output beams 112 that propagate at constant angles that are different from each other. Other embodiments of element 100 (e.g., certain other embodiments of reflective stair-stepped element 100C) generate an array of constant angular deflection output beams 112 that are translationally offset from each other, but propagate in the same constant angular direction (i.e., the output beams 112 are parallel to each other).

Thus, with constant angular deflection sectors 104, if device 10 is held stationary relative to the user's skin, each output beam 112 generated by a respective sector 104 of element dwells at a (different) particular point on the skin 40. Thus, if device 10 is held stationary relative to the user's skin, the plurality of constant angular deflection sectors 104 provide a sequentially-delivered series of stationary or substantially stationary treatment spots 70 on the skin, each stationary or substantially stationary treatment spot 70 corresponding to one of the constant angular deflection sectors 104.

However, as discussed above, in at least some embodiments or operational modes, device 10 is designed to be glided across the surface of the skin during operation, in a manner similar to a shaver being glided across the skin. Thus, in a system with constant angular deflection sectors 104, each output beam 112 moves relative to the skin as device 10 glides across the skin, such that each treatment spot moves relative to the skin, resulting in elongation, "smearing," or "blurring" in the direction of the gliding. However, despite this smearing of individual treatment spots, sufficient thermal energy may be provided to the treatment spots on a delivered energy per volume basis to provide the desired affect in the skin 40, at least within a range of operating parameters. For example, the desired effect may be provided as long as the device 10 is not glided across the skin extremely rapidly. Further, some amount of smearing may actually be beneficial for achieving a desired level of delivered energy per volume of irradiated or affected tissue, as a function of selected design and/or operational parameters (e.g., spot size and/or shape, beam intensity, fluence, and/or intensity profile of the delivered output beams, pulse duration and/or frequency, rotational speed of rotating element 100, etc.). Thus, in certain embodiments, settings, or uses of device 10, "constant angular deflection" sectors may be used to achieve the desired treatment effects.

In some embodiments, smearing caused by gliding may be compensated for, either partially or entirely. For example, the sectors 104 may be configured to be (a) stationary or substantially stationary in the non-glide direction (for which there is no smearing) and (b) to move the beam in the glide direction (for which there is normally smearing) at the same rate or nearly the same rate as the gliding, thereby compensating or partially compensating for smearing. In some embodiments, a glide rate sensor may provide feedback to the user or the device to ensure that the gliding rate is within predefined ranges such that the smearing compensation is effective.

FIGS. 26A and 26B illustrate example treatment spot patterns generated by an element 100 having "constant angular deflection" sectors 104, in a stamping mode and gliding mode operation of device 10, respectively. In this example, it is assumed that each output beam 112 delivered to the skin has a circular cross-section.

FIG. 26A illustrates a row of three treatment spots 70 generated by an element 100 having "constant angular deflection" sectors 104, while device 10 is held stationary with respect to the skin (e.g., with device 10 being operated in a stamping mode). Each output beam 112 dwells over the skin in a stationary or substantially stationary manner as the corresponding constant angular deflection sector 104 rotates through the input beam 110, such that each resulting treatment spot has a circular shape corresponding to the circular cross-section of the respective output beam 112.

FIG. 26B illustrates a row of three treatment spots 70 generated by an element 100 having "constant angular deflection" sectors 104, while device 10 is moved across the surface of the skin (e.g., with device 10 being operated in a manual gliding mode). As shown, each treatment spot is elongated, or smeared, corresponding to the circular cross-section of each respective output beam 112 moving some distance X across the skin in the glide direction during the delivery of that output beam 112 to the skin. The ratio of length L to the width W of each treatment spot 70 is a function of various factors, e.g., the rate of glide of device 10 across the skin, the spot size and/or shape, beam pulse duration, etc. In some embodiments, one or more of such factors may be selected or adjusted in order to produce treatment spots of a predetermined shape or size (or within a predetermined range of shapes or sizes) to provide the desired effect in the tissue.

In other embodiments, each sector 104 (or least some of the sectors 104) may be a "shifting deflection" sector, which is defined as a sector that deflects the input beam 110 such that the deflection of the output beam 112 relative to the input beam 110 changes or "shifts" either angularly, translationally, or both, in at least one direction (e.g., the scan direction) as that corresponding sector 104 rotates through the input beam 110.

"Shifting deflection" sectors may be used in certain embodiments for achieving a desired level of delivered energy per volume of irradiated or affected tissue, as a function of selected design and/or operational parameters (e.g., beam width, intensity, fluence, and/or intensity profile of the delivered output beams, pulse duration and/or frequency, rotational speed of rotating scanning element 100, etc.). Thus, in certain embodiments, shifting deflection sectors may be used to achieve the desired treatment effects.

Shifting deflection sectors may be configured to shift the deflection of individual output beams 112 directly in the scan direction, or in a direction between the scan direction and the glide direction (such that the shift direction has one vector component along the scan direction and another vector component along the glide direction), or in the glide direction.

FIGS. 27A and 27B illustrate example treatment spot patterns generated by an element 100 having "shifting deflection" sectors 104, in a stamping mode and gliding mode operation of device 10, respectively. In this example, it is again assumed that each output beam 112 delivered to the skin has a circular cross-section.

FIG. 27A illustrates a row of three treatment spots 70 generated by an element 100 having "shifting deflection" sectors 104, while device 10 is held stationary with respect to the skin (e.g., with device 10 being operated in a stamping mode). Although device 10 is held stationary, each MTZ is elongated in the shift direction for a distance Y due to the shifting deflection caused by the specific shape/configuration of the respective sector 104. In other words, in some embodiments, the "shifting deflection" sectors 104 trace a short line segment or arc rather than dwelling on a spot during that sectors rotation through the incident beam. With reference to FIG. 27A, in some embodiments, the distance Y of the shift due to the sector optics (apart from any movement of device 10 relative to the skin, e.g., due to gliding) is (a) greater than or equal to the width W of the output beam 112 received at the skin but (b) less than or equal to half the distance of separation S between adjacent treatment spots in the scan direction. In particular embodiments, the distance Y of the shift due to the sector optics is (a) greater than or equal to width W of the output beam 112 but (b) less than or equal to 75% of the distance of separation S between adjacent treatment spots in the scan direction.

Further, in some embodiments in which element 100 generates output beams 112 that are angularly offset from each other (e.g., example elements 100A and 100B discussed below), in a particular time period during the rotation of a particular sector 104 through the input beam 110, the angular shift of the output beam 112 caused by that sector 104 (apart from any angular shift due to movement of device 10, etc.) is less than the angle of rotation of element 100 during that same time period. In more simple terms, the angular shift of the beam caused by a sector 104 is less than the corresponding angular rotation of element 100, during a particular time period. In some embodiments, the angular shift of the beam caused by a sector 104 is significantly less than the corresponding angular rotation of element 100, during a particular time period. For example, in some embodiments, the angular shift of the beam caused by a sector 104 is at least 50% less than the corresponding angular rotation of element 100, during a particular time period. In particular embodiments, the angular shift of the beam caused by a sector 104 is at least 75% less than the corresponding angular rotation of element 100, during a particular time period.

FIG. 27B illustrates a row of three treatment spots 70 generated by an element 100 having "shifting deflection" sectors 104, while device 10 is moved across the surface of the skin (e.g., with device 10 being operated in a gliding mode). As shown, each treatment spot is elongated simultaneously in both the deflection shift direction (by a distance Y) and the glide direction (by a distance X), resulting in a generally diagonal elongation. In some embodiments, one or more of such factors may be selected or adjusted in order to produce treatment spots of a predetermined shape or size (or within a predetermined range of shapes or sizes) determined to provide the desired effect in the tissue.

In the example shown in FIGS. 27A and 27B, the shift direction (i.e., the direction of the deflection shift due to the sectors) is in the scan direction. However, the shift direction may be in any other suitable direction, e.g., in the glide direction or any other angular direction. Further, the shift direction may be linear, as in the example shown in FIGS. 27A and 27B, or non-linear (e.g., tracing an arc or other non-linear path).

Radiation Modes

Radiation source 14 may generate radiation in any suitable manner relative to time, e.g., continuous wave (CW) radiation, pulsed radiation, or in any other manner relative to time. With respect to embodiments that include a rotating scanning element 100 having a plurality of reflection or deflection sectors (e.g., rotating elements 100A or 100B having a plurality of beam-deflecting lenslets, or rotating element 100C having a plurality of beam-reflection sectors), radiation may be delivered from radiation source 14 to scanning system 48 according to any one or more of the following modes (and/or one or more other modes not covered below), depending on the particular embodiments, device configuration, or device setting of device 10.

FIGS. 28A-28F illustrate the various radiation modes with respect to an example disc-shaped or cup-shaped rotating element 100A/100B having four deflecting lenslets 104A/104B. FIGS. 29A-29F illustrate the various modes with respect to an example stair-stepped rotating element 100C having four reflection sectors 104C.

(1) "Continuous" radiation mode (FIGS. 28A and 29A): radiation from radiation source 14 is delivered without interruption to scanning system 48 for a duration equal to or exceeding one full rotation of the rotating scanning element 100 (i.e., a rotation of 360 degrees). Such radiation may be generated as CW radiation (such that the radiation is continuously delivered for any number of multiple rotations of element 100), or as pulsed radiation (e.g., where the pulse duration of each pulse corresponds to one full rotation of element 100, with a pulse-off period between such pulses).

(2) "Inter-sector longer pulsed" radiation mode (FIGS. 28B and 29B): pulsed radiation is delivered to scanning system 48 such that:
  (a) the duration of individual pulses (i) is greater than or equal to the average duration of individual sectors 104 of the rotating scanning element 100 rotating through a reference point (i.e., a rotation of 360 degrees divided by the number of sectors 104 on the rotating scanning element 100), but (ii) less than the duration of one full rotation of the rotating scanning element 100 (i.e., a rotation of 360 degrees), and
  (b) individual pulses are incident on multiple sectors 104 of the rotating scanning element 100; i.e., individual pulses bridge at least one separation or transition between adjacent sectors 104.

(3) "Inter-sector shorter pulsed" radiation mode (FIGS. 28C and 29C): pulsed radiation is delivered to scanning system 48 such that:
  (a) the duration of individual pulses is less than the average duration of individual sectors 104 of the rotating scanning element 100 rotating through a reference point (i.e., a rotation of 360 degrees divided by the number of sectors 104 on the rotating scanning element 100), and
  (b) individual pulses are incident on multiple sectors 104 of the rotating scanning element 100; i.e., individual pulses bridge at least one separation or transition between adjacent sectors 104.

(4) "Intra-sector single pulsed" radiation mode (FIGS. 28D and 29D): pulsed radiation is delivered to scanning system 48 such that:
  (a) individual pulses are incident on only one reflection/deflection sector of the rotating scanning element 100; i.e., individual pulses do not bridge separations or transitions between adjacent sectors 104, and
  (b) a single pulse is delivered to individual sectors 104 during a revolution of the rotating scanning element 100.

(5) "Intra-sector constant multi-pulsed" radiation mode (FIGS. 28E and 29E): radiation from radiation source 14 is delivered to scanning system 48 in a pulsed manner such that:
  (a) multiple pulses are delivered to individual sectors 104 during a revolution of the rotating scanning element 100, and
  (b) the pulse frequency remains constant during a revolution of the rotating scanning element 100.

(6) "Intra-sector non-constant multi-pulsed" radiation mode (FIGS. 28F and 29F): pulsed radiation is delivered to scanning system 48 such that:

(a) multiple pulses are delivered to individual sectors 104 during a revolution of the rotating scanning element 100, and (b) the pulse frequency is not constant during a revolution of the rotating scanning element 100.

As mentioned above, FIGS. 28A-28F illustrate the various modes with respect to an example disc-shaped or cup-shaped rotating element 100A/100B having four deflecting lenslets 104A/104B.

Figure 28A:
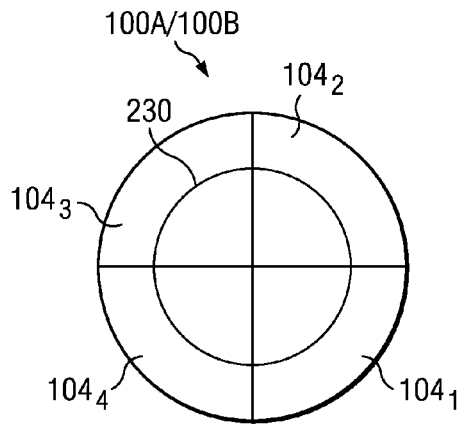
FIGS. 28A-28F illustrate the various radiation modes with respect to an example disc-shaped or cup-shaped rotating element having four deflection sectors, according to certain embodiments.

FIG. 28A illustrates a front view of example disc-shaped scanning element 100A or cup-shaped scanning element 100B, viewed along the rotation axis A, in which radiation is delivered to scanning system 48 according to a "continuous" radiation mode, according to an example embodiment. As shown, the radiation beam incident on rotating element 100A/100B traces a path 230 that extends around the full circumference of element 100A/100B as element 100A/100B rotates a full revolution.

Figure 28B:
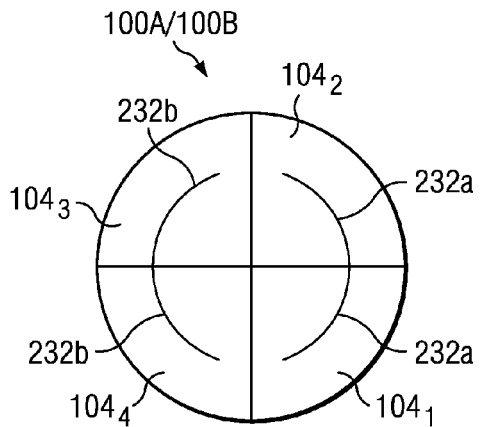

FIG. 28B illustrates a front view of example disc-shaped scanning element 100A or cup-shaped scanning element 100B, in which radiation is delivered to scanning system 48 according to an "inter-sector longer pulsed" radiation mode, according to an example embodiment. As shown, the radiation beam incident on rotating element 100A/100B is delivered in two pulses 232A and 232C during the full rotation of element 100A/100B, each pulse 232A and 232C tracing a path longer than a corresponding arc length of each individual lenslet $104_1$-$104_4$. (Or, in other words, the duration of each pulse 232A and 232C is greater than or equal to the average duration of an individual lenslet $104_n$ rotating through a reference point (i.e., in this embodiment, a 90 degree rotation of element 100A/100B). Further, as shown, each pulse 232A and 232C crosses over a transition between adjacent lenslets 104, thus rendering each pulse an "inter-sector" pulse.

Figure 28C:
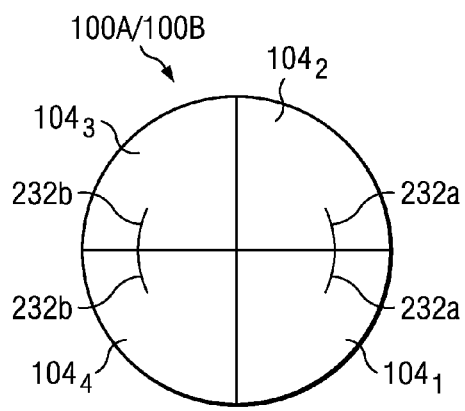

FIG. 28C illustrates a front view of example disc-shaped scanning element 100A or cup-shaped scanning element 100B, in which radiation is delivered to scanning system 48 according to an "inter-sector shorter pulsed" radiation mode, according to an example embodiment. As shown, the radiation beam incident on rotating element 100A/100B is delivered in two pulses 232A and 232C during the full rotation of element 100A/100B, each pulse 232A and 232C tracing a path shorter than a corresponding arc length of each individual lenslet $104_1$-$104_4$. (Or, in other words, the duration of each pulse 232A and 232C is less than the average duration of individual lenslet 104 rotating through a reference point (i.e., in this embodiment, a 90 degree rotation of element 100A/100B). Further, as shown, each pulse 232A and 232C crosses over a transition between adjacent lenslets 104, thus rendering each pulse an "inter-sector" pulse.

Figure 28D:
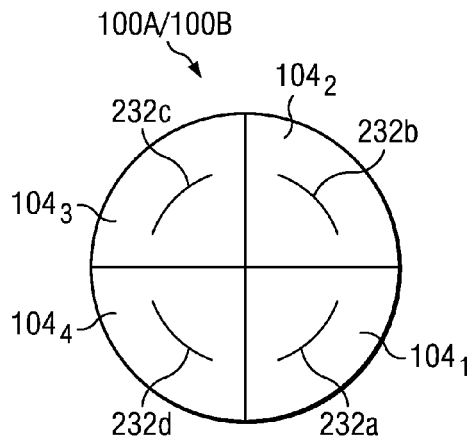

FIG. 28D illustrates a front view of example disc-shaped scanning element 100A or cup-shaped scanning element 100B, in which radiation is delivered to scanning system 48 according to an "intra-sector single pulsed" radiation mode, according to an example embodiment. As shown, the radiation beam incident on rotating element 100A/100B is delivered in pulses 232A-232d, such that a single pulse is delivered to each lenslet $104_1$-$104_4$, and such that the path traced by each pulse 232A-232d is located within its corresponding lenslet 104 (i.e., pulse 232A-232d do not cross over transitions between adjacent lenslets 104), thus rendering each pulse an "intra-sector" pulse.

Figure 28E:
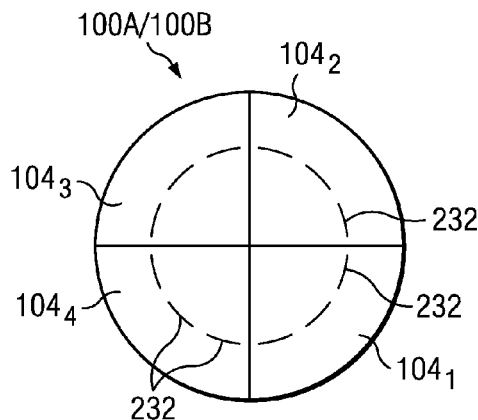

FIG. 28E illustrates a front view of example disc-shaped scanning element 100A or cup-shaped scanning element 100B, in which radiation is delivered to scanning system 48 according to an "intra-sector constant multi-pulsed" radiation mode, according to an example embodiment. As shown, the radiation beam incident on rotating element 100A/100B is delivered such that multiple pulses 232 are delivered to each lenslet $104_1$-$104_4$ during a revolution of the rotating element 100A/100B, and such that the pulse frequency remains constant during the revolution of the element 100A/100B.

Figure 28F:
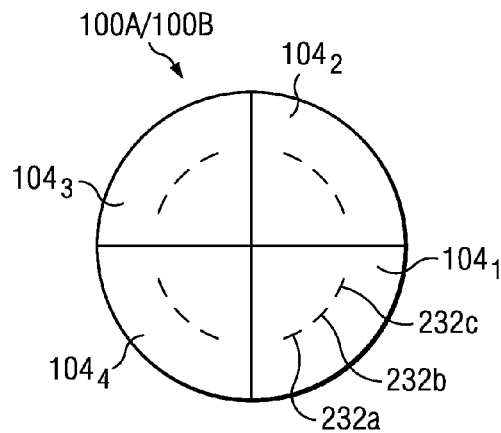

FIG. 28F illustrates a front view of example disc-shaped scanning element 100A or cup-shaped scanning element 100B, in which radiation is delivered to scanning system 48 according to an "intra-sector non-constant multi-pulsed" radiation mode, according to an example embodiment. As shown, the radiation beam incident on rotating element 100A/100B is delivered such that multiple pulses 232 are delivered to each lenslet $104_1$-$104_4$ during a revolution of the rotating element 100A/100B, but wherein the pulse frequency is not constant during the revolution of the element 100A/100B. In this example, a three-pulse burst 232A-232c is delivered to each lenslet $104_1$-$104_4$.

As mentioned above, FIGS. 29A-29F illustrate the various modes with respect to an example stair-stepped scanning element 100C having four reflection sectors 104C that define reflection surfaces $106_1$-$106_4$ offset from each other in the direction of the axis A.

FIG. 29A illustrates a front view of example stair-stepped scanning element 100C, viewed along the rotation axis A, in which radiation is delivered to scanning system 48 according to a "continuous" radiation mode, according to an example embodiment. As shown, the radiation beam incident on rotating element 100C traces a path 230 that extends around the full circumference of element 100C as element 100C rotates a full revolution. Due to the fact that reflection surfaces $106_1$-$106_4$ are offset from each other in the direction of the axis A, the portions of the radiation beam path 230 traced on the different reflection surfaces $106_1$-$106_4$ are located at varying distances from the center (i.e., axis A), which should be clear in view of FIGS. 12-14. Thus, although path 230 appears to "skip" when crossing the threshold between adjacent reflection surfaces $106_1$-$106_4$, it should be understood that the radiation beam is continuously delivered to element 100C for the full revolution of element 100C.

FIG. 29B illustrates a front view of example stair-stepped scanning element 100C, viewed along the rotation axis A, in which radiation is delivered to scanning system 48 according to an "inter-sector longer pulsed" radiation mode, according to an example embodiment. As shown, the radiation beam incident on rotating element 100C is delivered in two pulses 232A and 232C during the full rotation of element 100C, each pulse 232A and 232C tracing a path longer than a corresponding arc length of each individual reflection surface $106_1$-$106_4$. (Or, in other words, the duration of each pulse 232A and 232C is greater than or equal to the average duration of individual reflection surface $106_1$-$106_4$ rotating through a reference point (i.e., in this embodiment, a 90 degree rotation of element 100C). Further, as shown, each pulse 232A and 232C crosses over a transition between adjacent reflection surface $106_1$-$106_4$, thus rendering each pulse an "inter-sector" pulse.

Figure 29C:
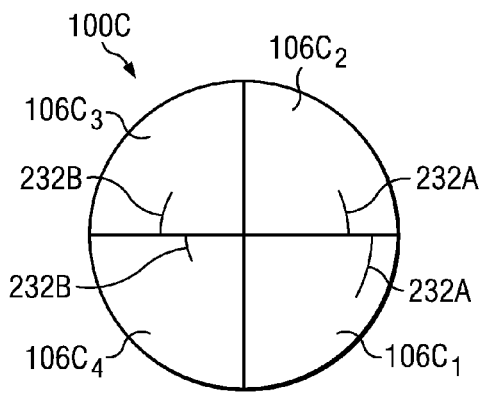

FIG. 29C illustrates a front view of example stair-stepped scanning element 100C, viewed along the rotation axis A, in which radiation is delivered to scanning system 48 according to an "inter-sector shorter pulsed" radiation mode, according to an example embodiment. As shown, the radiation beam incident on rotating element 100C is delivered in two pulses 232A and 232C during the full rotation of element 100C, each pulse 232A and 232C tracing a path shorter than a corresponding arc length of each individual reflection surface $106_1$-$106_4$. (Or, in other words, the duration of each pulse 232A and 232C is less than the average duration of individual reflection surface $106_1$-$106_4$ rotating through a reference point (i.e., in this embodiment, a 90 degree rotation of element 100C). Further, as shown, each pulse 232A and 232C crosses over a transition between adjacent reflection surface $106_1$-$106_4$, thus rendering each pulse an "inter-sector" pulse.

Figure 29D:
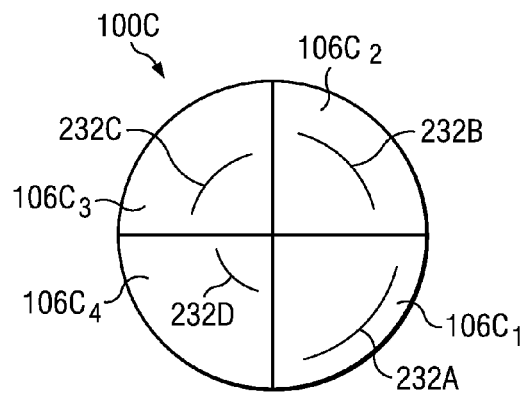

FIG. 29D illustrates a front view of example stair-stepped scanning element 100C, viewed along the rotation axis A, in which radiation is delivered to scanning system 48 according to an "intra-sector single pulsed" radiation mode, according to an example embodiment. As shown, the radiation beam incident on rotating element 100C is delivered in pulses 232A-232d, such that a single pulse is delivered to each reflection surface $106_1$-$106_4$, and such that the path traced by each pulse 232A-232d is located within its corresponding reflection surface $106_1$-$106_4$ (i.e., pulse 232A-232d do not cross over transitions between adjacent reflection surface $106_1$-$106_4$), thus rendering each pulse an "intra-sector" pulse.

Figure 29E:
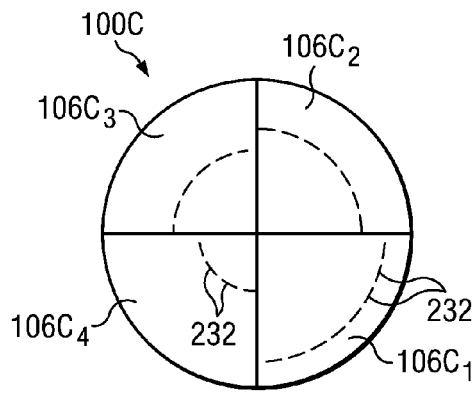

FIG. 29E illustrates a front view of example stair-stepped scanning element 100C, viewed along the rotation axis A, in which radiation is delivered to scanning system 48 according to an "intra-sector constant multi-pulsed" radiation mode, according to an example embodiment. As shown, the radiation beam incident on rotating element 100C is delivered such that multiple pulses 232 are delivered to each reflection surface $106_1$-$106_4$ during a revolution of the rotating element 100C, and such that the pulse frequency remains constant during the revolution of the element 100C.

Figure 29F:
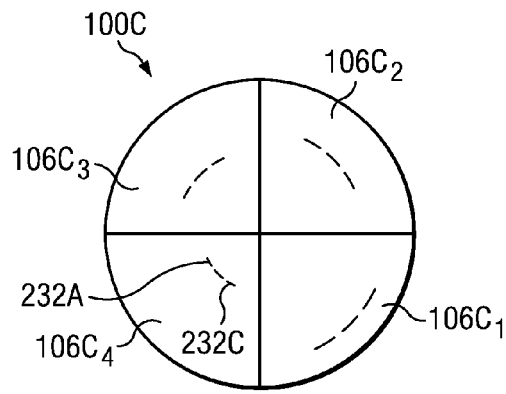

FIG. 29F illustrates a front view of example stair-stepped scanning element 100C, viewed along the rotation axis A, in which radiation is delivered to scanning system 48 according to an "intra-sector non-constant multi-pulsed" radiation mode, according to an example embodiment. As shown, the radiation beam incident on rotating element 100C is delivered such that multiple pulses 232 are delivered to each reflection surface $106_1$-$106_4$ during a revolution of the rotating element 100C, but wherein the pulse frequency is not constant during the revolution of the element 100C. In this example, a three-pulse burst 232A-232c is delivered to each reflection surface $106_1$-$106_4$.

Any of the radiation modes may continue uninterrupted for (a) less than a full rotation of the rotating scanning element 100 (except for continuous mode, which requires uninterrupted delivery of radiation for at least one full rotation), (b) one full rotation of the rotating scanning element 100, or (c) multiple rotations of the rotating scanning element 100.

For example, the current radiation mode may be interrupted after each full rotation of the rotating scanning element 100. As another example, the current radiation mode may be interrupted after a predetermined number of rotations of the rotating scanning element 100, after a predetermined time, or after a predetermined amount of radiation has been delivered to the skin 40, for example. In some embodiments, the current radiation mode may be interrupted and/or started or re-started in response to feedback from one or more systems of device 10, e.g., immediately (i.e., in the middle of a particular rotation of element 100/scan of input beam 110), at the end of the current rotation of element 100/scan of input beam 110, or in any other manner. For example, as discussed in greater detail below with respect to FIG. 38-46, the current radiation mode may be interrupted and/or started or re-started in response to:

(a) signals from one or more skin contact sensors 204 indicating whether application end 42 of device 10 is in contact with the skin;

(b) signals from displacement monitoring and control system 132, e.g., indicating the distance that device 10 has moved across the skin 40;

(c) signals from usability control system 133, e.g., indicating whether device 10 is in contact with the skin and experiencing a sufficient displacement or speed across the skin (e.g., based on signals from one or more displacements sensors 20 and skin contact sensors 204);

(d) signals from one or more sensors 26 or safety systems indicating a potentially unsafe condition; and/or (e) any other suitable automated feedback.

Further, in some embodiments or settings, the current radiation mode may be interrupted manually via a user interface 28, e.g., in response to the user pressing a button, releasing a button, or moving the device 10 away from contact with the skin 40.

An "interruption" of the current radiation mode may include any of (a) interrupting delivery of radiation to the skin 40 (e.g., by turning off the treatment radiation source 14, or preventing the radiation from being output from device 10, by blocking or redirecting the radiation within device 10), (b) switching to a different radiation mode, and (c) modifying one or more parameters of the delivered radiation, including fluence, power density, wavelength, pulse frequency, duty rate, pulse on time (pulse width), pulse off time, treatment spot size and/or shape, outlet beam focal plane, etc.

The duration of an interruption of the current radiation mode (before continuing radiation delivery) may be a predetermined time, a predetermined rotation of the rotating scanning element 100 (e.g., to skip or bypass a specific number of reflection sectors), or may be determined based on feedback from one or more systems of device 10. For example, as discussed in greater detail below with respect to FIG. 46, after an interruption of a particular radiation mode in response to signals from displacement monitoring and control system 132 or usability control system 133 (e.g., indicating that device 10 is not in contact with the skin or has not moved a threshold distance across the skin 40), the particular radiation mode may be continued in response to further signals from displacement monitoring and control system 132 or usability control system 133 (e.g., indicating that device 10 is back in contact with the skin and/or has moved the threshold distance across the skin 40).

In the example embodiments shown in FIGS. 28A-28F and 29A-29F, each example scanning elements 100 includes four reflection sectors 104. It should be understood that the illustrated embodiments are merely examples, for illustrative purposes. As discussed above, rotating element 100 may include any number of reflection sectors 104. For example, in some embodiments, rotating element 100 includes about 6 reflection sectors 104, or about 10-12 reflection sectors 104, or between 15-20 reflection sectors 104, more than 20 reflection sectors 104, or any other suitable number of reflection sectors 104.

Figure 30:
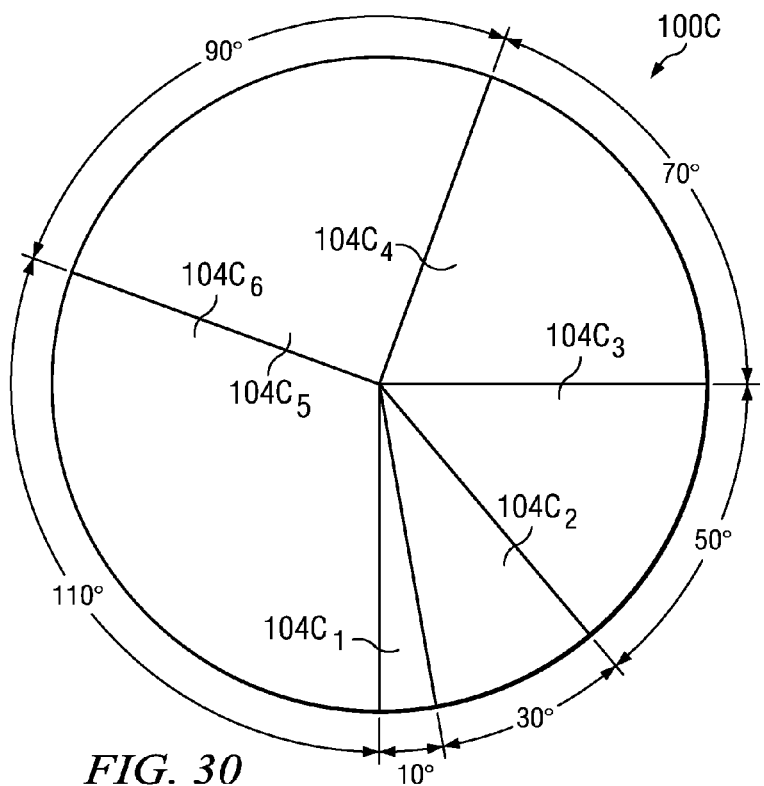
FIG. 30 illustrates an example scanning element having reflection sectors of different sizes, according to certain embodiments.

Further, in the example embodiments shown in FIGS. 28A-28F and 29A-29F 1, as well as those shown in FIGS. 7, 8, and 13, the reflection sectors 104 extend the same distance around the respective scanning element 100 (e.g., in the four-sector scanning elements 100 shown in FIGS. 28A-28F and 29A-29F, each reflection sector 104 extends 90 degrees around the respective rotating element 100, and in the 12-sector scanning elements 100 shown in FIGS. 7 and 8, each reflection sector 104 extends 30 degrees around the respective rotating element 100). Again, it should be understood that the illustrated embodiments are merely examples, for illustrative purposes. The reflection sectors 104 of any particular scanning element 100 may or may not extend the same distance or angle around the element 100. Thus, scanning element 100 may include n reflection sectors 104, each extending 360/n degrees around element 100; or alternatively, one or more of the n reflection sectors 104 may extend more or less than 360/n degrees around element 100. In some embodiments, the n reflection sectors 104 may extend $x_i$ degrees around scanning element 100, where the series $x_i, x_{i+1}, \ldots x_{n-1}, x_n$ increases linearly, according to an $n^{th}$ order equation, or other non-linear equation. For example, FIG. 30 illustrates a scanning element 100 with six deflection sectors $104C_1$-$104C_6$, which extend 10 degrees, 30 degrees, 110 degrees, 170 degrees, 90 degrees, and 110 degrees, respectively, around element 100.

Use of Non-Propagating Areas to Provide Constant-Input/ Pulsed-Output Effect

In some embodiments, adjacent reflection sectors 104 and/or reflection surfaces 106 may be separated from each other by areas that do not reflect input beam 110 for propagation toward the skin 40, such areas including non-reflective areas, or areas that reflect or deflect input beam 110 away from propagation toward the skin 40, for example. Such areas are referred to herein as "non-propagating areas." In some embodiments, non-propagating areas may be used to sample the treatment beam, such as to measure its power or energy with a photodiode, or for other purposes. In some embodiments, non-propagating areas may be used to control the duration or pulse width of individual output beams 112 to be delivered to the skin 40. For example, an input beam 110 may be delivered uninterrupted for a time period that spans the rotation of multiple reflection sectors 104 through the input beam 110. By including non-propagating areas between adjacent reflection surfaces 106, the uninterrupted input beam 110 may be effectively converted into a pulsed array of output beams 112. Such effect is referred to herein as a "constant-input/pulsed-output" effect. The relative size and shape of the reflection surfaces 106 and non-propagating areas may define at least in part the effective pulse-on time (i.e., pulse width) of each output beam 112, as well as the pulse-off time between output beams 112, and thus a pulse duty cycle.

Figure 31:
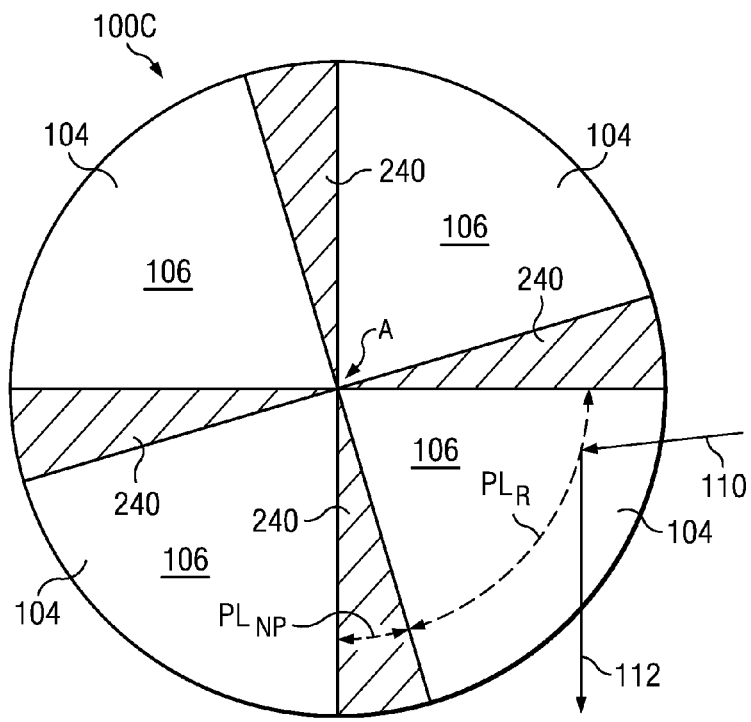
FIG. 31 illustrates an example rotating scanning element having four deflection sectors separated by non-propagating areas, according to an example embodiment.

FIG. 31 illustrates an end view, taken along the axis of rotation A, of an example rotating scanning element 100 (e.g., element 100A, 100B, or 100C) having four deflection sectors 104 separated by four non-propagating areas 240, according to an example embodiment.

An input beam 110 may be delivered uninterrupted for a time period that spans the rotation of multiple deflection sectors 104 (e.g., lenslets or mirrored sectors) through the input beam 110. Input beam 110 is incident to deflection sectors 104 and non-propagating areas 240 in an alternating manner. Each deflection sector 104 creates an output beam 112 defining a pulse-on time (pulse width), and each non-propagating areas 240 creates an interruption defining a pulse-off time between consecutive pulses. In this manner, a "constant-input/pulsed-output" effect can be generated. The pulse-on time (i.e., pulse width) of each output beam 112, and the pulse-off time between output beams 112, and thus the pulse duty cycle, may be defined by (a) the relative size and shape of the deflection sectors 104 and non-propagating areas 240, defined in the illustrated example by the respective path lengths $PL_R$ and $PL_{NP}$ traced by input beam 110 as element 100C rotates about axis A, and (b) the rotational speed of element 100C. The relative size and shape of the deflection sectors 104 and non-propagating areas 240 may be selected to provide any desired pulse-on time and pulse-off time, for a given rotational speed of element 100C.

In the illustrated example, the four deflection sectors 104 have the same shape and size, and the four non-propagating areas 240 have the same shape and size, such that the pulse-on time and pulse-off time is the same for each output beam 112, assuming a constant rotational speed of element 100C. In other embodiments, the different deflection sectors 104 may have different sizes and/or shapes, and/or the different non-propagating areas 240 may be may have different sizes and/or shapes, such that the pulse-on time for different output beams 112 and/or the pulse-off time between different output beams 112 may vary as desired.

The use of non-propagating areas 240 may be combined in any suitable manner with any radiation mode, e.g., any of the various continuous or pulsed radiation modes discussed above with reference to FIGS. 28A-28F and 29A-29F, in order to control one or more parameters of beams delivered to the skin 40.

On-Axis Vs. Off-Axis Output Beams; Optional Downstream Optics

A scanned array of beams may include "off-axis" and "on-axis" beams. "Off-axis" output beams 112 are output beams 112 in an array that have been deflected (by respective lenslets 104) by a relatively large amount, in contrast to "on-axis" output beams that have been deflected (by respective lenslets 104) by a relatively small amount or even not deflected at all. In some embodiments, the central output beam or beams 112 of an array are considered on-axis, while outer beams are of the array are considered off-axis. For example, in the examples arrangements shown in FIGS. 10A and 11A, output beam 112B is considered on-axis, while output beams 112A and 112C are considered off-axis.

The deflection of individual output beams 112 caused by lenslets 104 may affect the beam intensity profile of such beams. Generally, the greater the deflection, the greater the influence on the beam intensity profile. Thus, the beam intensity profiles of off-axis beams are generally influenced more than the profiles for on-axis beams. For example, off-axis output beams 112 of an array may have a defocused or widened intensity profile in at least one direction or axis, as compared to on-axis beams 112 in the same array, due to the deflection of such off-axis output beams 112 by the respective sectors 104 of element 100.

Figures 32A, 32B:
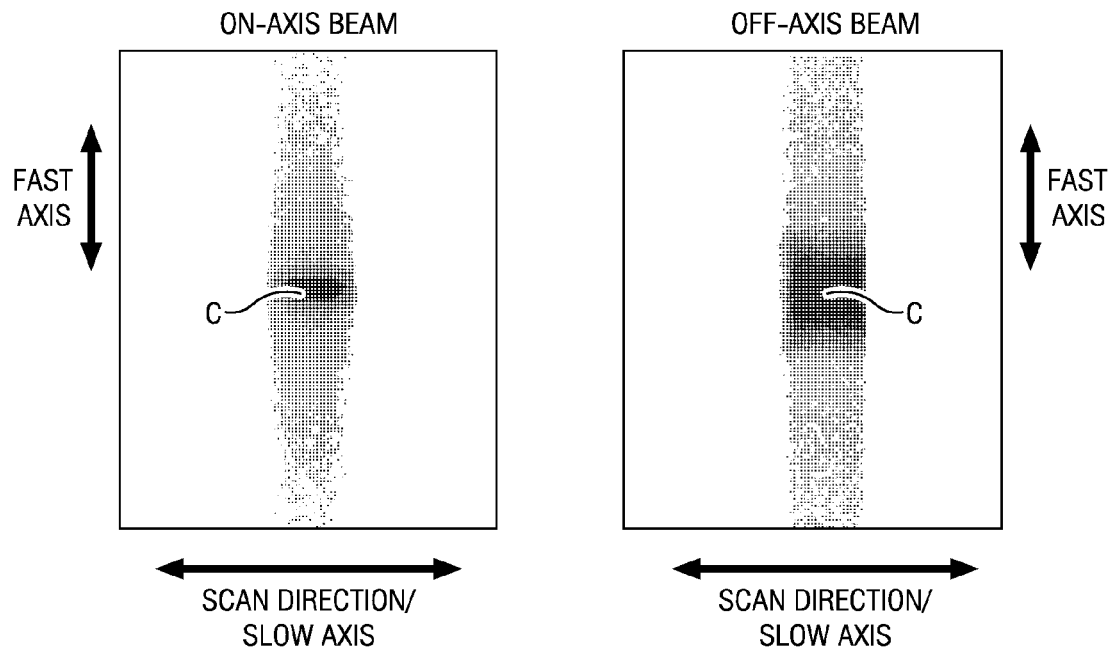
FIGS. 32A-32C illustrate beam intensity profiles in the slow and fast axis for on-axis scanned beams (FIG. 32A) and off-axis scanned beams (FIG. 32B), as well as a graph illustrating the fraction of "ensquared energy" as a function of the target area, for scanned-beam treatment devices according to certain embodiments.
Figure 32C:
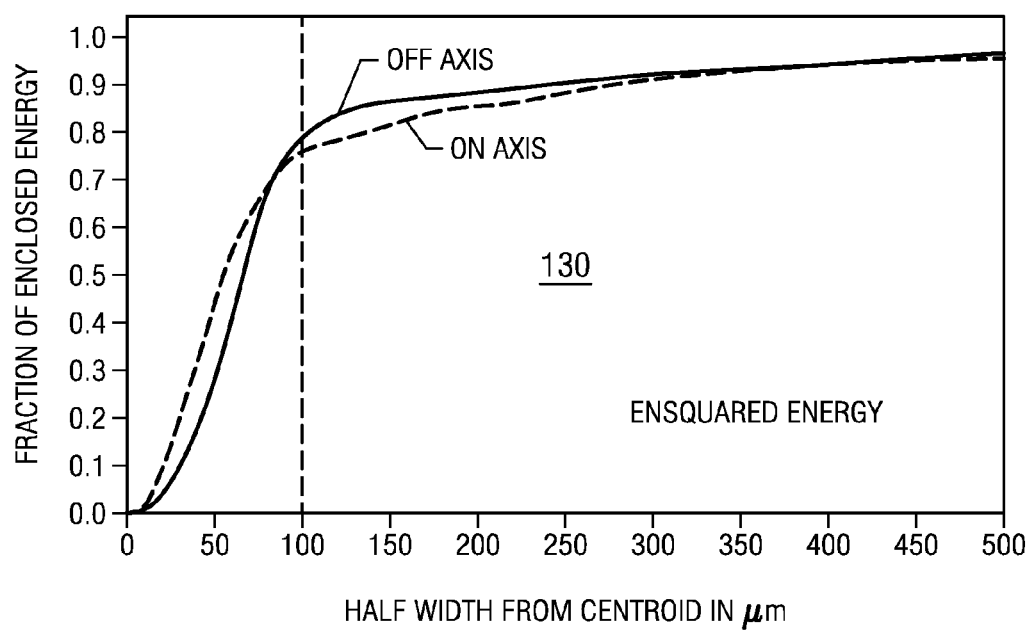

FIGS. 32 and 33 illustrate example intensity profiles of output beams 112, measured at the surface of the skin, for an on-axis output beam 112 and an off-axis output beam 112, respectively. For example, with reference to the arrangements shown in FIGS. 18 and 20, FIG. 32 may generally represent the beam intensity profile for on-axis output beam 112B, while FIG. 33 may represent the beam intensity profile for off-axis output beams 112A or 112C.

As shown, the intensity profile of the on-axis beam 112 is narrower in at least one direction (in this example, the fast axis direction), and may have a higher intensity peak (or peaks) as compared to the intensity profile of the off-axis beam 112. In some embodiments, the intensity profile of the on-axis beam 112 may also be narrower in the orthogonal direction (in this example, the slow axis direction) as compared to the off-axis beam 112.

Figure 33A:
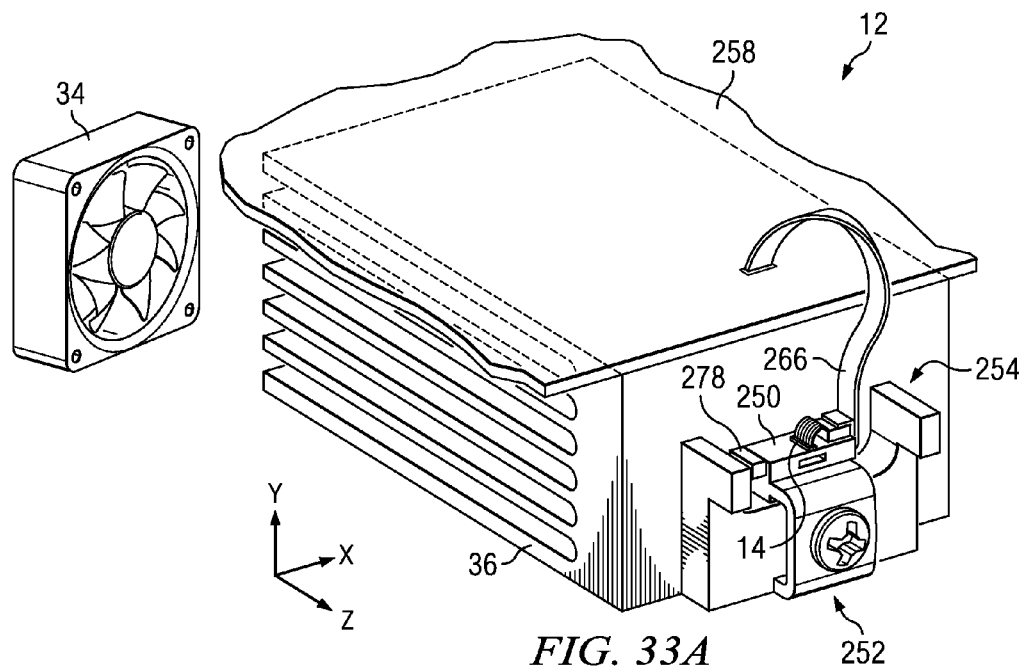
FIGS. 33A and 33B illustrate a first example embodiment of a radiation engine for use in a radiation-beam treatment device, according to certain embodiments.
Figure 33B:
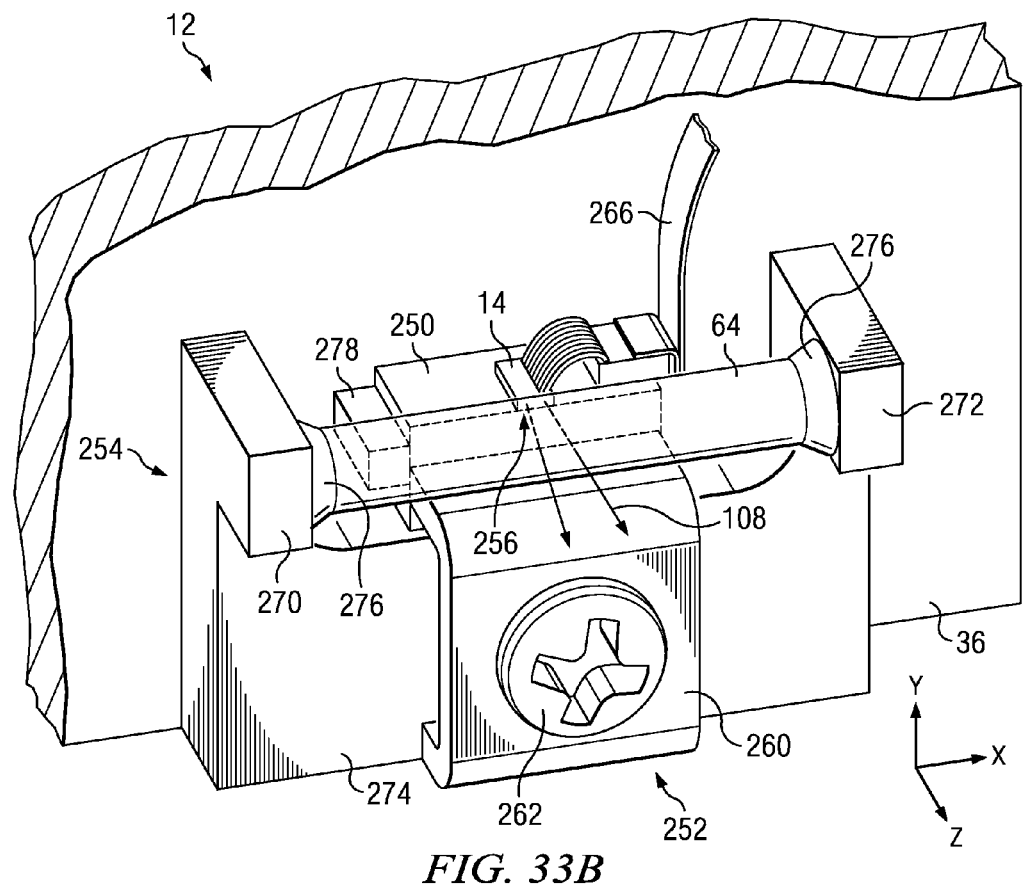
Figure 34:
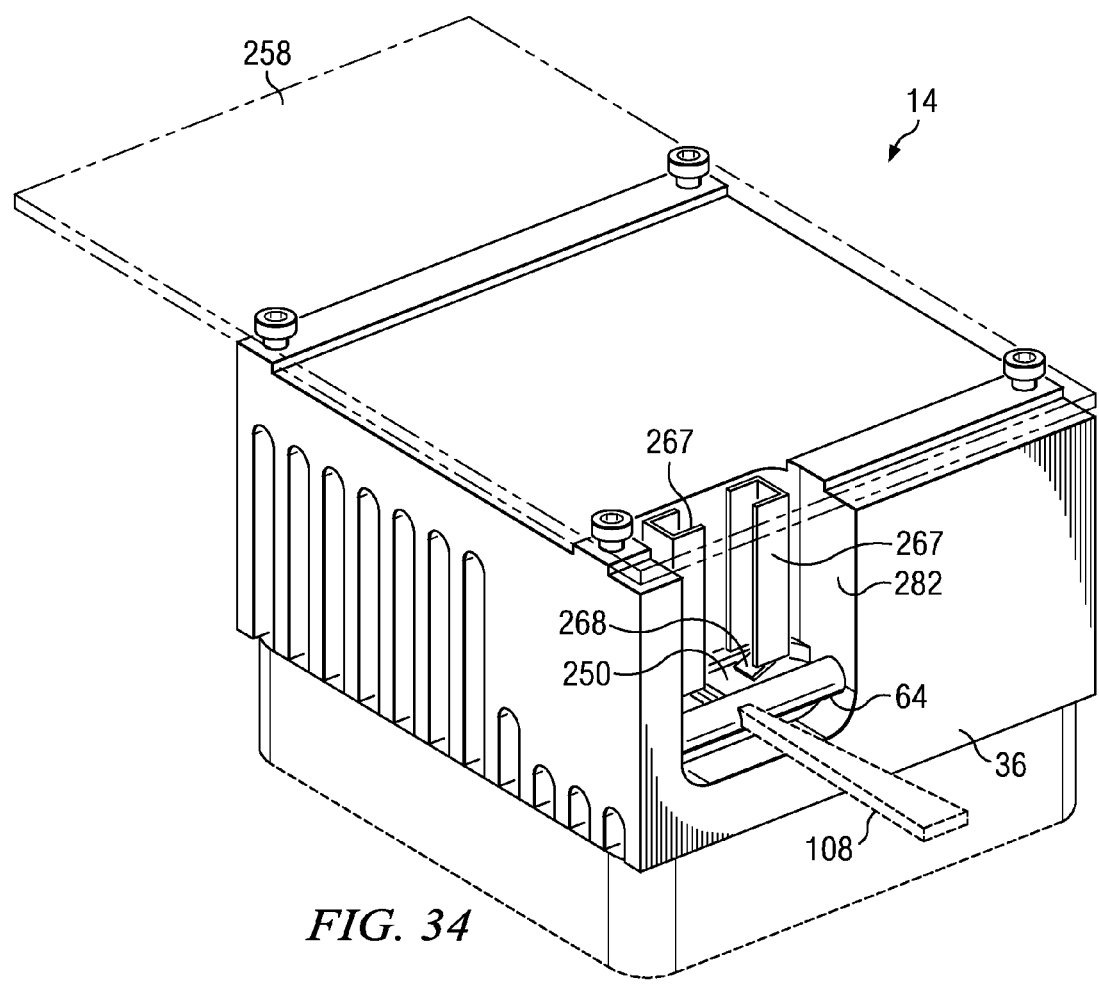
FIG. 34 illustrates a second example embodiment of a radiation engine for use in a radiation-beam treatment device, according to certain embodiments.

FIG. 34 illustrates a graph 130 of the fraction of the energy delivered to a target surface that is delivered within a square of a defined size on that target surface. The energy delivered within the square is referred to as the "ensquared energy." Graph 130 shows the fraction of ensquared energy as a function of square size, for an example on-axis beam (e.g., as shown in FIG. 32) and an example off-axis beam (e.g., as shown in FIG. 33). The square size is defined in terms of half width from a centroid of the intensity profile plane, e.g., points C indicated in the intensity profile plane shown in FIGS. 32 and 33. Thus, a half width of 50 µm in graph 130 refers to a 100 µm×100 µm square centered around centroid C.

As shown in graph 130, for small half widths (i.e., smaller squares), the ensquared energy for the on-axis beam is higher than that of the off-axis beam. For example, at a half width of 50 µm, the fraction of ensquared energy for the on-axis beam is about 0.43, compared to about 0.40 for the off-axis beam. However, for larger half widths (i.e., larger squares), the ensquared energy for the on-axis beam is similar to that of the off-axis beam (and in fact, may be smaller than that of the off-axis beam for certain half width). In one embodiment, an treatment spot diameter or width of about 0.2 mm (200 µm) is desired. The dashed line in graph 130 at 100 µm half width corresponds to a square width of 0.2 mm (200 µm). As shown, the ensquared energy for at that dimension is approximately the same for the on-axis beam and the off-axis beam. Thus, despite the defocused and/or widened intensity profile of the off-axis beam (as compared to the on-axis beam), the total energy delivered to an treatment spot of about 0.2 mm (200 µm) in width or diameter is about the same for both on-axis and off-axis beams in the same scanned array for this embodiment. Thus, the desired effect may be provided without needing further treatment optics to act on the off-axis beams.

The shape of the intensity profile of each output beam 112 along each axis (e.g., along the slow axis and fast axis for asymmetric profile beams, e.g., as generated by laser diodes) is determined at least by the type of treatment radiation source 14 and the particular elements of optical system 15. Thus, different embodiments may provide any of a variety of intensity profiles at the target plane (e.g., the surface of this skin) in any particular axis. Examples of such intensity profiles include, e.g., Gaussian, pseudo-Gaussian, flat-topped, pseudo-flat-topped, etc., and may include a single peak, two peaks, more than two peaks, or no significant peaks (e.g., flat-topped).

In some embodiments, one or more downstream optical elements 60B (e.g., with reference to FIG. 3C). Some example downstream optics 60B include: (a) downstream fast axis optic 64' (e.g., cylindrical lens) for focusing, aberration correction, and/or imaging and/or treatment of output beams 112, e.g., as discussed above with reference to FIGS. 10A-10B and 11A-11B; (b) mirrors 150A-150C for deflecting output beams 112, and (c) path length compensation elements 152 for providing equal total path lengths for output beam 112 generated by a stair-stepped scanning element 100C.

Downstream optics 60B may include any one or more planar mirrors, optically-powered lenses or mirrors, or other optical elements (as defined above) that influence output beams 112. Downstream optics 60B may be provided for a variety of purposes, e.g., to deflect one or more output beams 112 such that they are incident to the target surface at a desired angle (e.g., substantially normal to the target surface); to influence the focus of one or more output beams 112 (e.g., to provide a desired focal point or focal plane relative to the target surface); to influence the beam intensity profile of one or more output beams 112 at the focal point or focal plane of output beams 112; or for any other purpose.

For example, downstream fast axis optic 64', e.g., as shown in FIGS. 10 and 11, may be provided downstream of scanning system 48 for refocusing or reimaging or controlling or adjusting the intensity profile of output beams 112 as desired. In some embodiments, such downstream optics 60B may be particularly provided for refocusing or treating off-axis output beams 112, as such output beams 112 may have defocused and/or widened intensity profiles or otherwise different properties as compared to on-axis beams 112, as discussed above. For example, such downstream optics 60B may be provided for narrowing the intensity profile of off-axis output beams 112 along at least one axis. For instance, fast axis optic 64' shown in FIGS. 10 and 11, which may comprise, e.g., a rod lens, aspheric lens, or any other suitable optical element, may be provided to refocus or narrow the intensity profile of off-axis beams 112 in the fast axis direction. In some embodiments, such downstream optics 60B may be used to deliver a beam intensity profile to the skin that produces the desired effects in the tissue. In other embodiments, beam intensity profiles sufficient to provide the desired effects in the skin are provided without such downstream optics 60B (e.g., without fast axis optic 64'). For example, in some embodiments that utilize a laser diode, beam intensity profiles sufficient to provide the desired effects in the skin are provided using only a single fast axis optical element (e.g., a rod lens or aspheric lens) and a scanning element that both scans the beam and treats the beam in the slow axis direction.

Other embodiments of device 10 may include no downstream optics 60B. In some embodiments, the only element along the downstream beam path is a window 44 at the application end 42 that may comprise a clear glass or plastic film, plate, layer, or block. A window 44 may be provided to protect the internal components of device 10, as discussed above, or it could also be a spectral filter to allow only the treatment beam to pass through and provide the desired cosmetic visual effect. Output beams 112 may travel from scanning optics 62 through a chamber within housing 24, though window 44, and to the skin 40, with no optics 60B downstream of scanning optics 62. The chamber may be sealed and filled with air or other gas, or may comprise a vacuum. Alternatively the chamber may be open to ambient air, e.g., through one or more openings in housing 24 (e.g., to encourage heat transfer away from device 10). As another example, device 10 may include an open aperture, rather than window 44, in the application end 42, such that output beams 112 travel from scanning optics 62 through an open-air chamber and out through the aperture in application end 42, without being influenced by any downstream optics 60B or passing through any window or other element.

Radiation Engine

As discussed above, radiation engine 12 may include any number and or type(s) of radiation sources 14 configured to generate radiation to be delivered to the skin 40. For example, radiation sources 14 may include one or more laser diode, fiber laser, VCSEL (Vertical Cavity Surface Emitting Laser), LED, etc. Thus, depending on the particular type(s) of radiation source(s) 14 used, the radiation may have different properties, such as the radiation propagated by each treatment radiation source 14 may be symmetric about all axes, i.e., axis-symmetric (e.g., radiation produced by a fiber laser), or asymmetric about different axes, i.e., axis-asymmetric (e.g., radiation produced by a laser diode).

FIGS. 33A and 33B illustrate an example embodiment of a radiation engine 12 that includes a laser diode as the radiation source 14. In this example, radiation engine 12 includes a laser package 250 (which includes the laser diode 14), a heat sink 36, a laser package securing system 252, and a lens securing system 254 for securing a fast axis optic 64 (in this embodiment, a cylindrical lens) relative to the laser diode 14. FIG. 33A illustrates a full view of radiation engine 12, and FIG. 33B is a magnified view of a portion of radiation engine 12 illustrating the particular arrangement of laser package 250 (which includes the laser diode 14), laser package securing system 252, and lens securing system 254 for securing fast axis lens 64. Fast axis lens 64 is not shown in FIG. 33A, for illustrative purposes only.

In the illustrated embodiment, radiation source 14 is a single-emitter or multi-emitter laser diode 14 provided on a laser package 250. Laser package 250 may be, for example, a Q-Mount or B-Mount laser package, which may be particularly suitable for use with the illustrated example lens mounting system. However, other laser packages well suited for use with such lens mounting features include flat ceramic type packages and C-Mount packages and custom packages, among others. Other embodiments include any other suitable type(s) of radiation sources, e.g., other type(s) of laser sources (e.g., one or more laser diode bars, VCSELs, etc.) or any other type(s) of radiation sources.

As shown in FIG. 33A, laser diode 14 may be electrically coupled to a printed circuit board (PCB) 258 in any suitable manner. For example, laser diode 14 may be coupled to electronics on PCB 258 by an electrical connection 266, e.g., a flexible cable.

Laser diode 14 of the illustrated embodiment includes a single emitter that may include an emitting edge or surface 256, from which a beam 108 is emitted. In one embodiment, emitting edge/surface 256 is approximately 100 µm by 1 µm, extending lengthwise in the x-axis direction. In other embodiments, laser 14 may include multiple emitters or emitting edges/surfaces 256.

Heat sink 36 serves to cool the laser 14 and may be fabricated via an extrusion process or in any other suitable manner. Some embodiments include one or more fans to help maintain the laser temperature at a desired level. Heat sink 36 may include fins or other structures for promoting heat transfer. In some embodiments heat sink 36 may be passive and/or absorb and/or transfer heat by conduction only and/or combined with natural convection and/or combined with radiative heat transfer. In some embodiments, heat sink 36 in the fully assembled device 10 has a rating of about 2.5° C./W or lower. In particular embodiments, heat sink 36 in the fully assembled device 10 has a rating of about 1.5° C./W or lower.

In some embodiments, laser diode 14 also includes one or more fans 34 to actively cool heat sink 36, to further promote heat transfer from laser diode 14 and/or other powered components of device 10.

Laser package securing system 252 may comprise any devices used to secure laser diode package 24 to heat sink 36, e.g., via soldering, clamping, spring forces, or using thermally conductive adhesive. A bottom surface of laser package 250 may contact heat sink 36 either directly, or using thermal interface material (e.g., thermal grease), to promote heat transfer into heat sink 36.

Laser package 250 may include one or more laser diodes 14 directly mounted to heat sink 36 via suitable means (e.g., via soldering, clamping, or adhesive) or mounted to one or more subcarriers (e.g., a ceramic, plated ceramic, copper block, etc) to provide, among other things, electrical isolation and/or thermal conduction. Electrical connection to the laser diode emitter(s) may be made by wire bonding, clamping, or other suitable means between the emitter(s) and the subcarrier(s), to heat sink 36, or to other electrical connection point(s) (e.g., printed circuit board 258) in the device 10. Some example arrangements for mounting a laser diode 14 to heat sink 36 are shown in the embodiments of FIGS. 36 and 37, which are discussed below.

In the illustrated embodiment, laser package securing system 252 includes a clip 260 which is secured to heat sink 36 by a screw 262, in order to secure laser package 250 to heat sink 36. Mounting features may also be provided in heat sink 36 to assure repeatable positioning of the laser assembly. The laser mounting features may be modified to accommodate a variety of standard industry laser packages. Example embodiments of laser package securing system 252 that do not require a clip or screw are discussed below with reference to FIGS. 34-37.

Lens securing system 254 in this embodiment is configured for securing a fast axis lens 64 to heat sink 36, in order to secure fast axis lens 64 in a fixed position relative to laser diode 14. The beam 108 emitted by laser diode 14 may have a relatively large angular divergence in the fast axis (indicated as the y-axis in FIG. 33B). Thus, a high-numerical-aperture (high NA) short-focal-length cylindrical lens (or "rod lens") 64 may be provided to reduce the angular divergence of the fast axis profile of beam 108. Due to its high NA, the exact positioning of cylindrical lens 64 relative to laser diode 14 may be relatively important. In one embodiment, cylindrical lens 64 is about 12 mm long with a diameter of about 2 mm. However, lens 64 may have any other suitable dimensions. Further, in other embodiments, lens 64 may comprise a different shaped lens. For example, lens 64 may be an aspheric lens or a spherical lens.

Lenses are commonly attached to other structures using UV curing epoxy. However, UV curing epoxy experiences shrinkage during the curing process, which changes the position of the lens relative to the laser, which may negatively affect the desired beam output characteristics. Thus, lens securing system 254 may be configured for mounting fast axis optic 64 to heat sink 36 in a manner that minimizes or reduces the movement of optic 64 relative to laser diode 14, including during the mounting process, e.g., during a UV curing process.

In the illustrated embodiment, lens securing system 254 comprises a pair of lens support structures 270 and 272 that extend in the z-axis direction from a side of heat sink 36. Structures 270 and 272 may be formed integral with heat sink 36. Structures 270 and 272 extend past the front edge of laser package 250 in the z-axis direction, and may be separated by a distance of 1.5× to 2× the width of laser package 250 in the x-axis direction. The geometry of structures 270 and 272 may be at least partially generated in the heat sink extrusion direction, which may minimize or reduce the number of components and/or amount of post machining required, thus reduce the cost of the assembly.

In some embodiments, heat sink 36 and lens support structures 270 and 272 may be formed integrally by a single extrusion process, followed by a machining process to form an extended mounting portion 274 that includes support structures 270 and 272. In addition, locating features 278 for the laser package 250 may also be machined into the heat sink 36. Forming heat sink 36, lens support structures 270 and 272, and locating features 278 integrally creates a robust structure between the laser 14 and lens 64. In other embodiments, heat sink 36 may be formed by die-casting, forging, and/or any other suitable manufacturing process or processes.

As shown in FIG. 33B, high NA cylindrical lens 64 is mounted between support structures 270 and 272. Lens 64 may be secured to support structures 270 and 272 in any suitable manner. For example, lens 64 may be positioned between structures 270 and 272 and adhered to structures 270 and 272 using UV adhesive 276, e.g., UV epoxy 276 that is cured via a UV curing process.

To mount the lens 64, a small amount of UV adhesive 276 is applied to the ends of the lens 64 and/or to the inside surfaces of lens support structures 270 and 272. Lens 64 is then positioned between support structures 270 and 272, with a small space between each end of lens 64 and the respective support structure 270 and 272. Surface tension may hold the adhesive 276 in place while positioning lens 64 in between support structures 270 and 272. Alignment tool(s) and method(s), such as real time monitoring of the beam during the mounting of lens 64, may be used. Once in the proper location, the adhesive 276 wets to the lens support structures 270 and 272 and spans the gap between the support structures 270 and 272 and ends of lens 64. The adhesive 276 is then cured using a high intensity UV radiation source.

During curing, shrinkage of the epoxy may cause lens 64 to move in the x-axis direction, as lens 64 and support structures 270 and 272 are aligned in the x-axis direction. However, because cylindrical lens 64 has no optical power in the x-axis, movement of lens 64 in the x-axis does not substantially change the desired beam characteristics after the real time alignment of the lens 64 relative to the laser diode 14.

Cylindrical lens 64 may be positioned at any suitable distance from the laser emitting edge/surface 256. In one example embodiment, lens 64 is positioned about 260 um from the laser emitting edge/surface 256.

In some embodiments, radiation engine 12 formed or configured as discussed above may provide one or more advantages, as compared to certain known radiation engines. For example, using a single structure (heat sink 36) for cooling, alignment, and lens mounting features may be advantageous, e.g., for structural integrity, heat transfer, compactness, reducing the number of components, and/or reducing costs. As another example, the radiation engine 12 discussed above may minimize or reduce the required machining of parts. As another example, the radiation engine 12 discussed above may not require tight tolerances on lens support structures 270 and 272. As another example, the radiation engine 12 discussed above may allow for epoxy shrinkage without significantly affecting the resulting beam characteristics. As another example, the radiation engine 12 discussed above may allow for ease of adhesive application on either the lens or lens mounting features.

FIG. 34 illustrate another example configuration of a radiation engine 12. In this embodiment, laser package 250 and fast axis optic 64 are positioned within a recess 282 defined in heat sink 36. This may allow similar and/or additional benefits than the embodiment shown in FIG. 35, such as further reduction in number of components or greater structural integrity, among others. The embodiment of FIG. 34 also includes a pair of metal connector 267 between printed circuit board 258 and laser package 250 to provide an electrical path through laser diode 14. Each connector 267 may be mechanically-loaded to make good contact with the relevant portions of laser package 250 (e.g., using springs, flexures, bent tabs, etc.). This may provide a number of advantages included not requiring a soldered connection, connectors, pigtails, or flying leads.

Figure 35A:
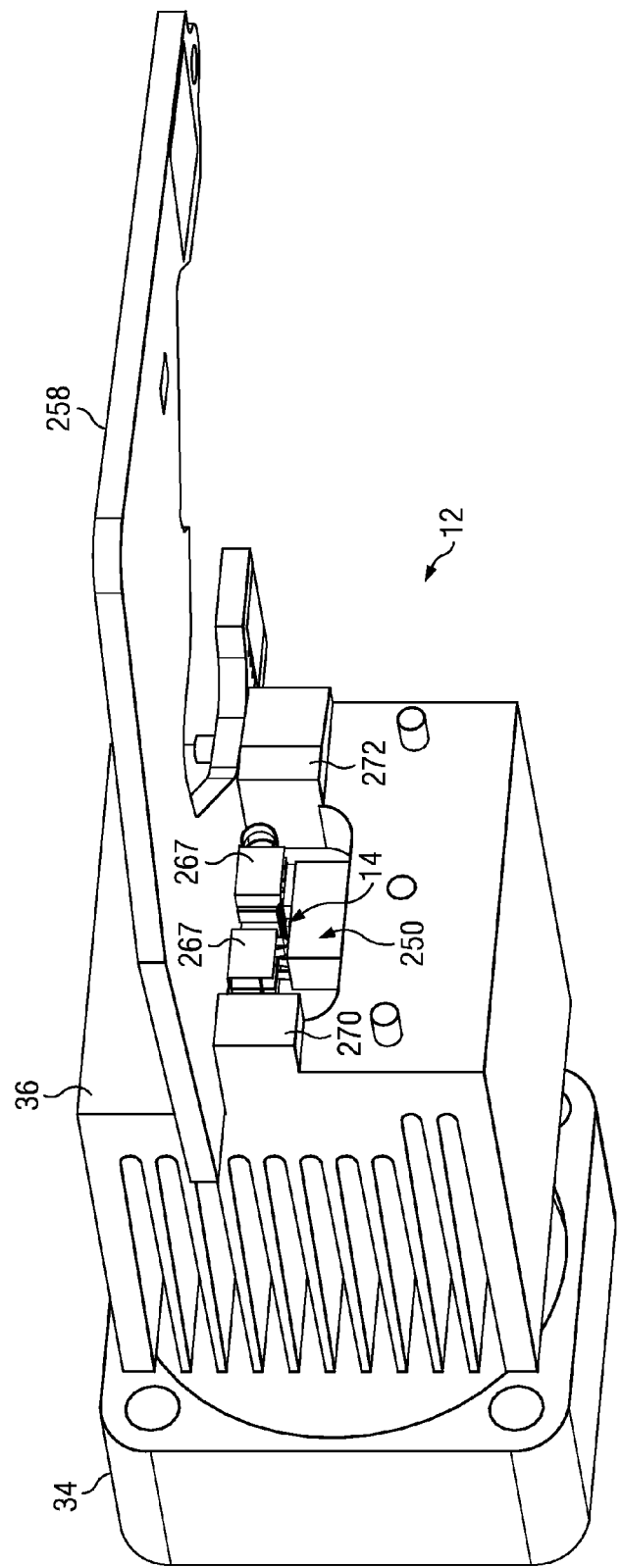
FIGS. 35A and 35B illustrate a third example embodiment of a radiation engine for use in a radiation-beam treatment device, according to certain embodiments.
Figure 35B:
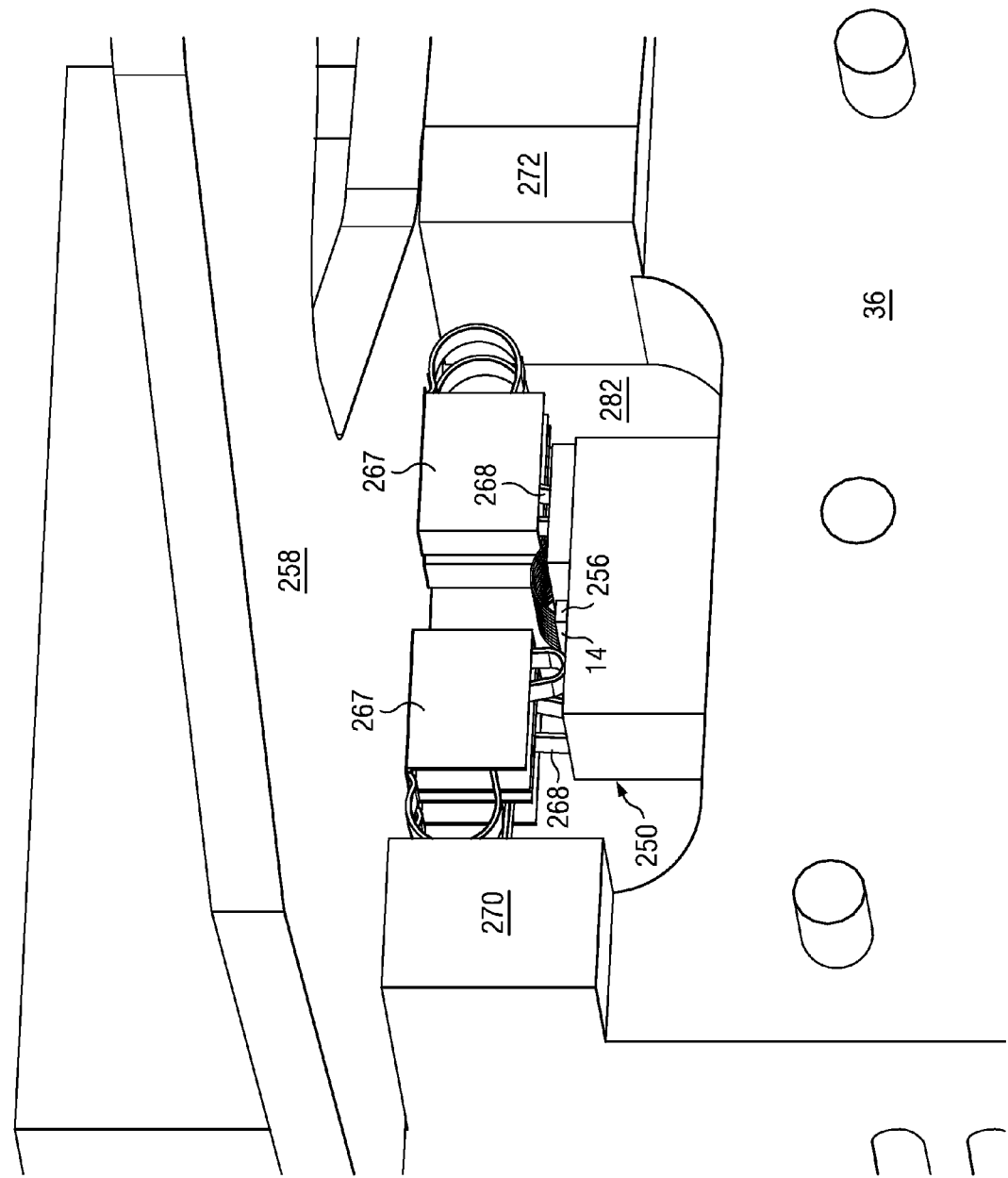

FIGS. 35A and 35B illustrate another example configuration of a radiation engine 12. FIG. 35A shows a full view of radiation engine 12, while FIG. 35B is a zoomed-in view of the arrangement of laser package 250. Similar to the embodiment of FIG. 34, in this embodiment, laser package 250 and fast axis optic 64 are positioned within a recess 282 defined in heat sink 36. Laser package 250 is secured to heat sink 36 by a pair of connection elements 267 extending from a bottom surface of printed circuit board 258, to provide an electrical path between PCB 258 and laser diode 14. Each connection element 267 includes a mechanically-loaded or spring-biased element 268 to ensure good contact with relevant contact portions of laser package 250, and to provide a downward securing force to secure laser package 250 to heat sink 36.

Figure 36A:
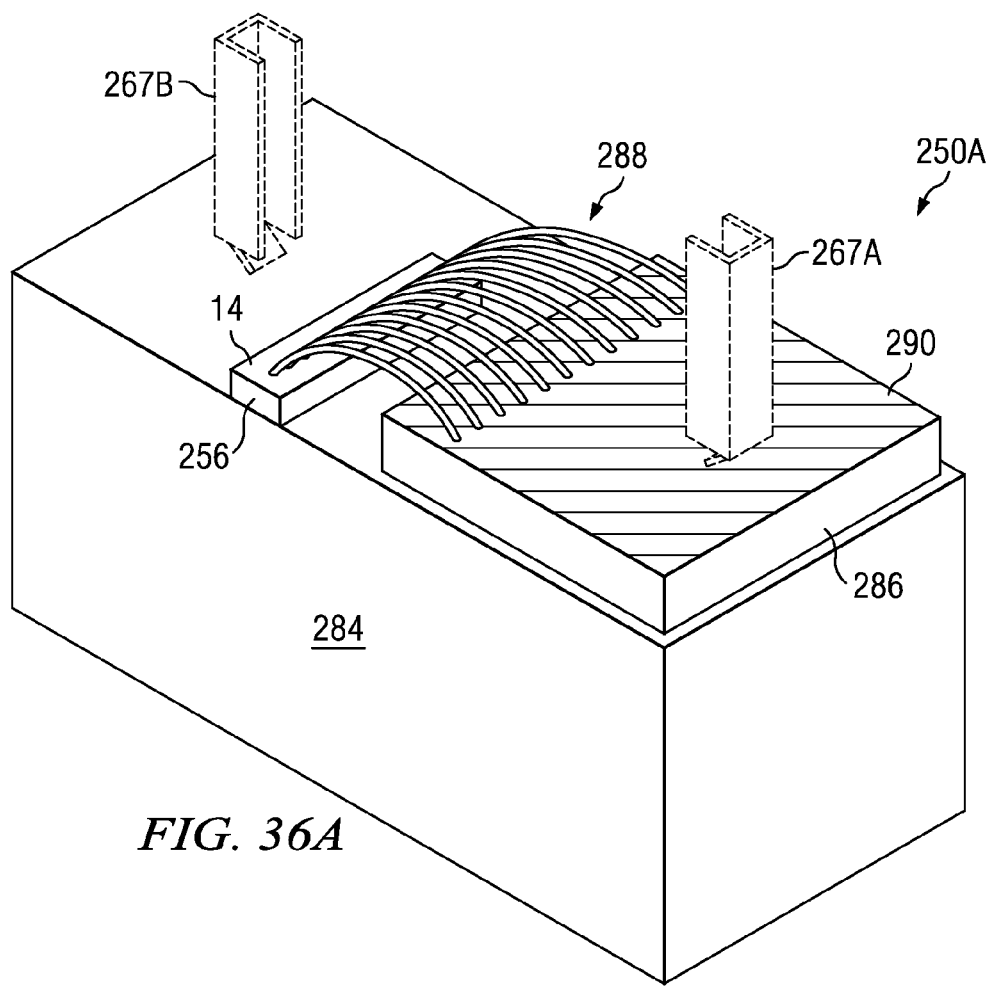
FIGS. 36A-36C illustrate a first example laser package for use in a radiation-beam treatment device, according to certain embodiments.
Figure 36B:
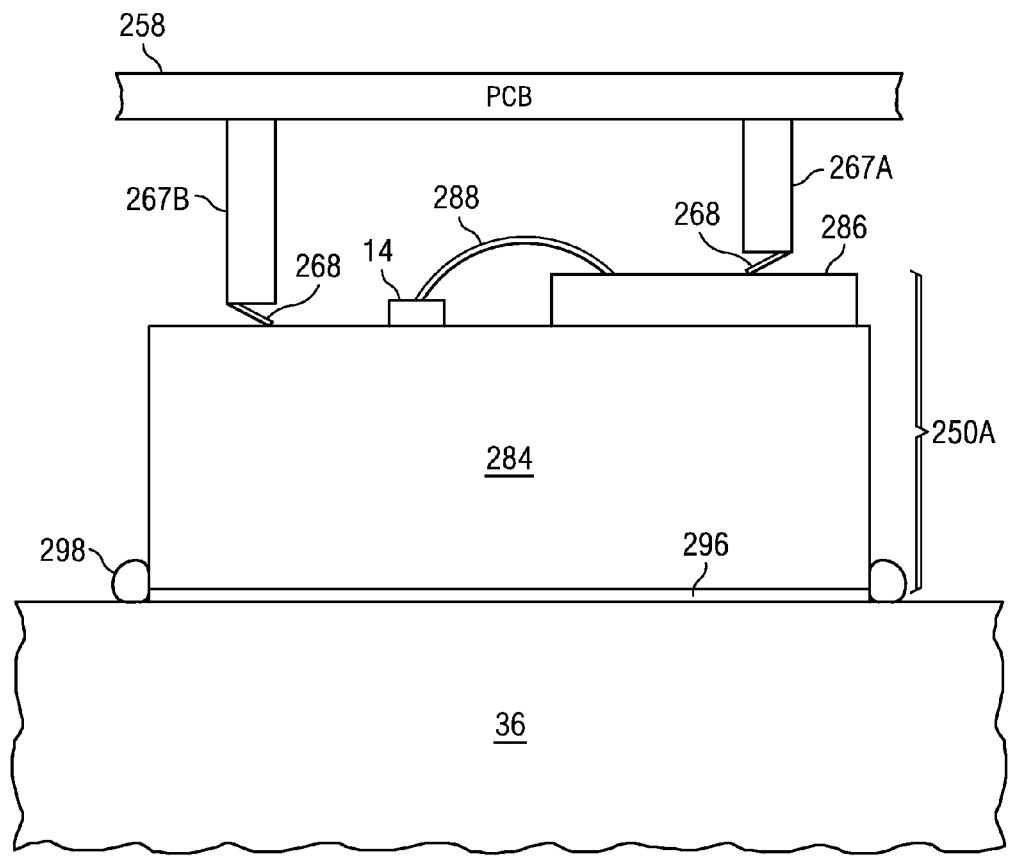
Figure 36C:
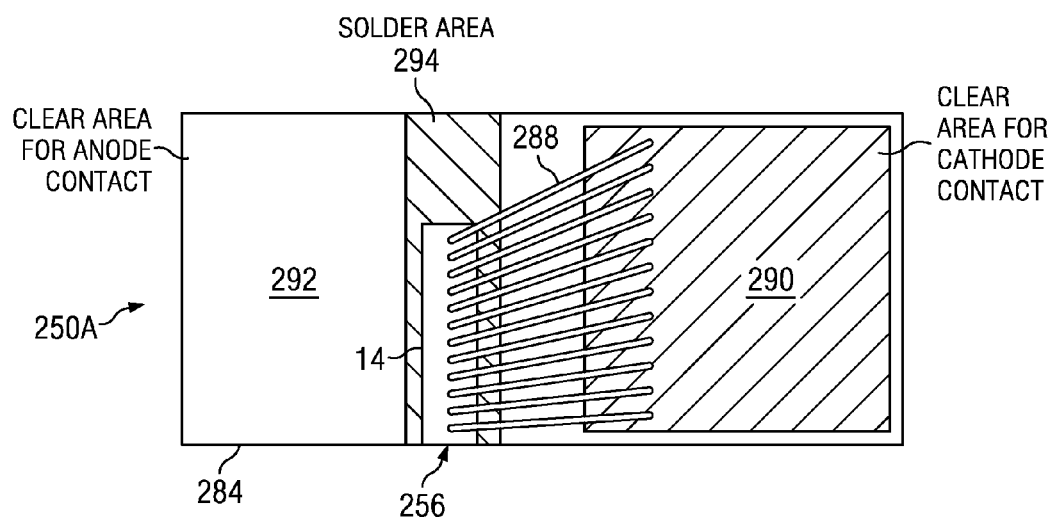
Figure 37:
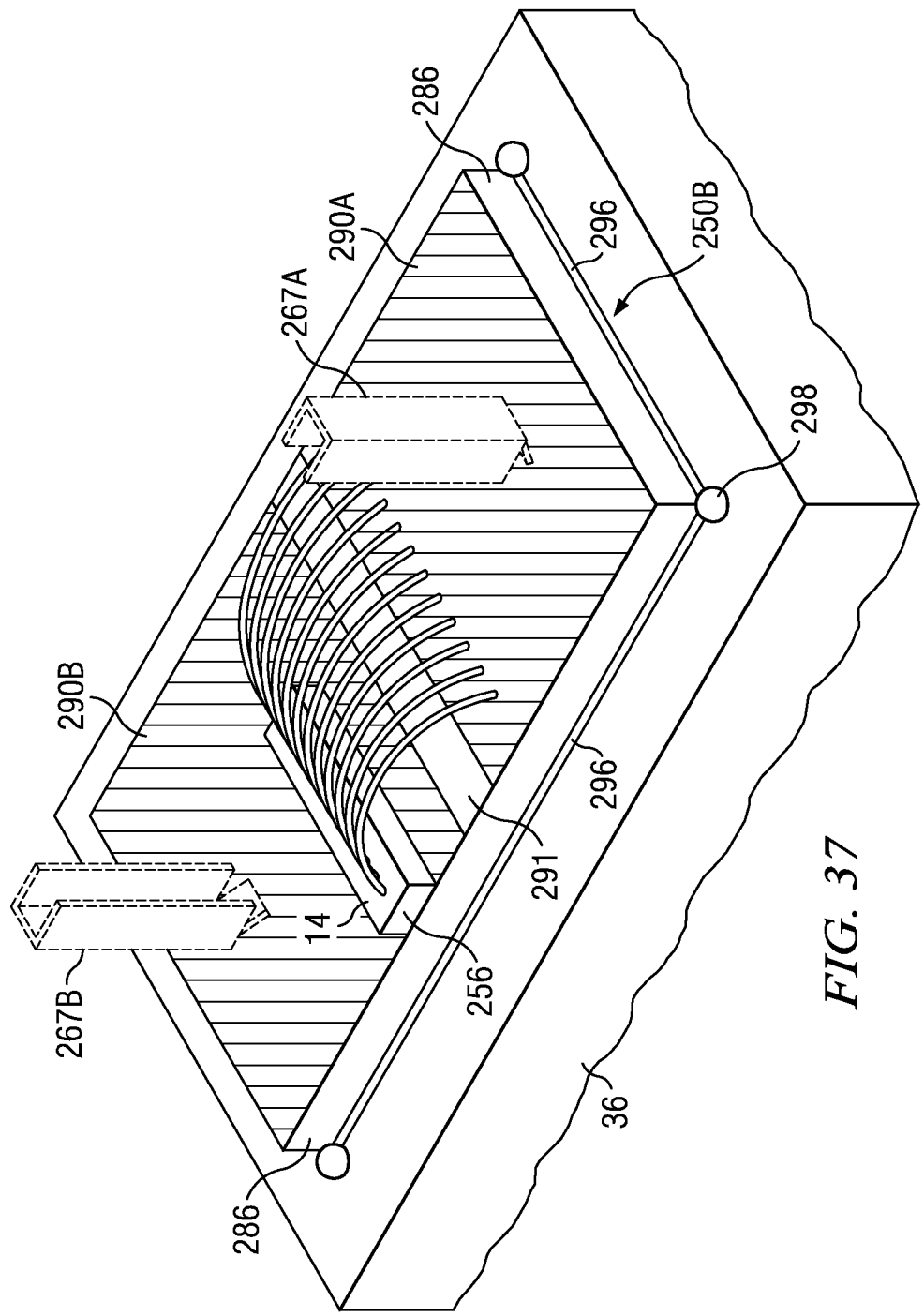
FIG. 37 illustrates a second example laser package for use in a radiation-beam treatment device, according to certain embodiments.

FIGS. 36A-36C illustrate one embodiment of a laser package 250A that may be used, e.g., in any of the example radiation engines 12 disclosed herein. As shown, laser package 250A includes a diode laser 14 mounted on a thermally and electrically conductive submount 284 (e.g., a copper block), which may be configured for mounting to heat sink 36. Laser package 250A also includes an electrically insulative contact pad 286 (e.g., formed from ceramic or other electrically insulative material) mounted to submount 284, which insulative contact pad 286 may include a metalized or otherwise electrically conductive top surface 290. Diode laser 14 may be electrically connected to the conductive top surface 290 of contact pad 286 by a number of connectors 288 (e.g., wire bonds).

Connection elements 267A and 267B may be provided to electrically couple laser package 250A (in particular, laser diode 14) to printed circuit board 258. In particular, connection element 267A may contact conductive top surface 290 of contact pad 286 (e.g., via a mechanically-loaded or spring-biased element 268) and connection element 267B may contact a top surface of conductive submount 284 (e.g., via a mechanically-loaded or spring-biased element 268), thus establishing a conductive path from PCB 258 through connection element 267A, conductive surface 290, connectors (e.g., wire bonds) 288, laser diode 14, conductive submount 284, connection element 267B, and back to PCB 258.

Submount 284 may be coupled to heat sink 36 either directly, or using thermal interface material 296 (e.g., thermal grease), to promote heat transfer into heat sink 36. Submount 284 may be secured to heat sink 36 in any suitable manner, e.g., via UV-cured epoxy 298.

FIG. 37 illustrates another example embodiment of a laser package 250B that may be used, e.g., in any of the example radiation engines 12 disclosed herein. As shown, laser package 250B includes a diode laser 14 mounted on an electrically insulative contact pad 286 (e.g., formed from ceramic or other electrically insulative material), which is in turn mounted to heat sink 36. A top surface of electrically insulative contact pad 286 includes first and second conductive area 290A and 290B having a metalized or otherwise electrically conductive top coating or surface, which are separated from each other by a non-conductive area 291 that is not metalized or otherwise electrically conductive. As shown, conductive connectors (e.g., wire bonds) 288 connect first conductive area 290A with laser diode 14, which is mounted on second conductive area 290B.

Connection elements 267A and 267B may be provided to electrically couple laser package 250A (in particular, laser diode 14) to a printed circuit board 258. In particular, connection element 267A may contact first conductive area 290A on the top surface of contact pad 286 (e.g., via a mechanically-loaded or spring-biased element 268) and connection element 267B may contact second conductive area 290B on the top surface of contact pad 286 (e.g., via a mechanically-loaded or spring-biased element 268), thus establishing a conductive path from PCB 258 through connection element 267A, first conductive area 290A, connectors (e.g., wire bonds) 288, laser diode 14, second conductive area 290B, connection element 267B, and back to PCB 258.

Contact pad 286 may be coupled to heat sink 36 either directly, or using thermal interface material 296 (e.g., thermal grease) to promote heat transfer into heat sink 36. Contact pad 286 may be secured to heat sink 36 in any suitable manner, e.g., via UV-cured epoxy 298.

Displacement-Based Control

As discussed above regarding FIG. 1, device 10 may include control system 18 configured to control various controllable operational parameters of device 10 (e.g., operational aspects of radiation source 14, scanning system 48, etc.). In some embodiments, control system 18 may include a displacement-based control system 132 configured to determine the displacement of device 10 relative to the skin as device 10 is moved across the surface of the skin (e.g., while operating device 10 in a gliding mode or a stamping mode), and control one or more controllable operational parameters of device 10 based on the determined displacement of device 10. For example, displacement-based control system 132 may control the one or more operational aspects radiation source(s) 14, such as for example, controlling the radiation mode of radiation source(s) 14, controlling the on/off status of radiation source(s) 14, controlling the timing of such on/off status (e.g., pulse trigger delay, pulse duration, pulse duty cycle, pulse frequency, temporal pulse pattern, etc.), controlling parameters of the radiation (e.g., wavelength, intensity, power, fluence, etc.), controlling parameters of optics 16, controlling parameters of beam scanning system 48 (e.g., controlling the on/off status, rotational speed, direction of rotation, or other parameters of motor 120), and/or any other controllable operational parameters of device 10.

In some embodiments, displacement-based control system 132 may also provide feedback to the user via a display 32 and/or one or more other user interfaces 28 based on (a) the monitored displacement of device 10 and/or (b) the automatic control of one or more controllable operational parameters by system 132. For example, system 132 may provide audio, visual, and/or tactile feedback to the user indicating data detected, or actions taken, by system 132, e.g., feedback indicating whether or not the displacement of device 10 exceeds a predetermined threshold distance, feedback indicating that treatment radiation source 14 or scanning system 48 (e.g., motor 120) has been turned on or off, feedback indicating that system 132 has automatically changed the radiation mode or other parameter of treatment radiation source 14, etc.

Displacement-based control system 132 may include, utilize, or otherwise cooperate with or communicate with any one or more of the control subsystems 52 discussed above with respect to FIG. 2 (e.g., radiation source control system 128, scanning system control system 132, usability control system 133, and user interface control system 134, including user interface sensor control subsystem 140 and user input/feedback control subsystem 142), as well as control electronics 30, any one or more sensors 26, user interfaces 28, and displays 32.

Figure 38:
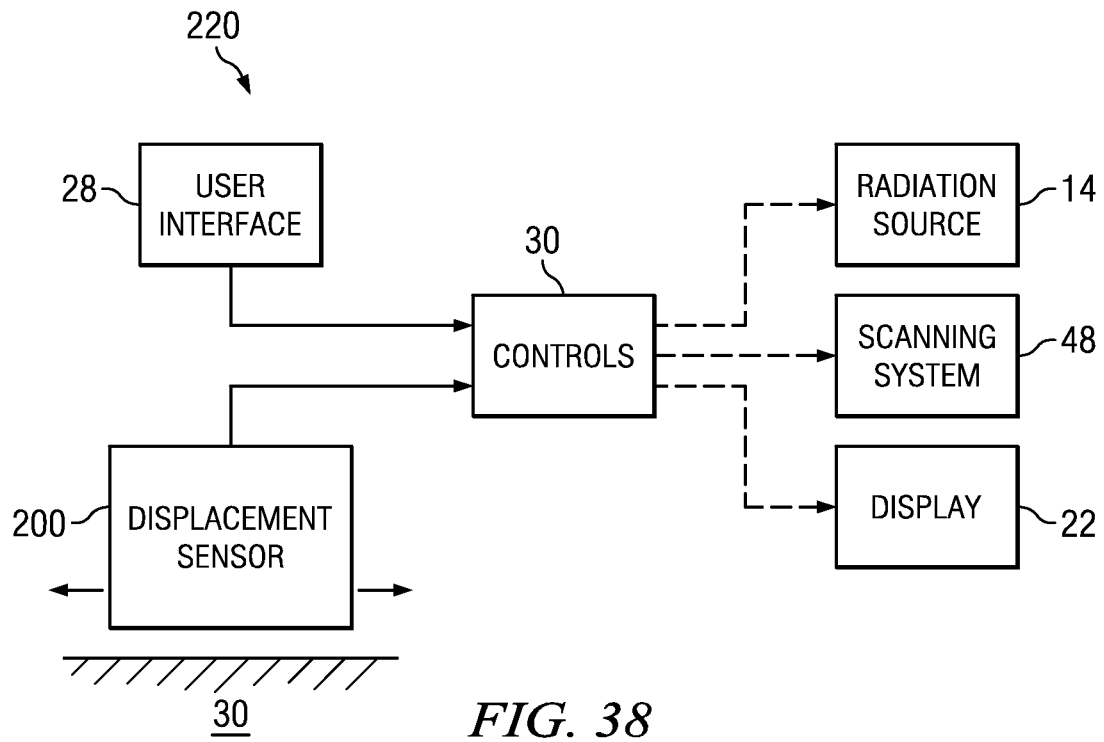
FIG. 38 illustrates a block diagram of an example displacement-based control system for a scanned-beam treatment device, according to certain embodiments.

FIG. 38 illustrates a block diagram of a displacement-based control system 132, according to certain embodiments. As shown, displacement-based control system 132 includes a displacement sensor 200, control electronics 30, and one or more of: treatment radiation source 14, scanning system 48, and display 32. In discussing various radiation-based sensors 26, radiation source 14 is referred to as "treatment radiation source 14" to distinguish from any radiation source of the particular sensor 26. In general, displacement sensor 200 collects data regarding the displacement of device 10 relative to the skin 40 and communicates such data to control electronics 30, which analyzes the data and controls or provides feedback via one or more of treatment radiation source 14, scanning system 48, and display 32. In some embodiments, control electronics 30 may also analyze particular user input received via one or more user interfaces 28 in conjunction with data received from sensor 200. For example, the appropriate control or feedback provided by control electronics 30 (e.g., as defined by a relevant algorithm 148) may depend on the current operational mode and/or other settings selected by the user. For instance, the minimum threshold displacement for triggering particular responses by control electronics 30 may depend on the current operational mode selected by the user.

Control electronics 30 may include any suitable logic instructions or algorithms 154 stored in memory 152 and executable by one or more processors 150 (e.g., as discussed above regarding FIG. 2) for performing the various functions of displacement-based control system 132. Displacement sensor 200 may be configured for detecting, measuring, and/or calculating the displacement of device 10 relative to the skin 40, or for generating and communicating signals to control electronics 30 for determining the displacement of device 10. In some embodiments, e.g., as discussed below with reference to FIGS. 40-43, displacement sensor 200 may be a single-pixel sensor configured to identify and count intrinsic skin features in the skin, and determine a displacement of the device 10 across the skin based on the number of identified intrinsic skin features. As used herein, "intrinsic skin features" include both (a) surface features of the skin, e.g., textural roughness, follicles, and wrinkles, and (b) sub-surface features, e.g., vascularity and pigmentation features.

In other embodiments, e.g., as discussed below with reference to FIG. 45, displacement sensor 200 may be a multiple-pixel sensor, such as a mouse-type optical sensor utilizing a two-dimensional array of pixels.

Depending on the particular embodiment, displacement sensor 200 (or a combination of multiple displacement sensors 200) may be used for (i) detecting, measuring, and/or calculating displacements of device 10 in one or more directions, or (ii) detecting, measuring, and/or calculating the degree of rotation traveled by device 10 in one or more rotational directions, or (iii) any combination thereof.

Displacement-based control system 132, and in particular control electronics 30, may control one or more controllable operational parameters of device 10 (e.g., operational aspects of treatment radiation source 14, fans 34, displays 32, etc.) to achieve any of a variety of goals. For example, control electronics 30 may control treatment radiation source 14 and/or scanning system 48 (a) in order to avoid overtreatment of the same area of skin, (b) to provide desired spacing between adjacent or sequential treatment spots 70 or arrays of spots 70, (c) to generate a relatively uniform pattern, or other desired pattern, of treatment spots 70, (d) to restrict the delivery of radiation to particular tissue, such as human skin (i.e., to avoid delivering radiation to eye or to other non-skin surfaces), (e) and/or for any other suitable goals, and (f) and combination of the above.

In some embodiments, displacement-based control system 132 may be used in both a gliding mode and a stamping mode of device 10.

Figure 39:
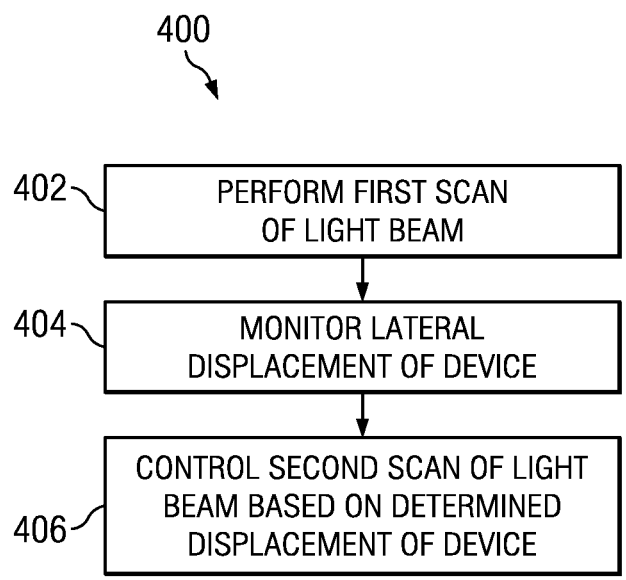
FIG. 39 illustrates a flowchart of an example method for controlling a device using a displacement-based control system, while the device is used either in a gliding mode or a stamping mode, according to certain embodiments.

FIG. 39 illustrates a flowchart of an example method 400 for controlling device 10 using displacement-based control system 132, while device 10 is used either in a gliding mode or a stamping mode, according to certain embodiments. At step 402, device 10 performs a first scan of input beam 110 to generate a first array (e.g., a row) of treatment spots onto the skin 40. If device 10 is being used in a gliding mode, the user may glide device 10 across the skin while the first array of treatment spots is generated. If device 10 is being used in a stamping mode, the user may hold device 10 stationary on the skin while the first array of treatment spots is generated. Although the scan as step 402 is called the "first" scan in this description, it should be understood that method 400 is a continuously repeating or looping process during a treatment session, and thus the "first" scan may be any particular scan during the treatment session (e.g., the $37^{th}$ scan during the process).

At step 404, displacement-based control system 132 performs a first monitoring process to monitor and analyze the displacement of device 10 across the surface of the skin using displacement sensor 200. For example, as discussed below, displacement-based control system 132 may analyze signal 360 to identify and count surface features 74 in the skin (e.g., in embodiments utilizing a single-pixel displacement sensor 200 (e.g., sensors 200A, 200B, or 200C discussed below)), or compare images scanned at different times (in embodiments utilizing a multi-pixel displacement sensor 200 (e.g., sensor 200D discussed below)), as device 10 is moved across the skin (e.g., in a gliding mode, during and/or after the generation of the first array of treatment spots; or in a stamping mode, after the generation of the first array of treatment spots). System 130 may begin the first monitoring process at the initiation of the first scan or upon any other predefined event or at any predetermined time.

At step 406, displacement-based control system 132 controls a second scan of input beam 110 (for generating a second array of treatment spots onto the skin 40) based on the displacement of device 10 determined in the at step 404 (i.e., during the first monitoring process). For example, displacement-based control system 132 may initiate the second scan only after system 130 determines at step 404 that device 10 has moved more than a predetermined minimum distance across the skin (e.g., 1 mm). Thus, in such embodiments, a minimum spacing in the glide direction (e.g., 1 mm) between corresponding treatment spots 70 of adjacent rows 72 can be achieved regardless of the manual glide speed.

Single Pixel Displacement Sensor

Figure 40A:
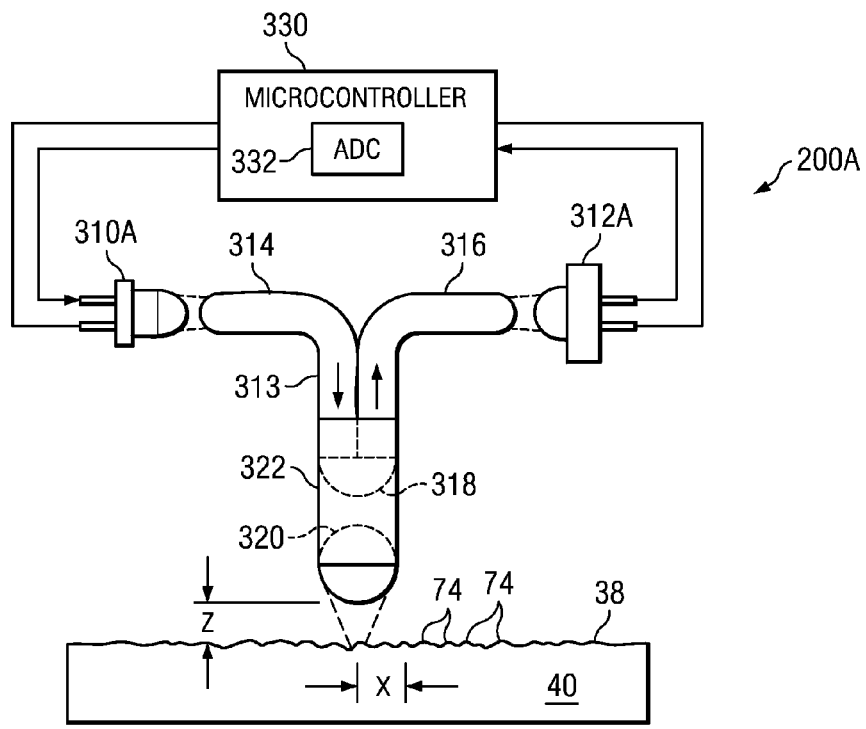
FIG. 40A illustrates a first example single-pixel displacement sensor for use in a displacement-based control system, according to certain embodiments.

FIG. 40A illustrates an example single-pixel displacement sensor 200A for use in displacement-based control system 132, according to certain embodiments. Displacement sensor 200A includes a light source 310A, a light detector 312A, a light guide 313 having an input and output portions 314 and 316, a half-ball lens 318, a ball lens 320, a housing 322 for housing at least lenses 318 and 320 (and/or other components of sensor 200A), and a and a microcontroller 330.

Light source 310A may be a light-emitting diode (LED) or any other suitable light source. Light source 310A may be selected for detecting fine details in the surface or volume of human skin. Thus, a wavelength may be selected that penetrates a relatively shallow depth into the skin before being reflected. For example, light source 310A may be a blue LED having a wavelength of about 560 nm, or a red LED having a wavelength of about 660 nm, or an infrared LED having a wavelength of about 940 nm. Red or infrared wavelength LEDs are relatively inexpensive and work well in practice. Alternatively, a semiconductor laser or other light source could be used.

Light detector 312A may be a photodiode, phototransistor, or other light detector. In some embodiments, a phototransistor has sufficient current gain to provide a directly usable signal, without requiring additional amplification.

Light guide 313 is configured to guide light from light source 310A (via input portion 314) and guide light reflected off the skin to detector 312A (via output portion 316). Input portion 314 and output portion 316 may comprises optical fibers or any other suitable light guides. Light guide 313 may be omitted in some embodiments in which light source 310A and detector 312A are close enough to the skin surface to image or convey the light directly onto the skin surface, or alternatively using suitable optics to image or convey light source 310A and detector 312A directly onto the skin surface.

Microcontroller 330 may be configured to drive light source 310A and receive and analyze signals from light detector 312A. Microcontroller 330 may include an analog-to-digital converter (ADC) 332 for converting and processing analog signals from light detector 312A.

In operation of this embodiment, light (for example, visible or near-IR energy) from light source 310A travels down input light guide 314 and through half-ball lens 318 and ball lens 320, which focuses the light on the skin surface 38. Some of this light is reflected and/or remitted by the skin and returns through ball lens 320, half-ball lens 318, and output light guide 316, toward light detector 312A, which converts the light into an electrical signal, which is then delivered to microcontroller 330. The light may be modulated to permit discrimination of a constant background ambient illumination level from the local light source.

Detector 312A may deliver analog signals to microcontroller 330, which may convert the signals to digital signals (using integrated ADC 332 or suitable alternatives), and perform computations regarding on the amplitude of the recorded signal over time to identify and count features in the skin and determine a relative displacement device 10 accordingly, as discussed below.

The amount of light that is returned to detector 312A is a strong function of the distance "z" between the sensor optics and skin surface 38. With no surface present only a very small signal is generated, which is caused by incidental scattered light from the optical surfaces. In addition to displacement sensor, this characteristic can be exploited to provide a contact sensor in another embodiment. When the skin surface 38 is within the focal distance of the lens 320, a much larger signal is detected. The signal amplitude is a function of distance z as well as surface reflectivity/remittance. Thus, surface texture features on the skin surface create a corresponding signal variation at detector 312A. Microcontroller 330 is programmed to analyze this signal and identify intrinsic skin features 74 that meet particular criteria. Microcontroller 330 may count identified features and determine an estimated displacement of sensor 200A relative to the skin 40 in the x-direction (i.e., lateral displacement), based on knowledge of estimated or average distances between intrinsic skin features 74 for people in general or for a particular group or demographic of people, as discussed below.

Displacement sensor 200A as described above may be referred to as a "single-pixel" displacement sensor 200A because it employs only a single reflected/remitted beam of light for generating a single signal 360, i.e., a single pixel. In other embodiments, displacement sensor 200 may be a multi-pixel sensor that employs two pixels (i.e., two reflected beams of light for generating two signals 360), three pixels, four pixels, or more. Multi-pixel displacement sensors 200 may be configured such that the multiple pixels are arranged along a single linear direction (e.g., along the glide direction, the scan direction, or any other direction), or in any suitable two-dimensional array (e.g., a circular, rectangular, hexagonal, or triangular pattern).

Figure 40B:
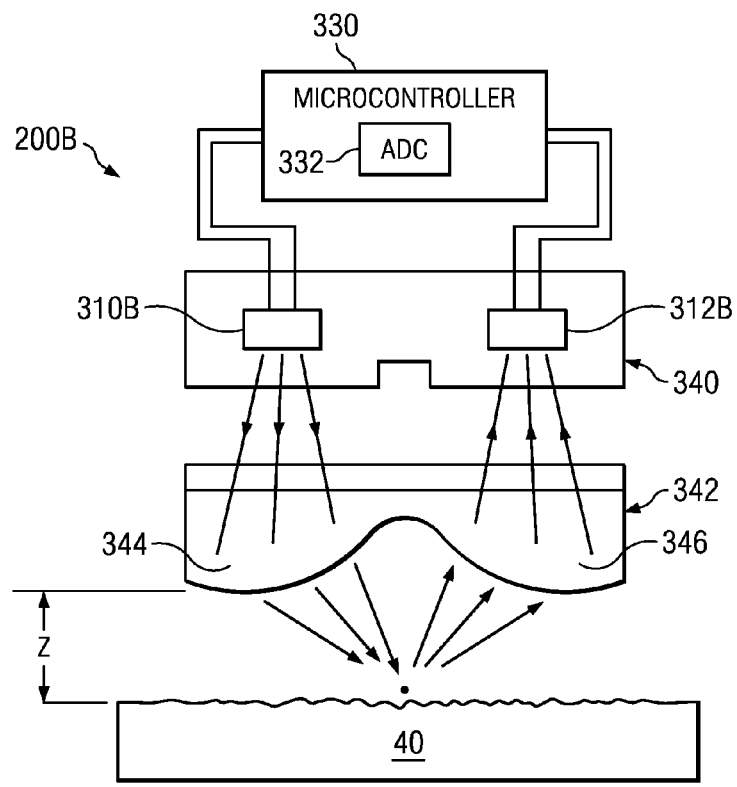
FIG. 40B illustrates a second example single-pixel displacement sensor for use in a displacement-based control system, according to certain embodiments.

FIG. 40B illustrates another example single-pixel displacement sensor 200B for use in displacement-based control system 132, according to certain embodiments. Displacement sensor 200B includes a light source 310B, a light detector 312B, optics 342, and a microcontroller 330.

Light source 310B and light detector 312B may be provided in an integrated emitter-detector package 340, e.g., an off-the-shelf sensor provided by Sharp Microelectronics, e.g., the Sharp GP2S60 Compact Reflective Photointerrupter. Light source 310B may be similar to light source 310A discussed above, e.g., a light-emitting diode (LED) or any other suitable light source. Light detector 312B may be similar to light source 310A discussed above, e.g., a photodiode, phototransistor, or other light detector.

Optics 342 may include one or more optical elements for directing light from light source 310B onto the target surface and for directing light reflected/remitted from the target surface toward light detector 312B. In some embodiments, optics 342 comprises a single lens element 342 including a source light focusing portion 344 and a reflected light focusing portion 346. As shown, source light focusing portion 344 may direct and focus light from light source 310B onto the skin surface 38, and reflected light focusing portion 346 may direct and focus reflected light onto detector 312B. Lens element 342 may have any suitable shape for directing and focusing the source light and reflected light as desired.

Microcontroller 330 may be configured to drive light source 310B and receive and analyze signals from light detector 312B. Microcontroller 330 may include an analog-to-digital converter (ADC) 332 for converting and processing analog signals from light detector 312B.

The operation of sensor 200B—including the operation of light detector 312B and microcontroller 330—may be similar to that described above with reference to sensor 200A of FIG. 40A. That is, detector 312B may record a signal having an amplitude or other property that corresponds to a distance z perpendicular to the target surface or other properties indicative of intrinsic skin features. Detector 312B may deliver analog signals to microcontroller 330, which may convert the signals to digital signals (using integrated ADC 332), and perform computations regarding the recorded signal over time to identify and count features in the skin and determine a relative displacement of device 10 accordingly.

Like displacement sensor 200A, displacement sensor 200B may be referred to as a "single-pixel" displacement sensor 200B because it employs only a single reflected beam of light for generating a single signal 360, i.e., a single pixel.

Figure 40C:
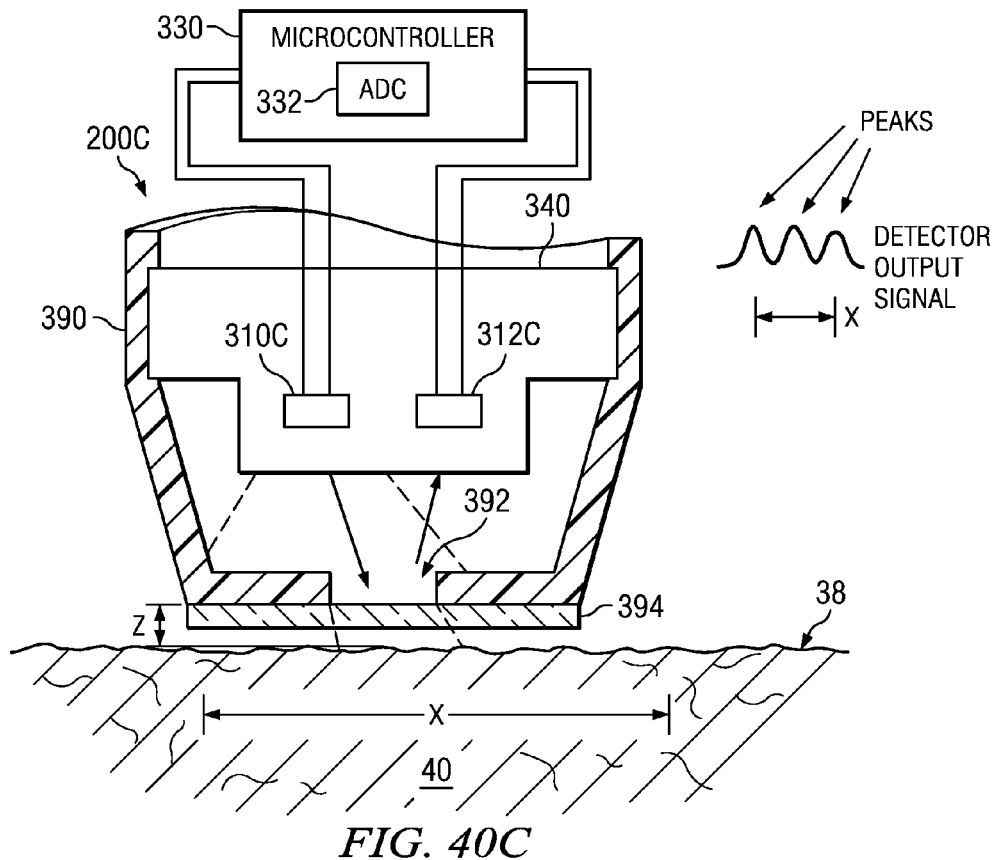
FIG. 40C illustrates a third example single-pixel displacement sensor for use in a displacement-based control system, according to certain embodiments.

FIG. 40C illustrates yet another example single-pixel displacement sensor 200C for use in displacement-based control system 132, according to certain embodiments. Displacement sensor 200C is generally similar to displacement sensor 200B shown in FIG. 40B, but omits the lens element 342 of displacement sensor 200B.

Displacement sensor 200C includes a light source 310C, a light detector 312C, and a microcontroller 330. Light source 310C and light detector 312C may be provided in an integrated emitter-detector package 340, e.g., an off-the-shelf sensor provided by Sharp Microelectronics, e.g., the Sharp GP2S60 Compact Reflective Photointerrupter, Light source 310C may be similar to light source 310A/310B discussed above, e.g., a light-emitting diode (LED) or any other suitable light source. Microcontroller 330 may be configured to drive light source 310C with a direct or modulated current. Light detector 312C may be similar to light source 310A discussed above, e.g., a photodiode, phototransistor, or other light detector.

The integrated (or non-integrated) emitter-detector package 340 may be housed in an opaque enclosure 390, having a clear aperture 392 in the front which is covered by a window 394 (for example a transparent plastic, or glass). Infrared light from light source 310C (e.g., LED) shines through the aperture 392 and impinges on the skin surface 38. Some of this light (reflected/remitted from the skin 40, as well as scattered from the interior volume of opaque enclosure 390, returns through aperture 392 and reaches detector 312C (e.g., photodetector), which converts the received light into an electrical signal. The light may be modulated to permit discrimination of a constant background ambient illumination level from the local light source.

The amount of light that is returned to detector 312C is a strong function of the distance "z" between the skin surface 38 and the optical aperture 392. When the skin surface 38 is close to or in contact with window 394, a larger signal is detected. With no surface presented to the detector, a smaller optical signal remains, due to reflections from the surface of opaque mask 390 and window 394, as well as background light from exterior illumination sources.

Thus, the signal amplitude recorded by detector 312C is a function of z-height as well as skin reflectivity/remittance. Surface texture features 74 create a corresponding signal variation at detector 312C. Detector 312C may deliver the recorded analog signals (with the amplitude being at least indicative of z-height) to microcontroller 330, which may convert the signals to digital signals (using integrated ADC 332), and perform computations regarding the recorded signal over time to identify features 74 in the skin (based on the signal amplitude), count or otherwise process such identified features 74, and determine a relative displacement of device 10 accordingly.

Integrated emitter-detector pairs used for the proximity detector may be compact, inexpensive, and readily available. It is also possible to use a separate emitter and detector. Any suitable wavelength range of light may be used, but infrared may be selected due to the sensitivity of the detector 312C (e.g., phototransistor), and ability to block out visible light with an IR-pass filter over the detector. Also, different skin types show more uniform reflectance levels in IR than in shorter wavelengths. Test results show that a phototransistor has sufficient current gain to provide a directly usable signal to the integrated ADC 332 of microcontroller 330, without requiring additional amplification.

Like displacement sensors 200A and 200B, displacement sensor 200C may be referred to as a "single-pixel" displacement sensor 200C because it employs only a single reflected beam of light for generating a single signal, i.e., a single pixel.

Figure 41:
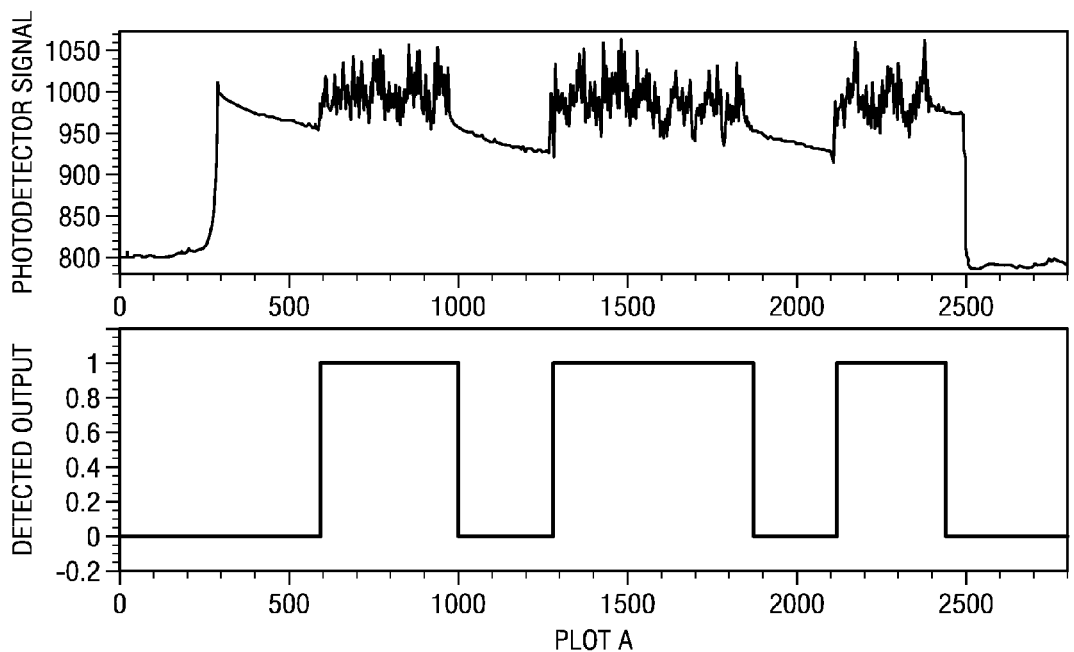
FIG. 41 illustrates a pair of experimental data plots for an embodiment of an optical displacement sensor being scanned above the skin surface of a human hand.

FIG. 41 illustrates a pair of experimental data plots for an embodiment of optical displacement sensor 200C being scanned above the skin surface 38 of a human hand. The photodetector signal (y-axis) is shown versus time (x-axis) in arbitrary units. The area without dense peaks indicates times in which the sensor aperture 392 is held against a fixed area of the skin. An algorithm takes as input the photodetector signal to generate the lower "detected output" plot, which is a signal suitable for controlling device 10. For example, microcontroller 330 may be programmed to analyze the photodetector signal and identify intrinsic skin features 74 that meet particular criteria, e.g., using any of the various techniques or algorithms disclosed herein, or any other suitable techniques or algorithms. In some embodiments, microcontroller 330 may count identified features and determine an estimated displacement of sensor 200C relative to the skin 40 in the x-direction (i.e., lateral displacement), based on knowledge of estimated or average distances between intrinsic skin features 74 for people in general or for a particular group or demographic of people, as discussed below.

Certain embodiments of single-pixel displacement sensor 200, e.g., sensors 200A, 200B, and/or 200C discussed above, may not require imaging optics, as compared to imaging-type sensors. Further, certain embodiments of single-pixel displacement sensor 200 may not require close proximity between the electronics (e.g., microcontroller) and the target surface to be sensed. For example, the light source and/or detector may be spaced away from the target surface, with light guides or relay optics used to convey light between the light source/detector and the target surface. As another example, the light source and/or detector may be spaced relative close to the target surface, but may be coupled to a relatively remote microcontroller by wiring.

Further, in certain embodiments of single-pixel displacement sensor 200, e.g., sensors 200A, 200B, and 200C discussed above, the active components (e.g., light source, detector, etc.) and the active sensing area are relatively small (e.g., as compared to a standard optical mouse-type imaging sensor). Thus, in embodiments in which single-pixel displacement sensor 200 is located at the application end 42 of device 10, sensor 200 may occupy relatively little real estate on the application end 42 (e.g., as compared to a standard optical mouse-type imaging sensor), which may allow the total size of application end 42 to be reduced in at least one dimension, which may be advantageous in certain embodiments.

Figure 42:
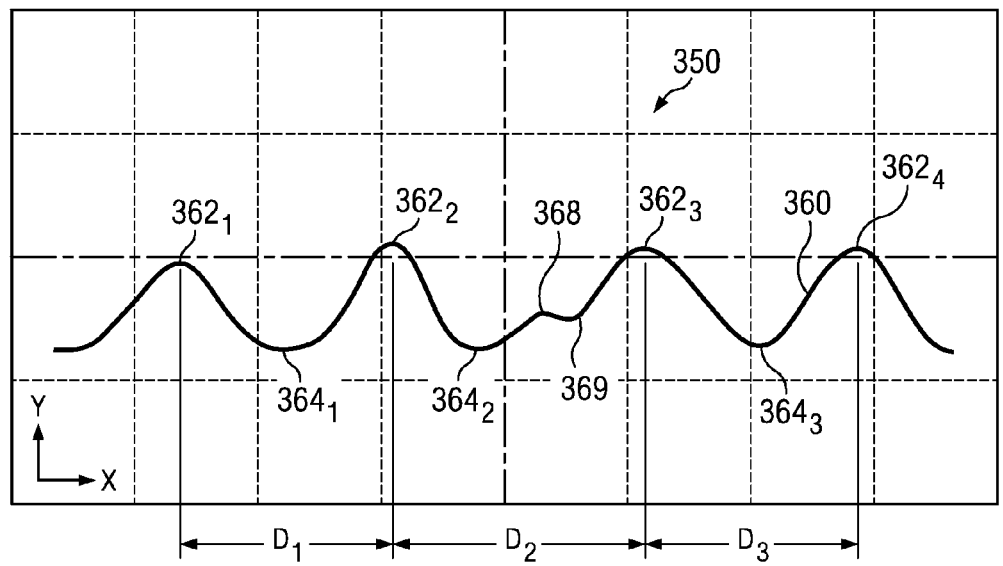
FIG. 42 represents an example plot of a signal generated by a detector as a displacement sensor is moved across the skin of a human hand.

FIG. 42 represents an example plot 350 of a signal 360 generated by detector 312A, 312B, or 312C as sensor 200A, 200B, or 200C is moved across the skin of a human hand in the x-direction. The x-axis of plot 350 may be scaled such that the movement of the signal 360 on the x-axis matches the distance of movement of sensor 200A/200B/200C across the skin.

The amplitude of the signal 360 corresponds with the texture of the skin surface, which includes numerous intrinsic skin features 74. As shown, signal 360 includes a series of peaks 362, valleys 364, and other characteristics. Intrinsic skin features 74 may be identified from signal 360 based on any suitable parameters or algorithms.

For example, one or more of the following criteria may be used for identifying intrinsic skin features 74 based on signal 360:

(a) the raw amplitude of a peak 362, (b) the amplitude of a peak 362 relative to the amplitude of one or more other peaks 362 (e.g., one or more adjacent peaks 362), (c) the amplitude of a peak 362 relative to the amplitude of one or more valleys 364 (e.g., one or more adjacent valleys 364), (d) the raw amplitude of a valley 364, (e) the amplitude of a valley 364 relative to the amplitude of one or more other valleys 364 (e.g., one or more adjacent valleys 364), (f) the amplitude of a valley 364 relative to the amplitude of one or more valleys 364 (e.g., one or more adjacent valleys 364), (g) the rate of increase in amplitude of signal 362 (i.e., positive slope of signal 360) for a particular portion of signal 360, (h) the rate of decrease in amplitude of signal 360 (i.e., negative slope of signal 360) for a particular portion of signal 362, (i) the x-direction distance between adjacent peaks 362 ($D_1$, $D_2$, $D_3$, etc), (j) the x-direction distance between adjacent valleys 364, or (k) any other suitable criteria.

An algorithm 154 may identify intrinsic skin features 74 based on any one or any combination of more than one of the criteria listed above. Such algorithm 154 may include (predefined or real-time calculated) threshold values to which one or more of the criteria listed above are compared. In some embodiments that identify intrinsic skin features 74 based on peaks 362 in signal 360, the algorithm 154 may be able to distinguish major or global peaks (e.g., peaks 362) from minor or local peaks (e.g., local peak 368), and use only the major or global peaks 362 for identifying intrinsic skin features 74. As another example, the algorithm 154 may distinguish major or global valleys (e.g., valleys 364) from minor or local valleys (e.g., local valley 369), and use only the major or global valleys 364 for identifying intrinsic skin features 74.

Figure 43:
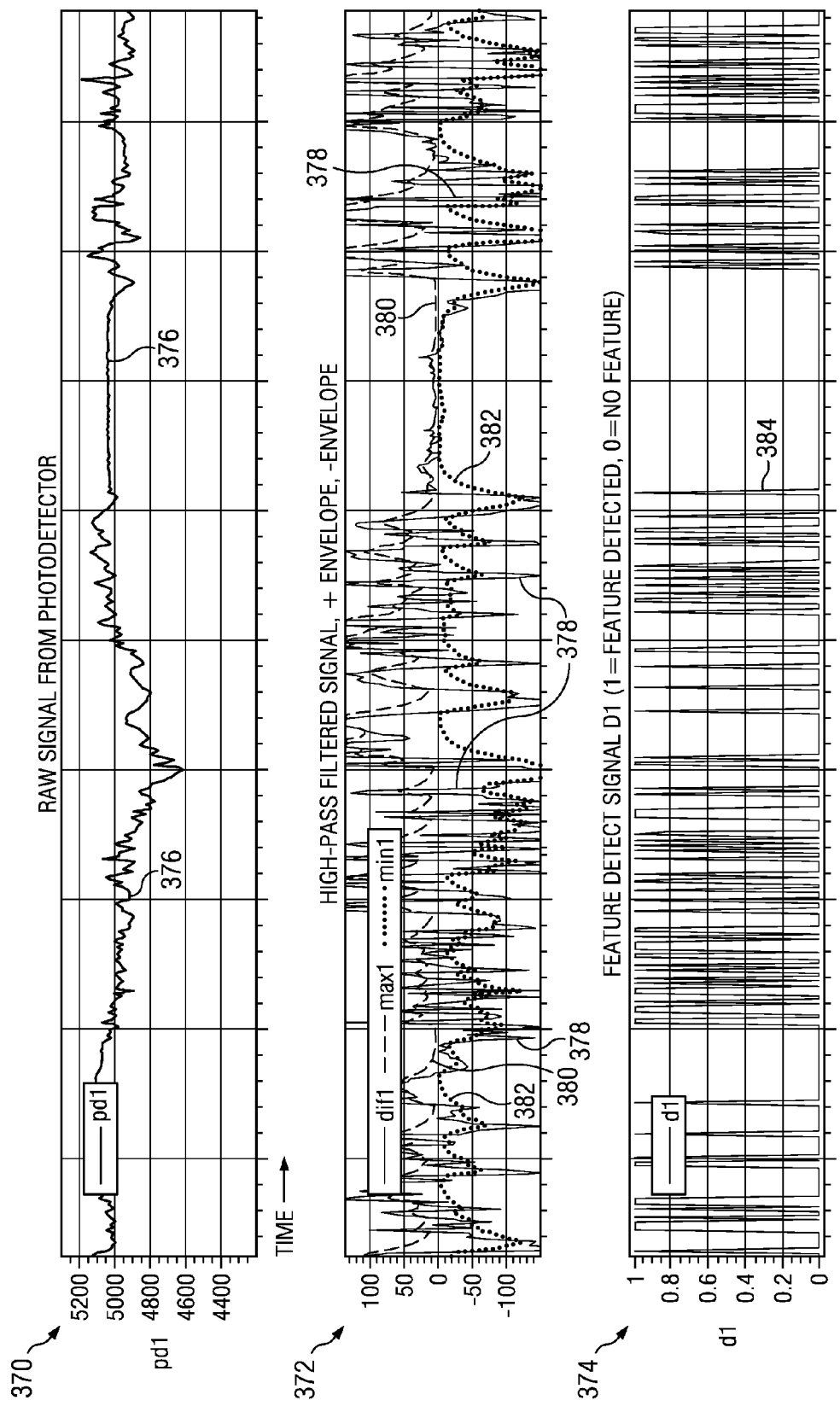
FIG. 43 illustrates three data plots: a raw signal plot, filtered signal plot, and a intrinsic skin feature detection plot, for detecting skin features based on signals from a displacement sensor, according to certain embodiments.

One example displacement algorithm that may be used with a single-pixel displacement sensor (e.g., sensor 200A, 200B, or 200C) to identify intrinsic skin features 74, and detect displacement of device 10, is discussed below with reference to FIG. 43. FIG. 43 illustrates three data plots: a raw signal plot 370, filtered signal plot 372, and an intrinsic skin feature detection plot 374. The example displacement algorithm takes as input a raw signal from a photodetector (representing reflectance/remittance vs. time), and generates as output a digital pulse "1" when a displacement has been detected, and "0" when no displacement has been detected. In FIG. 43, each plot 370, 372, and 374 shows the specified signals plotted against time on the horizontal axis.

Raw signal plot 370 shows the raw input signal "pd1" 376, which includes amplitude variations corresponding to displacement of the sensor across the skin (the amplitude variations correspond to intrinsic skin features 74 on the skin), and flatter areas corresponding to the sensor dwelling in the same place on the skin.

As shown in filtered signal plot 372, the algorithm extracts a high-pass filtered version "diff1" 378 of the raw signal pd1 and also a positive-tracking and negative-tracking envelope indicated as "max1" 380 and "min1" 382, respectively. The positive envelope "max1" 380 is created at each point in time by adding a fraction of the current high-pass-filtered positive signal "dif1$p$" to the previous time-step value of the positive envelope signal "max1", where "dif1$p$" is formed from the high-pass filtered signal "dif1":

$$dif1p = dif1(dif1 > 0)$$

$$dif1p = 0(dif1 <= 0)$$

Similarly, the negative envelope "min1" 382 is created the same way from "dif1$n$", which is the high-pass filtered negative signal:

$$dif1n = dif1(dif1 < 0)$$

$$dif1n = 0(dif1 >= 0)$$

Finally, as shown in the intrinsic skin feature detection plot 374, the feature-detect signal "d1" 384 is set to 1 at any time step in which "dif1" has a zero crossing (i.e., where previous time step and current time step have a different sign) AND "max1" exceeds a threshold value, AND "min1" exceeds a threshold value. Otherwise, "d1" is set to 0. The threshold limits may be designed to prevent non-desirable outputs (e.g., feature-detection false positives and/or false negatives) due to random sensor or circuit noise levels. The zero-crossing requirement may also be designed to prevent non-desirable outputs (e.g., feature-detection false positives and/or false negatives) when the photosignal dif1 is entirely positive or negative, as when the photosensor is initially brought up against a surface (signal shows large increase with time), or removed from it (signal decreases).

From feature detection plot 374, the displacement of the sensor relative to the skin can be determined by counting the number of detected features 74. The algorithm may then make control decisions by (a) comparing the number of detected features 74 to one or more predetermined threshold numbers (e.g., allow continued treatment if at least three features 74 have been detected), or (b) by multiplying the number of detected features 74 by a known nominal or average distance between features 74 (e.g., as determined based on experimental testing) to determine displacement distance (e.g., in millimeters), and then comparing the determined displacement distance to one or more predetermined threshold distances (e.g., allow continued treatment if the determined displacement exceeds 2 mm). It can be appreciated by one of ordinary skill in the art that, if desired, this embodiment could also be used to create a velocity sensor if rate information was also obtained and used or a dwell sensor.

In some embodiments, the example algorithm may be utilized in a system including a single sensor (e.g., single-pixel displacement sensor 200A, 200B, or 200C) having a single detector (e.g., detector 312A or 312B). In other embodiments, the example algorithm may be utilized in a system with more than one sensors (e.g., more than one sensor 200A, 200B, and/or 200C) or with a sensor 200 that includes more than one detector 312 (e.g., a sensor 200A, 200B, or 200C including more than one detector 312A, 312B, or 312C). Such embodiments may thus generate multiple feature detection signals 384, each corresponding to a different sensor 200 or detector 312 with the same type of features detected or different types of features detected.

In embodiments including multiple sensors 200 or detectors 312, the algorithm may make control decisions based on the multiple feature detection signals 384 in any suitable manner. For example, the algorithm may generate a control signal only if each of the multiple feature detection signals 384 detects a predetermined number of features 74 (which may provide relatively greater resistance to noise or possible fault conditions). Or, the algorithm may generate a control signal if any of the multiple feature detection signals 384 detects a predetermined number of features 74 (which may provide relatively greater detection sensitive for surfaces with less texture and smaller amplitude reflectance features). Or, the algorithm may generate control signals based on the total number of features 74 detected by the multiple feature detection signals 384. The algorithm can also be designed to the identify an outlier feature detection signal 384 (as compared to the other feature detection signal 384), and ignore such signal 384, at least while it remains an outlier.

A sample of humans was tested with a particular embodiment of sensor 200A, and identifying intrinsic skin features 74 according to the example algorithms discussed above. The testing involved moving sensor 200A in a straight line across the surface of the test subjects' skin, such as face or arm skin. The resulting test data using the particular embodiment of sensor 200A indicated that adjacent intrinsic skin features 74 (texture or roughness, in this case) are located about 0.3-0.4 mm apart on average. In other words, with reference to FIG. 42, the test data indicated an average spacing $D_1$, $D_2$, $D_3$, etc. of about 0.3-0.4 mm.

The displacement of device 10 can be determined or approximated using this experimental data, e.g., the average spacing between intrinsic skin features 74. For example, the displacement of device 10 can be determined or approximated by multiplying the number of intrinsic skin features 74 identified by system 132 by the experimentally determined average spacing between intrinsic skin features 74.

Thus, displacement-based control system 132 (e.g. by cooperation with radiation source control system 128 and/or scanning system control system 130) may control device 10 based on the determined or approximated displacement of device 10 across the skin. For example, displacement-based control system 132 may control one or more controllable operational parameters of device 10 (e.g., operational aspects of treatment radiation source 14 and/or scanning system 48) based on the number of surface features 74 identified by system 132 for a displacement of device 10 across the skin. For example, system 132 may control device 10 to deliver one scanned array of beams 114 each time device 10 is displaced X mm, as determined by identifying N surface features 74. For example, if experimental data indicates that surface features 74 are spaced by an average of 0.4 mm, system 132 may control device 10 to deliver one scanned array of treatment spots each time device 10 is displaced approximately 1.2 mm, as determined by identifying three surface features 74; the next scanned array of beams 114 is not delivered until/unless device 10 is displaced another approximately 1.2 mm (i.e., until three surface features 74 are identified by system 132).

Additional details and examples of the control of device 10 by system 132 are provided below.

Thus, in some embodiments, control systems 18, including displacement-based control system 132, controls operational aspects of device 10 (e.g., operational aspects of treatment radiation source 14) based on the displacement of device 10 across the skin, independent of the rate, speed, or velocity of device 10 moving across the skin. In some embodiments device 10, including displacement-based control system 132, is not configured for detecting or measuring any data indicative of the rate, speed, or velocity of device 10 moving across the skin, or for determining or attempting to determine the rate, speed, or velocity of device 10 moving across the skin. Rather, device 10 is configured for detecting or measuring data indicative of the lateral displacement of device 10 relative to the skin, and for determining the lateral displacement of device 10 using such data, e.g., as discussed above. In other words, device 10 can be moved at any rate, including very slowly, and beams 114 are delivered only if sufficient distance has been translated relative to the delivery of a particular prior beam 114 or some other predetermined event.

In other embodiments, device 10 may include a speed detection system, e.g., including a motion/speed sensor 202, for detecting or measuring data indicative of the rate, speed, or velocity of device 10 moving across the skin, and for determining or attempting to determine the rate, speed, or velocity of device 10 based on such data. Such speed detection sensor or system may be provided in addition to, or in place of, displacement-based control system 132 and displacement sensor 200.

In other embodiments, device 10 may include a dwell sensor 216 for measuring data indicative of whether device 10 is stationary or stationary within a certain tolerance with respect to the skin. Dwell sensor 216 may employ aspects of displacement sensor 200 described above but may be configured to provide information specifically about whether device 10 is stationary. For example, all or portions of the example algorithm described above for single-pixel displacement sensor 200A/200B may be used to determine when device 10 is substantially stationary (e.g., by recognizing the flat spots in the raw data signal 376 shown in FIG. 43) and device 10 may be controlled based on that information (e.g., radiation source 14 may be disabled if device 10 is determined to be stationary or dwelling).

Figure 44:
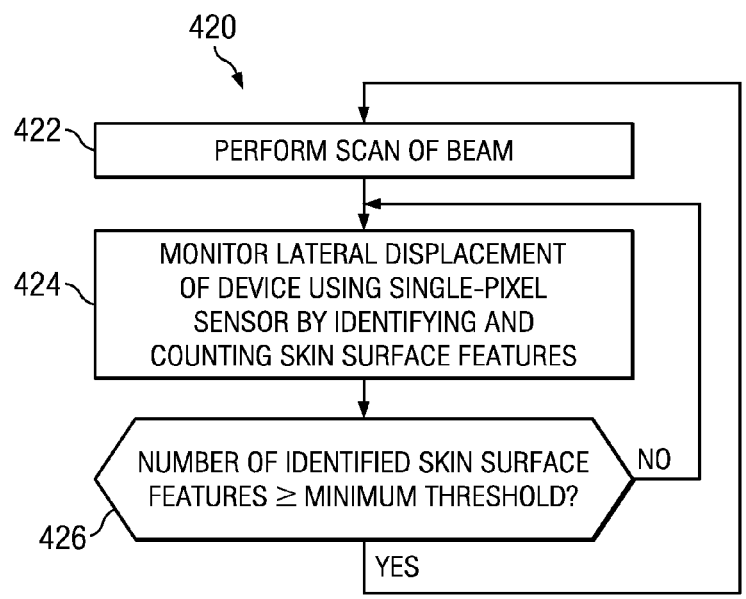
FIG. 44 illustrates a more specific example of the general method of FIG. 39 for controlling a device using a displacement-based control system, according to certain embodiments.

FIG. 44 illustrates a more specific example of the general method 400 of FIG. 39. In particular, FIG. 44 illustrates a method 420 for controlling device 10 using displacement-based control system 132 that employs a single-pixel displacement sensor 200A, while device 10 is used either in a gliding mode or a stamping mode, according to certain embodiments At step 422, device 10 initiates and performs a first scan of input beam 110 to generate a first array (e.g., a row 72) of treatment spots 70 onto the skin 40, as discussed above regarding step 402. As discussed above regarding method 400 of FIG. 39, although the scan in step 422 is called the "first" scan in this description, it should be understood that method 420 is a continuously repeating or looping process during a treatment session, and thus the "first" scan may be any particular scan during the treatment session (e.g., the $124^{th}$ scan during the process).

At step 424, displacement-based control system 132 initiates a monitoring process upon the initiation of the first scan, to monitor and analyze the lateral displacement of device 10 across the surface of the skin using sensor 200A. Displacement-based control system 132 analyzes signal 360 to identify and maintain a count of surface features 74 in the skin as device 10 is moved across the skin (e.g., in a gliding mode, during and/or after the generation of the first array (e.g., row 72) of treatment spots 70; or in a stamping mode, after the generation of the first array of treatment spots 70).

At step 426, system 132 determines whether a predetermined minimum number of surface features 74 (corresponding to a minimum lateral displacement of device 10) have been identified by the completion of the first scan of input beam 110. If so, the method returns to step 422 where the next (second) scan begins continuously upon completion of the first scan, and the process continues. If not, system 132 delays the initiation of the second scan and continues the first monitoring process (i.e., the method returns to step 424) until system 132 identifies the predetermined minimum number of surface features 74 (i.e., until system 132 determines that device 10 has traveled the minimum lateral displacement). Once system 132 has identified the predetermined minimum number of surface features 74, in some embodiments device 10 initiates the second scan of input beam 108 immediately, regardless of the rotational position of rotating scanning element 100 (i.e., the second scan may begin at any sector 104 of element 100). In other embodiments, device 10 waits until rotating scanning element 100 is positioned in a particular position to initiate the second scan immediately (e.g., such that the second scan begins at a predetermined "first" sector 104).

In this manner, system 132 ensures that each successively delivered array (e.g., row 72) of spots 70 is spaced apart from the previously generated array (e.g., row 72) in the glide direction by at least the predetermined distance corresponding to the predetermined minimum number of surface features 74 identified in the skin. As mentioned above, this method can be applied in both a gliding mode and a stamping mode of device 10.

In this example method, device 10 (e.g., operational aspects of treatment radiation source 14 and/or scanning system 48) is controlled based on the displacement of device 10 across the skin, regardless of the rate, speed, or velocity of device 10 moving across the skin. As discussed above, in some embodiments device 10 is not configured for detecting or measuring any data indicative of the rate, speed, or velocity of device 10 moving across the skin, or for determining or attempting to determine the rate, speed, or velocity of device 10 moving across the skin.

Multi-Pixel Displacement Sensor

As mentioned above, in some embodiments displacement sensor 200 is a multi-pixel displacement sensor 200 that employs two pixels (i.e., two reflected beams of light for generating two signals 360), three pixels, four pixels, or more. For example, some embodiments employ a multi-pixel imaging correlation sensor 200D, of the type used in optical mice for computer input, for detecting displacement along the skin.

Figure 45:
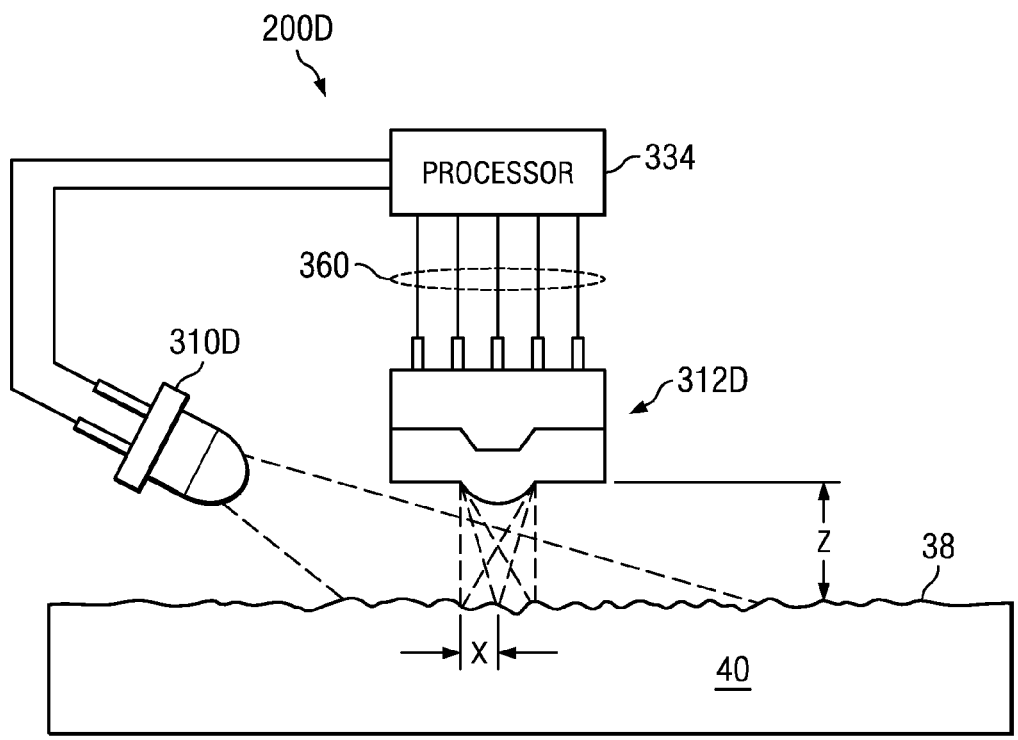
FIG. 45 illustrates an example multi-pixel imaging correlation sensor, of the type used in optical mice for computer input, for detecting displacement along the skin, according to certain embodiments.

FIG. 45 illustrates an example multi-pixel imaging correlation sensor 200D, of the type used in certain types of optical mouse for computer input, for detecting displacement along the skin, according to certain embodiments. Displacement sensor 200D may include a radiation source 310D, a light detector 312D, and a processor 334.

Radiation source 310D may be a light-emitting diode (LED) or any other suitable radiation source, e.g., as discussed above regarding radiation source 310A. Radiation source 310D may be arranged to deliver light at an oblique angle with respect to the skin surface 38, as shown in FIG. 45.

Light detector 312D may include a molded lens optic 336 and an imaging chip 338. In some embodiments, sensor 200C is configured such that the skin is within the focal plane of molded lens optic 336, which focal plane may be located several millimeters away from the surface of molded lens optic 336, as indicated by distance z in FIG. 45. Optionally, a system of relay lenses may be added between detector 312D and skin surface 38 to extend the total distance from the external focal plane to detector 312D.

Detector 312D may be configured to generate a two-dimensional multi-pixel "image" of the area of skin surface 38 illuminated by radiation source 310D. The image may consists of a two-dimensional array of pixels, each pixel having a signal 360 similar to signal 360 of single-pixel sensor 200A, 200B, OR 200c. Imaging chip 338 may be configured to generate a digital output stream to processor 334 corresponding to the multi-pixel signal array.

Processor 334 may be configured to drive radiation source 310D and receive and analyze the multi-pixel array of signals from light detector 312D. In particular, processor 334 may compare different multi-pixel images received from detector 312D (e.g., successively received images) to determine linear displacements in one or more directions, rotational displacements, and/or lateral displacements of sensor 200D across the skin surface 38.

Figure 46:
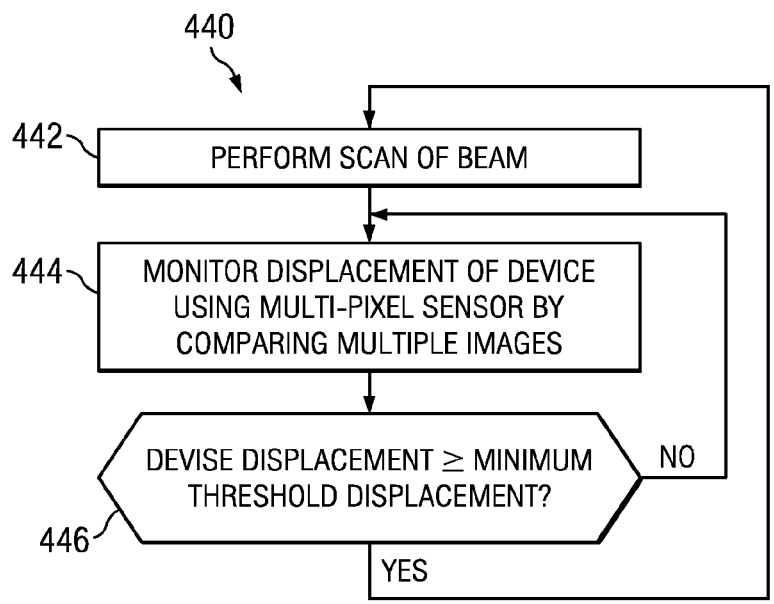
FIG. 46 illustrates an example method for controlling a device using a displacement-based control system that employs a multi-pixel displacement sensor, while the device is used either in a gliding mode or a stamping mode, according to certain embodiments.

FIG. 46 illustrates an example method 440 for controlling device 10 using displacement-based control system 132 that employs a multi-pixel displacement sensor 200C, while device 10 is used either in a gliding mode or a stamping mode, according to certain embodiments.

At step 442, device 10 initiates and performs a first scan of input beam 110 to generate a first array (e.g., a row 72) of treatment spots onto the skin 40, as discussed above regarding step 402. Again, as discussed above regarding methods 400 and 420, although the scan in step 442 is called the "first" scan in this description, it should be understood that method 440 is a continuously repeating or looping process during a treatment session, and thus the "first" scan may be any particular scan during the treatment session.

At step 444, displacement-based control system 132 initiates a monitoring process upon the initiation of the first scan of input beam 110, to monitor and analyze the lateral displacement of device 10 across the surface of the skin using sensor 200C. Displacement-based control system 132 analyzes signals 360 as device 10 is moved across the skin (e.g., in a gliding mode, during and/or after the generation of the first array of treatment spots; or in a stamping mode, after the generation of the first array of treatment spots).

At step 446, system 132 determines whether device 10 has been displaced a predetermined minimum distance along the skin by the completion of the first scan of input beam 110. If so, the method returns to step 442 where the next (second) scan begins continuously upon completion of the first scan, and the process continues. If not, system 132 delays the initiation of the second scan and continues the first monitoring process (i.e., the method returns to step 444) until system 132 determines that device 10 has traveled the predetermined minimum distance across the skin. Once system 132 determines that device 10 has traveled the predetermined minimum distance, in some embodiments device 10 initiates the second scan of input beam 110 immediately, regardless of the rotational position of rotating scanning element 100 (i.e., the second scan may begin at any sector 104 of element 100). In other embodiments, device 10 waits until rotating scanning element 100 is positioned in a particular position to initiate the second scan immediately (e.g., such that the second scan begins at a predetermined "first" sector 104).

In this manner, system 132 ensures that each successively delivered array (e.g., row 72) of spots 70 is spaced apart from the previously generated array (e.g., row 72) in the glide direction by at least the predetermined distance corresponding to the predetermined minimum number of surface features 74 identified in the skin. As mentioned above, this method can be applied in both a gliding mode and a stamping mode of device 10.

In this example method, device 10 (e.g., operational aspects of treatment radiation source 14 and/or scanning system 48) is controlled based on the displacement of device 10 across the skin, regardless of the rate, speed, or velocity of device 10 moving across the skin. As discussed above, in some embodiments device 10 is not configured for detecting or measuring any data indicative of the rate, speed, or velocity of device 10 moving across the skin, or for determining or attempting to determine the rate, speed, or velocity of device 10 moving across the skin.

Treatment Sessions

In some embodiments, control system 18 defines and controls individual treatment sessions based on one or more "treatment delimiters" such as (a) a total number of treatment spots/MTZs generated in the skin 40, (b) a total number of scans of beam 110, (c) a total amount of energy delivered to the skin 40, (d) a total treatment time, or any other suitable delimiter(s).

In some embodiments, treatment delimiters are specified for different "types" of treatments. Different types of treatments may include (a) treatments for different areas of the body (e.g., periorbital area, areas near the mouth, the back of the hand, the stomach, the knees, etc.), (b) different treatment energy or intensity levels (e.g., high energy treatment, medium energy treatment, low energy treatment), (c) different treatments for different stages of a multi-session treatment plan (e.g., a first session treatment, a mid-stage session treatment, or a final-session treatment), or any other different types of treatments.

Further, treatment delimiters may be specified for different combinations of treatment types. For example, different values for a total treatment spot/MTZ delimiter may be specified for different combinations of treatment area and treatment energy level. For example, device 10 may enforce the following delimiter value: (a) for a full-face treatment (e.g., based on an assumed area of 300 cm2), 39,000 MTZs for a high energy full-face treatment; 21,600 MTZs for a medium energy full-face treatment; and 10,800 MTZs for a low energy full-face treatment; (a) for a periorbital area treatment (e.g., based on an assumed area of 20 cm2), 2,600 MTZs for a high energy periorbital treatment; 1,440 MTZs for a medium energy periorbital treatment; and 720 MTZs for a low energy periorbital treatment; and (c) for treatment of both hands (e.g., based on an assumed area of 150 cm2), 19,500 MTZs for a high energy hand treatment; 10,800 MTZs for a medium energy hand treatment; and 5,400 MTZs for a low energy hand treatment; and (c)

Treatment delimiters for different treatment types (or combinations of different treatment types) may be predetermined and programmed into device 10, set or modified by a user via a user interface 18, determined by device 10 based on user input, settings stored in device 10, and/or algorithms 148 stored in device 10, or determined in any other suitable manner. In some embodiments, treatment delimiters for different treatment types are determined based on experimental testing and preprogrammed into device 10. For example, experimental testing may determine that an appropriate treatment session for the full face involves 10,000-45,000 treatment spots, an appropriate treatment session for a periorbital region involves 700-3,000 treatment spots, an appropriate treatment session for a mouth region involves 2,700-11,000 treatment spots, and an appropriate treatment session for the back of the hand involves 5,400-22,000 treatment spots. These treatment delimiters may be stored in device 10 and implemented by control system 18 as appropriate when a user selects from a "full face treatment," "periorbital treatment," "mouth treatment," or "hand treatment" via user interface 18.

Where treatment sessions are defined by treatment delimiters that are not time-based, such as treatment sessions defined by (a) a total number of treatment spots, (b) a total number of beam scans, or (c) a total amount of energy delivered to the target, the rate or speed at which the user moves device 10 across the skin (e.g., glide speed)—with the possible exception of extremely fast gliding velocities—may be largely or substantially irrelevant to the effectiveness of the treatment delivered during the session, at least in certain embodiments or configurations of device 10. For example, the glide speed may influence the number of times device 10 must be glided across the skin 40 to complete the treatment session (e.g., the faster the glide speed, the more glides are required to complete the session), but does not affect the specified treatment delimiter for the session, e.g., the total number of treatment spots or the total amount of energy delivered to the skin 40.

Further, in some embodiments, the effectiveness of the treatment, as related to the spacing between treatment spots, is generally not affected by the glide speed of device 10. In embodiments that include displacement-based control system 132, which controls beam delivery, and thus treatment spot generation, based on the determined displacement of device 10 across the skin, system 132 ensures at least a minimum spacing between successive scanned treatment spot rows/arrays, which reduces or substantially eliminates the chances of over-irradiation of any area. In particular, displacement-based control system 132 may ensure at least a minimum spacing between successive scanned treatment spot rows/arrays during slow glide velocities, and without detecting or determining the glide speed. Thus, displacement-based control system 132 may reduce or substantially eliminate the chances of over-irradiation of any particular area, even for very slow glide velocities.

Further, where the treatment session involves multiple glides of device 10 across the skin 40, the treatment spots generated during different glides typically will not align with other, which generally results in an treatment spot pattern with sufficient or desirable randomness and/or density uniformity to provide the desired treatment effects, without over-irradiating any areas. Thus, although rapid glide velocities may require the user to perform more glides to reach the relevant treatment delimiter (e.g., total treatment spots generated or total energy delivered), rapid glide velocities may provide a sufficient or desirable treatment spot patterns, without over-irradiating any areas.

It should be noted that the glide speed may influence the shape of individual treatment spots, e.g., the extent of elongation, "blurring," or "smearing" of treatment spots, such as described above with respect to FIG. 26B. Thus, operational aspects of device 10 may be configured such that within a reasonable range of glide velocities (i.e., less than very fast glide velocities), the elongation or smearing of treatment spots does not substantially affect the physiological effectiveness of the treatment spots. In some embodiments or configurations of device 10, at very high glide velocities, the elongation or smearing of treatment spots may significantly reduce the effectiveness of the treatment. For example, the energy density within a very elongated treatment spot may be too low to provide the intended effects. Thus, the user may be provided general guidance (e.g., via display 32 or in a user manual) regarding the rate or speed at which to move device 10 to ensure the desired treatment effects. For example, the user may be instructed to glide device 10 across the skin 40 at a rate or speed of roughly three seconds per glide.

Figure 47:
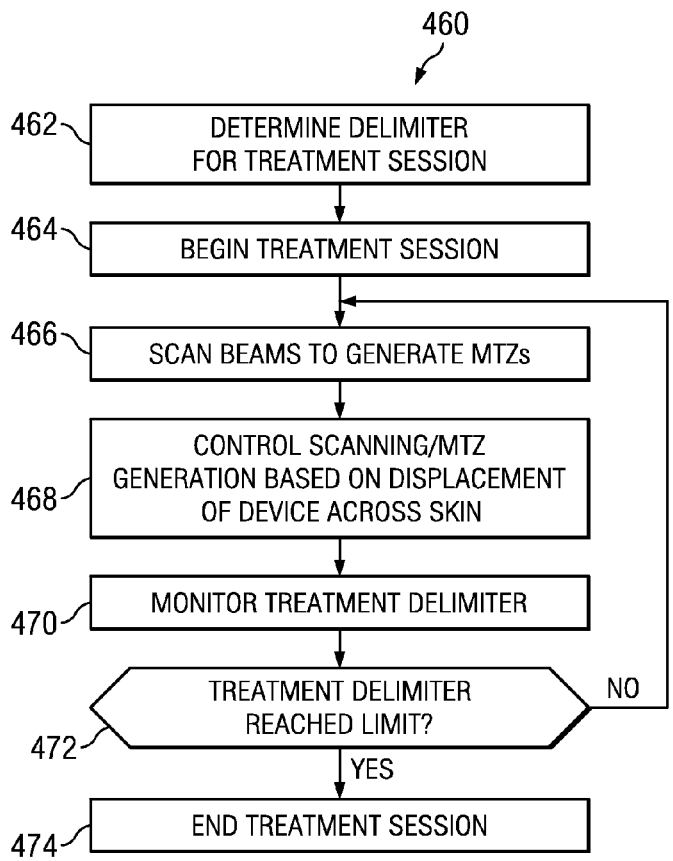
FIG. 47 illustrates an example method for executing a treatment session for providing treatment (e.g., fractional light treatment) to a user in certain embodiments and/or settings of the device.

FIG. 47 illustrates an example method 460 for executing a treatment session for providing treatment (e.g., fractional treatment) to a user with device 10. At step 462, one or more delimiters for a treatment session to be performed are determined in any suitable manner, e.g., as discussed above. For the purposes of this discussion it is assumed that a single treatment delimiter is determined. For example, control system 18 may determine a predefined total number of treatment spots for the treatment session based on a treatment area (e.g., full face or periorbital area) selected by the user via a user interface 18: for example, 1200 treatment spots. (The number of treatment spots may be assumed to be equal to the number of output beams 112 output by device 10).

At step 464, after the user has positioned device 10 against the skin 40, device 10 may begin the treatment session. In particular, control system 18 may deliver scanned arrays (e.g., rows 72) of beams 114 to the skin 40, thus generating an array of treatment spots 70, as indicated at step 466. If device is operating in a gliding mode, device 10 may glided across the skin continuously during the beam-scanning and delivery process. If device is operating in a stamping mode, device 10 may held in place during each scan, and then moved, or glided, across the surface of skin to the next treatment location for performing the next scan. The user may be instructed (e.g., by audible, visible, or tactile notifications) when each scan of input beam 110 begins and ends, and/or whether or when device 10 has been moved a sufficient distance for performing the next scan (as determined by displacement monitoring and control system 132). In either the gliding mode or the stamping mode, the user may glide or move the device across the skin 40 any number of times (e.g., to "paint" a desired area of skin) during the treatment session.

During the treatment session, as indicated as step 468, displacement monitoring and control system 132 may monitor the lateral displacement of device as it moves across the skin and control the delivery of output beams/generation of treatment spots accordingly, as discussed above. For example, system 132 may ensure that consecutive rows of treatment spots are spaced apart in the glide direction by at least a minimum distance.

Also during the treatment session, control system 18 may monitor the treatment delimiter determined at step 462, as indicated at step 470. For example, control system 18 may maintain a running count of the number of treatment spots generated during the treatment session. Steps 468 and 470 may be performed concurrently throughout the duration of the treatment session.

At step 472, control system 18 determines whether the treatment delimiter has reached the predetermined limit. For example, control system 18 may determine whether the number of treatment spots that have been generated during the session has reached the predefined number of treatment spots determined at step 462 (e.g., 1200 treatment spots). If so, the treatment session is completed at step 474. For example, control system 18 may turn off treatment radiation source 14 and/or scanning system 48. If not, steps 466-472 are continued until the treatment delimiter is reached.

In some embodiments, a treatment session for providing treatment (e.g., fractional treatment) to a user may be completed according to method 460 without regard to the rate or speed at which device 10 is moved across the skin, e.g., as discussed above.

Roller-Type Displacement Sensor or Motion/Speed Sensor

In some embodiments, device 10 may include one or more roller-based sensors 218 that function as a displacement sensor 200, or dwell sensor 216 or as a motion/speed sensor 202, or all. Roller-based sensor 218 may be arranged at or near the treatment tip 42 of device 10, and may include a roller 480 having a leading surface that is generally flush with, or projects slightly forward from the leading surface of the surrounding or adjacent portion of housing 24. In some embodiments, the leading surface of roller 480 may define a skin-contacting surface 74, which may or may not affect the distance (if any) of the treatment window 44 from the skin surface, e.g., depending on the closeness of the roller 405 to the window 44 and/or the force at which device 10 is pressed against the skin by the user.

FIGS. 48A-48G illustrate some example embodiments of a roller-based sensor 218A-118G that may be used in certain embodiments of device 10. Each embodiment includes a roller 480 coupled (e.g., mechanically, optically, magnetically, electrically, etc.) to a detection system 482 configured to generate signals indicative of (a) the displacement of device 10 (e.g., based on a detected amount of angular rotation of roller 45), or (b) the manual glide speed of device 10 (e.g., based on a detected speed of rotation of roller 45), or (c) a dwell sensor (e.g., based on rotation or not rotation), or (d) all of the above.

As device 10 is manually moved across the skin, roller 480 turns or "rolls" by a degree and at a speed corresponding to the lateral displacement and manual glide speed, respectively, of the device relative to the skin surface. Detection system 482, via its coupling or interaction with roller 480, generates signals indicative of the lateral displacement and/or manual glide speed, and communicates such signals to processor 150, which may convert and/or process such signals to determine the displacement and/or glide speed and/or stationary status of device 10. The determined displacement and/or glide speed and/or stationary status of device 10 may then be used for controlling one or more controllable operational parameters of device 10 (e.g., control operational parameters of radiation source 14), e.g., as discussed herein.

In some embodiments, roller-based sensor 218 is configured to operate as a displacement sensor 200 for use in displacement-based control system 132, and may be used for any of the displacement-based control techniques discussed herein. In some embodiments, roller-based sensor 218 measures, detects, or generates signals indicative of, the displacement of device 10, but does not measure, detect, or generate signals indicative of, the manual glide speed of device 10.

In an example embodiment, roller 480 has a diameter of about 4 mm, such that a 29 degree rotation of roller 480 corresponds to 1 mm displacements of device 10 (assuming no slipping between roller 480 and skin). In some embodiments, detection system 482 may be sensitive to device displacements to a granularity of about 1 mm.

Figure 48A:
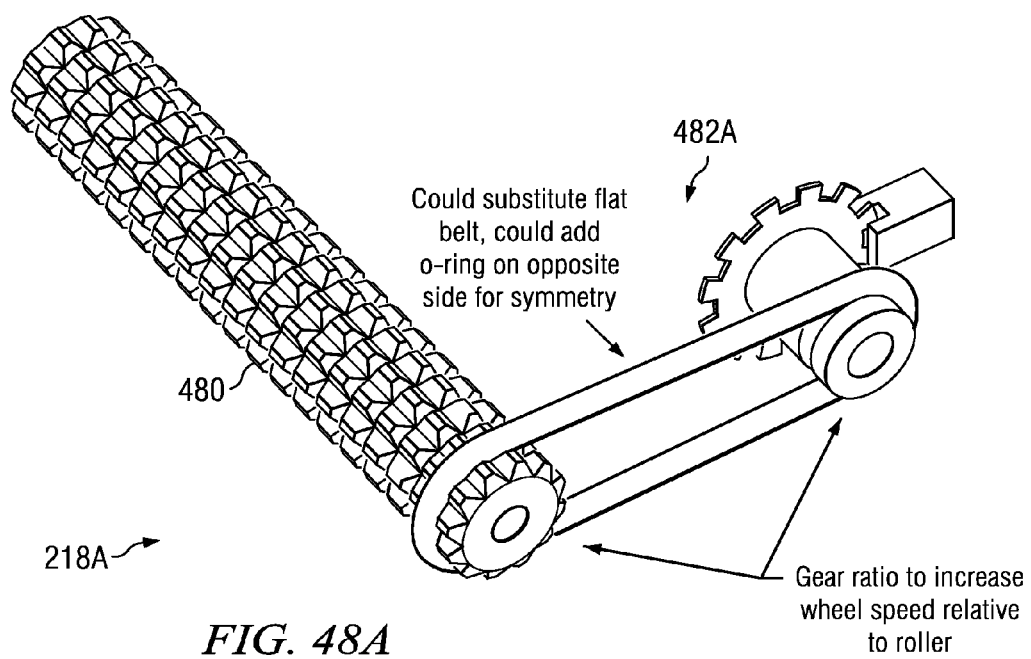
FIGS. 48A-48G illustrate example embodiments of a roller-based sensor that may be used a displacement sensor, or a motion/speed sensor, or both, for use in certain embodiments.

FIG. 48A illustrates an example roller-based sensor 218A that includes a belt-driven optical-interrupt detection system 482A to generate signals indicative of the displacement and/or glide speed of device 10.

Figure 48B:
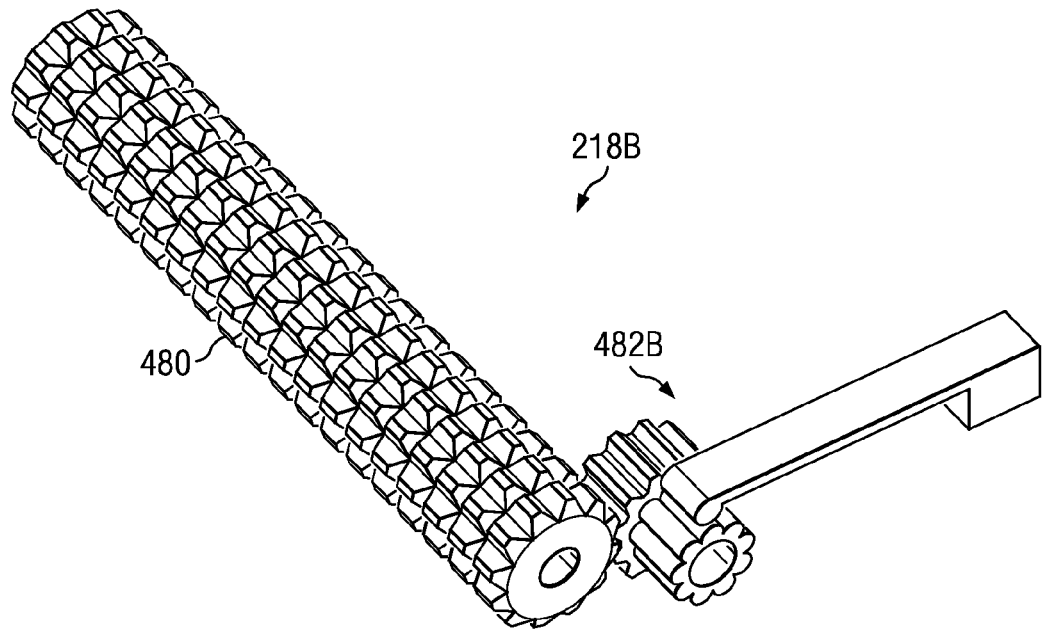
Figure 48C:
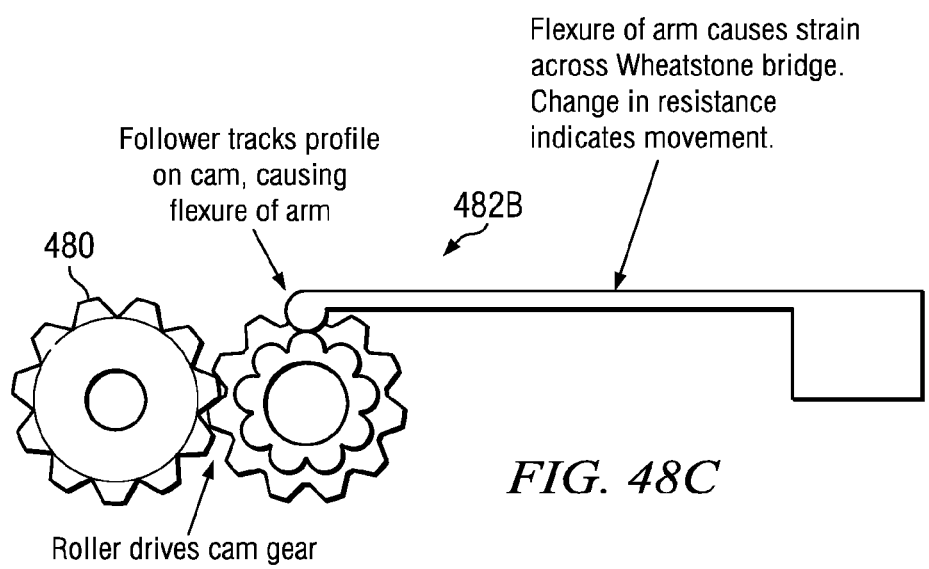

FIGS. 48B and 48C illustrate an example roller-based sensor 218B that includes a detection system 482B that generates signals indicative of the displacement and/or glide speed of device 10 based on the flexure of a physical arm, which causes strain across a Wheatstone bridge, thus causing changes in resistance corresponding to device movement.

Figure 48D:
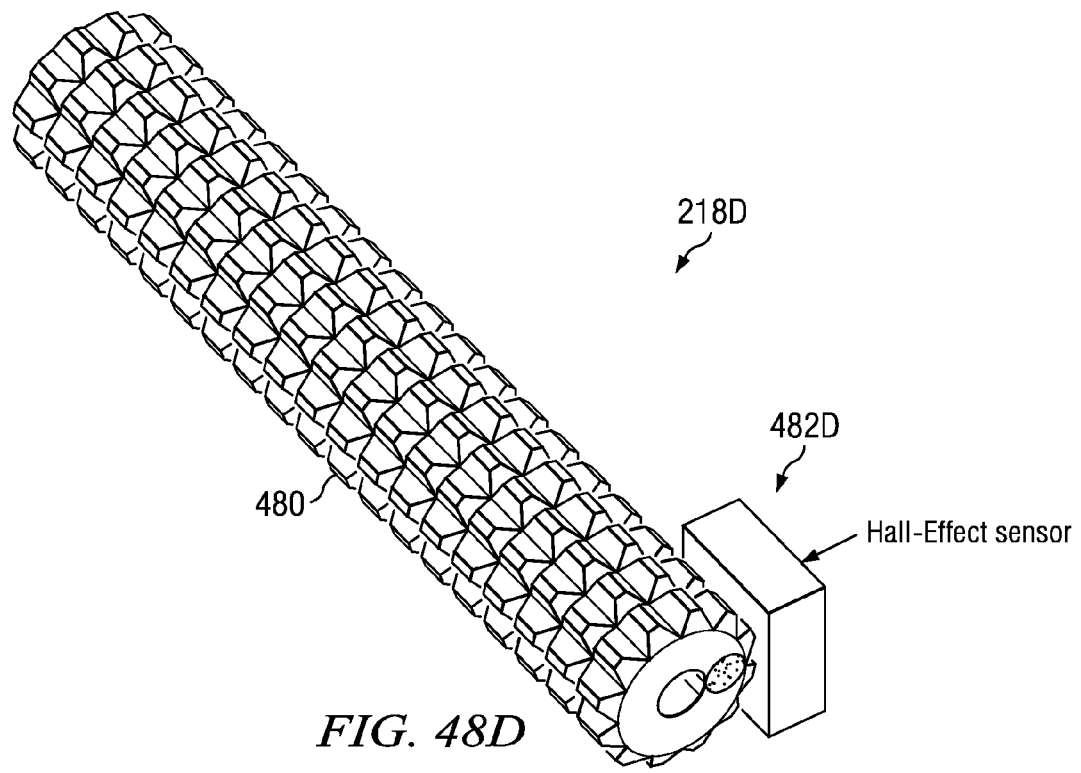

FIG. 48D illustrates an example roller-based sensor 218D that includes a detection system 482D that generates signals indicative of the displacement and/or glide speed of device 10 based on an interaction between a Hall-effect sensor and one or more magnets around the perimeter of roller 480.

Figure 48E:
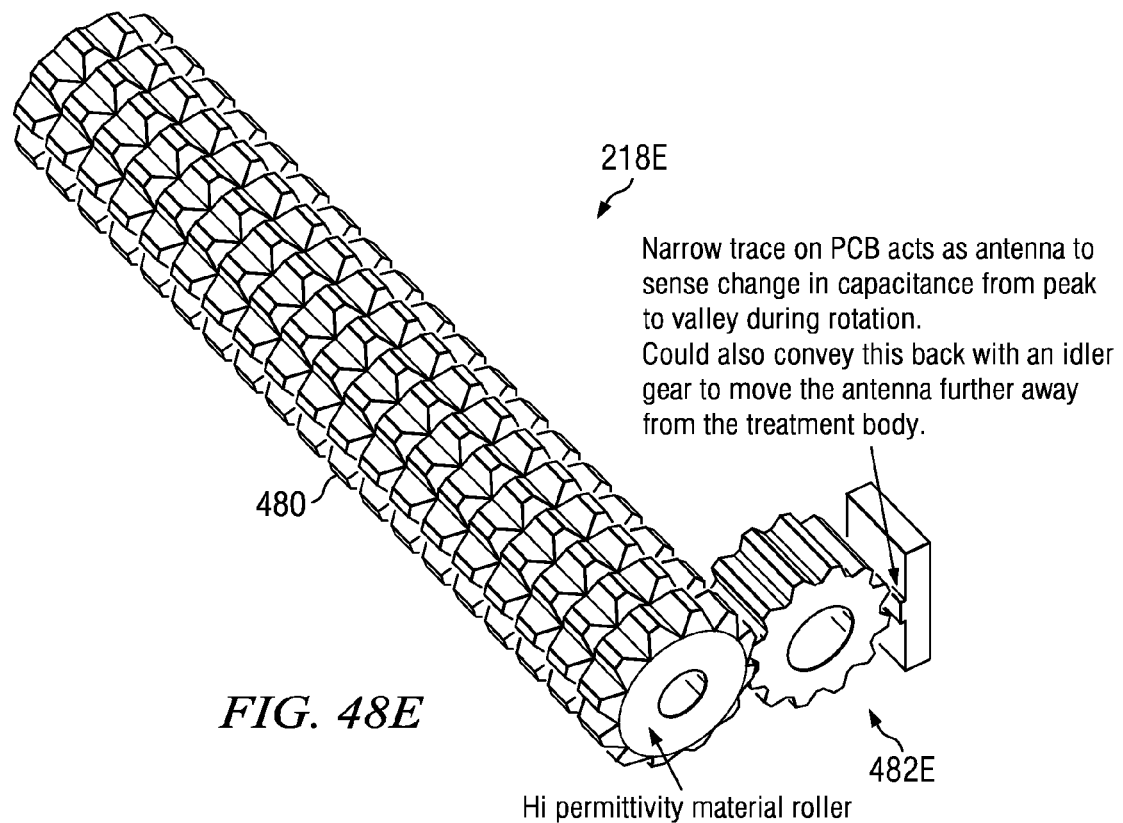

FIG. 48E illustrates an example roller-based sensor 218E that includes a detection 482E to generate signals indicative of the displacement and/or glide speed of device 10 based on a measured capacitance between an "antenna" and a gear or other rotating element.

Figure 48F:
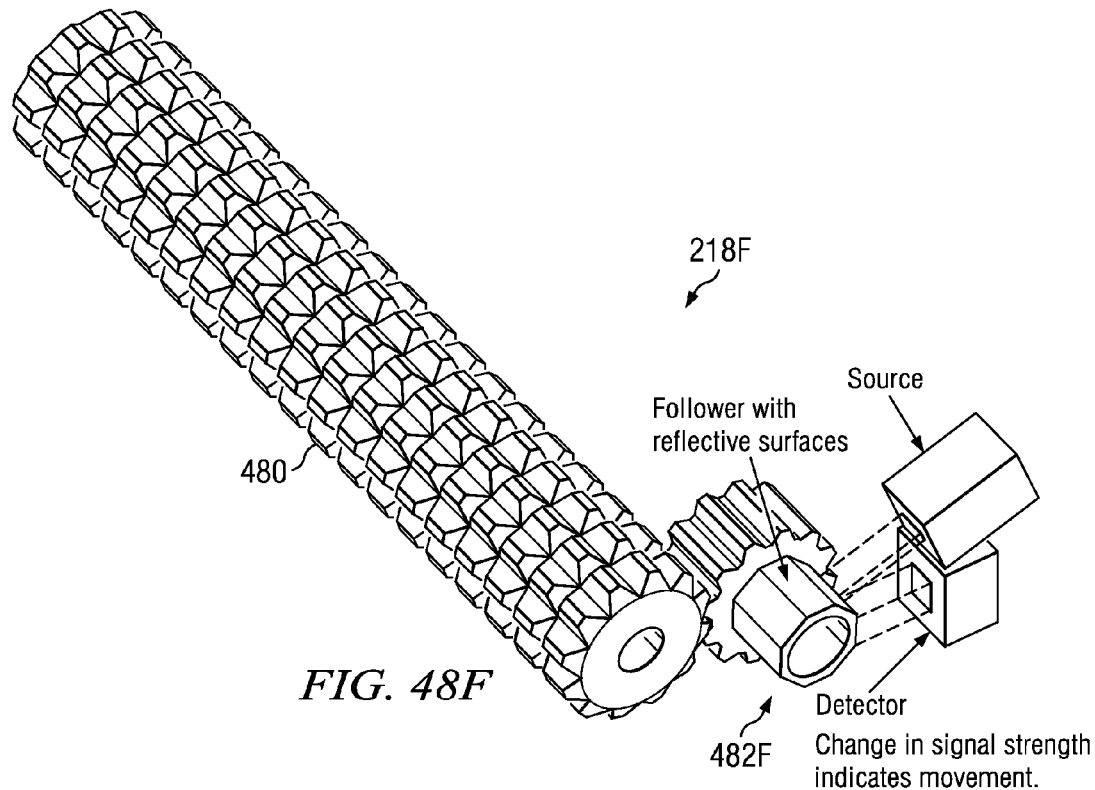

FIG. 48F illustrates an example roller-based sensor 218F that includes a detection system 482F to generate signals indicative of the displacement and/or glide speed of device 10 based on measurements of reflected optical radiation.

Figure 48G:
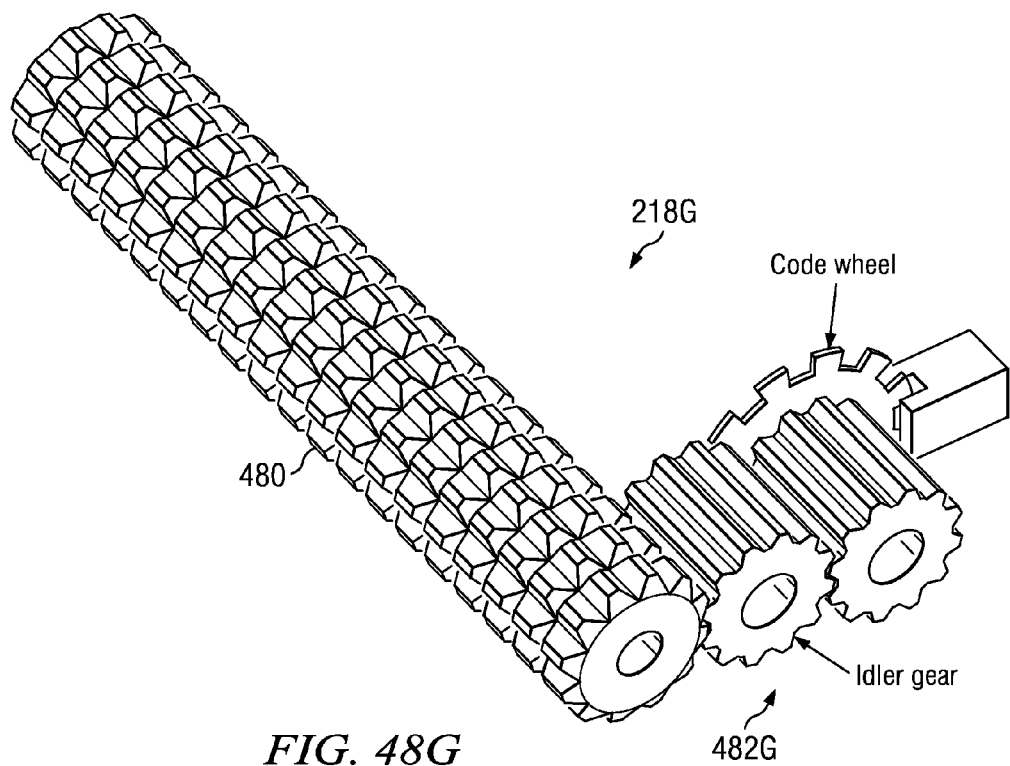

Finally, FIG. 48G illustrates an example roller-based sensor 218G that includes a gear-driven optical-interrupt detection system 482G to generate signals indicative of the displacement and/or glide speed of device 10.

Capacitive Sensors

One or more sensors 26 of device 10 may be, or may include, capacitive sensors. As discussed above, skin-contact sensor 204 may be a capacitive sensor, in which the signal amplitude is analyzed to determine whether sensor 204 is in contact or sufficient proximity with the skin. In addition, any of displacement sensor 200, motion/speed sensor 202, and/or dwell sensor 216 may be capacitive sensors, or may include capacitive sensors in addition to other types of sensors (e.g., a sensor 200, 202, or 216 may include an optical reflectance/remittance sensor in addition to a capacitive sensor for providing the desired functionality, e.g., to provide redundancy).

A capacitive sensor in contact with the skin (e.g., a capacitive sensor located at the application end 42 of device 10 may generate a signal (e.g., a high-frequency signal) indicating a measure of capacitance associated with the contact between the sensor and the skin. For example, a capacitive sensor's signal may be inversely proportional to the relative displacement between the sensor and the target surface. Because the surface of a human's skin is not perfectly smooth and/or because a human cannot achieve perfectly steady motion during manual movement of device 10, static friction (stiction) between device 10 and the skin and/or other physical principles may result in "stick-and-slip" movement of device 10 across the skin, which causes micro-displacement between the sensor and the skin surface. This micro-displacement due to stick-and-slip movement of device 10 may result in a translational signal added to the nominal steady-state capacitance signal of the sensor, to provide a total capacitance signal. The amplitude and/or other aspects of the total capacitance signal may be analyzed to determine whether the device is moving across the skin, or dwelling at the same location. Thus, a capacitive sensor may be used as a dwell sensor 216. Such analysis may include any suitable algorithms, e.g., comparing the signal to one or more threshold values.

As another example, the total capacitance signal may be analyzed to determine or estimate the speed of device 10 moving across the skin. Thus, a capacitive sensor may be used as a glide speed sensor 202. As another example, the total capacitance signal may be analyzed to determine or estimate the displacement of device 10 moving across the skin. Thus, a capacitive sensor may be used as a displacement sensor 200.

Usability Control

As discussed above regarding FIG. 1, device 10 may include control system 18 configured to control various controllable operational parameters of device 10 (e.g., operational aspects of radiation source 14, scanning system 48, etc.). In some embodiments, control system 18 may include a usability control system 133 configured to control the operation of device 10 (e.g., the generation and/or delivery of radiation) based on whether the device 10 is both (a) in contact with the skin and (b) sufficiently moving across the skin (e.g., based on a minimum displacement or glide speed of device 10). Usability control system 133 may be provided in addition to, or in place of, displacement-based control system 132, depending on the particular embodiment.

In some embodiments, usability control system 133 may control the one or more operational aspects radiation source(s) 14, such as for example, controlling the radiation mode of radiation source(s) 14, controlling the on/off status of radiation source(s) 14, controlling the timing of such on/off status (e.g., pulse trigger delay, pulse duration, pulse duty cycle, pulse frequency, temporal pulse pattern, etc.), controlling parameters of the radiation (e.g., wavelength, intensity, power, fluence, etc.), controlling parameters of optics 16, controlling parameters of beam scanning system 48 (e.g., controlling the on/off status, rotational speed, direction of rotation, or other parameters of motor 120), and/or any other controllable operational parameters of device 10.

In some embodiments, usability control system 133 may also provide feedback to the user via a display 32 and/or one or more other user interfaces 28 based on (a) the monitored skin contact and displacement status of device 10 and/or (b) the automatic control of one or more controllable operational parameters by system 133. For example, system 133 may provide audio, visual, and/or tactile feedback to the user indicating data detected, or actions taken, by system 133, e.g., feedback indicating whether device 10 is in contact with the skin and/or feedback indicating whether device 10 is sufficiently moving across the skin, or feedback indicating whether device 10 is both in contact with and sufficiently moving across the skin.

Usability control system 133 may include, utilize, or otherwise cooperate with or communicate with displacement-based control system 132 and/or any other control subsystems 52 discussed above with respect to FIG. 2 (e.g., radiation source control system 128, scanning system control system 132, and user interface control system 134, including user interface sensor control subsystem 140 and user input/feedback control subsystem 142), as well as control electronics 30, any one or more sensors 26, user interfaces 28, and displays 32.

In some embodiments, usability control system 133 may include one or more skin contact sensors 204, one or more displacement sensors 200, control electronics 30, and one or more of: treatment radiation source 14, scanning system 48, and display 32. In general, skin contact sensor(s) 204 and displacement sensor(s) 200 collects data regarding the contact and displacement of application end 42 of device 10 relative to the skin 40 and communicates such data to control electronics 30, which analyzes the data and controls or provides feedback via one or more of treatment radiation source 14, scanning system 48, and display 32. In some embodiments, control electronics 30 may also analyze particular user input received via one or more user interfaces 28 in conjunction with data received from sensor(s) 200 and 204. For example, the appropriate control or feedback provided by control electronics 30 (e.g., as defined by a relevant algorithm 148) may depend on the current operational mode and/or other settings selected by the user.

In some embodiments, usability control system 133 controls the starting and stopping (e.g., interruption) of radiation delivery based on signals from one or more skin contact sensors 204 and one or more displacement sensors 200 indicating whether application end 42 of device 10 is in contact with the skin and moved across the skin with sufficient displacement to allow generation and delivery of radiation. In other words, usability control system 133 may be configured to start/stop the delivery of radiation based on whether device 10 is being properly positioned and moved for a dermatological treatment.

In some embodiments, usability control system 133 defines different standards for starting/stopping radiation delivery based on the particular operation situation. For example, usability control system 133 may define a first set of conditions required to initiate radiation delivery (e.g., to turn on radiation source 14) and a different second set of conditions required to maintain radiation delivery after initiation. As another example, usability control system 133 may define a first set of conditions required to initiate radiation delivery (e.g., to turn on radiation source 14), a different second set of conditions required to maintain radiation delivery after initiation, and a different third set of conditions required to restart radiation delivery after an interruption of radiation delivery.

Figure 50:
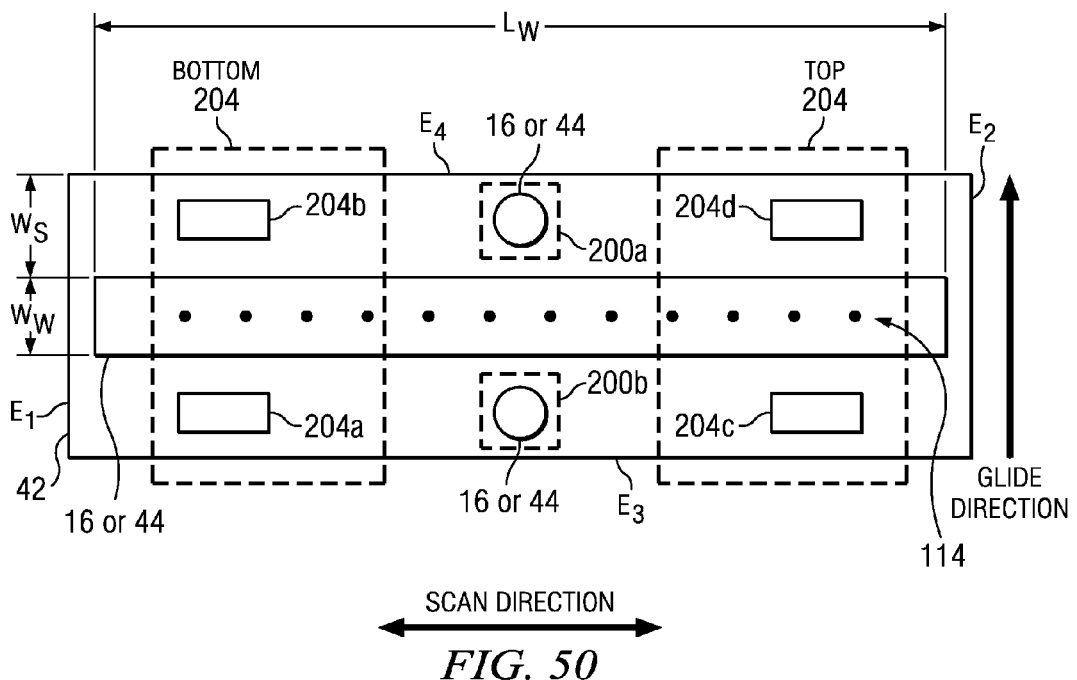
FIG. 50 illustrates an example configuration of the application end of a scanned-beam treatment device, indicating an arrangement of contact sensors and displacement sensors, according to an example embodiment.

In an example embodiment, device 10 includes two displacement sensors 200a and 200b and four skin contact sensors 204a-200d at the application end 42 of device 10, e.g., in the example arrangement shown in FIG. 50. Usability control system 133 may define conditions for initiating, maintaining, interrupting, and restarting radiation delivery as follows:

(1) Generation of the initial pulse/beam of a treatment session requires (a) signals from all four skin contact sensors 204 independently indicating contact with the skin, and (b) signals from both displacement sensors 200 independently indicating that devices 10 has been moved a predetermined displacement across the skin.

(2) After the initial pulse, continued pulsing/beam delivery requires (a) signals from at least one of the two "bottom" skin contact sensors 204a and 204b (see FIG. 50) indicating contact with the skin, and (b) signals from at least one of the two "top" skin contact sensors 204c and 204d (see FIG. 50) indicating contact with the skin, and (c) signals from at least one of two displacement sensors 200a and 200b independently indicating that devices 10 has been moved a predetermined displacement across the skin.

(3) If any of the conditions in condition set (2) are violated (i.e., any of conditions (2)(a), (2)(b), or (2)(c)), system 133 interrupts pulsing immediately or substantially immediately. System 133 then continues to apply condition set (2) to determine whether to re-start pulsing. However, if any of the conditions in condition set (2) is violated for a consecutive duration of one second, system 133 instead applies the more stringent conditions of condition set (1) in order to re-start pulsing.

This algorithm using different sets of conditions for initiating, maintaining, interrupting, and restarting the radiation delivery may allow some imperfect contact and/or sensing interface between sensors 200/204 and the skin (e.g., when gliding over boney features or other contoured features of the body), without discontinuing radiation delivering due to such imperfect contact. In other words, once the device has initially determined proper skin contact and device movement, the algorithm relaxes the skin contact/displacement detection standards to account for some imperfect contact with the skin for brief durations (e.g., less than one second). This may improve the practical "usability" of the device 10, so that the start/stop control of radiation delivery may better match the actual use of device 10 in a real world application.

Figure 49:
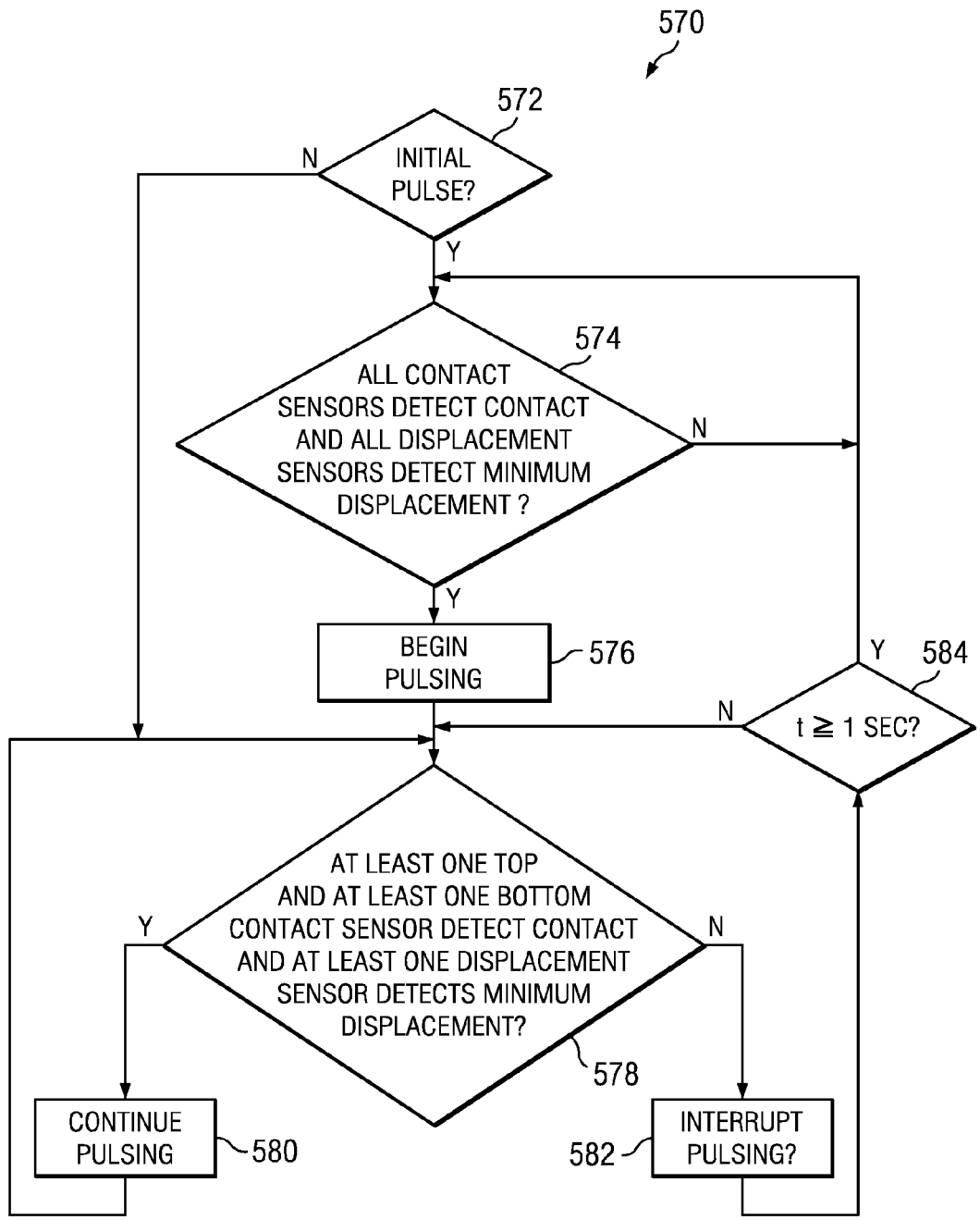
FIG. 49 illustrates an example method for providing "usability" control of radiation delivery based on feedback from contact sensors and displacement sensors, according to an example embodiment.

FIG. 49 illustrates an example flowchart of the algorithm discussed above, which may be stored as an algorithm 148 and implemented by usability control system 133, e.g., using any suitable control electronics 30. System 133 first determines whether the current control decision regards an initial pulse by radiation source 14, at step 572. If so, at step 574, system 133 determines whether all contact sensors 204a-204d currently detect contact and all (both) displacement sensors 200a-200b currently detect a predetermined minimum displacement of device 10 across the skin. If so, system 133 begins pulsing the radiation source 14 at step 576. If not, system 133 continues to receive and analyze signals from sensors 200 and 204 until the conditions at step 574 are met.

After the initial pulse is delivered, system 133 applies less stringent conditions to continue pulsing. In particular, at step 578, system 133 determines whether at least one bottom contact sensor 204a-204b currently detects skin contact, and at least one top contact sensor 204c-204d currently detects skin contact, and at least one displacement sensor 200a-200b currently detects the predetermined minimum displacement of device 10 across the skin. If these conditions are met, system 133 continues pulsing, indicated at 580. In one or more of these conditions are met, system 133 interrupts pulsing at 582. If the violation of the condition(s) at step 578 has continued consecutively for one second, system 133 reverts back to the more stringent standards at step 574, for re-starting pulsing. If the violation of the condition(s) at step 578 has not yet continued for one second, system 133 may continue to apply the less stringent standards at step 578, for re-starting pulsing.

It should be understood that algorithm 570 is an example only, and that usability control system 133 may employ any other suitable control algorithm or algorithms.

FIG. 50 an end view of example application end 42 (e.g., as seen by the skin) of device 10, e.g., for use with displacement-based control system 132 and/or usability control system 133, according to one embodiment. In this example, application end 42 is elongated in the scan direction and includes (a) an elongated optical element 16 or window 44 through which scanned beams 114 are delivered to the skin, (b) four capacitive skin contact sensors 204a-204d, (c) a pair of displacement sensors 200a and 200b, each configured to interface with the skin through an optic 16 or window 44. In other embodiments, one or more displacement sensors 200 (and/or other types of sensors) interface with the skin through the same optic 16 or window 44 as scanned beams 114.

In this embodiment, skin contact sensors 204a-204d are provided near the corners of application end 42. This arrangement allows for the detection of any edge of application end 42 being lifted off the skin. For example, sensors 204a and/or 204b can detect if edge E1 is lifted off the skin, sensors 204c and/or 204d can detect if edge E2 is lifted off the skin, sensors 204a and/or 204c can detect if edge E3 is lifted off the skin, and sensors 204b and/or 204d can detect if edge E4 is lifted off the skin. In other embodiments, any other number and arrangement of skin contact sensor(s) 204 may be provided. As discussed above, contact sensors 204 may be capacitive sensors or any other suitable type of sensors for detecting contact with the skin.

Each optic 16 or window 44 may provide any suitable optical path for delivering light to and/or receiving reflected light from the skin. Alternatively, any sensor 26 and/or the beam delivery aperture may be open to the air, i.e., without an optic 16 or window 44 at application end 42. In the illustrated example, 12 scanned beams 114 pass through optic 16 or window 44 in a linear row pattern extending in the scan direction. Thus, optic 16 or window 44 may be sized and shaped based on the locations of the 12 scanned beams 114. In an example embodiment that uses an output window 44, the window 44 may be rectangular with dimensions of about 20 mm length ($L_W$) by 2 mm width ($W_W$), with a width of about 3 mm ($W_S$) on each side of window 44, for locating various sensors 26 and/or rollers, and/or other features. In an example embodiment that uses an output optic 16, the optic 16 may comprise a rod lens having a diameter of about 5 mm and length ($L_W$) of about 20 mm.

Eye Safety

Some embodiments of device 10 provide eye safe radiation, e.g., by delivering scanned, divergent beams 114 from the application end 42 of the device, and/or using an eye safety control system including one or more sensors 26 including one or more eye safety sensors 214 and/or other types of sensors 26, and/or by any other suitable manner. For example, in some embodiments or settings, device 10 meets the Class 1M or better (such as Class 1) eye safety classification per the IEC 60825-1, referred to herein as "Level 1 eye safety" for convenience. In other embodiments or settings, the device exceeds the relevant Accessible Emission Limit (AEL) (for 1400-1500 nm or 1800-2600 nm wavelength radiation) by less than 50%, referred to herein as "Level 2 eye safety" for convenience. In still other embodiments or settings, the device exceeds the relevant AEL (for 1400-1500 nm or 1800-2600 nm wavelength radiation) by less than 100%, referred to herein as "Level 3 eye safety" for convenience. The Accessible Emission Limit (AEL), as specified in IEC 60825-1, e.g., for 1400-1500 nm or 1800-2600 nm wavelength radiation, is discussed below. In other embodiments or settings, device 10 meets the next highest eye safety classification after Class 1M per the IEC 60825-1, i.e., Class 3B, referred to herein as "Level 4 eye safety" for convenience.

Such levels of eye safety may be provided based on a combination of factors, including for example, one or more of the following: (a) the scanning of an input beam, (b) the divergence of delivered beams (e.g., in embodiments that use laser diode radiation source(s)), (c) the emitted power, (d) the wavelength of the delivered beams, (e) the pulse duration, and (f) the total energy per delivered beam. Thus, in some embodiments, one, some, or all of such factors may be selected or adjusted to provide Level 1, Level 2, Level 3, or Level 4 eye safety, as defined above.

In the wavelength ranges of 1400-1500 nm and 1800-2600 nm (e.g., for providing certain fractional treatments), corneal damage is typically the primary concern for eye safety. In some embodiments that radiate in such wavelength ranges using a laser diode source, the beam scanning and divergence inherently provided by a scanned divergent laser diode source, alone or in combination with other eye safety features, may provide a desired eye safety for device 10. For example, it may provide Level 1, Level 2, Level 3, or Level 4 eye safety, depending on the other selected parameters. An analysis of relevant issues is discussed below.

A scanned, divergent, intense-radiation source (e.g., certain laser diode sources) may provide eye safe radiation. For certain wavelengths greater than 1400 nm (including, e.g., typical wavelengths used in fractional laser treatment), the radiation source is greatly attenuated by the water absorption in the eye anterior chamber. Thus, there is substantially little or no retinal hazard in this wavelength range. The emission limit is determined by the potential corneal damage. Moreover, since there is no focusing effect by the eye lens, the hazard is further minimized by beam scanning to avoid compounding the laser energy on the corneal surface. For Class 1M eye safety classification per IEC 60825-1, the Accessible Emission Limit (AEL) in the wavelength range of 1400 to 1500 nm and 1800 to 2600 nm is described by a simple equation in Table 4 of IEC 60825-1:2007:

$$AEL = 4.4 t^{0.25} \text{ mJ} \qquad \text{Equation 1}$$

For a scanned beam system, the AEL energy is measured at 100 mm from the source with a circular aperture of 1 mm in diameter (Condition 3 measurement setup described in Table 11 of IEC 60825-1:2007, applicable for scanned beams viewed by unaided eye). In this equation, t (in unit of seconds) is the source pulse duration in the range of 1 ms to 350 ms. For example embodiments that include a scanned laser diode source, this pulse duration may be in the range of 1 to 10 ms. The corresponding AEL is 0.8 to 1.4 mJ.

The actual source AE (Accessible Energy) can be estimated for given scanned beam characteristics including the beam's divergence in both axes. It can also be measured experimentally with the appropriate aperture stop (1-mm wide) and measurement distance (100-mm from the source). The AE at a distance 100-mm from the treatment aperture is given by (this is approximately correct for a Gaussian beam from a diffraction limited laser):

$$AE = 2.5 \times 10^{-5} Q / [\tan(\Phi_F/2) \tan(\Phi_S/2)] \text{ mJ} \qquad \text{Equation 2}$$

where Q (in unit of mJ) is the source energy at the treatment plane, and $\Phi_F$ and $\Phi_S$ are the beam divergence in the fast and slow axis, respectively. To achieve the Class 1M eye safety classification, AE must be lower than the AEL for the corresponding pulse duration.

Table 1 below provides several example configurations and device settings for providing Level 1 eye safety (Class 1M or better per standard IEC 60825-1) for certain embodiments of device 10 that provide pulsed radiation in the 1400-1500 nm or 1800-2600 nm wavelength ranges (e.g., for fractional treatment) using a scanned laser diode source 14, wherein each pulse is scanned to a different location.

TABLE 1

| Parameter | Example Design 1 | Example Embodiment Example Design 1 | Example Design 2 | Example Embodiment Example Design 2 |
| --- | --- | --- | --- | --- |
| Configuration | No downstream fast-axis rod lens | No downstream fast-axis rod lens | With downstream fast-axis rod lens | With downstream fast-axis rod lens |
| Radiation source | scanned laser diode | scanned laser diode | scanned laser diode | scanned laser diode |
| Radiation mode | Pulsed (one pulse per delivered beam) | Pulsed (one pulse per delivered beam) | Pulsed (one pulse per delivered beam) | Pulsed (one pulse per delivered beam) |
| wavelength | 1400-1500 nm or 1800-2600 nm | 1400-1500 nm or 1800-2600 nm | 1400-1500 nm or 1800-2600 nm | 1400-1500 nm or 1800-2600 nm |
| beam divergence at skin surface (fast axis, slow axis) | 0.3°-2° fast axis, 2°-4° slow axis | 1.5° fast axis 3° slow axis | 4°-8° fast axis, 2°-4° slow axis | 6° fast axis 3° slow axis |

TABLE 1-continued

| Parameter | Example Design 1 | Example Embodiment Example Design 1 | Example Design 2 | Example Embodiment Example Design 2 |
|---|---|---|---|---|
| Pulse/delivered beam duration (ms) | 3-10 | about 8 | 3-10 | about 8 |
| Power (W) | 0.5-3 | about 1.5 | 0.5-3 | about 1.5 |
| Total energy per pulse/delivered beam (mJ) | 5-15 | about 12 | 5-15 | about 12 |
| AEL (mJ) | 1.0-1.4 | about 1.3 | 1.0-1.4 | about 1.3 |
| AE (mJ) | 0.2-8.2 | about 0.9 | 0.05-0.6 | about 0.2 |
| Eye safety classification | Class 1M for AE < AEL | Class 1M | Class 1M | Class 1M |

Because certain embodiments or device settings may provide Level 1, Level 2, Level 3, or Level 4 eye safety based on the appropriate selection of parameters discussed above, in some such embodiments an eye safety sensor or system may be omitted. However, some such embodiments, even those providing Level 1 eye safety, may include one or more eye safety sensors (e.g., one or more eye safety sensors 214 described below) and/or an eye safety system to provide redundancy, to meet particular regulatory standards, or for other reasons.

In at least some embodiments additional eye safety is provided by incorporating one or more skin contact sensors 204 that enable pulsing of the radiation source 14 only when device 10 in contact with the skin. Thus, in such embodiments, the likelihood of corneal eye injury may be reduced or substantially eliminated unless device 10 is literally pressed to the eye surface.

Eye Safety Sensor

In some embodiments, device 10 includes an optical eye safety sensor 214 configured to detect the presence of a cornea (or other eye tissue or feature) near a treatment output aperture of device 10, in order to help prevent unintended eye exposure to light from the treatment radiation source 14. For example, optical eye safety sensor 214 may be configured to distinguish between the presence of skin and the cornea, and enable device 10 to treat only the intended treatment area 40. Eye safety sensor 214 may be especially important for infrared treatment light of wavelength greater than 1400-nm, for which the eye injury risk is primarily in the cornea or for UV, visible, and/or near-IR where retinal hazards exist. In some embodiments, optical eye safety sensor 214 is relatively low cost, compact, easily packaged within a handheld enclosure (e.g., small and lightweight), and assembled from commonly available parts. Another example embodiment of an eye safety sensor is an imaging sensor with pattern recognition for shape, color, or other feature of the eye.

Figure 51A:
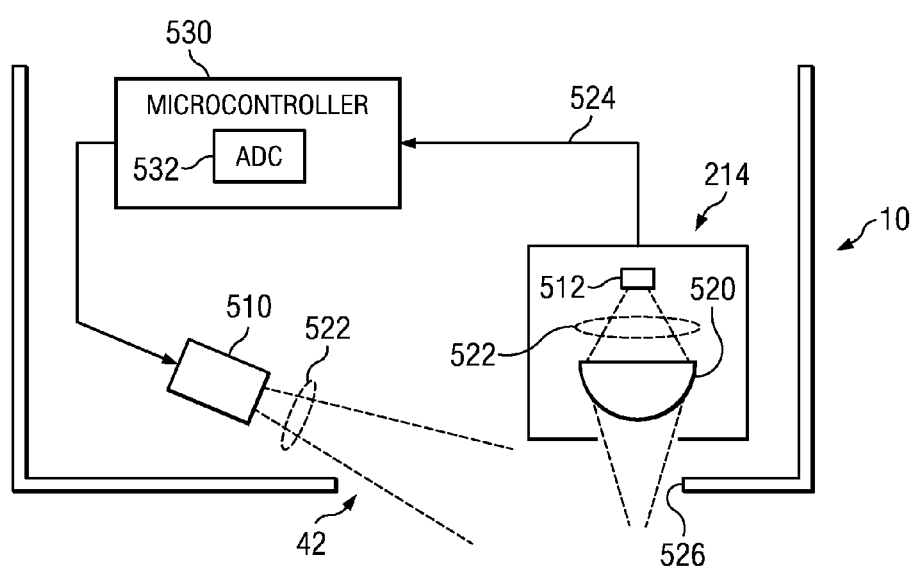
FIGS. 51A-51D illustrate an example optical eye safety sensor (FIGS. 51A and 51B) according to certain embodiments, as well as representation of local surface normal directions for example corneas of different shapes (FIGS. 51C and 51D).

FIG. 51A illustrates an example optical eye safety sensor 214, according to certain embodiments. Optical eye safety sensor 214 may include a light source 510, a light detector 512, detector optics 520, relay optics 522 (in some embodiments), and a microcontroller 530.

Light source 510 may be a light-emitting diode (LED) or any other suitable light source. Light source 510 may be selected for showing fine details in the surface of human skin. Thus, a wavelength may be selected that penetrates a relatively shallow depth into the skin before being reflected. For example, light source 510A may be a blue LED having a wavelength of about 560 nm, or a red LED having a wavelength of about 660 nm, or an infrared LED having a wavelength of about 940 nm. Red or infrared wavelength LEDs are relatively inexpensive and work well in practice. Alternatively, a semiconductor laser could be used.

Light detector 512 may be a photodiode, phototransistor, or other light detector. In some embodiments, a phototransistor has sufficient current gain to provide a directly usable signal, without requiring additional amplification. Light detector optics 520, e.g., a half-ball lens, may be coupled to or carried with light detector 512. Light detector optics 520 may be configured to allow light detector 512 to "view" a target surface location.

Further, in some embodiments, sensor 214 may include relay optics 522 for relaying light from light source 510 and/or relay optics 522 for relaying reflected light to detector 512. Relay optics 522 may be used to relay light for any desired distance, such that one, some, or all of light source 510, detector optics 520, and/or detector 512 may be located at any desired distance from an aperture 526 in housing 24 that may be configured to be positioned on or near the skin surface 38 during use. Also, microcontroller 530 and/or other electronics associated with sensor 214 may be located at any distance from aperture 526 and/or from the other components of sensor 214 (e.g., light source 510, detector 512, detector optics 520, and optional relay optics 522). In some embodiments, locating components of sensor 214 away from aperture 526 may reduce or minimize the space occupied by sensor 214 at application end 42 of device 10, which may allow for a reduced or minimized size of application end 42, which may be desirable or advantageous.

In other embodiments, components of sensor 214 may be located near aperture 526 (e.g., in the application end 42 of device 10), such that relay optics 520 are not included.

Light source 510 may be oriented to illuminate a surface (e.g., skin surface 38) at a very low angle of incidence (e.g., θ shown in FIG. 51B may be between about 5 and 40 degrees), while detector 512 may be aligned at a normal or near-normal angle of incidence relative to the illuminated surface.

Microcontroller 530 may be configured to drive light source 510 (e.g., an LED) with a direct or modulated current, record a signal 524 from detector 512 using an integrated ADC 532, and analyzes the amplitude of the recorded detector signal 524 to determine if the surface below detector 512 is skin 40 or cornea 500.

The signal 524 from detector 512 may be referred to as a "reflectance feedback signal." The amplitude of the reflectance feedback signal 524 corresponds to the intensity of reflected light from light source 510 received by detector 512: the more light from light source 510 that is reflected into detector 512, the higher the amplitude of reflectance feedback signal 524. As discussed below, due to the configuration of light source 510 and detector 512, skin (which is relatively diffuse) reflects more of light from light source 510 into detector 512 than the cornea (which is relatively specular). Thus, microcontroller 530 may analyze the amplitude of reflectance feedback signal 524 (e.g., using threshold or window comparisons) to determine whether the surface below detector 512 is skin 40 or cornea 500.

Signals from microcontroller 530 indicating whether a treatment window 44 of device is located above skin or the cornea may be used by control systems 18 for controlling one or more controllable operational parameters of device 10.

For example, treatment (e.g., delivery of radiation to a treatment area 40) may be initiated, such as to begin a treatment session, or re-initiated after an interruption during a treatment session if microcontroller 530 detects a "skin presence," e.g., by determining that reflectance feedback signal 524 is above a predefined skin/cornea threshold or within a predefined reflectance window corresponding with skin. In such situation, control systems 18 may enable or power on treatment radiation source 14 (or control other aspects of device 10) to begin radiation delivery to the treatment area 40. The treatment may continue as long as microcontroller 530 continues to detect a skin presence. The treatment may be interrupted upon detection of a "possible cornea presence" or upon other treatment interrupting events.

If microcontroller 530 determines that reflectance feedback signal 524 is below the predefined skin/cornea or outside the reflectance window corresponding with skin, microcontroller 530 may detect a "possible cornea presence" (which is essentially a detection of a non-skin surface, which could be a cornea, other non-diffuse surface, or lack of a target surface, for example). Control systems 18 may disable treatment radiation source 14 (or control other aspects of device 10) in response to a possible cornea presence detected by microcontroller 530, in order to prevent a possible unintended eye exposure (and possible eye damage).

Figure 51B:
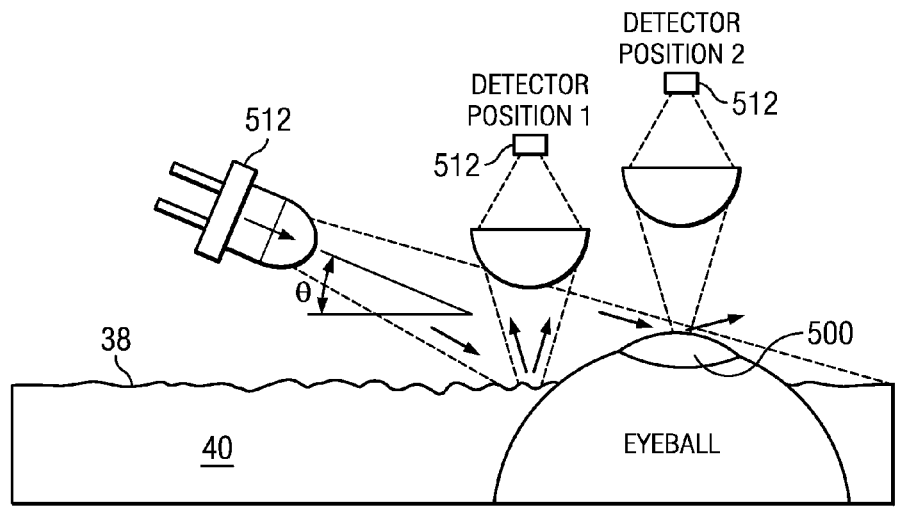
Figure 51C:
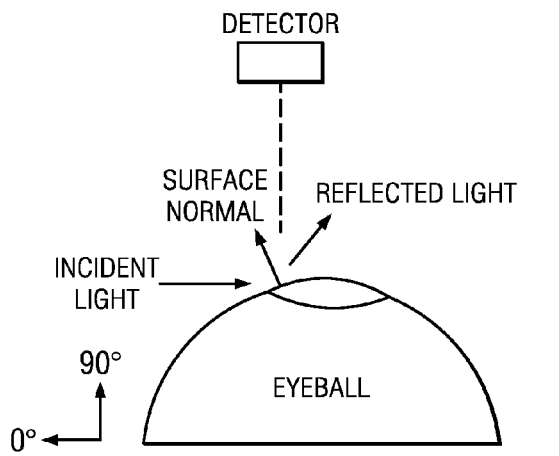
Figure 51D:
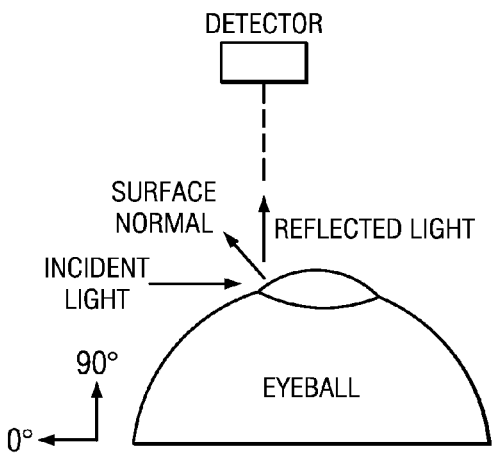

The operation of sensor 214 is described below with reference to FIGS. 51B-51D. FIG. 51B illustrates light source 510 and two different positions of detector 512. FIGS. 51C and 51D illustrate the local surface normal directions for example corneas of different shapes.

Detector 512 receives a larger amount of reflected light (and thus generates a larger amplitude of signal 524) from diffuse surface materials, due to light scattering, than from smoother, more specular reflection materials. Skin is relatively diffuse, while the corneal surface is generally smooth and specular, such that the corneal surface has a much lower diffuse component of reflection than the skin. This difference can be used to determine whether detector 512 is positioned over an area of skin 40 or over the cornea 500.

This technique of discriminating between diffuse and specular materials using a single beam source 510 and single detector 512 may assume that the angles between the target surface normal and both the beam source 510 and detector 512 are known at least to an extent. In particular, the angles at which beam source 510 and detector 512 are aligned relative to the target surface may be selected such that the reflectance feedback signal 524 can be reliably used to distinguish reflection off the skin from reflection off the cornea, for a known range of corneal curvatures, as discussed below with respect to FIGS. 51C and 51D.

In general, the local surface normal vector of a surface (e.g., skin or corneal surface) will vary relative to a larger-scale average surface normal, depending on the local curvature of the surface. For example, near the edge of the cornea, the local surface normal will be at least several degrees offset from the normal vector at the center of the cornea, because the cornea is a curved surface.

Assume a light beam source illuminates a surface at an incidence of near-grazing (~0 degrees) and a detector views this surface at near normal incidence (~90 degrees). For less curved surfaces, the local surface normals are relatively close to 90 degrees, as shown in FIG. 51C. In an extreme case shown in FIG. 51D, in which curvature provides a local surface normal of 45 degrees, a specular reflection propagates directly into the detector. It may be assumed for the purposes of sensor 214 that the exposed corneal surface forms an angle of less than 45 degrees with the larger surface normal of the face (i.e., skin adjacent the eye), such that a direct specular reflection from beam source to detector does not occur for any practical configuration of sensor 214/device 10 relative to the face. It is also known that for a normal eye, the most extreme angle near the corneal edge is less than 40 degrees. (See, e.g., James D. Doss, "*Method for Calculation of Corneal Profile and Power Distribution*", Arch Ophthalmol, Vol. 99, July 1981). Moreover, this angle quickly decreases to near 20 degrees within 60% of the central cornea region, i.e., the curvature is not large near the cornea center. Therefore, for the central 60% cornea region, the specular reflection from the cornea will not be intercepted by the detector with a large margin.

Thus, assuming light source 510 is arranged at a sufficiently low angle of incidence (e.g., $\theta$ shown in FIG. 51B between about 5 and 40 degrees), for all practical cases the cornea will not reflect the light from light source 510 directly into detector 512. Thus, for all practical cases, the cornea will reflect less light from light source 510 into detector 512 than will the skin. Thus, for practical cases, the cornea can be distinguished from skin, assuming the proper signal amplitude thresholds are utilized by microcontroller 530. Thus, to summarize, assuming the proper orientation of light source 510 and detector 512, as well as the proper selection of threshold(s) for comparing the amplitude of reflectance feedback signal 524, sensor 214 is able to reliably discriminate between the skin and the cornea, especially for the central cornea region which may be the most important for vision.

It has been shown experimentally that the scattering coefficient of skin dermis $\mu m_{s\_skin}$ is substantially greater than that of the cornea $\mu m_{s\_cornea}$. In particular, the scattering coefficient of skin dermis $\mu m_{s\_skin} \approx 60$ cm$^{-1}$ for 500-nm wavelength (see Steven L. Jacques, "*Skin Optics*", Oregon Medical Laser Center News, January 1998), whereas the scattering coefficient of skin dermis $\mu m_{s\_cornea} \approx 10$ cm$^{-1}$ for 500-nm wavelength (see Dhiraj K. Sardar, "*Optical absorption and scattering of bovine cornea, lens, and retina in the visible region*", Laser Med. Sci., 24(6), November 2009). Based on these respective scattering coefficients, the expected diffused reflectance of the cornea is about 8%, while the expected diffused reflectance for a typical Fitzpatrick Type I to VI skin ranges from 70% to 10% respectively. Thus, for most skin types, the reflectance contrast is large enough discriminating the cornea from the skin, again assuming the proper comparison thresholds or windows are utilized by sensor 214.

Multi-Sensor Eye Safety System

In some embodiments, device 10 includes a multi-sensor control/safety system that includes one or more eye safety sensor 214 and one or more skin contact sensors 204.

Figure 52:
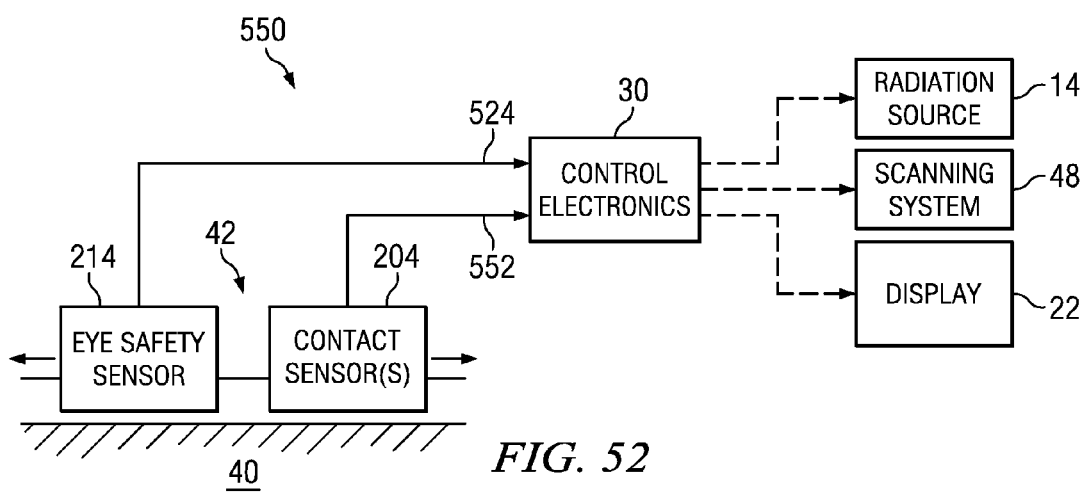
FIG. 52 illustrates an example multi-sensor control/safety system that includes one or more eye safety sensors and one or more skin contact sensors arranged on or near the application end of the device, according to certain embodiments.

FIG. 52 illustrates an example multi-sensor control/safety system 550 that includes one or more eye safety sensor 214 and one or more skin contact sensors 204 arranged on or near device application end 42. System 550 combines the functionality of eye safety sensor 214 and skin contact sensor(s) 204 to provide more reliable and/or redundant eye safety functionality as compared to eye safety sensor 214 or skin contact sensor(s) 204 acting alone.

System 550 may configured to control device 10 (e.g., turn treatment radiation source 14 on/off) based on independent determinations made by eye safety sensor 214 and skin contact sensor(s) 204, in any suitable manner. The independent determinations made by eye safety sensor 214 and skin contact sensor(s) 204 may be based on comparisons of signals detected by such sensors to respective thresholds, referred to herein as "independent determination thresholds."

For example, system 550 may trigger a control signal to turn on treatment radiation source 14 if either (a) eye safety sensor 214 determines a "skin presence" (discussed above), independent of any determinations or signal analysis by contact sensor(s) 204, or (b) all contact sensors 204 determine a contact status with the skin, independent of any determinations or signal analysis by eye safety sensor 214. Thus, system 550 may trigger a control signal to turn off treatment radiation source 14 only if both (a) eye safety sensor 214 determines a "possible cornea presence" (discussed above), independent of any determinations or signal analysis by contact sensor(s) 204, and (b) at least one contact sensor 204 determines a non-contact status with the skin, independent of any determinations or signal analysis by eye safety sensor 214.

Alternatively, system 550 may trigger a control signal to turn on treatment radiation source 14 only if both (a) eye safety sensor 214 determines a skin presence (discussed above), independent of any determinations or signal analysis by contact sensor(s) 204, and (b) all contact sensors 204 determine a contact status with the skin, independent of any determinations or signal analysis by eye safety sensor 214. Thus, system 550 may trigger a control signal to turn off treatment radiation source 14 if either (a) eye safety sensor 214 determines a possible cornea presence, independent of any determinations or signal analysis by contact sensor(s) 204, or (b) any contact sensor 204 determines a non-contact status with the skin, independent of any determinations or signal analysis by eye safety sensor 214.

Alternatively or in addition, system 550 may be configured to control device 10 (e.g., turn treatment radiation source 14 on or off) based on inter-dependent analysis of signals from eye safety sensor 214 and signals from skin contact sensor(s) 204. For example, system 550 may utilize algorithms that analyze signals detected by eye safety sensor 214 (e.g., reflectance feedback signal 524 from detector 512) and signals detected by contact sensor(s) 204 (e.g., signal 552 detected by contact sensor(s) 204) to determine whether to trigger a particular control signal. For example, such algorithms may incorporate thresholds that are lower than the independent determination thresholds discussed above. Such thresholds are referred to herein as "inter-dependent sensor analysis thresholds."

To illustrate by example, system 550 may specify the following independent determination thresholds:
  (a) 10 mV eye safety threshold: eye safety sensor 214 determines a possible cornea presence if the amplitude of reflectance feedback signal 524 falls below 10 mV, and
  (b) 50 pF contact sensor threshold: contact sensor 204 determines a non-contact status if the amplitude of contact sensor signal 552 falls below 50 pF.

Further, system 550 may specify the following inter-dependent sensor analysis thresholds:
  (a) 15 mV eye safety threshold for reflectance feedback signal 524, and
  (b) 70 pF contact sensor threshold for signal 552.

System 550 may utilize an algorithm 154 that incorporates the inter-dependent sensor analysis thresholds (15 mV and 70 pF). For example, an algorithm may specify a control signal to turn off treatment radiation source 14 if both (a) reflectance feedback signal 524 falls below 15 mV and (b) contact sensor signal 552 falls below 70 pF.

As another example of controlling device 10 based on inter-dependent analysis of signals from eye safety sensor 214 and signals from skin contact sensor(s) 552, an algorithm 154 may calculate an index, referred to herein as an "eye safety factor index," or ESF index from reflectance feedback signal 524 and contact sensor signal 552. The algorithm may weight reflectance feedback signal 524 and contact sensor signal 552 in any suitable manner. An example algorithm is provided as equation (1):

$$\text{ESF index} = \text{signal 524 amplitude} * W1 + \text{signal 552 amplitude} * W2 \tag{1}$$

where W1 and W2 represent any suitable constants (including 0).

Another example algorithm is provided as equation (2):

$$\text{ESF index} = (\text{signal 524 amplitude} + C1) * (\text{signal 552 amplitude} + C2) \tag{2}$$

where C1 and C2 represent any suitable constants (including 0).

Any other suitable algorithms may be used for calculating an ESF index based on reflectance feedback signal 524 and contact sensor signal 552.

ESF index may then be compared to a predefined threshold to determine whether to trigger a particular control signal (e.g., to turn off treatment radiation source 14), or compared to multiple different predefined thresholds for triggering different control signals. Such algorithms (using the same or different threshold values) may be used for triggering any suitable control signals, such as control signals for turning on treatment radiation source 14, turning on treatment radiation source 14, changing the current treatment mode, or adjusting any controllable operational parameter of device 10.

Figure 53:
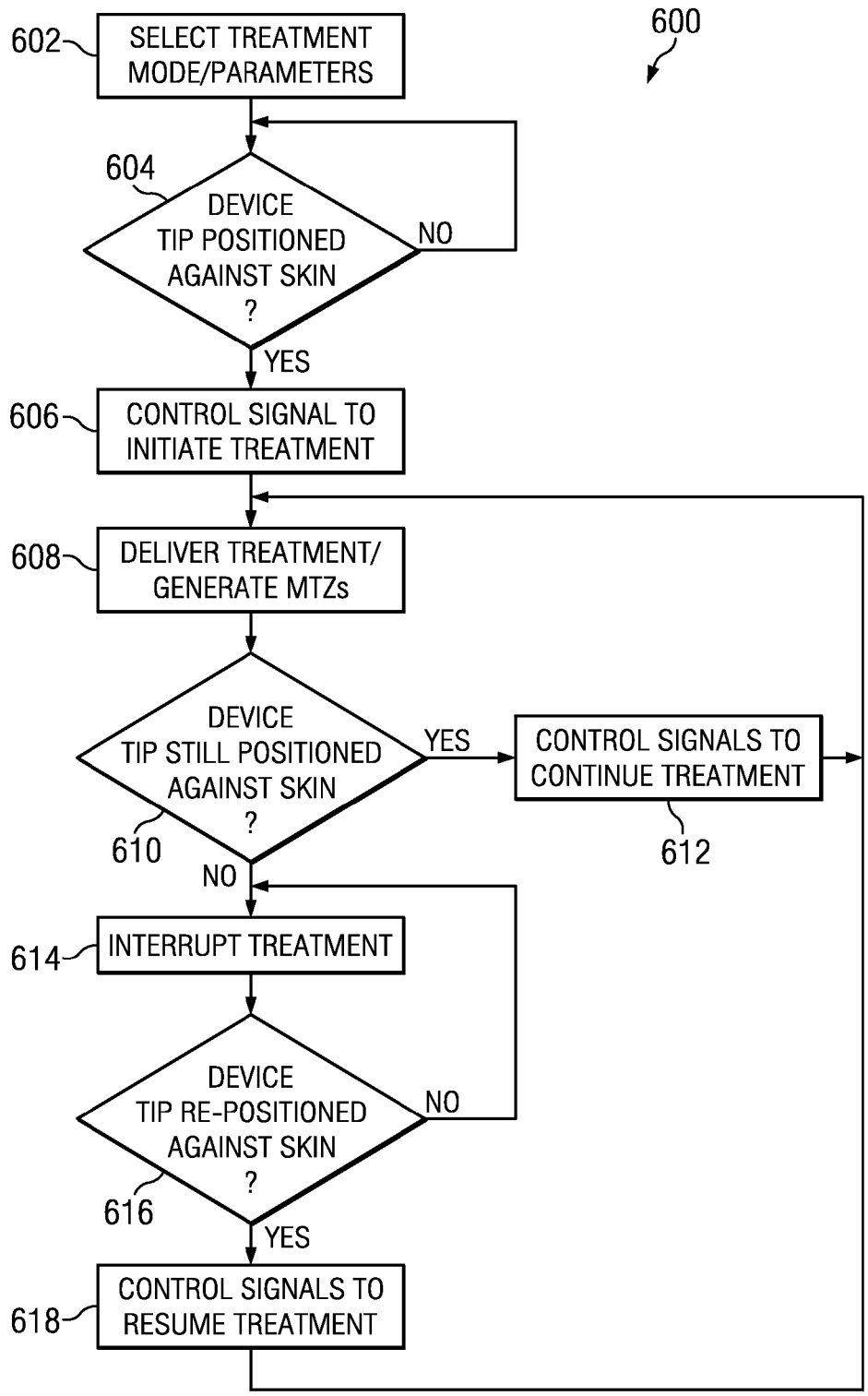
FIG. 53 illustrates an example method for controlling a device using a multi-sensor control/safety system, according to certain embodiments.

FIG. 53 illustrates an example method 600 for controlling device 10 (e.g., controlling treatment radiation source 14) using a multi-sensor control/safety system 550, according to certain embodiments. At step 602, a user prepares for a treatment session by selecting a treatment mode and/or other treatment parameters, and places the application end 42 of device 10 against the skin.

At step 604, system 550 determines whether the application end 42 is correctly positioned against the skin for treatment, e.g., using any of the techniques discussed above or any other suitable technique.

If system 550 determines that the application end 42 is correctly positioned against the skin for treatment, system 550 may generate a control signal for beginning a treatment session automatically or upon a defined user input (e.g., pressing a treatment button), as indicated at step 606. Control systems 18 may also generate feedback to the user indicating that treatment has been initiated or that treatment is ready for initiation upon the defined user input (e.g., pressing a treatment button).

Device 10 may then activate radiation source 14 to generate beam 108 for delivery to the skin 40 as delivered beams 114 to generate treatment spots 70, as indicated at step 608. The user may operate device 10 in a gliding mode or a stamping mode, depending on the configuration and/or selected treatment mode of device 10.

During the treatment, system 550 continually or repeatedly determines whether the application end 42 is still correctly positioned against the skin for treatment, as indicated at step 610. As long as system 550 determines that application end 42 is correctly positioned against the skin for treatment, system 550 may continue to generate control signals for continuing the treatment session (i.e., such that control systems 18 continue to deliver beams 114 to generate treatment spots 70 on the skin 40), as indicated at step 612.

However, during the treatment, if system 550 determines that application end 42 is not correctly positioned against the skin for treatment (e.g., if system 550 determines that application end 42 is located over the cornea or moved out of contact with the skin), system 550 may generate a control signal for automatically stopping or interrupting the treatment session, e.g., by turning off or disabling treatment radiation source 14), as indicated at step 614. Control systems 18 may also generate feedback, e.g., audible or visual feedback, to the user indicating the status of device 10. For example, control systems 18 may provide general feedback indicating that the treatment has been stopped or interrupted, or may provide more specific feedback indicating the reason that the treatment has been stopped or interrupted, such as feedback distinguishing between eye detection, non-contact detection, and device malfunction, for example.

System 550 may continue to monitor the positioning of application end 42 at step 616. If system 550 determines that application end 42 has again become correctly positioned against the skin for treatment, system 550 may resume the treatment session, e.g., by generating a control signal to resume treatment (e.g., by turning on treatment radiation source 14), as indicated at step 618, and resuming the generation of treatment spots 70 in the skin, as indicated by the method returning to step 608.

The treatment session may end upon reaching a treatment delimiter (such as discussed above regarding FIG. 47), or after a predefined time, or based on any other parameters defining the treatment session. It should be understood that this example and FIG. 53 can apply to sensors other than contact sensor in a similar manner.

Calibration of Eye Safety Sensor

Figure 54:
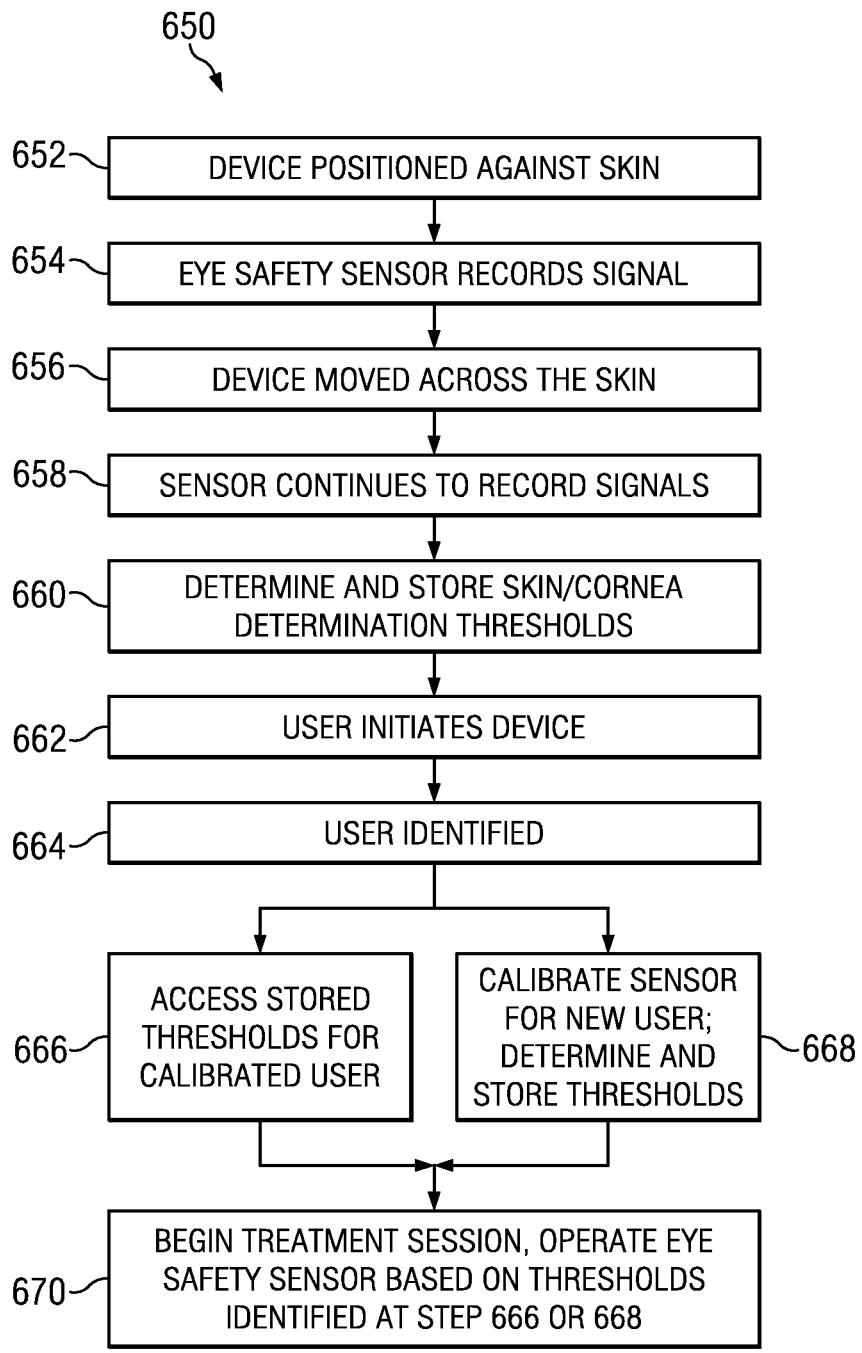
FIG. 54 illustrates an example method for calibrating an eye safety sensor for one or multiple users, according to certain embodiments.

In some embodiments, eye safety sensor 214 can be individually calibrated to the current user of device 10. FIG. 54 illustrates an example method 650 for calibrating eye safety sensor 214 for one or multiple users. A calibration process is performed at steps 652-660. At step 652, a user positions the application end 42 of device 10 against the user's skin, e.g., upon instruction from device 10. Device 10 may instruct the user to position application end 42 against a certain part of the body, e.g., the face or back of the hand. Sensor 214 is activated and records a reflectance feedback signal 524 at step 654. At step 656, the user may move the application end 42 of device 10 across the skin, e.g., upon instruction from device 10. Sensor 214 may continue to record reflectance feedback signal 524 at various locations of application end 42 on the skin, at step 658.

At step 660, microcontroller 530 may analyze signal 524 recorded at steps 654, 658 to calibrate sensor 214. For example, microcontroller 530 may execute one or more algorithms to determine one or more appropriate threshold values (e.g., threshold voltages) for distinguishing between skin and the cornea, e.g., for determining a "skin presence" or "possible cornea presence," as discussed above. Such threshold values may be stored by sensor 214 or control system 18.

At step 662, the same user or a different user may initiate device 10 for a treatment session. The user may identify him or herself via a user interface 18, e.g., by scrolling and selecting from a list of names, or entering a new name, at step 664. Device 10 may then determine whether eye safety sensor 214 has been calibrated for that user, and if so, access the skin/cornea determination thresholds stored for that user, at step 666. If the user is a new user or eye safety sensor 214 has not been calibrated for that user, device 10 may calibrate sensor 214 for that user to determine and store skin/cornea determination thresholds for that user, at step 668 (e.g., by leading the user through the calibration process of steps 652-660).

After the skin/cornea determination thresholds for the user have been accessed (or in the case of a new user, determined and stored), the user may select various operational parameters and begin a treatment session using device 10. During the treatment session, at step 670, eye safety sensor 214 may continually or repeatedly monitor the surface under application end 42 using the user-specific thresholds accessed at step 666 or 668.

In other embodiments, device 10 may require eye safety sensor 214 to be recalibrated before each treatment session.

Dual-Function Sensors

In some embodiments, in addition to providing eye safety functionality, eye safety sensor 214 may also be used as a displacement sensor, operating in a similar manner as discussed above regarding single-pixel displacement sensor 200A, 200B, or 200C shown in FIGS. 40A-40C. The functionality of eye safety sensor 214 and a displacement sensor 200A/200B/200C may be integrated into a single sensor 200/214. Thus, a single radiation source and single detector may be used to provide both the eye safety and displacement monitoring functions described above. The integrated eye safety/displacement sensor 200/214 includes one or more microcontrollers or other processors for providing the functionality of both sensors.

In other embodiments, device 10 may include both eye safety sensor 214 and one or more displacement sensors 200 (e.g., one or more single-pixel displacement sensors 200A/200B/200C and/or one or more multi-pixel displacement sensors 200D), wherein eye safety sensor 214 provides (in addition to its eye safety functionality) device displacement monitoring functionality to supplement or provide a backup to the displacement sensor(s) 200A/200B/200C/200D.

Radiation Pulse and Scanning Element Motor Control

In some embodiments, device 10 includes a pulsed laser radiation source 14 and a motor/pulse control system 139 configured to monitor and control the operation of pulsed laser radiation source 14 and beam scanning system 48, e.g., scanning system motor 120. Motor/pulse control system 139 may combine aspects of any of the various control systems discussed above, e.g., radiation source control system 128, scanning system control system 130, displacement-based control system 132, usability control system 133, user interface control system 134, and temperature control system 136. For example, motor/pulse control system 139 may control pulsed laser radiation source 14 to control the pulse duration, pulse on time, pulse off time, trigger delay time, duty cycle, pulse profile, or any other parameters of generated pulses; and may control scanning system motor 120 of scanning system 48 (e.g., to control the speed, position, etc. of a rotating beam-scanning element 100), etc. Motor/pulse control system 139 may control such parameters based on signals from various sensors 26 and/or by monitoring the rotation and/or position of an encoder 121, which may be arranged to indicate the rotation and/or position of a rotating beam-scanning element 100. An example of such encoder 121 is shown in FIGS. 68A and 68B, discussed below.

Motor/pulse control system 139 may provide various control redundancies, which may be designed, for example, to ensure accuracy of energy dose per laser pulse, as well as to provide eye safety and skin safety aspects.

Figure 55:
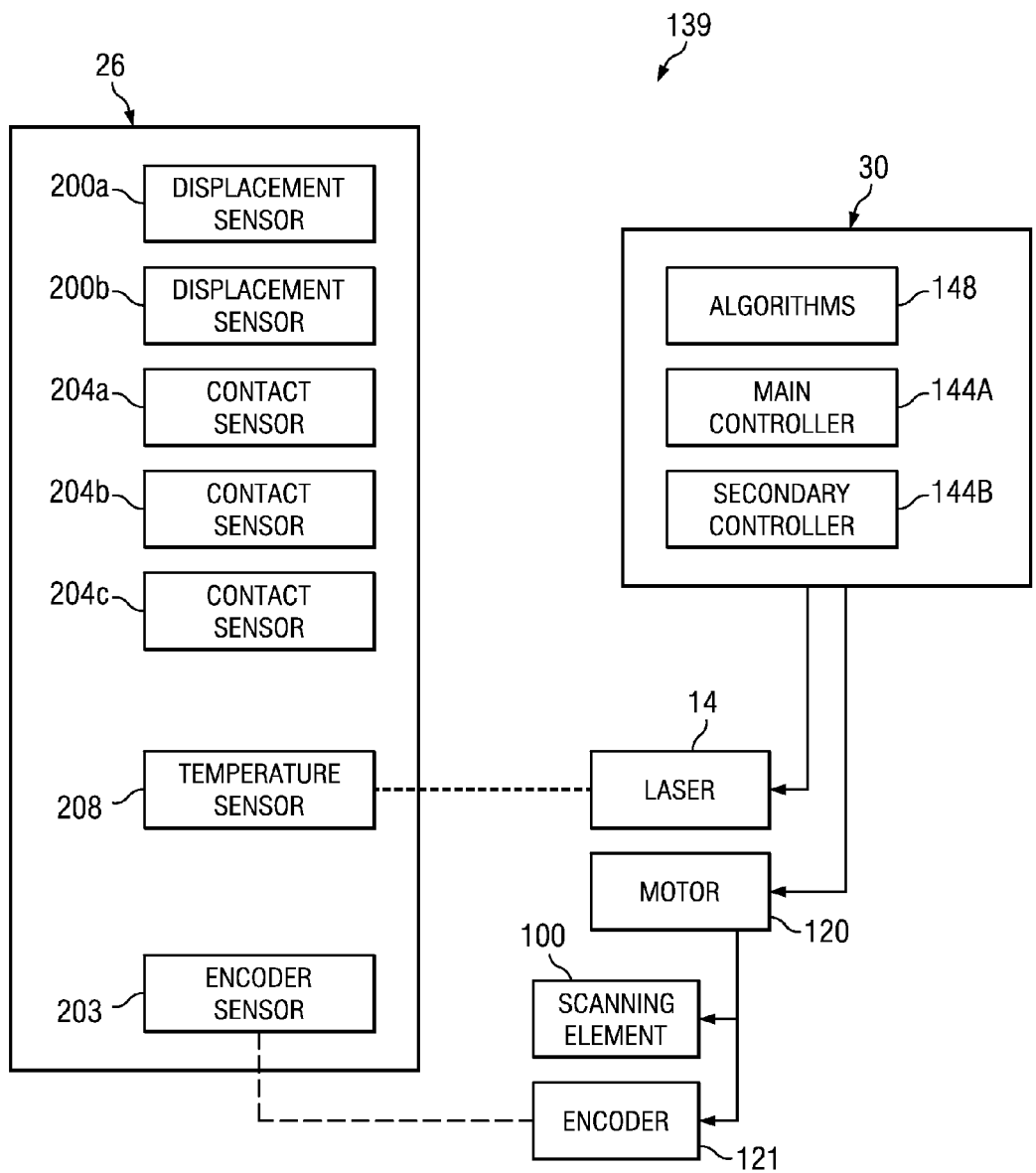
FIG. 55 illustrates an example system for controlling a scanning system motor and laser pulse parameters, for certain example embodiments that utilize a pulsed laser source.

FIG. 55 illustrates components of an example motor/pulse control system 139, according to an example embodiments. Motor/pulse control system 139 may include a number of sensors 26 for providing input to control electronics 30 for controlling laser 14 and scanning system motor 120, which is configured to drive the rotation of beam scanning element 100 and encoder 121.

Sensors 26 of system 139 may include, for example, four independent contact sensors 204a-204d for detecting skin contact, two independent displacement sensors 200a and 200b for detecting displacement of device 10 relative to the skin, a temperature sensor for detecting a temperature of or related to the laser 14 (e.g., a temperature of laser package 250 or heat sink 36), an optical encoder sensor 203 for monitoring the speed of the scanning system motor 120 and for detecting the rotation and/or position of rotating scanning element 100 (by monitoring encoder 121).

Control electronics 30 may include a main processor or controller 144A, an independent secondary processor or controller 144B, and executable logic or algorithms 148 stored in any suitable storage medium 146. Main controller 144A may generally be configured to control the various parameters of system 139, while secondary controller 144B may provide independent error checking for integrity verification, thus providing redundancy, e.g., to provide an additional aspect of safety.

The speed of scanning system motor 120 and the trigger timing (e.g., trigger delay time) for each individual laser pulse must be well coordinated depending on multiple factors, including the desired laser pulse duration and the operating laser temperature. Thus, system 139 provides appropriate temperature compensation to ensure accurate pulse energy control, as discussed below regarding FIGS. 56 and 57A-57B.

Figure 56:
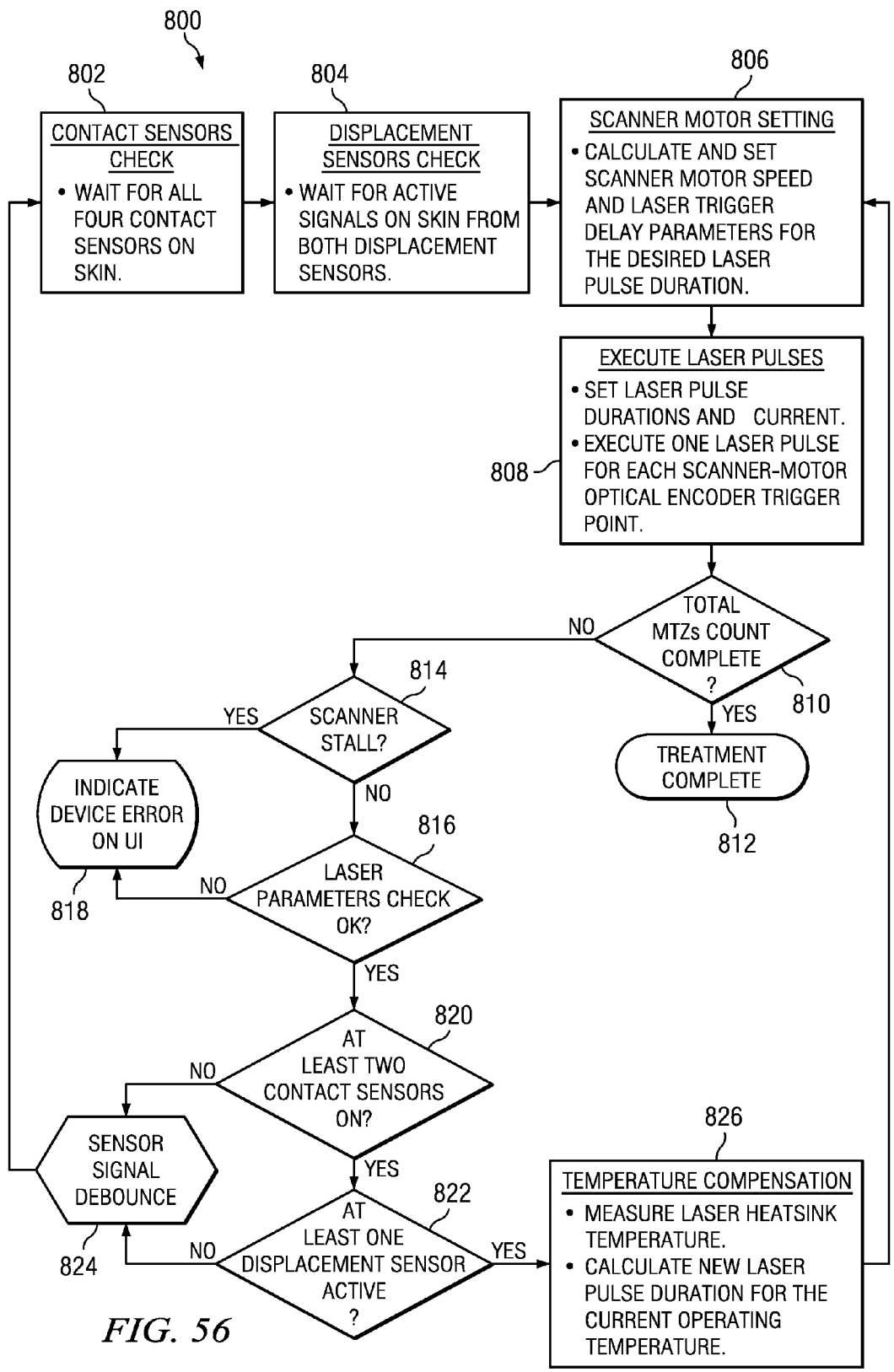
FIG. 56 illustrates an example algorithm for controlling the radiation source and scanning system motor in a scanned-beam treatment device, according to certain example embodiments.

FIG. 56 illustrates an example algorithm 800 employed by motor/pulse control system 139 for controlling scanning system motor 120 and the pulsing of laser source 14. It may be recognized that example algorithm 800 employs the usability control algorithm discussed above.

System 139 may initiate algorithm 800 once device 10 is in a ready state after passing initial start-up self-tests for verifying the appropriate functionality of various control elements. At steps 802 and 804, system 139 waits for all four contact sensors 204a-204d to indicate contact with the skin and both displacement sensors 200a and 200b to indicate a displacement that meets the predetermined minimum displacement threshold (e.g., 1 mm). The predetermined displacement threshold may be defined by a predetermined number of identified surface features 74 of the skin, e.g., as discussed above regarding FIGS. 38-46. Both conditions must be satisfied before initiating a laser pulsing command.

When both conditions are met, the algorithm advances to step 806, where main controller 144A calculates (a) an appropriate scanning system motor speed and (b) an appropriate trigger delay time relative to a transition edge of each lenslet of the scanning element. The input for this calculation is the target laser pulse duration for a given desired pulse energy output. It is important for the motor speed and the laser trigger timing (as defined by the trigger delay time) to be properly synchronized in order for each laser pulse to be delivered within an optically usable portion of each respective lenslet of the rotating scanning optic. This process is discussed in greater detail below with respect to FIGS. 57A and 57B.

After calculating the parameters at step 806, system 139 begins pulsing laser 14 at step 808, with each pulse being deflected by a different sector of the rotating scanning element 100 to provide an individual output beam 112 that is delivered to create a treatment spot on the skin. The laser pulses are executed with the appropriate scanning system motor speed and trigger delay time relative to a detected optical encoder signal, which is a square-wave pulse train generated by encoder sensor 203 monitoring an encoder wheel 121 rotated by motor 120. Encoder wheel 121 may have a number of detectable features (e.g., slotted openings), each corresponding to one sector of multi-sector scanning element 100, and each aligned with a transition edge of the corresponding sector (e.g., a transition edge between adjacent lenslets). Thus, system 139 can monitor the optical encoder signal generated by encoder sensor 203 to detect each detectable feature (e.g., slotted opening) rotating through a particular location, and thereby detect a transition edge of each sector of the rotating scanning element.

Accordingly, system 139 commands the generation of one laser pulse for each detected sector of scanning element 100 (based on the signal from encoder sensor 203). Throughout the laser pulsing, controller 144A maintains a count of the total pulses delivered, as indicated at step 810, and determines a completion of the treatment when the pulse count reaches a predetermined pulse count for the particular treatment session, as indicated at step 812. Thus, the total energy dose delivered during the treatment session is independent of the glide speed of the device 10.

During the treatment session, controllers 144A and/or 144B continually check for various safety fault conditions. For example, at step 814, controller 144A checks for a motor stall condition, which may be detected when the motor speed (e.g., as detected based on signals from encoder sensor 203) either (a) differs from the motor speed commanded at step 804 by more than a predetermined amount (e.g., ±20%) or (b) falls below a predetermined stall threshold (e.g., 240 rpm). Further, at step 816, secondary controller 144B may provide an independent check of various laser parameters (e.g., pulse duration, current, and voltage) to monitor for laser over-pulse-duration, laser over-current, or degraded laser (based on laser diode voltage), for example. If any of the fault conditions are detected at step 814 or 816, the laser pulsing will stop immediately and the device will report an error condition on the display user interface, as indicated at 816. The checks at steps 814 and/or 816 may be performed in any suitable frequency, e.g., after each pulse, after each scan of the input beam, or at a frequency unrelated to the pulse or scan frequencies (e.g., every 200 ms).

Assuming no fault condition at step 814 or 816, the controller 144A applies the usability control conditions for continuing the pulsing of laser 14 at step 820 and 822, which conditions are less stringent than the conditions at steps 802 and 804 for allowing the initial pulse, e.g., as discussed above regarding the usability control algorithm of FIG. 49. In this example, valid inputs from only two of the four contact sensors 204a-204 (specifically, valid input from at least one of "bottom" contact sensors 204a and 200b and valid input from at least one of "top" contact sensors 204c and 200d), combined with valid input from only one of the two displacement sensors 200a and 200b are required for continued pulsing. Therefore, the laser pulsing will continue as long as any pair of contact sensors along the critical scan-beam edges indicate contact with the skin and either one of the two displacement sensors indicate the required displacement of device 10. However, if the conditions at steps 820 and 822 are not met for a continuous period referred to as the "signal de-bouncing period" (e.g., one second), the conditions reset to the more stringent standard for allowing an initial pulse, as indicated as step 824 and the return to steps 802 and 804. The different standards for initiating pulsing and for continuing pulsing once initiated may achieve both safety and usability for the gliding movement of the application end 42 of device 10 across the skin. That is, due to the expected treatment skin curvature and the bony structure underneath, it is often usually difficult to obtain perfect skin contact and displacement in a gliding treatment motion, except for during the initial contact and movement.

In the illustrated example algorithm 800, system 139 also compensates for temperature variations of laser 14, due to the fact that laser performance (e.g., output power or wavelength) typically varies with temperature. Thus, the temperature compensation provided by system 139 may ensure accurate control of the laser pulse energy (i.e., energy output per pulse). Laser diode optical output power varies with its operating temperature. This variation normally corresponds to about 1% power drop per degree C. of temperature rise. To maintain a constant laser pulse energy, either the laser drive current or the pulse duration can be varied. Because of the linear nature of the pulse energy relative to the pulse duration (e.g., as opposed to the generally non-linear relationship between current and pulse energy), adjusting the laser pulse duration may be the preferred option, particularly when the compensation range is not large, e.g., less than 25 degree C. temperature change. In this example implementation, the new laser power is recalculated in each control loop based on the actual measured temperature of heat sink 36, as indicated at 826. The resulting required laser pulse duration to achieve the set target pulse energy is then fed back as input for calculating the scanning system motor speed and trigger delay time at step 806. The entire algorithm 800 working in real-time is designed to achieve closed-loop control of scanning system motor speed and laser pulsing parameters based on the dynamic operating temperature of laser 14.

Figure 57A:
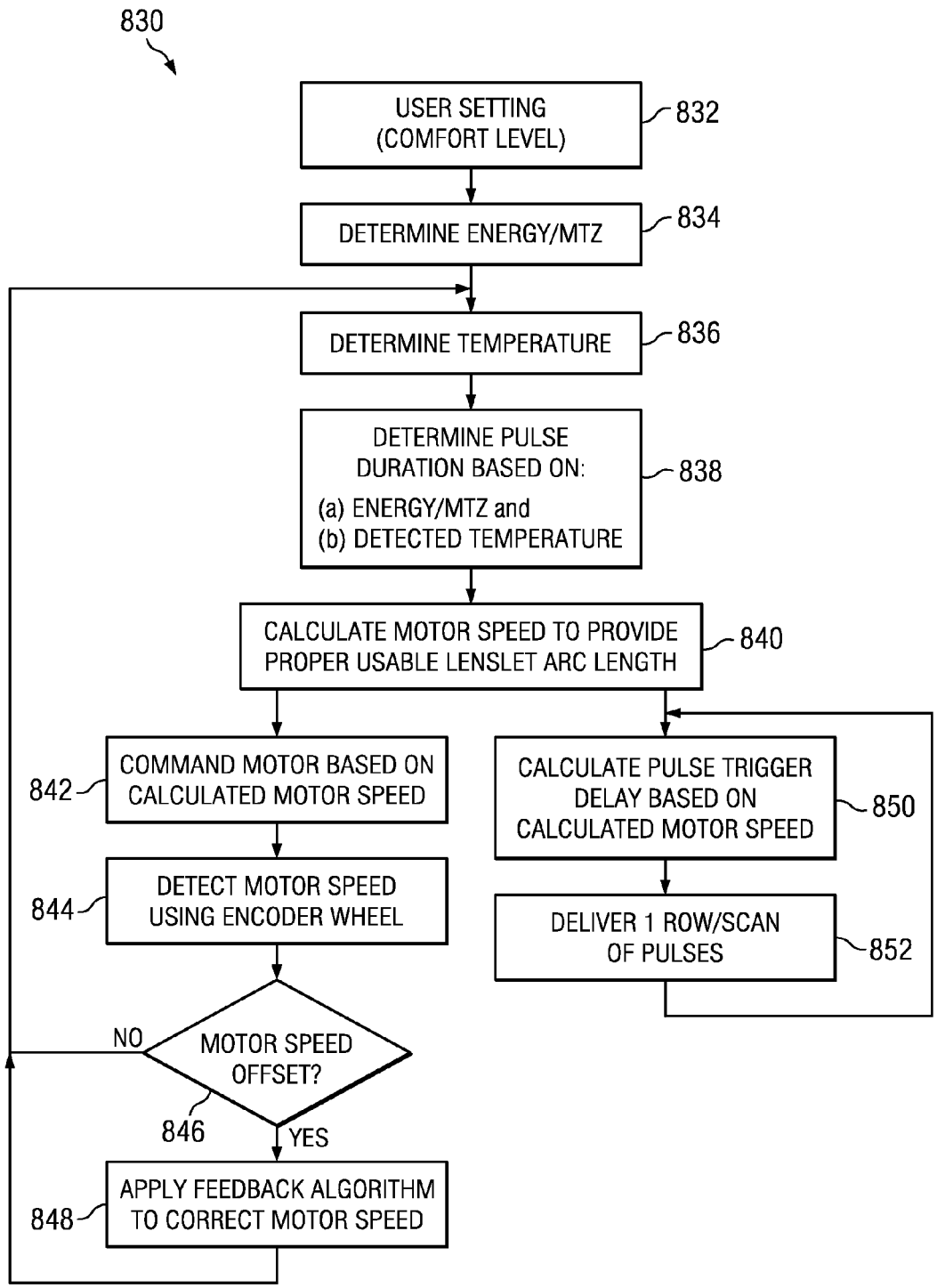
FIG. 57A illustrates a more specific algorithm for controlling parameters of the scanning motor and radiation source in a scanned-beam treatment device, according to an example embodiment.
Figure 57B:
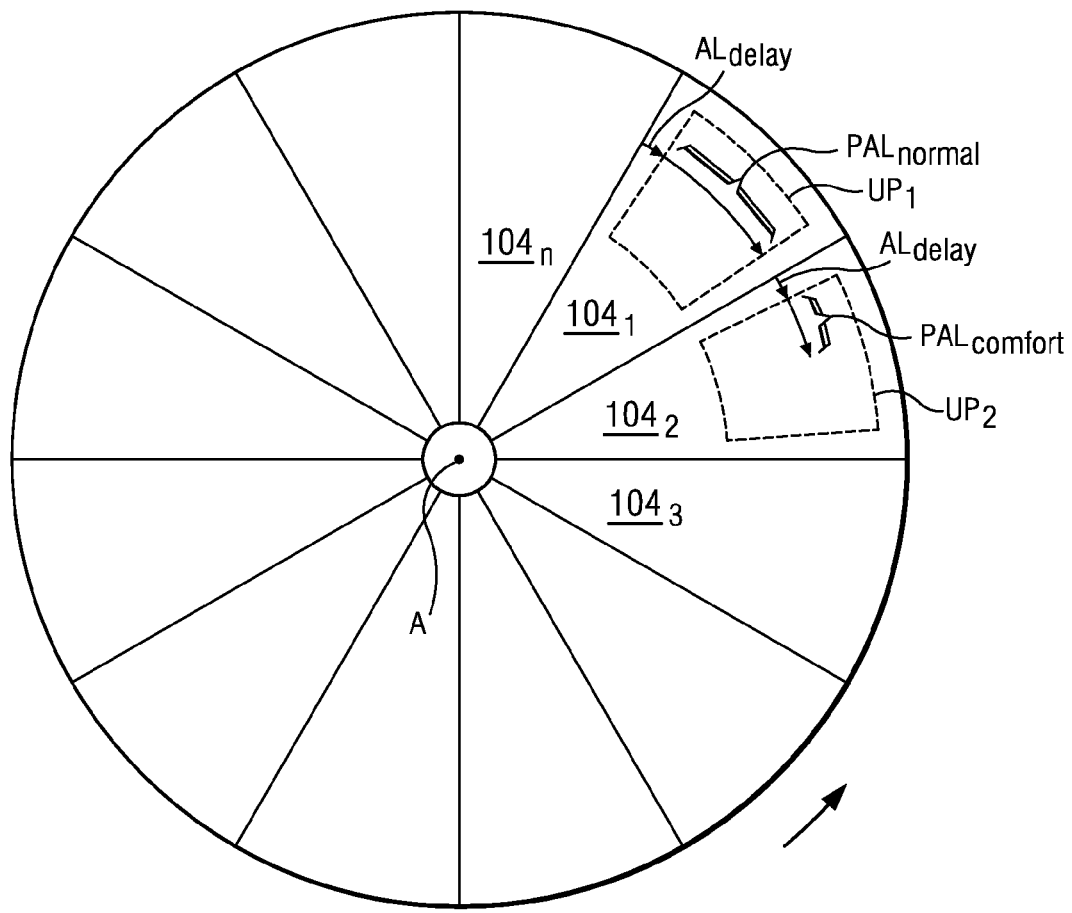
FIG. 57B illustrates radiation pulse parameters with respect to a rotating beam-scanning element, e.g., for the example control algorithm shown in FIG. 56, according to an example embodiment.

FIG. 57A illustrates an example algorithm 830 corresponding to steps 804 and 806 of algorithm 800, according to an example embodiment. FIG. 57B illustrates radiation pulse parameters with respect to a rotating beam-scanning element 100, with reference to control algorithm 830 of FIG. 56, according to an example embodiment.

At step 832, device 10 receives a user setting, e.g., a treatment level or a "comfort level" (discussed below in more detail) for a treatment session, via any suitable user interface 28, e.g., a treatment level selection button or switch 220.

At step 834, motor/pulse control system 139 determines a target energy/MTZ corresponding to the selected treatment level or comfort level. As an example only, device 10 may allow the user to select between a low level treatment, a medium level treatment, and a high level treatment, which are programmed to deliver 5 mJ/MTZ, 10 mJ/MTZ, and 12 mJ/MTZ, respectively.

At step 836, system 139 determines a current actual temperature of or related to the laser 14 (e.g., a temperature of laser package 250 or heat sink 36), e.g., from one or more temperature sensors 208.

At step 838, system 139 calculates a target pulse duration required to provide the target energy/MTZ determined at step 834, and adjusts based on the temperature measured at step 836, e.g., based on known temperature/performance relationships for the particular laser 14 of device 10 stored in memory 146. Thus, system 139 calculates the target pulse duration based on the target energy/MTZ and the current temperature of related to laser 14.

Based on the calculated pulse duration, system 139 calculates a target motor speed for scanning system motor 120 that will provide a pulse arc length on a deflection sector 140 of rotating scanning element 100 that matches a predetermined usable portion for that deflection sector 140, at step 840. The length and/or rotational location of the usable portion of each deflection sector 140 of element 100 may be the same, or may be different, e.g., depending on the physical geometry of element 100. In some embodiments, a common usable portion may be predetermined and used for all sectors, to simplify the control process.

FIG. 57B illustrates a representation of a scanning element 100 having multiple deflection sectors 104 (e.g., lenslets 104). In particular, FIG. 57B shows a usable portion, UP, for a particular deflection sector $104_1$. The remaining portions of the sector $104_1$ may be unusable for generating the corresponding output beam 112 due to interference or other affects related to the transitions between sector $104_1$ and its adjacent sectors 104. In other embodiments, the entire width of each sector 104 may be usable.

Thus, at step 840 system 139 calculates the target motor speed based on the pulse duration calculated at step 838 that will provide a pulse arc length, $PAL_{normal}$, on deflection sector 140 equal to the usable portion UP of that sector 140. In some embodiments, device 10 may provide for an alternative operational mode (e.g., a "comfort" mode), in which the frequency of treatment spot/MTZ generation is reduced by reducing the motor speed, but maintaining the pulse delivery parameters of the normal mode operation. Thus, FIG. 57B also shows a pulse arc length, $PAL_{comfort}$, that is delivered to sector $104_1$ in an example "comfort mode" operation in which the motor speed of motor 120 is reduced by 50%, while maintaining the pulse parameters.

At step 842, system 139 commands motor 120 to operate at the target motor speed. At step 844, system 139 determines the actual speed of motor 120, e.g., based on signals from an optical encoder sensor 203 that reads detectable features of encoder 121 as they pass by a particular point in space. In other embodiments, device 10 may utilize any other suitable type of motor speed sensor.

At step 846, system 139 compares the actual motor speed determined at step 844 with the target motor speed calculated and commanded at steps 840 and 842 to determine a resulting motor speed offset, if any. If the motor speed offset is above a predetermined threshold, (e.g., zero, a predetermined percentage (e.g., 1%) of the target motor speed, a predetermined speed offset (e.g., 10 rpm), or any other suitable threshold), the algorithm loops back to step 836 to determine the current temperature and repeat steps 836-844 based on the current temperature. If the motor speed offset is below the predetermined threshold, system 139 may apply a feedback algorithm at step 848 to correct the motor speed, and the algorithm loops back to step 836.

In this manner, system 139 executes a closed-loop algorithm for controlling the motor speed of motor 120 to compensate for temperature changes of laser 14 in real-time.

As shown in FIG. 57A, in parallel with the command and control of the motor speed at steps 842-848, system 139 commands laser 14 to generate pulses at steps 850-852. In particular, at step 850, system 139 calculates a pulse trigger delay time such that the delivered pulse (of the duration calculated at step 838) begins at the start of the usable portion UP of the respective sector 104, as opposed to the transition point between sectors 104. The arc through which sector 1041 passes during the pulse trigger delay time is indicated in FIG. 57B as arc length $AL_{delay}$. System 139 may calculate the pulse trigger delay time based on the motor speed calculated at step 840, and with knowledge of arc length $AL_{delay}$.

System 139 then pulses laser 14 at step 252 according to the pulse duration and pulse trigger delay time determined at steps 838 and 850, wherein the pulse trigger delay time and pulse activation for each pulse is triggered based on the signal from encoder sensor 203. For example, each detection of a detectable feature of encoder 121 (e.g., each corresponding to a transition point between adjacent sectors 104 of element 100) by encoder sensor 203 initiates the pulse trigger delay time, after which laser 14 is pulsed for the duration calculated at step 838. Thus, in such embodiments, encoder 121 operates as the trigger for each pulse.

In some embodiments, each of the various steps of algorithm 830 may be repeated at any desired frequency, e.g., after each pulse, after each scan of the input beam, or at a frequency unrelated to the pulse or scan frequencies (e.g., every 50 ms). For example, in the illustrated example, the pulse trigger delay time is updated after each scan of the input beam (i.e., after each rotation of element 100).

By calculating a pulse duration that fills up the usable portion of each sector 104 as discussed above, system 139 may maximize the usable portions of element 100, which may allow for an efficient use of laser 14 and scanning system 48 to provide the desired treatment.

Laser Control Circuits

In some embodiments, device 10 may include two (or more) independent laser current switch controls for safety redundancy, one connected to the laser anode side and the other to the cathode side. For example, FIGS. 58 and 59 illustrate electrical schematics for two independent laser current switch controls of an example device 10, including a first digital control circuit connected to the laser anode side (FIG. 58) and a second dimmer-type control circuit connected to the cathode side (FIG. 59).

Figure 58:
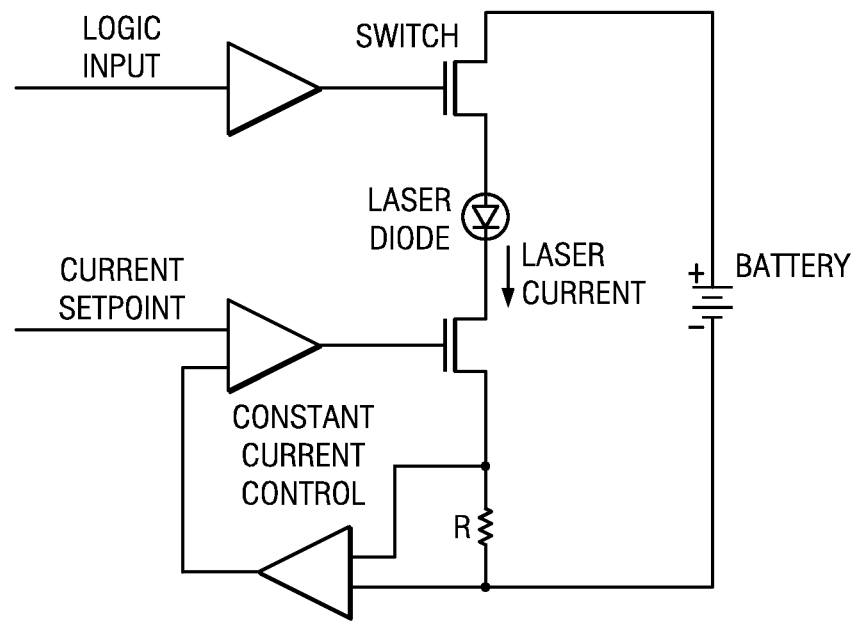
FIGS. 58 and 59 illustrate electrical schematics for two independent laser current switch controls of an example laser-based treatment device, including a first digital control circuit connected to the laser anode side (FIG. 58) and a second dimmer-type control circuit connected to the cathode side (FIG. 59).
Figure 59:
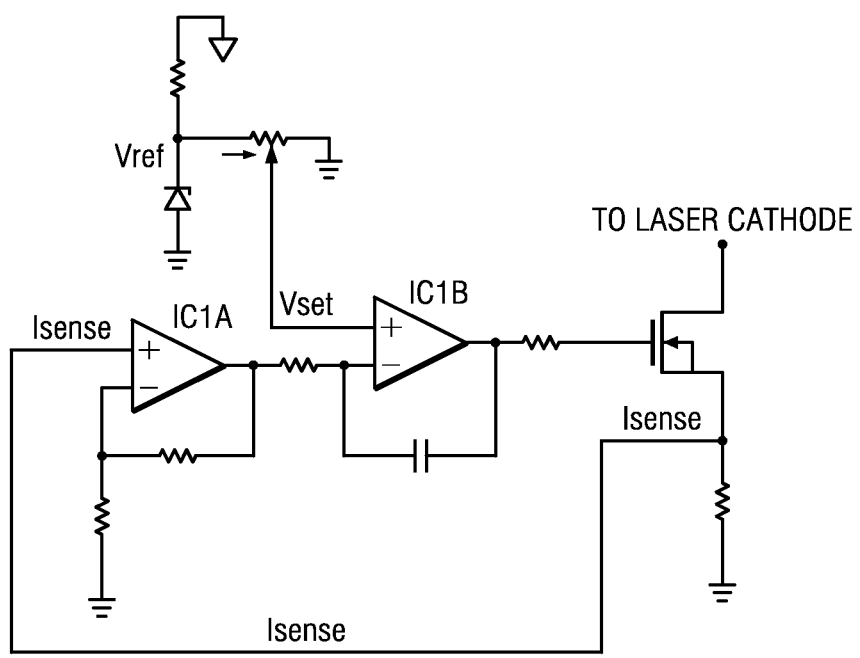

With reference to FIG. 58, the anode side switch is a digital switch, referred to as the sentinel FET switch. The circuit switches the laser current completely on or off. This digital switch may be used to turn off the laser quickly whenever a safety related error condition is detected. In contrast, with reference to FIG. 59, the cathode side switch functions as a linear dimmer control, referred to as the control FET. This circuit can adjust the laser current from zero to any set value within the design range, and may be used to set the target laser power for compensating for any significant inherent variations among different laser diodes (e.g., based on manufacturing differences). The cathode side switch may also be used as a secondary safety switch to turn down the laser current to zero value when the sentinel switch on the anode side is off.

One simple yet stable circuit implementation of the constant pulse current control is shown in the schematics with two OpAmp stages. The first OpAmp IC1A may be a fixed gain preamp to boost the laser current sense signal flowing through the cathode side control FET. The second OpAmp IC1B may be a control stage acting as an integrator to match the laser current to the set-point established at the positive input side of the OpAmp, i.e., the voltage set by the potentiometer or any other means. The IC1B input voltage set-point may be used to adjust the laser current from zero to any desired value within the design range. For example, with an appropriate set of circuit component values, the laser pulse current can be adjusted from 0 to 6 A with a pulse rise and fall time less than 0.4 ms. These may be desirable or even ideal operating conditions for fractional treatment laser diode control, for certain embodiments of device 10.

Prevention of Treatment Spot Overlap

As discussed above, in some embodiments, device 10 may be configured to prevent, limit, or reduce the incidence or likelihood of treatment spot overlap, e.g., based on feedback from one or more sensors 26 (e.g., a displacement sensor 200, speed/motion sensor 202, and/or a dwell sensor 216). For example, displacement-based control system 132 and/or usability control system 133 discussed above may operate to prevent, limit, or reduce the incidence or likelihood of treatment spot overlap. In addition or in the alternative to displacement-based control system 132 and/or usability control system 133, device 10 may include further controls or features for preventing, limiting, or reducing the incidence or likelihood of treatment spot overlap.

For example, in some embodiments, the pulse rate may be automatically adjustable by device 10 and/or manually adjustable by the user, e.g., to accommodate different manual movement speeds and/or different comfort levels or pain tolerance levels of the user.

Some embodiments include other devices or techniques that individually or in combination provide over-treatment protection, e.g., to prevent pulse stacking, firing on the same area(s), an excessive treatment spot 70 density, or other non-desirable treatment conditions. For example, in some embodiments, device 10 ceases to operate (e.g., generate or deliver beams) when stationary condition of device 10 is detected. A stationary condition may be determined using one or more sensors, e.g., any one or more displacement sensors, motion sensors, speed sensors, dwell sensors, vibration and tilt sensors, and/or accelerometers. Such sensors may generate signals based on capacitance, optical reflection, remittance, scattering variation, acoustical reflection variation, acoustical impedance, galvanic potential, potential difference, dielectric constant variation, or any other parameter.

In some embodiments, device 10 uses local pyrometry (alone or in combination with other techniques mentioned above) to detect a stationary condition. The treatment area may be optically measured by local thermal imaging of the skin, and a stationary condition may be detected where local heating of the skin exceeds a threshold temperature or other parameter value.

In some embodiments, device 10 delivers an "encouragement beam" or a scanned row of encouragement beams when a stationary condition is detected. For example, a single beam or scanned row of beams at a non-damaging but higher than normal energy (e.g., causing discomfort but not damage) may be delivered if a stationary condition is detected, to encourage the user to move device 10.

A stationary condition may further be measured by bulk heating measurement, for example. If the tip of the treatment delivery device or the sensed skin temperature or region of skin temperature begins to heat above a threshold, loss of motion is detected, or excessive treatment in the area is detected.

As another example, device 10 may deliver heat or cold to the skin to encourage motion, as dwelling in one location may become uncomfortable. As another example, mechanical rollers may be used to detect a non-motion condition. Alternatively, motorized rollers may drive motion of device 10 across the skin, thus physically avoiding a non-motion condition.

In some embodiments, physiological feedback based on beam characteristics may be exploited, e.g., by designing the output for treatment efficacy as well as perception of the presence of treatment. For example, discomfort may be exploited such that overtreatment is discouraged by pain feedback that increases with excessive treatment.

In some embodiments, photobleaching may be used with indigenous or exogenous substances. For example, the skin may be treated with a dye that is photobleached by the treatment beam or by a separate bleaching beam used to bleach the treated area and potentially its surrounding areas. In this example, device 10 may be configured to detect the presence of the unbleached dye and would allow treatment only on areas with unbleached dye, thus preventing repetitive scanning on the same areas (since that would be photobleached).

Example Embodiments of Device 10 for Providing Fractional Treatment

In some embodiments, device 10 is a fractional skin treatment device, which delivers scanned beams 114 to the skin, e.g., to treat wrinkles, pigmentation and coarse skin. Each delivered beam 114 creates a treatment spot 70 on the skin 40, which produces a corresponding micro-thermal zone (MTZ), as discussed above. The device application end 42 may be manually glided across the skin 40 (in a gliding mode or a scanning mode, for example) any suitable number of times to create an array of treatment spots 70. The skin's healing response in turn rejuvenates the skin. In some embodiments, device 10 may yield results similar to professional devices, but leverages a home daily use model to gradually deliver the equivalent of a single professional dose over multiple treatments or days (e.g., a 30 day treatment routine).

Figure 60:
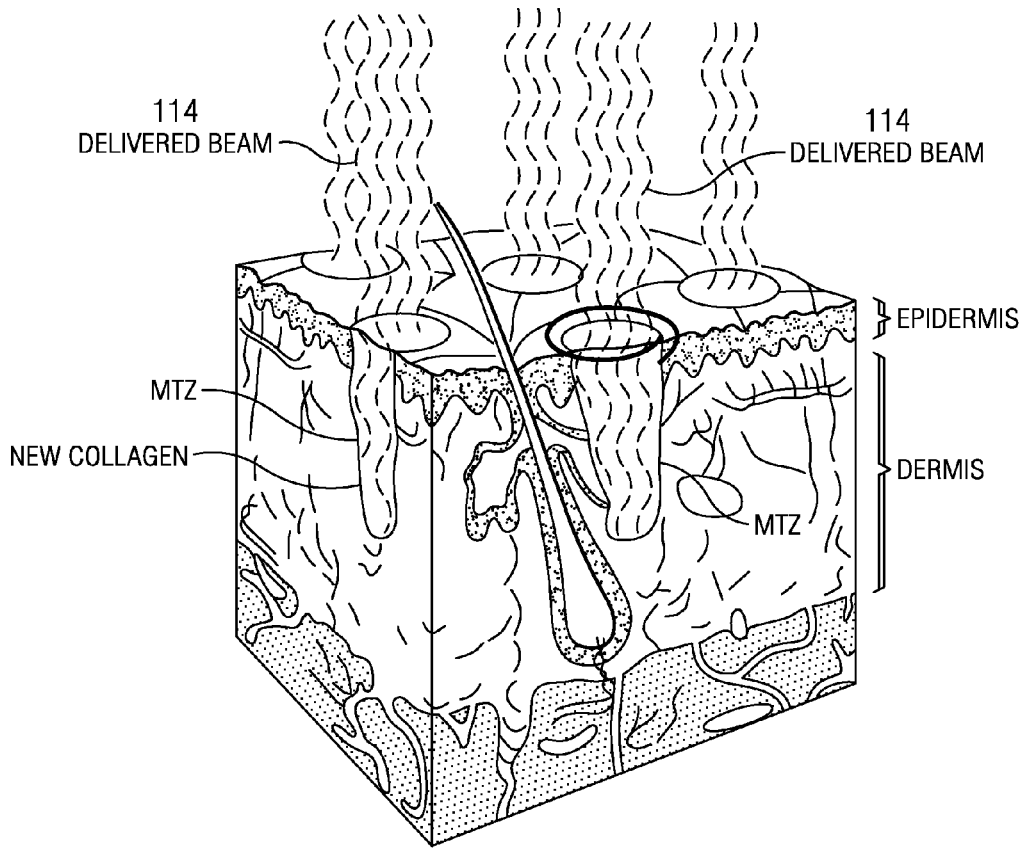
FIG. 60 illustrates a three-dimensional cross-section of a volume of skin for illustrating the process of a non-ablative fractional treatment.

FIG. 60 shows a three-dimensional cross-section of a volume of skin for illustrating the process of a non-ablative fractional treatment consisting of an array of MTZs in the skin, with each MTZ corresponding to treatment spot 70 created by a delivered beam 114 from device 10. Each MTZ is a small volume of denatured (or otherwise influenced, such as photochemical or photobiological) epidermis and dermis generally shaped as a column or elongated bowl and extending downward from the skin surface or subsurface in a direction substantially orthogonal to the skin surface. The damaged skin of the MTZ is surrounded by untreated (and thus not denatured, in this example) skin. Because of the proximity of healthy skin cells, the damaged skin of the MTZ heals relatively quickly (as compared to traditional non-fractional treatments, such as CO2 laser resurfacing) and reduces wrinkles, scarring, and/or uneven pigmentation as part of the healing process. During the healing process, MENDS (microscopic epidermal necrotic debris) may be formed. Since the MTZs typically cover only a fraction (e.g., less than 1% to about 70% of the skin surface, side effects may be substantially reduced as compared to traditional non-fractional treatments, such as CO2 laser resurfacing. In some home-use embodiments of this disclosure, coverage fraction may be between 0.25% and 5% of the skin per treatment. In some embodiments, device 10 is configured such that the size and shape (e.g., height and width and depth) of the MTZs spare many of the stem cells and melanocytes in the papillary dermis.

Figure 61:
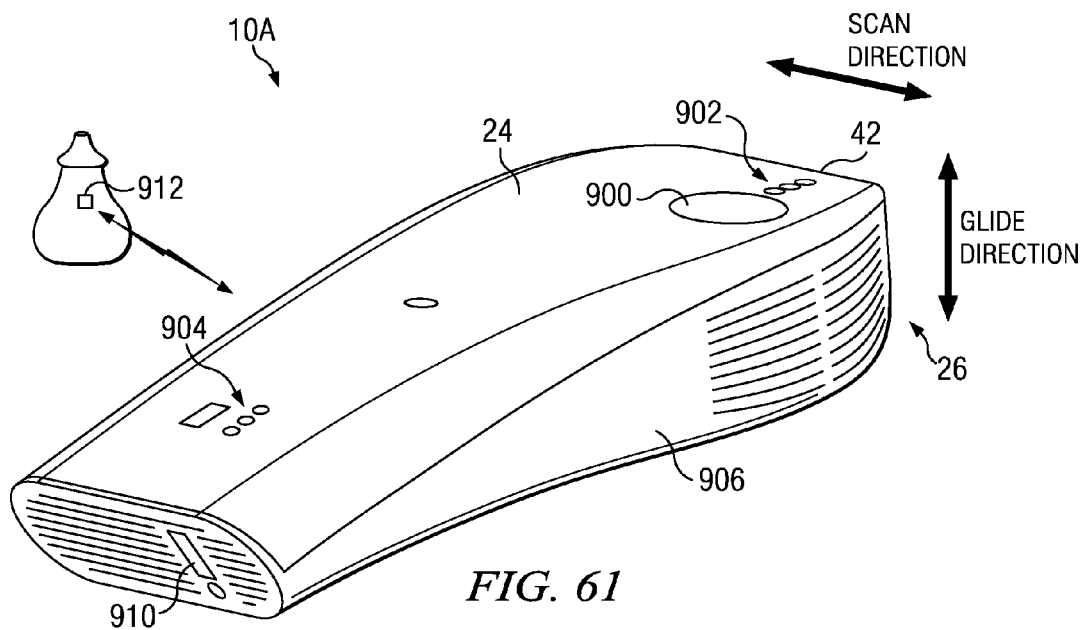
FIG. 61 illustrates an example scanned-beam radiation-based treatment device, according to one example embodiment.

FIG. 61 illustrates an example hand-held device 10A according to certain embodiments of the present disclosure. Device 10A includes a device housing 24, which houses a radiation source 14 and optics 16 (including a scanning system 48) for delivering scanned beams to the skin. Device 10A includes a tip portion 42 configured to be placed in contact with the skin and glide across the skin during a treatment session. Tip portion 42 may include a window (e.g., window 44 discussed above) through which the scanned beams are delivered to the skin.

In addition, any number and type(s) of sensors 26 may be located on the tip portion 42, e.g., as discussed above. For example, device 10A may include a displacement sensor 200, such as the single-pixel type displacement sensor 200A, 200B, or 200C discussed above, or the mouse-type displacement sensor 200D discussed above. In addition, one or more skin contact sensors 204 may be provided to detect the presence of a target in close proximity to the device application end 42, prior to delivery of laser pulses. In some embodiments, the skin contact sensor(s) 204 may include pressure switches, capacitive touch sensors, or other sensor technologies. In certain embodiments, capacitive touch sensors are preferred as they may be less likely to be actuated by surfaces other then the user's skin.

In some embodiments, one or more roller devices are provided on the device application end 42. Due to the scan line nature of treatment it may be preferred that device 10A is glided in a glide direction that generally perpendicular to the scan direction (i.e., analogous to shaving with a liner cutting head, or a blade). Roller devices oriented on device application end 42 and configured to contact the skin may help guide the gliding of device 10A in the desired glide direction. Also, roller devices may help device 10A glide smoothly across the dry skin, both for user comfort and even application of laser pulses. In some embodiments, roller devices may reduce stiction between the device application end 42 and the skin. Roller devices may also provide a good visual indication of proper glide direction.

Device 10A may be configured to provide any number of different treatment levels (e.g., low, medium, and high) or modes, which may be defined by one or more different parameters, such as, for example:

Energy per beam 112: by controlling radiation source 14,

Beam wavelength: e.g., by controlling the temperature of radiation source 14, or by selectively controlling the activation of radiation sources or emitters configured for different wavelengths.

treatment spot array density: by controlling a minimum threshold distance used by displacement-based control system 132 for enabling delivery of output beams 112 (and thus generation of treatment spots), e.g., as discussed above regarding FIGS. 38-46. As discussed above, such minimum threshold distance may be expressed as a measured distance or as a number of identified surface features of the skin.

treatment spot size or shape: for example by adjusting the position of radiation source 14 and/or one or more optical elements.

One or more treatment session delimiters, such as discussed above with respect to FIG. 47 (e.g., total number of treatment spots in a treatment session).

Radiation mode: e.g., any of the modes discussed above regarding FIGS. 28-29.

Beam scanning speed, e.g., by controlling the speed of scanning system motor 120.

Further, in embodiments/operational modes in which radiation source 14 is pulsed:

Pulse on time (i.e., pulse width): by controlling radiation source 14,

Pulse off time (i.e., pulse delay): by controlling radiation source 14,

Pulse frequency: by controlling radiation source 14,

Pulse wave profile (e.g., square wave, sine wave, etc.): by controlling radiation source 14.

Each selectable treatment level or mode may be defined by combination of one or more of such parameters, or other parameters. In some embodiments, the selectable treatment levels or modes are predefined and stored in device 10 to accommodate a range of user preferences with respect to treatment sensation and pain, treatment time, or other aspect of a treatment. For example, device 10 may provide selectable treatment levels of low, medium, and high. The low level may be defined by a relatively low energy/pulse and relatively large minimum distance between scanned rows (e.g., as enforced by displacement-based control system 132), whereas the high level may be defined by a relatively high energy/pulse and relatively small minimum distance between scanned rows (e.g., as enforced by displacement-based control system 132). The low level may be suitable for pain sensitive users, while the high level may be suitable for more aggressive users. In other embodiments, individual parameters that define treatment levels or modes may be selectable or adjusted by a user, e.g., via a suitable user interface 28.

The treatment levels or modes provided by device 10 may be selected in any suitable manner, e.g. automatically by control system 18 or by a user. Control system 18 may automatically select a treatment level or mode based on any suitable information, e.g., feedback from one or more sensors 26, or according to a predefined multi-session treatment plan, or based on any other relevant information. Alternatively, control system 18 may automatically select a treatment level or mode based on selections made by a user, e.g., a selected body part to be treated, a selected treatment time, a selected energy level, etc.

Alternatively, the user may select the current treatment level or mode via any suitable user interface 28, e.g., one or more buttons, switches, knobs, or a touch screen. For example, device 10A includes a power/treatment control button 900 that allows selection between different treatment levels or modes, as well as turning device on/off. For example, button 900 may be a single momentary pushbutton control that powers on device 10 when pressed. Subsequent presses then cycle through different power settings. For example, pressing button 900 may progress through the following sequence of settings in order:

[off]→[on:low]→[on:medium]→[on:high]→[off]

As another example, pressing button 900 may progress through the following sequence of settings in order:

[off]→[on:last used treatment level]→[on: next treatment level] . . . →[on: next treatment level] with a long press required to turn the device back off.

Lighted setting indicators 902 may indicate the currently selected treatment level or mode, as selected using power/treatment control button 900. In one embodiment, an array of three light emitting diodes (LEDs) indicates the on/off state and treatment level setting according to the following code:
all three off=device off; one on=level 1 or low two on=level 2 or medium; all three on=level 3 or high A lighted battery indicator 904 may indicate the charge status of a battery 20 provided in device 10A. In some embodiments, indicator 904 is a multicolor LED for indicating battery status, e.g., a red/green LED indicator in which green indicates full/good charge, flashing green indicates need to recharge soon, and red indicates depleted battery/must recharge prior to using.

In some embodiments, device 10A includes a tactile feedback device within housing 24 to provide tactile feedback to the user, e.g., vibration type feedback, to indicate various events (e.g., button presses, proper usage, the pausing of a treatment session due to particular sensor feedback, etc.). Such tactile feedback is indicated generally by reference number 906.

Because device 10A may likely be used in front of a mirror, and held in a variety of positions by different users, placement of visual indicators, such as LED's, in a manner that provide universal visibility can be difficult. Thus, device 10A may include one or more "wide area" type indicators, such as light rings, glowing housings, or other wide area lighting device that are visible from a wide range of positions of the user and device 10A. Alternatively, or in addition, the visual indicator(s) may be carefully placed to provide good viewing under many conditions, for example, visible lights around the treatment beam aperture that could be seen for example as a glow around the skin in both direct visualization, peripheral visualization such as when treating around the eyes, or in a mirror.

Device 10A may include "proper usage" feedback in any suitable manner, to indicate to the user that they are using the device properly (e.g., using proper technique) and that the device is operating properly (e.g., proper laser output). For example, device 10 may provide audible "happy sounds," LED indications, both discreet and wide area type indicators as described above, tactile feedback 906 (e.g., vibrations), and/or any other suitable feedback. Control system 18 may provide such feedback when all sensors 26 are satisfied and laser pulses are enabled.

Device 10A may also provide pacing assistance and automatic shutoff functionality. A desired full face treatment may consist of a substantially uniform patter of treatment spots across a target area (e.g., the face). To facilitate uniform treatment of the target area, device 10A may provide feedback to the user indicating when to move from one region of the target area to another, e.g., after a predetermined fraction of the total treatment spots for the session have been generated on the target area. For example, one embodiment provides 36 treatment spot/cm2, which corresponds to about 10,000 treatment spots for an average face of 300 cm2. The face may be considered as consisting of four quadrants. For a full face treatment of 10,000 treatment spots, 2,500 treatment spots should be generated in each quadrant to provide uniform treatment. Thus, device 10A may provide feedback to the user to facilitate movement from one quadrant to the next, after 2,500 treatment spots have been generated, after 5,000 total treatment spots have been generated, and after 7,500 total treatment spots have been generated. The user may know (e.g., from a user manual or from instructions provided by device 10A, e.g., via a display 32) to move from quadrant to quadrant upon each such feedback. The feedback may be audible, visual, and/or tactile feedback. Device 10A may then automatically power down after delivering the full 10,000 treatment spots.

In some embodiments, device 10A may require communication with a removable cartridge 910 or a separate item 912 in order to enable activation of device 10A. For example, a bottle of topical solution may include an RFID tag 912 configured to communicate an ID to device 10A in order to enable operation of device 10A. As another example, device 10A may require a specialized battery that has a limited lifetime, or the device may have a hardware cartridge that provides a preset number of treatments or minutes or other parameter. In still other examples, the device may require communication with an external system, like a PC monitor through visual signals on the PC monitor or the internet through TCP/IP or other protocols. Topical consumables, hardware consumables, or electronic keys like these may be configured to provide recurring revenue associated with device use.

In some embodiments, device 10A may include devices for inductive coupling of the electrical charger 720 to handheld device 10. This may be coupled in a receptacle/stand type arrangement 730, or a pad or tray on which the hand piece lies for storage between treatments. Such configuration may help avoid the need to manually plug device 10 in for recharging on a frequent basis. With the inductive charging stand or pad, the features of a wall plug-in charger may be incorporated into the charging stand 730 and inductively provide A/C charging current to the device charge circuit.

Figure 62A:
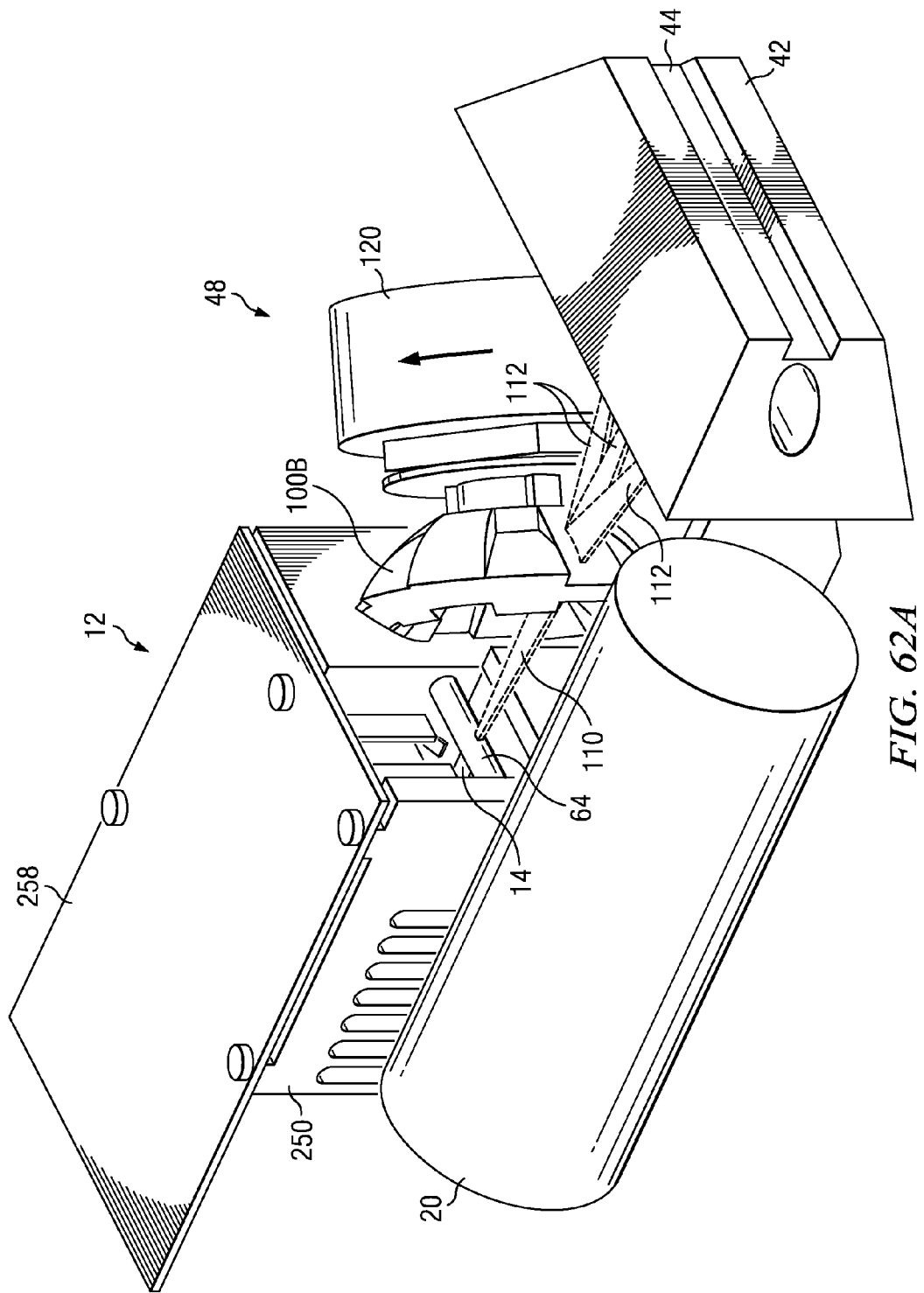
FIGS. 62A-62B illustrate an example arrangement of components for an example scanned-beam treatment device including a cup-shaped rotating scanning element, according to an example embodiment.
Figure 62B:
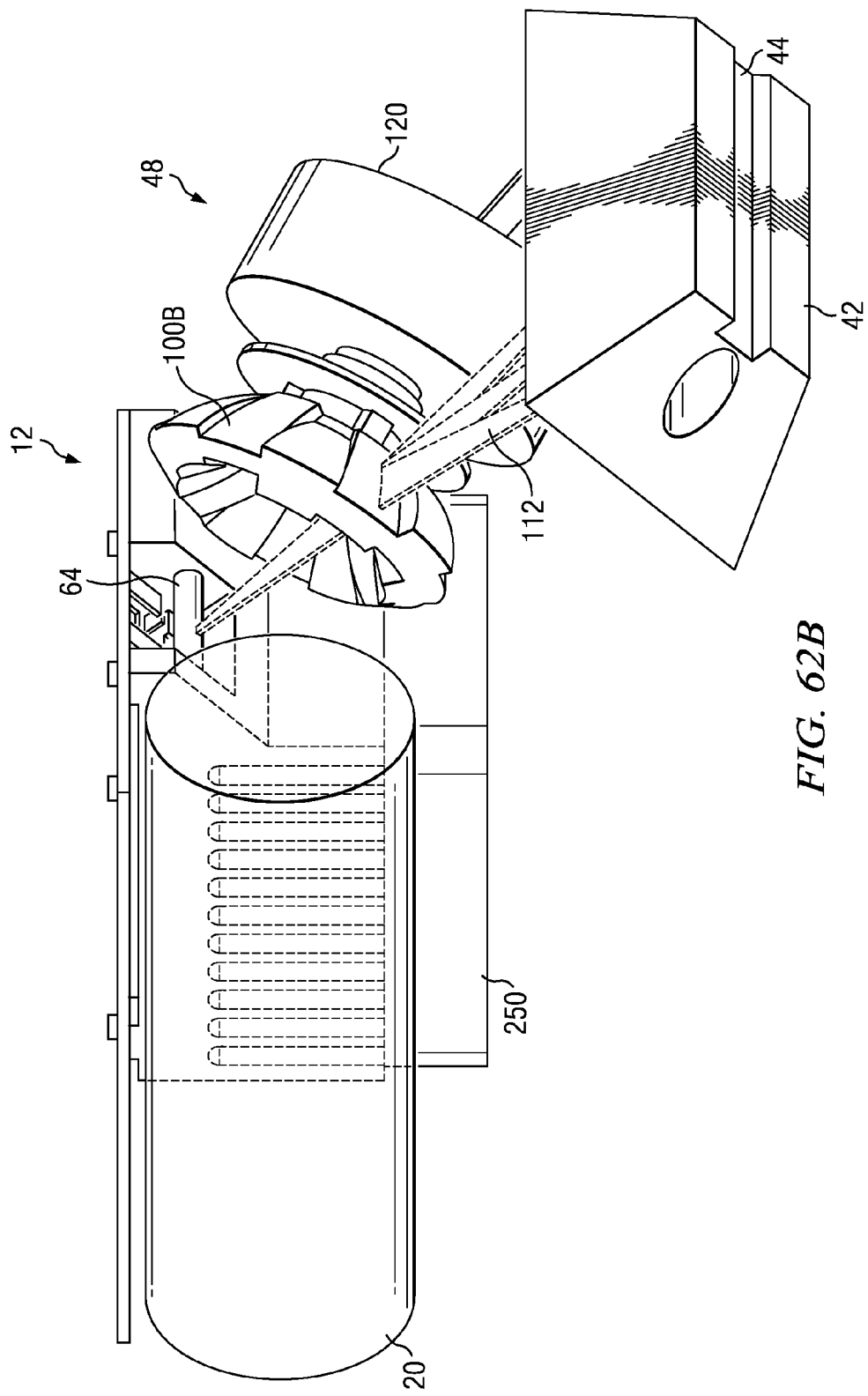

FIGS. 62A and 62B illustrate example configurations of particular components of device 10 according to certain embodiments. In particular, FIGS. 62A and 62B illustrate example arrangements of a radiation engine 12 similar to that shown in FIG. 34, an upstream optic 64, a cup-shaped rotating scanning element 100B, a battery 20, and an application end 42 including a window 44.

Figure 63:
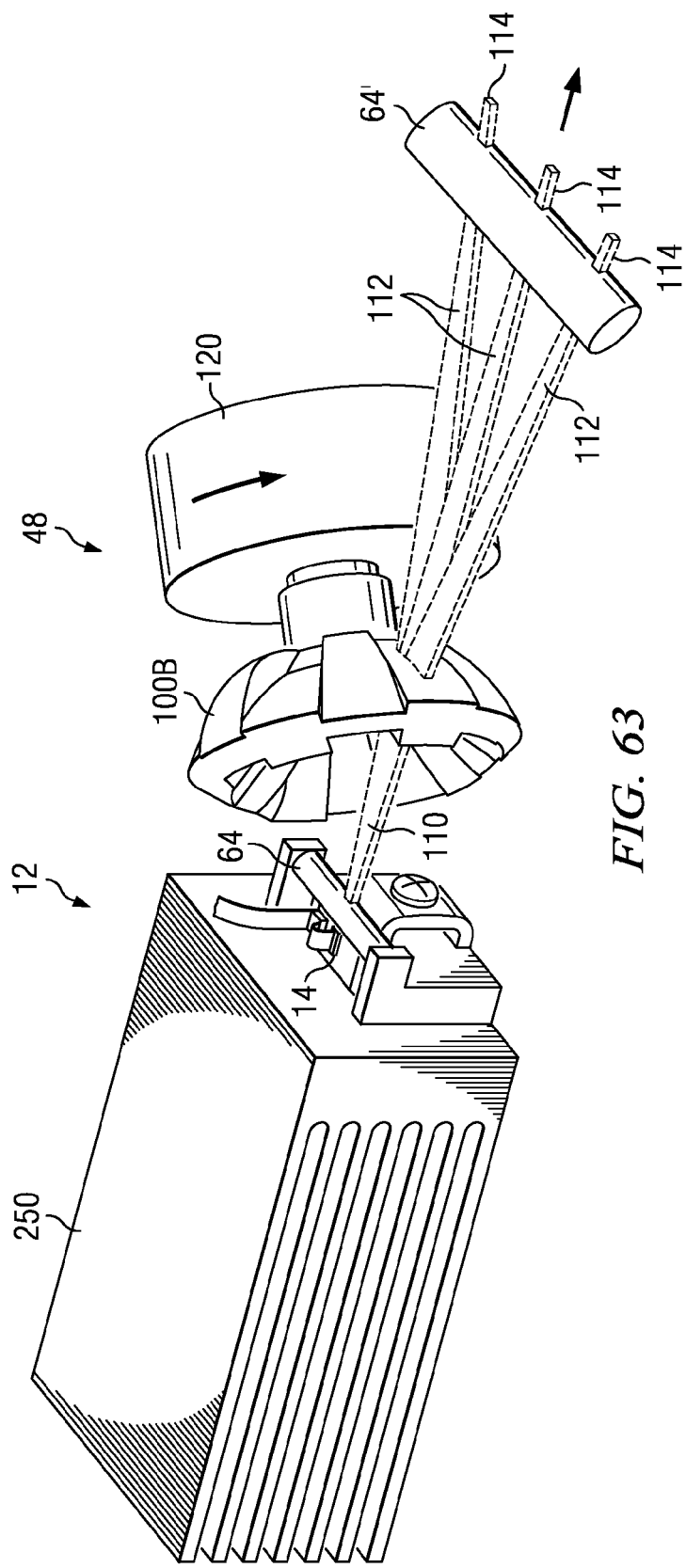
FIG. 63 illustrates an example arrangement of components for an example scanned-beam treatment device including a cup-shaped rotating scanning element, according to another example embodiment.
Figure 64A:
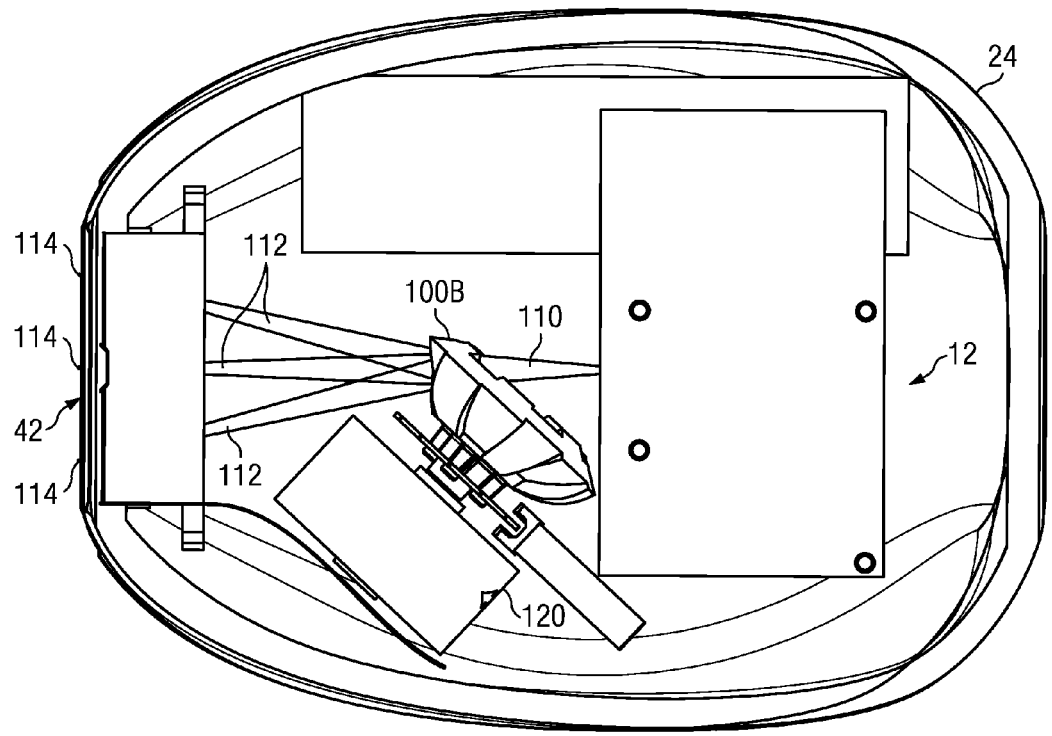
FIGS. 64A-64D illustrate an example arrangement of components for an example scanned-beam treatment device including a cup-shaped rotating scanning element, according to an yet example embodiment.
Figure 64B:
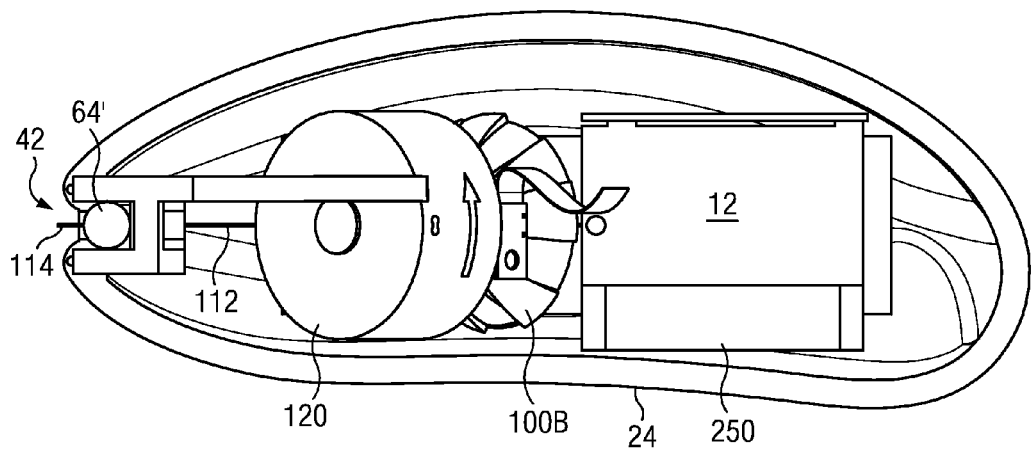
Figure 64C:
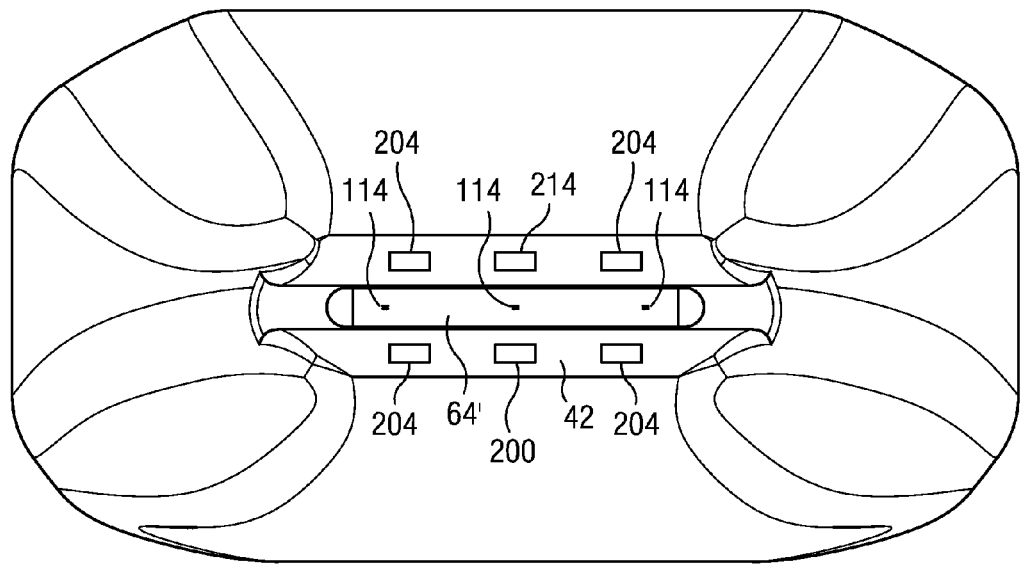
Figure 64D:
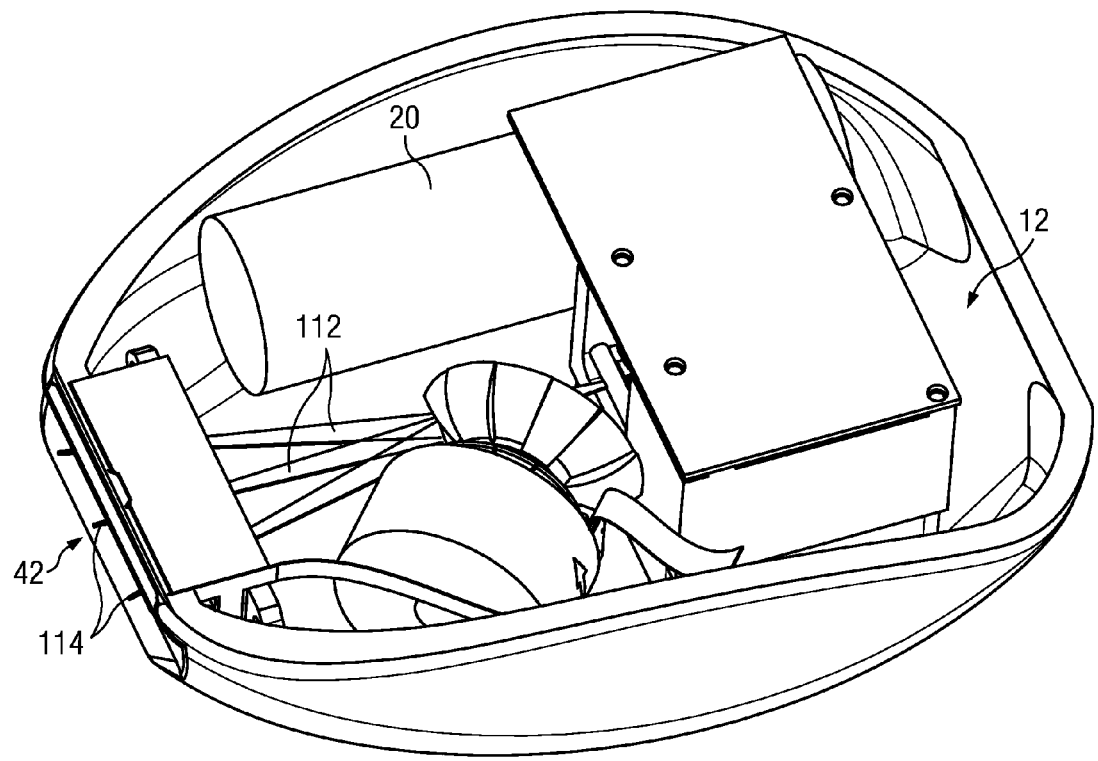
Figure 65A:
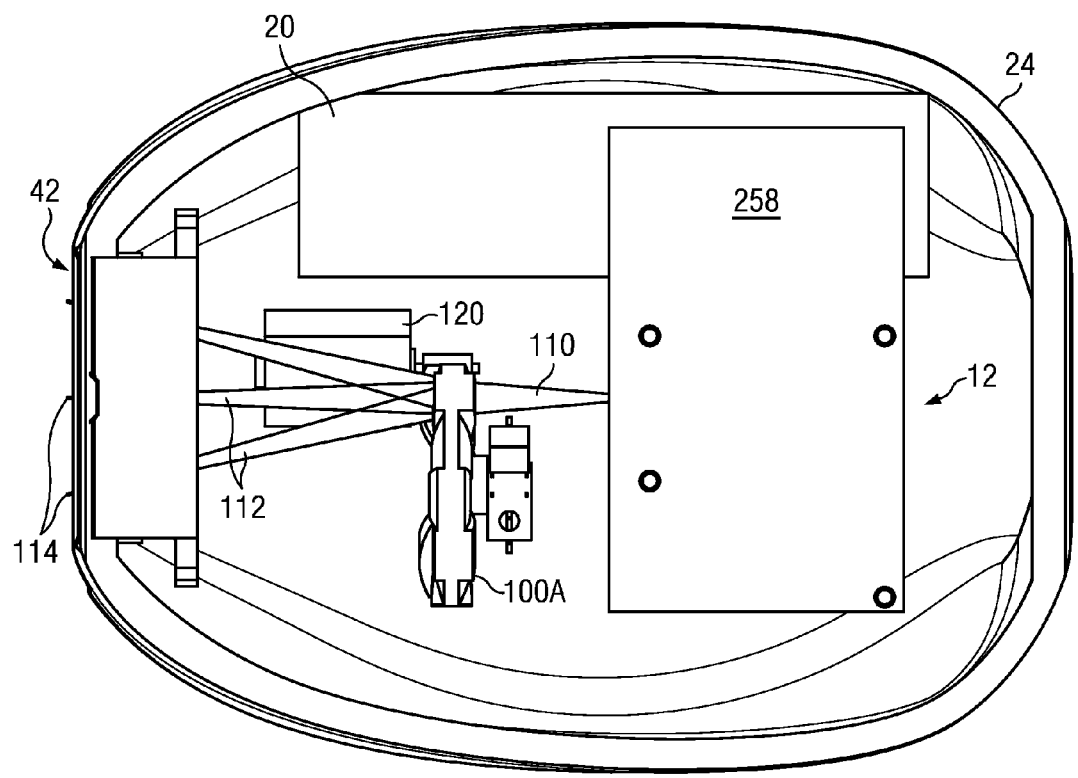
FIGS. 65A-65D illustrate an example arrangement of components for an example scanned-beam treatment device including a disk-shaped rotating scanning element, according to an example embodiment.
Figure 65B:
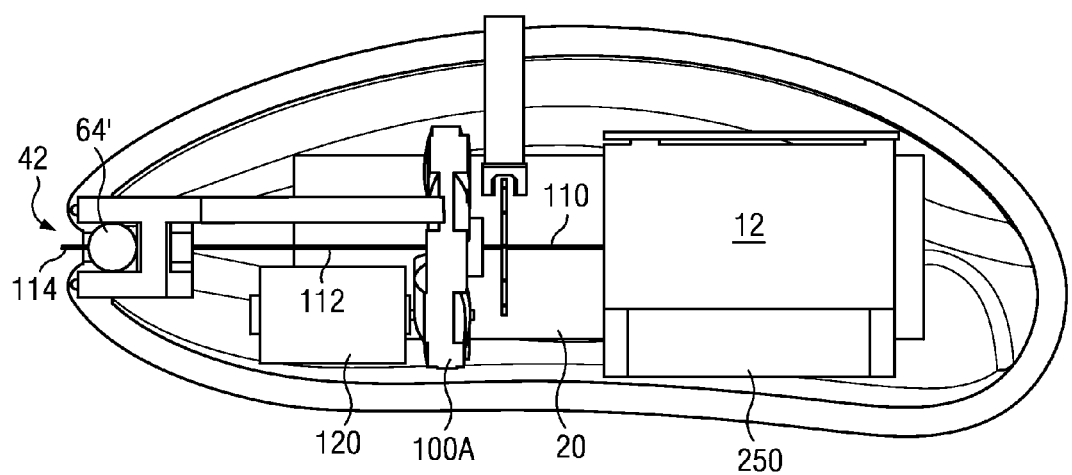
Figure 65C:
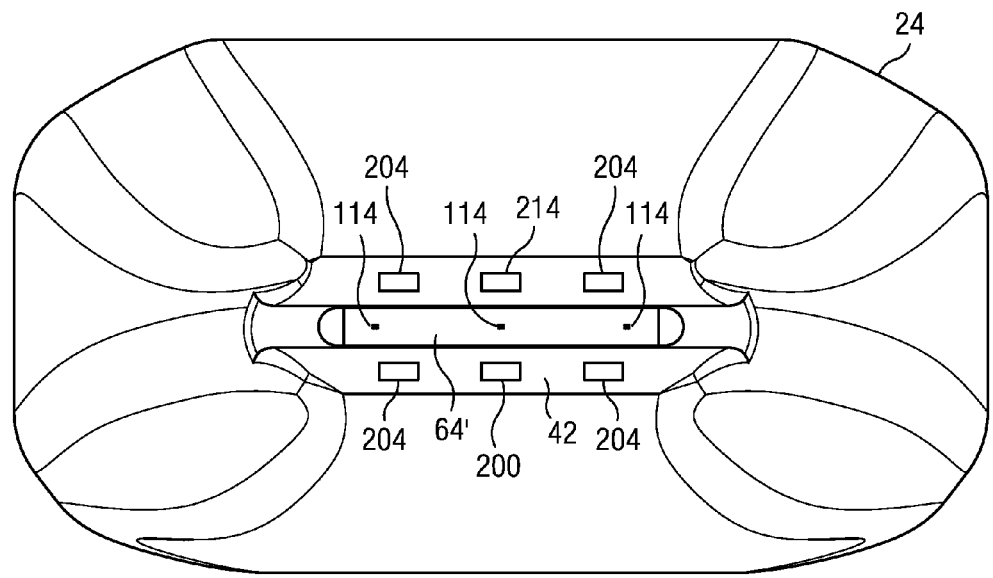
Figure 65D:
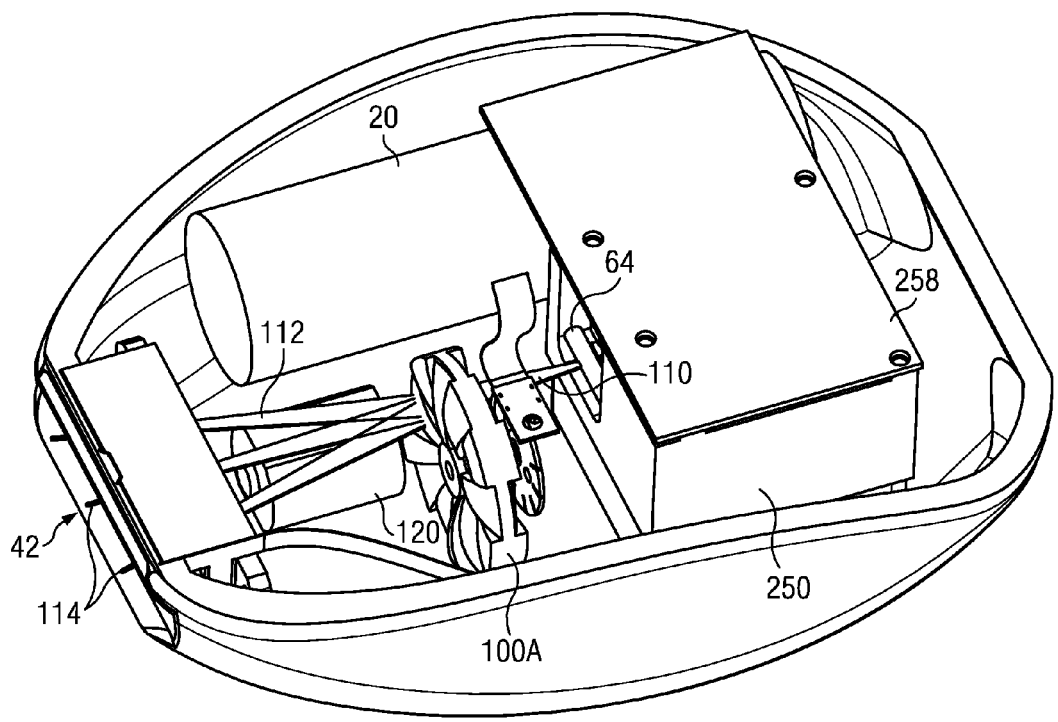

FIG. 63 illustrates another example configuration of particular components of device 10 according to certain embodiments. In particular, FIG. 58 illustrate an example arrangement of a radiation engine 12 similar to that shown in FIGS. 33A-33B, an upstream optic 64, a cup-shaped rotating scanning element 100B, and an optional downstream optic 64' proximate an application end of the device.

FIGS. 64A-64D illustrate various views of an example device 10 that utilizes a cup-shaped rotating scanning element 100B, according to certain embodiments. In particular, FIGS. 64A-64D illustrate an example arrangement of a cup-shaped rotating scanning element 100B, a radiation engine 12 similar to that shown in FIG. 34, an optional downstream optic 64', a battery 20, and an application end 42 that includes various sensors 200, 204, and 214 disposed around optional downstream optic 64'.

FIGS. 65A-65D illustrate various views of an example device 10 that utilizes a disc-shaped rotating scanning element 100A, according to certain embodiments. In particular, FIGS. 65A-65D illustrate an example arrangement of a disc-shaped rotating scanning element 100A, a radiation engine 12 similar to that shown in FIG. 34, an optional downstream optic 64', a battery 20, and an application end 42 that includes various sensors 200, 204, and 214 disposed around optional downstream optic 64'.

Figure 66A:
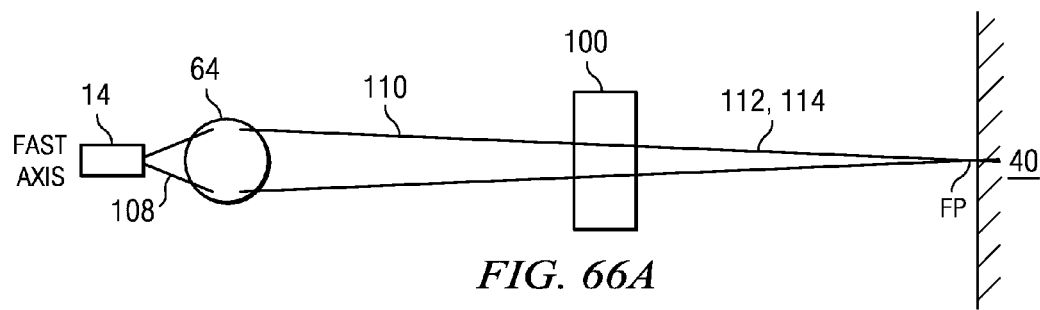
FIGS. 66A and 66B illustrate the optical system and its affects on the fast axis beam profile (FIG. 66A) and slow axis beam profile (FIG. 66B) for embodiments of the device according to FIGS. 64A-64D or FIGS. 65A-65D that omit a downstream lens.
Figure 66B:
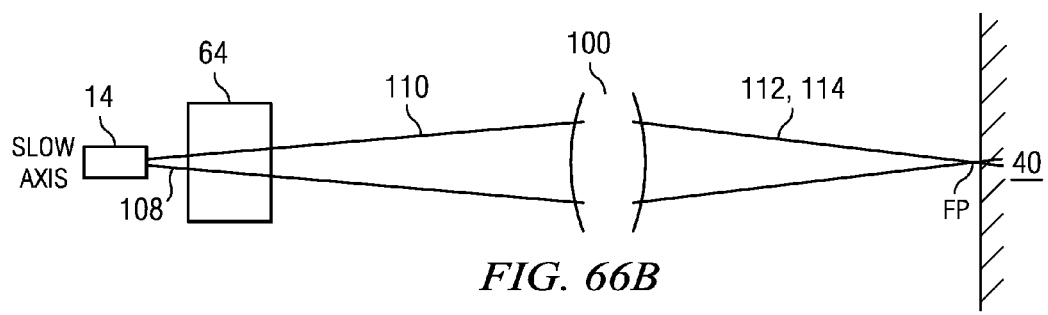
Figure 67A:
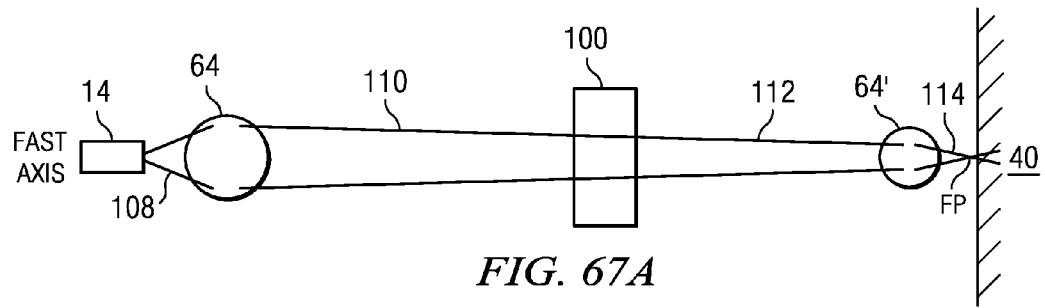
FIGS. 67A and 67B illustrate the optical system and its affects on the fast axis beam profile (FIG. 67A) and slow axis beam profile (FIG. 67B) for embodiments of the device according to FIGS. 64A-64D or FIGS. 65A-65D that include a downstream lens.
Figure 67B:
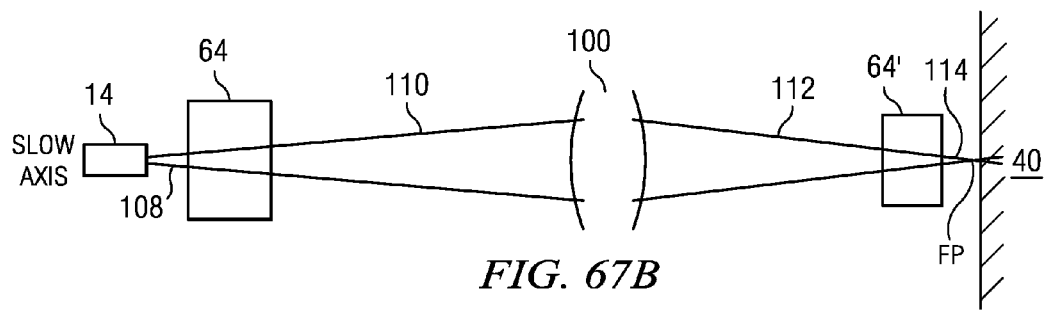

FIGS. 66A-66B and 67A-67B illustrate representations of the optical system 15 of example devices 10 shown in FIGS. 64A-64D and FIGS. 65A-65D, according to various embodiments. In particular, FIGS. 66A and 66B illustrate the optical system 15 of example devices 10 shown in FIGS. 64A-64D and FIGS. 65A-65D, according to embodiments in which optional downstream optic 64' is omitted. In contrast, FIGS. 67A and 67B illustrate the optical system 15 of example devices 10 shown in FIGS. 64A-64D and FIGS. 65A-65D, according to embodiments that include optional downstream optic 64'.

Referring to FIGS. 66A and 66B, FIG. 66A shows optical system 15 in the fast axis profile, while FIG. 66B shows optical system 15 in the slow axis profile, orthogonal to the fast axis profile. As shown, upstream optic 64 is a rod lens that influences (converges) the fast axis profile of the beam, but does not significantly influence the slow axis profile of the beam, while scanning element 100 (e.g., element 100A or 100B) influences (converges) the slow axis profile of the beam, but does not significantly influence the fast axis profile. In this example, each delivered beam 114 has a focal point or focal plane that is slightly above the surface of the skin 40. In other embodiments, the focal point or focal plane of each delivered beam 114 may be co-planar with the surface of the skin 40, or alternatively may be below the surface of the skin 40.

Referring now to FIGS. 67A and 67B, FIG. 67A shows optical system 15 in the fast axis profile, while FIG. 67B shows optical system 15 in the slow axis profile. As shown, upstream optic 64 is a rod lens that influences (slightly converges or collimates) the fast axis profile of the beam, but does not significantly influence the slow axis profile of the beam; scanning element 100 (e.g., element 100A or 100B) influences (converges) the slow axis profile of the beam, but does not significantly influence the fast axis profile; and downstream optic 64' is a second rod lens that further converges the fast axis profile of the beam, but does not significantly influence the slow axis profile of the beam. As with the example discussed above, each delivered beam 114 has a focal point or focal plane that is slightly above the surface of the skin 40. In other embodiments, the focal point or focal plane of each delivered beam 114 may be co-planar with the surface of the skin 40, or alternatively may be below the surface of the skin 40.

In some embodiments, downstream optic 64' provides a divergence of beam 114 of at least 50 mrad. In particular embodiments, downstream optic 64' provides a divergence of beam 114 of at least 75 mrad. In specific embodiments, downstream optic 64' provides a divergence of beam 114 of at least 100 mrad. For example, downstream optic 64' may comprise a rod lens that provides a divergence of beam 114 of about 100 mrad. Such divergence may provide various level of inherent eye safety, with eye safety increasing with increased beam divergence.

Figure 68C:
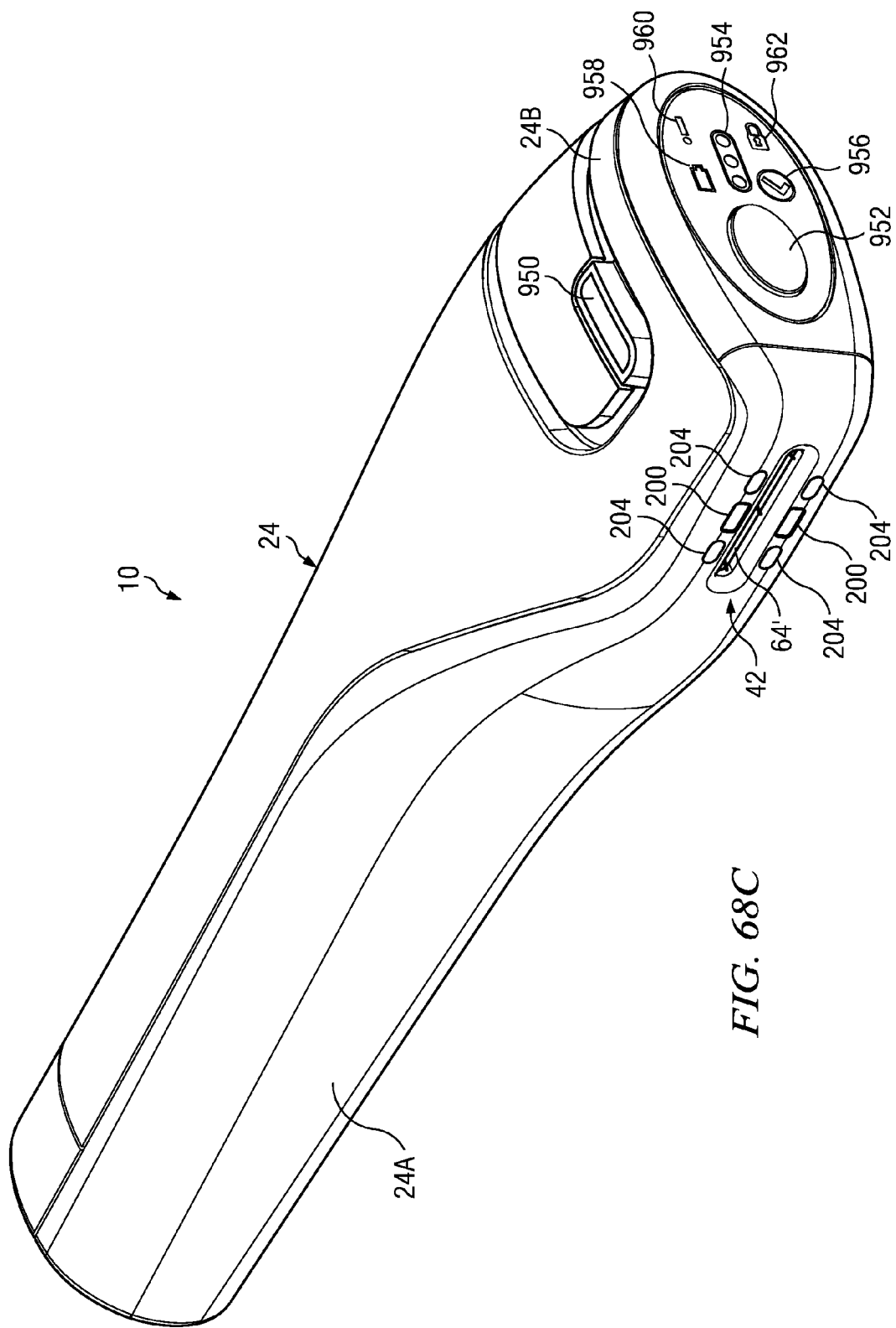

FIGS. 68A-68C illustrate various views of an example device 10 that utilizes a cup-shaped rotating scanning element 100B, according to certain embodiments. In particular, FIG. 68A illustrates an example arrangement of internal components of device 10, including a battery 20, a fan 34, and a radiation generation and delivery system including a radiation engine 12, an upstream optic 64, a cup-shaped rotating scanning element 100B, a turning mirror 65, and an optional downstream optic 64' proximate an application end 42 of the device. FIG. 68B is a zoomed-in view of FIG. 68A, showing the optics system 15 and general beam propagation directions. Finally, FIG. 68C shows the assembled device 10, with the assembly shown in FIG. 68A being contained with an outer housing 24, and showing beams 114 being delivered from the application end 42 of the device.

As shown in FIG. 68B, radiation engine 12 includes a laser package 250 mounted to a heat sink 36, and including a diode laser 14. Radiation engine 12 may be configured similar to any of the arrangements shown in FIG. 33A-33B, FIG. 34, or FIG. 35A-35B, or in any other suitable manner. As shown, optical system 15 includes (a) an upstream fast axis rod lens 64, (b) a cup-shaped multi-sector rotating scanning element 100B driven by a motor 120 and having a rotational axis arranged at a non-zero, non-90 degree angle with respect to the propagation direction of input beam 110 (e.g., as discussed above with respect to FIG. 11A); (c) a downstream planar turning mirror 65 configured to redirect, or "turn," the array of output beams 112 output by rotating scanning element 100B; and (d) an optional downstream fast axis rod lens 64'.

An encoder 121, e.g., in the form of a wheel or disk, may be fixed to rotating scanning element 100B such that the rotation of encoder wheel 121 remains synchronized with element 100B. Encoder wheel 121 may be used for detecting or monitoring the rotation and/or rotational position of scanning element 100B, which information may be used by control system 18 for various functions. Thus, encoder 121 may include a number of detectable features around a circumference or perimeter of encoder 121. The number of detectable features may be equal to or a multiple of the number of sectors of scanning element 100B, and may be fixed in a desired rotationally alignment relative to such sectors. Thus, information regarding the rotation and/or rotational position of scanning element 100B may be determined or monitored by detecting the detectable features of encoder 121.

For example, as discussed above regarding FIGS. 56-57, encoder wheel 121 may be used for triggering each beam pulse from radiation source 14. For instance, in an embodiment in which encoder 121 includes one detectable feature corresponding to each sector of scanning element 100B, the detection of each detectable feature passing by a particular point may be used to trigger a pulse from radiation engine 14 to be delivered through the sector of scanning element 100B corresponding to that detectable feature. Each pulse may be triggered instantaneously upon detection of the next detectable feature as encoder 121 rotates, or may be triggered after some predetermined or dynamically determined delay time after the detection of the next detectable feature, e.g., as discussed above regarding FIGS. 56-57. Encoder 121 may also be monitored for safety features of device 10, e.g., to instantaneously turn off radiation source 14 if it is determined that scanning element 100B has stopped rotating.

Turning mirror 65 may be provided to redirect, or "turn," the array of output beams 112 in order to provide a desired size, shape, or form factor of device 10, e.g., to reduce the size of device 10 and/or to provide an ergonomic hand-held shape. With reference to FIG. 68C, example device 10 includes an elongated handle portion 24A configured to be gripped by a hand, a head portion 24B, and an optical system 15 configured to deliver beams 114 in a direction generally perpendicular to the elongated direction of handle portion 24A. Further, as shown in FIG. 68C, the scan direction extends generally parallel to the elongated direction of handle portion 24A. This configuration may be more comfortable or ergonomic for a user while operating device 10, e.g., as compared to a configuration in which the beams are delivered in same direction as the elongated direction of handle portion 24A, e.g., out of the end of device at which user interfaces 952-962 are located.

Figure 69A:
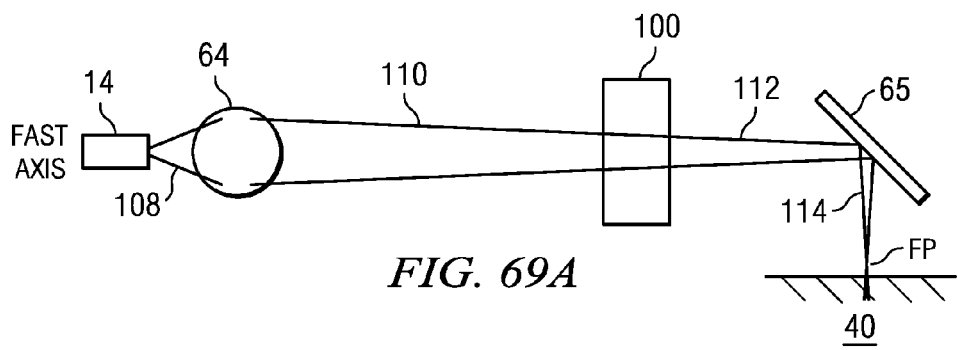
FIGS. 69A and 69B illustrate the optical system and its affects on the fast axis beam profile (FIG. 69A) and slow axis beam profile (FIG. 69B) for an embodiment of the device according to FIGS. 68A-68C that omits a downstream lens.
Figure 69B:
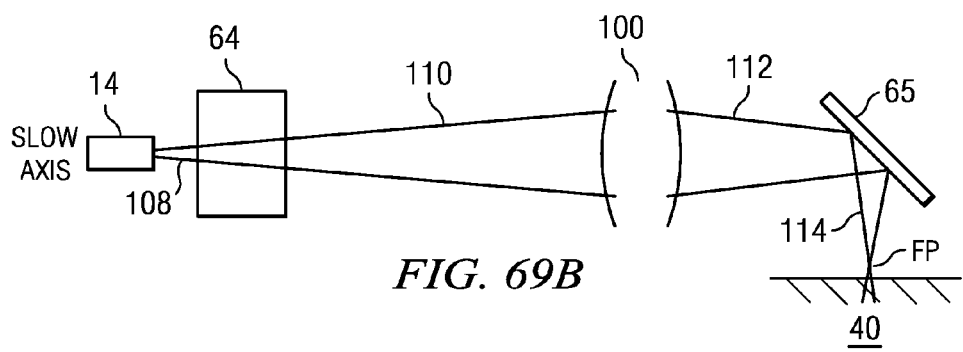
Figure 70A:
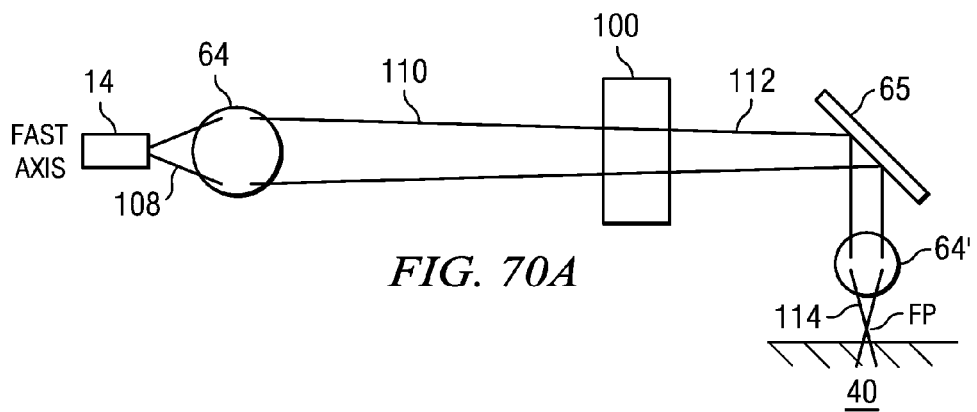
FIGS. 70A and 70B illustrate the optical system and its affects on the fast axis beam profile (FIG. 70A) and slow axis beam profile (FIG. 70B) for an embodiment of the device according to FIGS. 68A-68C that includes a downstream lens.
Figure 70B:
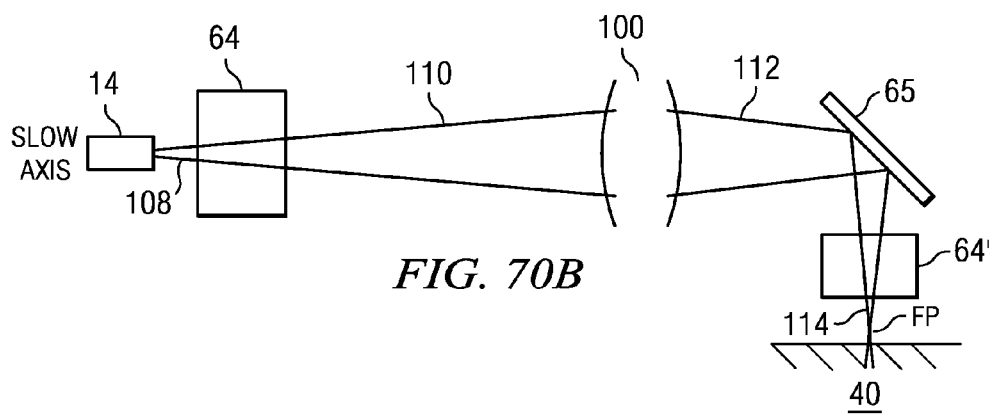

FIGS. 69A-69B and 70A-70B illustrate representations of the optical system 15 of example device 10 shown in FIGS. 68A-68C, according to certain embodiments. In particular, FIGS. 69A and 69B illustrate the optical system 15 of device 10 shown in FIGS. 68A-68C, according to embodiments in which optional downstream optic 64' is omitted. In contrast, FIGS. 70A and 70B illustrate the optical system 15 of device 10 shown in FIGS. 68A-68C, according to embodiments that include optional downstream optic 64'.

Referring to FIGS. 69A and 69B, FIG. 69A shows optical system 15 in the fast axis profile, while FIG. 69B shows optical system 15 in the slow axis profile, orthogonal to the fast axis profile. As shown, upstream optic 64 is a rod lens that influences (converges) the fast axis profile of the beam, but does not significantly influence the slow axis profile of the beam, while scanning element 100 (e.g., element 100A or 100B) influences (converges) the slow axis profile of the beam, but does not significantly influence the fast axis profile. Turning mirror 65 may be a planar mirror that redirects but does not otherwise influence the output beams 112. In this example, each delivered beam 114 has a focal point or focal plane that is slightly above the surface of the skin 40. In other embodiments, the focal point or focal plane of each delivered beam 114 may be co-planar with the surface of the skin 40, or alternatively may be below the surface of the skin 40.

Referring now to FIGS. 70A and 70B, FIG. 70A shows optical system 15 in the fast axis profile, while FIG. 70B shows optical system 15 in the slow axis profile. As shown, upstream optic 64 is a rod lens that influences (slightly converges or collimates) the fast axis profile of the beam, but does not significantly influence the slow axis profile of the beam; scanning element 100 (e.g., element 100A or 100B) influences (converges) the slow axis profile of the beam, but does not significantly influence the fast axis profile; and downstream optic 64' is a second rod lens that further converges the fast axis profile of the beam, but does not significantly influence the slow axis profile of the beam. Again, turning mirror 65 may be a planar mirror that redirects but does not otherwise influence the output beams 112. As with the example discussed above, each delivered beam 114 has a focal point or focal plane that is slightly above the surface of the skin 40. In other embodiments, the focal point or focal plane of each delivered beam 114 may be co-planar with the surface of the skin 40, or alternatively may be below the surface of the skin 40.

Returning to FIG. 68C, device 10 may include various user interface features 28 at any suitable locations on device 10. In this embodiment, device 10 includes user interface features 950-962, including a use indicator 950, a power/mode selector 952, a selected mode indicator 954, a treatment completion indicator 956, a battery charge indicator 958, an alarm indicator 960, and a device lock indicator 962.

Use indicator 950 may comprise any indicator (e.g., an LED) that indicates when device 10 is delivering radiation from application end 42. Use indicator 950 may be positioned on device 10 at a location that is likely to be viewable by the user during a treatment.

Power/mode selector 952 may be any suitable interface (e.g., a depressible button, movable switch, capacitive switch, touch screen, etc.) used to turn device 10 on and off, and to select a operational mode of device 10 (e.g., a particular treatment mode, power level, "comfort level," etc.) for a treatment session. For example, selector 952 may be a single momentary pushbutton control that powers on device 10 when pressed. Subsequent presses then cycle through different treatment levels. For example, pressing button 900 may progress through the following sequence of settings in order:

[off]→[on:Level 1 operational mode]→[on:Level 3 operational mode]→[on:hi Level 3 operational mode]→[off]

Selected mode indicator 954 may indicate the currently selected treatment operational mode of device 10 (e.g., a particular treatment mode, power level, "comfort level," etc.), as selected using power/mode selector 952. In one embodiment, selected mode indicator 954 includes three LEDs, each corresponding to one of three different operational modes of device 10, such that the currently selected operational mode can be indicated, e.g., by lighting the corresponding LED, or according to the following code:

all three LEDs off=device off; one LED lighted=Level 1 operational mode; two LEDs lighted on=Level 2 operational mode; all three LEDs lighted=Level 3 operational mode Treatment completion indicator 956 comprise any suitable interface for indicating an the successful completion of a particular recommended treatment session, e.g., which may be defined based on one or more treatment session delimiters, as discussed above.

Battery charge indicator 958 may indicate the charge status of a battery 20 provided in device 10. For example, indicator 958 may be a multicolor LED for indicating battery status, e.g., a red/green LED indicator in which green indicates full/good charge, flashing green indicates need to recharge soon, and red indicates depleted battery/must recharge prior to using. As another example, indicator 958 may indicate the fraction of remaining charge of battery 20 by lighting a corresponding fraction of a battery icon.

Alarm indicator 960 may comprise any suitable interface for indicating an error condition regarding device 10, e.g., an error condition identified by any control system 18 or electronics 30. For example, alarm indicator 960 may comprise a multicolor LED configured to display different colors corresponding to different error conditions. In some embodiments, device 10 may also provide audible feedback to indicate the error condition.

Device lock indicator 962 may comprise any suitable interface for indicating whether device 10 is locked from operation (e.g., a child lock safety feature). In some embodiments, device 10 may be locked and/or unlocked by predetermined user interactions with one or more user interface 28. For example, device 10 may be locked and/or unlocked by pressing a predetermined combination of buttons. As another example, device 10 may be locked and/or unlocked by holding one or more predetermined buttons by a predetermined time period, which time period may be indicated by visual, audible, or tactile feedback. For instance, in one embodiment, device 10 is locked and unlocked in the following manner. When the user presses and holds power/mode button 952, the device 10 begins emitting a series of audible tones, one each second. The device can be locked by releasing button 952 after the fourth tone, but before the fifth tone. In response, device lock indicator 962 is illuminated and the operation and use of device 10, including user interfaces 28, are locked until device 10 is unlocked. Device 10 can be unlocked in the same way that the device is locked, by pressing and holding power/mode button 952 and then releasing after a period of between 4 and 5 seconds.

In addition to the above, device 10 may provide additional visual, audible, and/or tactile feedback regarding the status, settings, and/or operation of device 10. For example, in embodiments in which scanning system motor 120 is turned on and off corresponding to on/off periods of treatment, the rotation of the motor 120 may provide an inherent tactile feedback (e.g., a slight vibration) indicating to the user that the device is operating. As another example, device 10 may be programmed to provide visual, audible, and/or tactile feedback at the completion of a treatment session, as well as at the completion of predetermined portions of the treatment session. For instance, device 10 may emit a tone after each 25% of a treatment session (e.g., indicating 25% completion, 50% completion, 75% completion, and 100% completion). Thus, for a full-face treatment, for example, the user may treat one quadrant of the face during each 25% of the treatment session. As discussed above, the treatment session may be defined by a predetermined treatment session delimiter, e.g., total number of beams 114 delivered, total number of scans, total energy delivered, etc. Thus, the predetermined portions (e.g., 25%) of the treatment may be defined based on such treatment session delimiter. For example, for a full-face treatment defined by delimiter of 20,000 total MTZs, device 10 may emit a tone after each 5,000 delivered beams 114.

Operation Modes/"Comfort Levels"

As discussed above, device 10 may be configured to operate according to multiple different operational modes, which may be manually selectable by the user and/or automatically selectable by control system 18 of device 10. Operational modes may include, for example, treatment modes (e.g., gliding mode vs. stamping mode), power levels (e.g., low delivered energy/MTZ, medium delivered energy/MTZ, or high delivered energy/MTZ), "comfort levels" (e.g., comfort level 1, comfort level 2, comfort level 3, etc.). Device 10 may be configured for any suitable number of selectable treatment modes, e.g., two, three, four, five, or more selectable treatment modes.

In one example embodiment, device 10 is configured for providing three selectable treatment levels, according to Table 2 below.

TABLE 2

| | Level 1 | Level 2 | Level 3 |
|---|---|---|---|
| Raw laser power (i.e., emitted) (approximate) | 3 W | 3 W | 3 W |
| Pulse duration (approximate) | 3 ms | 6 ms | 7 ms |
| Total optical efficiency of device (approximate) | 55% | 55% | 55% |
| Energy per delivered beam 114/MTZ (approximate) | 5 mJ | 10 mJ | 12 mJ |
| Treatment spot size, assuming no smearing (approximate) | 0.06 mm$^2$ | 0.06 mm$^2$ | 0.06 mm$^2$ |
| Treatment spot size, including smearing effects at typical manual glide speed of 4 cm/sec (approximate) | 0.10 mm$^2$ | 0.13 mm$^2$ | 0.14 mm$^2$ |
| Energy density at each MTZ, assuming typical manual glide speed of 4 cm/sec (approximate) | 5 J/cm$^2$ | 8 J/cm$^2$ | 9 J/cm$^2$ |
| MTZ depth (approximate) | 100 μm | 250 μm | 300 μm |
| Minimum displacement of device 10 between consecutive scanned rows of MTZs | 1 mm (or n identified skin features, where n = 2 or 3, for example) | 1 mm (or n = 2 or 3 skin features) | 1 mm (or n = 2 or 3 skin features) |
| scanning frequency (assuming uninterrupted scanning) | 110 MTZ/sec | 110 MTZ/sec (comfort mode, e.g., achieved by reducing speed of motor 120 by 50%) | 90 MTZ/sec |
| Total MTZs for full-face treatment (300 cm$^2$) (e.g., enforced as a treatment session delimiter) | 10,800 MTZ | 21,600 MTZ | 39,000 MTZ |
| Treatment spot density (approximate) | 36 MTZ/cm$^2$ | 72 MTZ/cm$^2$ | 130 MTZ/cm$^2$ |
| Treatment time for full-face treatment (approximate) | 2 min | 5 min | 10 min |

Focal Plane of Delivered Beams

Figure 71:
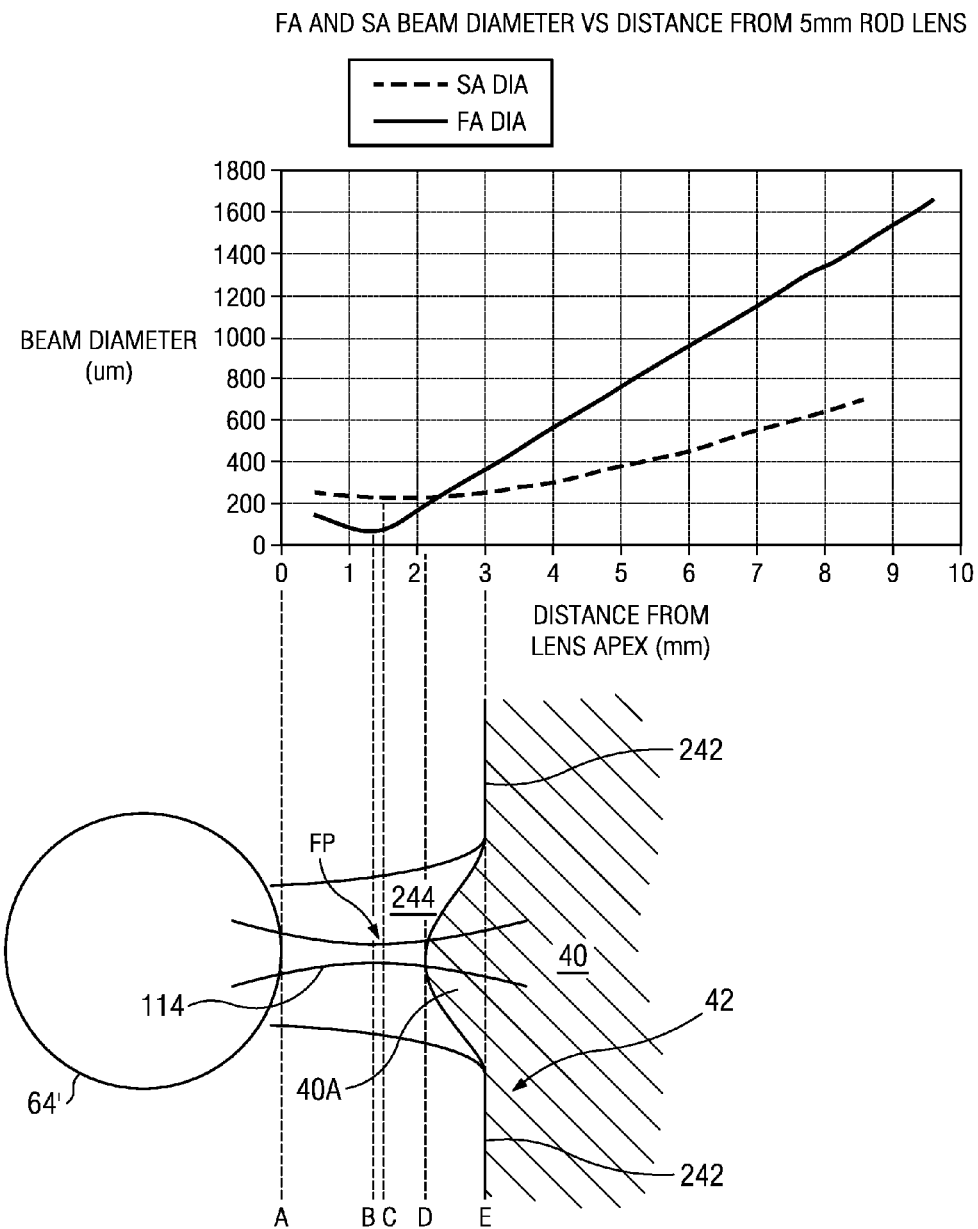
FIG. 71 illustrates a graph and cross-sectional representation of the fast axis and slow axis beam profile of a delivered beam, illustrating the focal plane with respect to the surface of the skin, according to certain example embodiments.

FIG. 71 illustrates a graph and cross-sectional representation of the fast axis and slow axis beam profile of a delivered beam 114, illustrating the focal plane (FP) with respect to the surface of the skin 40, according to certain example embodiment. For example, FIG. 71 may correspond to embodiments of device 10 that use a laser diode as radiation source 14, and include a downstream fast axis optic (e.g., rod lens) 64', such as the embodiment shown in FIGS. 68A-68C, for example.

The top portion of FIG. 71 illustrates a graph of the beam diameter in both the fast axis and slow axis, as a function of distance beyond (downstream of) fast axis optic 64'. The bottom portion of FIG. 71 shows a cross-sectional representation of the application end 42 of device 10, including an outer surface 242 of application end 42, fast axis optic 64', and an open recessed area 244 through which beam 114 is delivered to the skin 40. When application end 42 is pressed against the skin, a portion 40A of the skin may press into the open recessed area 244, as illustrated. The bottom portion of FIG. 71 also identified various parallel planes A-E, wherein plane A is the plane of the apex of optic 64', plane B is the plane corresponding to the minimum width, or waist, of the fast axis profile of beam 114. plane C is the plane corresponding to the minimum width, or waist, of the slow axis profile of beam 114, plane D is the plane corresponding to the maximum penetration of skin portion 40A within the open recessed area 244 of the application end 42 of device 10, and plane E is the plane corresponding to the outer surface 242 of the application end 42.

In the illustrated example, optical system 15 of device 10, including downstream fast axis optic 64', scanning element 62, and any other optical elements 16 of optical system 15, are configured to converge the output beam in the fast and slow axes, respectively, such that each delivered beam 114 has a focal point or focal plane FP located slightly above the surface of the skin (i.e., outside the skin). As discussed above, the "focal point" or "focal plane" of each delivered beam is defined as the plane perpendicular to the propagation axis of the beam having the minimum cross-sectional area. In this embodiment, the focal plane FP lies between the waist of the fast axis beam profile (plane B) and the waist of the slow axis beam profile (plane C).

Thus, in this embodiment, beam 114 is slight diverging upon incidence with the skin, and creates a treatment spot of about 200-250 μm (in the fast axis direction) by about 200-250 μm (in the slow fast axis direction), which may be suitable, e.g., for a fractional treatment. In other embodiments, device 10 may be configured to provide any other suitable treatment spot sizes and/or other treatment spot shapes, e.g., by varying the details of the fast axis optics, slow axis optics, distances between optical elements, power of optical elements, etc.

Further, in other embodiments, device 10 may be configured such that the focal plane FP of delivered beams 114 is at the surface of the skin 40, or below the surface of the skin 40 by any suitable distance, e.g., as suitable for various types of dermatological treatments.

What is claimed is:

1. A self-contained, hand-held device for providing a dermatological treatment, the device comprising:
    a device body configured to be handheld by a user;
    a radiation source supported in the device body;
    an automated scanning system configured to receive an input beam generated by the radiation source and scan the received input beam to provide a series of output beams for delivery to the skin to form a pattern of treatment spots on the skin, wherein each treatment spot is defined by a contiguous area on the skin surface receiving at least $1/e^2$ times the maximum intensity of a respective output beam delivered to the skin;
    an application end at which the output beams are delivered to the skin, the application end configured to be manually moved across the surface of the skin during a treatment session; and
    a displacement control system including:
        a displacement sensor that generates displacement sensor signals based on an interaction with the skin during movement of the application end across the surface of the skin; and
        a processor; and
        computer instructions stored in a non-transitory computer-readable medium and executable by the processor to:
            receive the displacement sensor signals from the displacement sensor;
            successively identify from the displacement sensor signals a series of skin features in the skin as the device moves across the skin;
            count the number of successively-identified skin features as the device moves across the skin;
            determine the displacement of the device relative to the skin based on the counted number of identified skin features;
            compare the determined displacement of the device to a predefined minimum displacement; and
            generate displacement-based control signals that control at least one operational parameter of the device based on the results of the comparison of the determined displacement of the device to the predefined minimum displacement.

2. The device of claim 1, wherein the computer instructions are executable to control at least one operational parameter of the radiation source based at least on the determined displacement of the device relative to the skin.

3. The device of claim 2, wherein the computer instructions are executable to interrupt or delay operation of the radiation source based at least on the determined displacement of the device relative to the skin.

4. The device of claim 3, wherein the computer instructions are executable to interrupt or delay pulsing of the radiation source based at least on the determined displacement of the device relative to the skin.

5. The device of claim 1, wherein the computer instructions are executable to control at least one operational parameter of the automated scanning system based at least on the determined displacement of the device relative to the skin.

6. The device of claim 5, comprising:
    a motor associated with the automated scanning system; and
    wherein the computer instructions are executable to control at least one operational aspect of the motor associated with the an automated scanning system based at least on the determined displacement of the device relative to the skin.

7. The device of claim 1, wherein the computer instructions of the displacement control system are executable to generate the displacement-based control signals to prevent or reduce the likelihood of over-treatment of a location on the skin.

8. The device of claim 1, wherein the computer instructions of the displacement control system are executable to generate the displacement-based control signals to prevent or reduce the likelihood of treatment spots overlapping each other.

9. The device of claim 1, wherein:
the automated scanning system is configured to repeatedly scan the received input beam, each scan of the input beam creating an array of output beams for delivery to the skin to form a corresponding array of treatment spots on the skin; and
the computer instructions of the displacement control system are executable to generate the displacement-based control signals to provide a defined non-zero minimum spacing between adjacent arrays of treatment spots in a direction of manual movement of the device.

10. The device of claim 9, wherein:
each scan of the input beam creating a row of output beams for delivery to the skin to form a corresponding row of treatment spots on the skin; and
the computer instructions of the displacement control system are executable to generate the displacement-based control signals to provide the defined non-zero minimum spacing between adjacent rows of treatment spots in the direction of manual movement of the device.

11. The device of claim 1, wherein the displacement control system is configured to control the radiation source based on the counted number of identified skin features.

12. The device of claim 1, wherein the displacement control system is configured to enable the radiation source only if the counted number of identified skin features reaches a predetermined minimum number of skin features.

13. The device of claim 1, wherein the device does not detect or determine a speed of movement of the device.

14. The device of claim 1, wherein the displacement sensor is a single-pixel displacement sensor.

15. The device of claim 14, wherein the single-pixel displacement sensor is a lensless sensor including:
a light emitter configured to deliver light toward the skin;
a light detector configured to detect light reflected and/or remitted from the skin, and generate a signal; and
hardware circuitry configured to analyze a signal from the detector.

16. The device of claim 1, further including a control system for:
determining a delimiting value of a delimiting parameter for a treatment session;
monitoring the delimiting parameter during the treatment session; and
automatically terminating the treatment session upon reaching the delimiting value of the delimiting parameter.

17. The device of claim 16, wherein the delimiting parameter comprises either a total number of treatment spots or a total amount of delivered energy for the treatment session.

18. The device of claim 1, wherein comparing the determined displacement of the device to the predefined minimum displacement comprises comparing the determined displacement of the device to a predefined minimum displacement greater than a length of each treatment spot along a direction of manual movement of the device, such that the displacement-based control signals generated by the execution of the computer instructions by the processor provide a defined non-zero minimum spacing between corresponding treatment spots of adjacent rows of treatment spots on the skin in the direction of the manual movement of the device across the skin, such that treatment spots of sequentially-delivered rows of treatment spots on the skin are spaced apart from each other in the direction of the manual movement of the device by areas of non-treated skin that receive insufficient radiation to qualify as a treatment spot.

19. A self-contained, hand-held device for providing a dermatological treatment, the device comprising:
a device body configured to be handheld by a user;
a radiation source supported in the device body;
an automated scanning system configured to receive an input beam generated by the radiation source and scan the received input beam to provide a series of output beams for delivery to the skin to form a pattern of treatment spots on the skin, wherein each treatment spot is defined by a contiguous area on the skin surface receiving at least $1/e^2$ times the maximum intensity of a respective output beam delivered to the skin;
an application end at which the output beams are delivered to the skin, the application end configured to be manually moved across the surface of the skin during a treatment session; and
a displacement control system including:
a displacement sensor that generates displacement sensor signals based on an interaction with the skin during movement of the application end across the surface of the skin; and
a processor; and
computer instructions stored in a non-transitory computer-readable medium and executable by the processor to:
receive the displacement sensor signals from the displacement sensor;
successively identify from the displacement sensor signals a series of skin features in the skin as the device moves across the skin;
count the number of successively-identified skin features as the device moves across the skin;
compare the counted number of successively-identified skin features to a predefined minimum number; and
generate displacement-based control signals that control at least one operational parameter of the device based on the results of the comparison of the number of successively-identified skin features to the predefined minimum number.

* * * * *